(12) United States Patent
Mousa et al.

(10) Patent No.: US 9,750,709 B2
(45) Date of Patent: Sep. 5, 2017

(54) NANOPARTICLE AND POLYMER FORMULATIONS FOR THYROID HORMONE ANALOGS, ANTAGONISTS, AND FORMULATIONS THEREOF

(71) Applicant: NanoPharmaceuticals LLC, Rensselaer, NY (US)

(72) Inventors: Shaker A. Mousa, Wynantskill, NY (US); Faith B. Davis, West Sand Lake, NY (US); Paul J. Davis, West Sand Lake, NY (US)

(73) Assignee: NANOPHARMACEUTICALS LLC, Rensselaer, NY (US)

( * ) Notice: Subject to any disclaimer, the term of this patent is extended or adjusted under 35 U.S.C. 154(b) by 305 days.

(21) Appl. No.: 14/185,010

(22) Filed: Feb. 20, 2014

(65) Prior Publication Data

US 2014/0314665 A1     Oct. 23, 2014

Related U.S. Application Data

(63) Continuation of application No. 11/786,723, filed on Apr. 11, 2007, now Pat. No. 8,668,926, which is a continuation-in-part of application No. 11/663,047, filed on Oct. 9, 2007, now Pat. No. 8,071,134, which is a continuation-in-part of application No. 10/943,072, filed as application No. PCT/US2005/032813 on Sep. 15, 2005, now Pat. No. 7,785,632, which is a continuation of application No. 10/943,072, filed on Sep. 15, 2004, now Pat. No. 7,785,632.

(60) Provisional application No. 60/502,721, filed on Sep. 15, 2003, provisional application No. 60/670,534, filed on Apr. 13, 2005, provisional application No. 60/856,450, filed on Nov. 2, 2006, provisional application No. 60/831,740, filed on Jul. 17, 2006,
(Continued)

(51) Int. Cl.

| | |
|---|---|
| A61K 31/198 | (2006.01) |
| A61K 47/48 | (2006.01) |
| C07K 16/28 | (2006.01) |
| A61K 9/51 | (2006.01) |
| A61K 9/00 | (2006.01) |
| A61K 31/35 | (2006.01) |
| A61K 49/00 | (2006.01) |
| A61K 49/08 | (2006.01) |
| A61K 49/10 | (2006.01) |
| A61K 49/12 | (2006.01) |
| A61K 51/04 | (2006.01) |
| A61K 51/06 | (2006.01) |
| A61K 31/192 | (2006.01) |
| A61K 31/195 | (2006.01) |
| A61K 31/4365 | (2006.01) |
| A61K 31/60 | (2006.01) |
| A61K 31/7076 | (2006.01) |
| A61K 31/727 | (2006.01) |
| A61K 31/65 | (2006.01) |
| A61K 39/44 | (2006.01) |

(52) U.S. Cl.
CPC ......... *A61K 31/198* (2013.01); *A61K 9/0048* (2013.01); *A61K 9/5153* (2013.01); *A61K 31/192* (2013.01); *A61K 31/195* (2013.01); *A61K 31/4365* (2013.01); *A61K 31/60* (2013.01); *A61K 31/65* (2013.01); *A61K 31/7076* (2013.01); *A61K 31/727* (2013.01); *A61K 39/44* (2013.01); *A61K 47/482* (2013.01); *A61K 47/4823* (2013.01); *A61K 47/48176* (2013.01); *A61K 47/48215* (2013.01); *A61K 47/48246* (2013.01); *A61K 47/48915* (2013.01); *A61K 47/48923* (2013.01); *A61K 49/0008* (2013.01); *A61K 49/085* (2013.01); *A61K 49/10* (2013.01); *A61K 49/12* (2013.01); *A61K 51/0402* (2013.01); *A61K 51/0497* (2013.01); *A61K 51/065* (2013.01); *C07K 16/2848* (2013.01); *C07K 2317/76* (2013.01); *Y10T 428/2982* (2015.01)

(58) Field of Classification Search
CPC ............ A61K 31/198; A61K 47/48923; A61K 9/5153; A61K 9/0048; A61K 31/65; A61K 39/44; A61K 47/48915; A61K 49/12; A61K 47/48176; A61K 47/482; A61K 47/48215; A61K 47/4823; C07K 16/2848
See application file for complete search history.

(56) References Cited

U.S. PATENT DOCUMENTS

| | | |
|---|---|---|
| 3,625,214 A | 12/1971 | Higuchi |
| 4,205,058 A | 5/1980 | Wagner et al. |

(Continued)

FOREIGN PATENT DOCUMENTS

| | | |
|---|---|---|
| CA | 2673133 A1 | 11/2008 |
| CN | 1126589 | 7/1996 |

(Continued)

OTHER PUBLICATIONS

Restriction Requirement (Mail Date Dec. 2, 2015) for U.S. Appl. No. 14/184,889, filed Feb. 20, 2014.

(Continued)

*Primary Examiner* — Snighda Maewall
(74) *Attorney, Agent, or Firm* — Schmeiser, Olsen & Watts, LLP

(57) ABSTRACT

Disclosed are methods of treating subjects having conditions related to angiogenesis including administering an effective amount of a polymeric Nanoparticle form of thyroid hormone agonist, partial agonist or an antagonist thereof, to promote or inhibit angiogenesis in the subject. Compositions (Continued)

of the polymeric forms of thyroid hormone, or thyroid hormone analogs, are also disclosed.

13 Claims, 65 Drawing Sheets

Related U.S. Application Data provisional application No. 60/791,235, filed on Apr. 11, 2006.

(56) References Cited

U.S. PATENT DOCUMENTS

| | | | |
|---|---|---|---|
| 4,650,751 A | 3/1987 | Siegel et al. |
| 4,789,734 A | 12/1988 | Pierschbacher |
| 4,801,504 A | 1/1989 | Burdick et al. |
| 4,801,575 A | 1/1989 | Pardridge |
| 4,906,474 A | 3/1990 | Langer et al. |
| 4,925,673 A | 5/1990 | Steiner et al. |
| 4,968,590 A | 11/1990 | Kuberasampath et al. |
| 5,011,486 A | 4/1991 | Aebischer et al. |
| 5,091,513 A | 2/1992 | Huston et al. |
| 5,104,895 A | 4/1992 | Spinelli et al. |
| 5,158,978 A | 10/1992 | Rubin |
| 5,225,204 A | 7/1993 | Chen et al. |
| 5,231,000 A | 7/1993 | Majocha et al. |
| 5,304,121 A | 4/1994 | Sahatjian |
| 5,410,016 A | 4/1995 | Hubbell et al. |
| 5,438,126 A | 8/1995 | DeGroot et al. |
| 5,449,665 A | 9/1995 | Sollevi |
| 5,482,719 A | 1/1996 | Guillet et al. |
| 5,571,840 A | 11/1996 | Mayor et al. |
| 5,591,709 A | 1/1997 | Lindenbaum |
| 5,593,688 A | 1/1997 | Baldeschwieler |
| 5,648,506 A | 7/1997 | Desai et al. |
| 5,733,871 A | 3/1998 | Alps et al. |
| 5,766,635 A | 6/1998 | Spenleuhauer et al. |
| 6,013,641 A | 1/2000 | Lussow et al. |
| 6,139,870 A | 10/2000 | Verrecchia |
| 6,316,412 B1 | 11/2001 | Ginsberg et al. |
| 6,414,037 B1 | 7/2002 | Pezzuto et al. |
| 6,482,406 B1 | 11/2002 | Stewart |
| 6,677,473 B1 | 1/2004 | Madison et al. |
| 6,740,680 B1 | 5/2004 | Danforth, Jr. et al. |
| 6,818,620 B2 | 11/2004 | Bhatnagar |
| 6,821,947 B2 | 11/2004 | Iozzo |
| 7,166,155 B2 | 1/2007 | Ishikawa |
| 7,638,558 B2 | 12/2009 | Breitenkamp et al. |
| 7,785,632 B2 | 8/2010 | Mousa et al. |
| 7,807,621 B2 | 10/2010 | Mazar et al. |
| 8,026,209 B2 | 9/2011 | Gaillard et al. |
| 8,071,134 B2 | 12/2011 | Mousa et al. |
| 8,242,171 B2 | 8/2012 | Sinclair et al. |
| 8,518,451 B2 | 8/2013 | Mousa et al. |
| 8,668,926 B1 | 3/2014 | Mousa et al. |
| 8,802,240 B2 | 8/2014 | Davis et al. |
| 9,180,107 B2 | 11/2015 | Mousa et al. |
| 9,198,887 B2 | 12/2015 | Mousa et al. |
| 9,220,788 B2 | 12/2015 | Davis et al. |
| 9,272,049 B2 | 3/2016 | Alexander-Bridges et al. |
| 9,289,395 B2 | 3/2016 | Davis et al. |
| 2001/0021763 A1 | 9/2001 | Harris |
| 2001/0046521 A1 | 11/2001 | Zasloff et al. |
| 2002/0049247 A1 | 4/2002 | Chen |
| 2002/0137676 A1 | 9/2002 | Hsiang et al. |
| 2002/0151594 A1 | 10/2002 | Morkin et al. |
| 2003/0027940 A1 | 2/2003 | Lang et al. |
| 2003/0138557 A1 | 7/2003 | Allison |
| 2003/0157098 A1 | 8/2003 | Laug |
| 2003/0162758 A1 | 8/2003 | Schwartz et al. |
| 2003/0165576 A1 | 9/2003 | Fujii et al. |
| 2004/0013728 A1 | 1/2004 | Oh et al. |
| 2004/0033259 A1 | 2/2004 | Hanshew, Jr. et al. |
| 2005/0124862 A1 | 6/2005 | Mousa et al. |
| 2005/0158376 A1 | 7/2005 | Sardi et al. |
| 2005/0171027 A1 | 8/2005 | Sinclair et al. |
| 2005/0222387 A1 | 10/2005 | Debatin et al. |
| 2005/0249721 A1 | 11/2005 | Houston et al. |
| 2005/0272817 A1 | 12/2005 | Heino |
| 2006/0166303 A1 | 7/2006 | Spanuth |
| 2006/0210539 A1 | 9/2006 | Zhang |
| 2007/0117841 A1 | 5/2007 | Ozes et al. |
| 2007/0190160 A1 | 8/2007 | Turos et al. |
| 2008/0081074 A1 | 4/2008 | Gu et al. |
| 2008/0124280 A1 | 5/2008 | Mousa et al. |
| 2008/0193377 A1 | 8/2008 | Line et al. |
| 2008/0199850 A1 | 8/2008 | Sutter et al. |
| 2009/0022806 A1 | 1/2009 | Mousa et al. |
| 2009/0175862 A1 | 7/2009 | Silverio et al. |
| 2010/0112079 A1 | 5/2010 | Mousa et al. |
| 2010/0159021 A1 | 6/2010 | Davis et al. |
| 2010/0209382 A1 | 8/2010 | Alexander-Bridges et al. |
| 2010/0255108 A1 | 10/2010 | Lin et al. |
| 2011/0052715 A1 | 3/2011 | Davis et al. |
| 2011/0142941 A1 | 6/2011 | Davis et al. |
| 2012/0258069 A1 | 10/2012 | Alexander-Bridges et al. |
| 2012/0315320 A1 | 12/2012 | Davis et al. |
| 2014/0072635 A1 | 3/2014 | Mousa et al. |
| 2014/0072646 A1 | 3/2014 | Mousa et al. |
| 2014/0199376 A1 | 7/2014 | Mousa et al. |

FOREIGN PATENT DOCUMENTS

| | | |
|---|---|---|
| WO | 9500135 | 1/1995 |
| WO | 9640048 | 12/1996 |
| WO | 9833942 | 8/1998 |
| WO | 9856771 | 12/1998 |
| WO | 9958119 A1 | 11/1999 |
| WO | 9959548 A1 | 11/1999 |
| WO | 9962549 | 12/1999 |
| WO | 0064431 A1 | 11/2000 |
| WO | 0078815 A1 | 12/2000 |
| WO | 0113031 A2 | 2/2001 |
| WO | 0113936 A1 | 3/2001 |
| WO | 0176589 A1 | 10/2001 |
| WO | 0203914 A2 | 1/2002 |
| WO | 0249501 A2 | 6/2002 |
| WO | 02060389 A2 | 8/2002 |
| WO | 03075741 A2 | 9/2003 |
| WO | 2004013728 A2 | 2/2004 |
| WO | 2004069201 A2 | 8/2004 |
| WO | 2005027895 A2 | 3/2005 |
| WO | 2006003014 A2 | 1/2006 |
| WO | 2006031922 A2 | 3/2006 |
| WO | 2007035612 A2 | 3/2007 |
| WO | 2008051291 A2 | 5/2008 |
| WO | 2008140507 A2 | 11/2008 |
| WO | 2010120506 A2 | 10/2010 |
| WO | 2010148007 A2 | 12/2010 |

OTHER PUBLICATIONS

Notice of Allowance (Mail Date Nov. 16, 2015) for U.S. Appl. No. 12/947,389, filed Nov. 16, 2010.
Final Office Action (Mail Date Oct. 9, 2015) for U.S. Appl. No. 13/975,725, filed Aug. 26, 2013.
Adyisory Action (Mail Date Dec. 31, 2015) for U.S. Appl. No. 13/975,725, filed Aug. 26, 2013.
Notice of Allowance (Mail Date Nov. 2, 2015) for U.S. Appl. No. 13/256,047, filed Jun. 8, 2011.
Final Office Action (Mail Date Oct. 16, 2015) for U.S. Appl. No. 14/242,041, filed Apr. 1, 2014.
Restriction Requirement (Mail Date Nov. 4, 2015) for U.S. Appl. No. 14/546,440, filed Nov. 18, 2014.
A.D.A.M. Medical Encyclopedia, www.ncbi.nlm.nih.gov/pubmedhealth/PMH0001308/, downloaded Jul. 12, 2012. 6 pages.
Abdollahi et al., "Inhibition of α□β3 Integrin Survival Signaling Enhances Antiangiogenic and Antitumor Effects of Radiotherapy", Clin. Cancer Research., 11(17):6270-6279 (2005) 10 pages.
Albert et al., "Integrin α□β3 Antagonist Cilengitide Enhances Efficacy of Radiotherapy in Endothelial Cell and Non-Small-Cell

(56) References Cited

OTHER PUBLICATIONS

Lung Cancer Models", Int. J. Radiat. Oncol. Biol. Phys., 65(5):1536-1543 (2006) 8 pages.
Alexis et al., "Nonocclusive Common Carotid Artery Thrombosis in the Rat Results in Reversible Sensorimotor and Cognitive Behavorial Deficits", Stroke, 26:2338-2346 (1995) 16 pages.
Ali et al., "Angiogenesis as a potential biomarker in prostate cancer chemoprevention trials", Urology, 57(Suppl 4A):143-147 (2001) 5 pages.
Ali et al., "Apoptosis-Inducing effect of erlotinib is potentiated by 3,3'-diindolylmethane in vitro and in vivo using an orthotopic model of pancreatic cancer", Mol. Cancer Ther., 7(6):1708-1719(2008) 12 pages.
Ali et al., "High levels of oestrogen receptor-$\alpha$ in tumorigenesis: inhibition of cell growth and angiogenic factors", Cell Prolif., 34(4):223-231 (2001) 10 pages.
Allen, A.R., "Surgery of experimental lesion of spinal cord equivalent to crush injury of fracture dislocation of spinal column", J. Am. Med. Assoc., 57(11):878-880 (1911) 4 pages.
Almog et al., "Transcriptional Switch of Dormant Tumors to Fast-Growing Angiogenic Phenotype", Cancer Res., 69 (3):836-844 (2009).
Amirkhosravi et al., "Antimestatatic effect of tinzaparin, a low-molecular-weight heparin", J. Thromb. Haemost., 1:1972-1976 (2003) 5 pages.
Amirkhosravi et al., "Inhibition of tumor cell-induced platelet aggregation and lung metastasis by the oral GpIIb/IIIa antagonist XV454", J. Thrombosis and Haemostasis, 3:549-554 (2003) 6 pages.
Ando et al., "Induction by carbon-ion irradiation of the expression of vascular endothelial growth factor in lung carcinoma cells", Int. J. Radiat. Biol., 76(8):1121-1127 (2000) 7 pages.
Application No. PCT/US2004/030583, International Search Report and the Written Opinion of the International Searching Authority, or the Declaration dated Mar. 7, 2005. 11 pages.
Application No. PCT/US2005/032813, International Search Report dated Dec. 22, 2006. 6 pages.
Application No. PCT/US2007/009026, International Search Report dated Nov. 7, 2008. 5 pages.
Application No. PCT/US2009/069104, International Search Report dated Mar. 4, 2010 5 pages.
Application No. PCT/US2007/026167, International Search Report dated Oct. 30, 2008. 3 pages.
Application No. PCT/US2010/038700, International Search Report dated Mar. 21, 2011. 4 pages.
Application No. PCT/US2006/036243, International Search Report dated Jul. 30, 2007. 7 pages.
Application No. PCT/US2010/029371, International Search Report dated Aug. 24, 2010. 5 pages.
Audus et al., "Bovine Brain Microvessel Endothelial Cell Monolayers as a Model System for the Blood-Brain Barrier", in Biological Approaches to the Controlled Delivery of Drugs, Ann. N.Y. Acad. Sci., 507:9-18 (1987) 11 pages.
Avis, K.E., "Parenteral Preparations", in Remington's Pharmaceutical Sciences, 15th Ed., Chapter 84, pp. 1461-1487, Mack Publishing Co., Easton, Pennsylvania (1975) 29 pages.
Balestrazzi et al., "Leaf-associated bacteria from transgenic white poplar producing resveratrol-like compounds: isolation, molecular characterization, and evaluation of oxidative stress tolerance", Can. J. Microbiol., 55:829-840 (2009) 12 pages.
Balin-Gauthier et al., "In vivo and in vitro antitumor activity of oxaliplatin in combination with cetuximab in human colorectal tumor cell lines expressing different level of EGFR", Cancer Chemother. Pharmacol., 57:709-718 (2006) 8 pages.
Baur et al., "Resveratrol improves health and survival of mice on a high-calorie diet", Nature, 444:337-342 (2006) 6 pages.
Baur et al., "Therapeutic potential of resveratrol: the in vivo evidence", Nat. Rev. Drug Discov., 5:493-506 (2006) 14 pages.

Bederson et al., "Rat Middle Cerebral Artery Occlusion: Evaluation of the Model and Development of a Neurologic Examination", Stroke, 17(3):472-476 (1986) 6 pages.
Belenky et al., "NAD+ metabolism in health and disease", Trends Biochem. Sci., 32(1):12-19 (2007) 9 pages.
Benedetti et al., "Life Tables and Survivor Functions", in BMDP Statistical Software Manual, BMDP Statistical Software, Inc., vol. 2, p. 573 and 689-718 (1988) 33 pages.
Ben-Hur et al., "Thermally Enhanced Radioresponse of Cultured Chinese Hamster Cells: Inhibition of Repair of Sublethal Damage and Enhancement of Lethal Damage", Radiat Res., 58:38-51 (1974) 14 pages.
Bennett et al., "A peptide derived from $\alpha$-fetoprotein prevents the growth of estrogen-dependent human breast cancers sensitive and resistant to tamoxifen", Proc. Natl, Acad. Sci. USA, 99(4):2211-2215 (2002) 5 pages.
Bergers et al., "Modes of resistance to anti-angiogenic therapy", Nat. Rev. Cancer, 8(8):592-603 (2008) 23 pages.
Bergh et al., "Integrin $\alpha v \beta 3$ contains a cell surface receptor site for thyroid hormone that is linked to activation of mitogen-activated protein kinase and induction of angiogenesis", Endocrinology, 146(7):2864-2871 (2005) 8 pages.
Bergstrom et al., "Iodine-123 labelled Z-(R,R)-IQNP: a potential radioligand for visualization of M1 and M2 muscarinic acetylcholine receptors in Alzheimer's disease", Eur. J. Nucl. Med., 26(11):1482-1485 (1999).
Bergstrom et al., "Reduction of fibrinogen absorption on PEG-coated polystyrene surfaces", J. Biomed. Mat. Res., 26:779-790 (1992) 12 pages.
Beum et al., "Binding of Rituximab, Trastuzumab, Cetuximab, or mAb T101 to Cancer Cells Promotes Trogocytosis Mediated by THP-1 Cells and Monocytes", J. Immunol., 181:8120-8132 (2008) 13 pages.
Bhat et al., "NCAM-180, the largest component of the neural cell adhesion molecule, is reduced in dysmyelinating quaking mutant mouse brain", Brain Res., 452:373-377 (1988) 5 pages.
Bilello et al., "Effect of 2', 3'-Didehydro-3'-Deoxythymidine in an In Vitro Hollow-Fiber Pharmacodynamic Model System Correlates with Results of Dose-Ranging Clinical Studies", Antimicrob Agents Chemother., 38(6):1386-1391 (1994) 6 pages.
Blaszczyk-Thurin et al., "An Experimental Vaccine Expressing Wild-Type p53 induces Protective Immunity Against Glioblastoma Cells with High Levels of Endogenous p53", Scand. J. Immunol., 56:361-375 (2002) 15 pages.
Blight, A.R., "Macrophages and Inflammatory Damage in Spinal Cord Injury", J. Neurotrauma, 9(Suppl. 1):S83-S91 (1992) 10 pages.
Blood et al., "Tumor interactions with the vasculature: angiogenesis and tumor metastasis", Bioch. Biophys. Acta, 1032:89-118 (1990) 30 pages.
Bokemeyer et al., "Fluorouracil, Leucovorin, and Oxaliplatin With and Without Cetuximab in the First-Line Treatment of Metastatic Colorectal Cancer", J. Clin. Oncol., 27(5):663-671 (2009) 9 pages.
Bornebroek et al., "Potential for imaging cerebral amyloid deposits using 123I-labelled serum amyloid P component and SPET", Cucl. Med. Commun., 17:929-933 (1996) 6 pages.
Bozarth et al., "An improved method for the quantitation of cellular migration: Rose of $\alpha v \beta 3$ integrin in endothelial and smooth muscle cell migration", Meth. Cell Sci., 19(3):179-187 (1997) 9 pages.
Brachmann et al., "The SIR2 gene family, conserved from bacteria to humans, functions in silencing, cell cycle progression, and chromosome stability", Genes Dev. 9:2888-2902 (1995) 15 pages.
Braughler et al., "Involvement of Lipid Peroxidation in CNS Injury", J. Neurotrauma, 9(Suppl. 1):S1-S7 (1992) 8 pages.
Breier et al., "The role of vascular endothelial growth factor in blood vessel formation", Trends in Cell Biol., 6:454_456 (1996) 3 pages.
Bridoux et al., "Semisynthesis and pharmacological activities of Tetrac analogs: Angiogenesis modulators", Bioorg. Med. Chem. Lett., 19:3259-3263 (2009) 5 pages.
Bridoux et al., "Semisynthesis and pharmacological activities of thyroxine analogs: Development of new angiogenesis modulators", Bioorg. Med. Chem. Lett, 20(11):3394-3398 (2010) 5 pages.

(56) References Cited

OTHER PUBLICATIONS

Brockhoff et al., "Differential impact of Cetuximab, Pertuzumab and Trastuzumab on BT474 and SK-BR-3 breast cancer proliferation", Cell Prolif., 40:488-507 (2007) 20 pages.
Brooks et al., "Antintegrin α□β3 blocks human breast cancer growth and angiogenesis in human skin", J. Clin. Invest., 96(4):1815-1822 (1995) 8 pages.
Bulitta et al., "Development and Qualification of a Pharmacodynamic Model for the Pronounced Inoculum Effect of Ceftazidime against Pseudomonas aeruginosa", Antimicrob. Agents Chemother., 53(1):46-56 (2009) 11 pages.
Burgman et al., "Effect of Inhibitors of Poly(ADP-Ribose)Polymerase on the Radiation Resposne of HeLa S3 Cells", Radiat. Res., 119:380-386 (1989) 7 pages.
Carmeliet et al., "Molecular Basis of Angiogenesis Role of VEGF and VE-Cadherin", Ann. N.Y. Acad. Sci., 902:249-264 (2000) 16 pages.
Chanoine et al., "The role of transthyretin in the transport of thyroid hormone to cerebrospinal fluid and brain", Acta Medica Austriaca, 19(Suppl. 1):25-28 (19920) 5 pages.
Charness et al., "Ethanol Increases the Expression of Functional Delta-Opioid Receptors in Neurblastoma x Glioma NG108-15 Hybrid Cells", J. Biol. Chem., 261(7):3164-3169 (1986) 6 pages.
Charo et al., "The Vitronectin Receptor α□β3 Binds Fibronectin and Acts in Concert with α5β1 in Promoting Cellular Attachment and Spreading on Fibronectin", J. Cell Biol., 111(6 Pt. 1): 2795-2800 (1990) 6 pages.
Chase et al., "Principles of Radioisotope Methodology", 2nd Ed., Minneapolis, MN. Burgess Publ. Co., 1962, pp. 68, 87-90. 7 pages.
Chavakis et al., "Kinetics of integrin expression in the mouse model of proliferative retinopathy and success of secondary intervention with cyclic RGD peptides", Diabetologia, 45:262-267 (2002) 6 pages.
Cheng et al., "Molecular Aspects of Thyroid Hormone Actions", Endocri. Rev., 31(2): 139-170 (2010) 32 pages.
Cheresh et al., "Biosynthetic and Functional Properties of an Arg-Gly-Asp-directed Receptor Involved in Human Melanoma Cell Attachment to Vitronectin, Fibrinogen and von Willibrand Factor", J. Biol. Chem., 262(36):17703-17711 (1987) 9 pages.
Cheresh, D.A., "Human endothelial cells synthesize and express an Arg-Gly-Asp-directed adhesion receptor involved in attachment to fibrinogen and von Willibrand factor", Proc. Natl. Acad. Sci. U.S.A., 84:6471-6475 (1987) 9 pages.
Chiaguri et al., "Anoikis: A necessary death program for anchorage-dependent cells", Biochem. Pharmacol., 76:1352-1364 (2008) 13 pages.
Chinese Office Action for Application No. 2004800331846 dated Mar. 5, 2010 7 pages.
Chinese Office Action for Application No. 2004800331846, mailed Nov. 30, 2007, cited CN 1126589. 6 pages.
Clifton et al., "Marked Protection by Moderate Hypothermia After Experimental Traumatic Brain Injury", J. Cereb. Blood Flow Metab., 11(1):114-121 (1991) 9 pages.
Cody et al., "Molecular modeling of the thyroid hormone interactions with α□β3 integrin", Steriods, 72:165-170 (2007) 6 pages.
Cohen-Jonathan et al., "Radioresistance Induced by the High Molecular Forms of the Basic Fibroblast Growth Factor Is Associated with an increased G2 Delay and a Hyperphosphorylation of p34CDC2 in HeLa Cells", Cancer Res., 57:1364-1370 (1997) 7 pages.
Cohen-Jonathan et al., "α□β3 integrin pathway controls glioma radioresistance through ILK", Proc. Amer. Assoc. Cancer Res., 47:5180 (2006) (Abstract Only) 2 pages.
Cox et al., "The repair of potentially lethal damage in X-irradiated cultures of normal and ataxia telangiectasia human fibroblasts", Int. J. Radiat. Biol., 39(4):357-365 (1981) 9 pages.
Cristofanilli et al., "Thyroid Hormone and Breast Carcinoma. Primary Hypothyroidism is Associated with a Reduced Incidence of Primary Breast Carcinoma", Cancer, 103(6):1122-1128 (2005) 7 pages.

D'Arezzo et al., "Rapid Nongenomic Effects of 3,5,3'-Triiodo-L Thyronine on the Intracellular pH of L-6 Myoblasts are Mediated by Intracellular Calcium Mobilization and Kinase Pathways", Endocrinol., 145(12):5694-5703 (2004) 10 pages.
Database BIOSIS [Online], Accession No. PREV20040016159, Abstract, Mousa et al., "Discovery of pro-angiogenic effects of thyroid hormone and analogs", Blood, 102(11):77b-78b (2003) 1 page.
Davis et al., "Acting via a Cell Surface Receptor, Thyroid Hormone is a Growth Factor for Glioma cells," Cancer Res., 66(14):7270-7275 (2006) 6 pages.
Davis et al., "Cell-surface receptor for thyroid hormone and tumor cell proliferation", Expert Reviews in Endicrinology and Metabolism, 1(6):753-761 (2006) 10 pages.
Davis et al., "Mechanisms of nongenomic actions of thyroid hormone", Frontiers Neuroendocrinol., 29:211-218 (2008) 8 pages.
Davis et al., "Proangiogenic Action of Thyroid Hormone is Fibroblast Growth Factor-Dependent and is initiated at the Cell Surface." Cir. Res., 94(2004):1500-1506 7 pages.
Davis et al., "Promotion by thyroid hormone of cytoplasm-to-nucleus shutting of thyroid hormone receptors", Steroids, 73:1013-1017 (2008) 5 pages.
Davis et al., "Thyroxine Promotes Association of Mitogen-activated Protein Kinase and Nuclear Thyroid Hormone Receptor (TR) and Causes Serine Phosphorylation of TR", J. Biol. chem., 275(48):38032-38039 (2000) 8 pages.
Davis et al., "Translational implications of nongenomic actions of thyroid hormone initiated at its integrin receptor", Am. J. Physiol. Endocrinol. Metab., 297:E1238-E1246 (2009) 9 pages.
De la Cruz et al., "Effect of Aspirin Plus Dipyridamole on the Retinal Vascular Pattern in Experimental Diabetes Mellitus", J. Pharmacol. Exp. Ther., 280(1):454-459 (1997) 6 pages.
Deardorff, D.L., "Isotonic Solutions", in Remington's Pharmaceutical Sciences, 15th Ed., Chapter 79, pp. 1405-1412, Mack Publishing Co., Easton (1975) 10 pages.
DeFesi et al., "3,5,3'-Triiodothyronine Effects on the Growth Rate and Cell Cycle of Cultured GC Cells", Endocrinol., 108(1):259-267(1981) 9 pages.
Demediuk et al., "Traumatic Spinal Cord Injury in Rats Causes Increases in Tissue Thromboxane but Not Peptidoleukotrienes", J. Neurosci. Res., 20:115-121 (1988) 7 pages.
DeRyck et al., "Neocortical localization of tactile/proprioceptive limb placing reactions in the rat", Brain Res., 573 (1):44-60 (1992) 18 pages.
Di Chiro et al., "Glucose utilization of cerebral gliomas measured by [18F] fluorodeoxyglucose and positron emission tomography", Neurology, 32(12):1323-1329 (1982) 8 pages.
Dietrich et al., "Post-traumatic brain hypothermia reduces histopathological damage following concussive brain injury in the rat", Acta Neuropathol., 87(3):250-258 (1994) 10 pages.
Ding et al., "Radioprotection of Hematopoietic Tissue by Fibroblast Growth Factors in Fractionated Radiation Experiments", Acta Onocol., 36(3):337-340 (1997) 4 pages.
Dixon et al., "A fluid percussion model of experimental brain injury in the rat", J. Neurosurg., 67(1):110-119 (1987) 11 pages.
Drusano et al., "Pharmacodynamics of Abacavir in an In Vitro Hollow-Fiber Model System", Antimicrob. Agents Chemother., 46(2):464-470 (2002) 7 pages.
Dupont et al., "Antiangiogenic and antimetastatic properties of Neovastat (•-941), an orally active extract derived from cartilage tissue", Clin. Experim. Metastasis, 19:145-153 (2002) 9 pages.
Edwards et al., "Trypsinized BHK21 cells aggregate in the presence of metabolic inhibitors and in the absence of divalent cations", J. Cell Sci., 19(3):653-667 (1975) 16 pages.
Elkind et al., "Radiation Response of Mammalian Cells Grown in Culture. 1. Repair of X-Ray Damage in Surviving Chinese Hamster Cells", Radiat. Res., 13:556-593 (1960) 38 pages.
Elvin et al., "Cell Adhesiveness and the Cell Cycle: Correlation in Synchronized Balb/c 3T3 Cells", Biol. Cell, 48:1-10 (1983) 10 pages.
Ely and Berne, "Protective Effects of Adenosine in Myocardial Ischemia", Circulation, 85:893-904 (1992) 13 pages.

(56) References Cited

OTHER PUBLICATIONS

Ethier et al., "Adenosine stimulates proliferation of human endothelial cells in culture", Am. J. Physiol., 265:H131-H138 (1993) 8 pages.

Everts et al., "Uptake of 3,3',5.5'-Tetraiodothyroacetic Acid and 3,3',5'-Triiodothyronine in Cultured Rat Anterior Pituitary Cells and Their Effects on Thyrotropin Secretion", Endocrinol., 136(10):4454-4461 (1995) 8 pages.

Faden et al., "Endogenous Opioid Immunoreactivity in Rat Spinal Cord Following Traumatic Injury", Ann. Neurol., 17 (4):386-390 (1985) 5 pages.

Faden, A.I., "Experimental Neurobiology of Central Nervous System Trauma", Crit. Rev. Neurobiol., 7(3/4):175-186 (1993) 13 pages.

Feeney et al., "Amphetamine, Haloperidol, and Experience Interact to Affect Rate of Recovery After Motor Cortex Injury", Science, 217(4562):855-857 (1982) 4 pages.

Fei et al., "P53 and radiation responses", Oncogene, 22:5774-5783 (2003) 10 pages.

Felding-Habermann et al., "Integrin activation controls metastasis in human breast cancer", Proc. Natl. Acad. Sci. U.S.A., 98(4):1853-1858 (2001) 6 pages.

Feng et al., "Fibrin and Collagen Differentially Regulate Human Dermal Microfascular Endothelial Cell Integrins: Stablization of $\alpha\Box/\beta3$ mRNA by Fibrin", J. Invest. Dermatol., 113(6):913-919 (1999) 7 pages.

Fife et al., "Effects of tetracyclines on angiogenesis in vitro", Cancer Letters, 153:75-78 (2000) 4 pages.

Folkman, J., "Angiogenesis in cancer, vascular, rheumatoid and other disease", Nat. Med., 1(1):27-31 (1995) 5 pages.

Freese et al., "Characterization and mechanism of glutamate neurotoxicity in primary striatal cultures", Brain Res., 521 (1/2):254-264 (1990) 12 pages.

Frye, R.A., "Characterization of Five Human cDNAs with Homonology to the Yeast SIR2. Gene: Sir2-like Proteins (Sirtuins) Metabolize NAD and May Have Protein ADP-Ribosyltransferase Activity", Biochem. Biophys. Res. Comm., 260:273-279 (1999) 7 pages.

Fujii et al., "Crystal Structure of Trimestatin, a Disintegrin Containing a Cell Adhesion Recognition Motif RGD", J. Mol. Biol., 332:1115-1122 (2003) 8 pages.

Gavrieli et al., "Identification of Programmed Cell Death In Situ via Specific Labeling of Nuclear DNA Fragmentation", J. Cell. Biol., 119(3):493-501 (1992) 9 pages.

GenBank Accession No. AF083106, Apr. 14, 2000 5 pages.
GenBank Accession No. AF083107, Mar. 21, 2001. 3 pages.
GenBank Accession No. NM_002210, Jun. 15, 2008 8 pages.
GenBank Accession No. NM_012238, Apr. 25, 2010. 8 pages.
GenBank Accession No. NM_030593, Mar. 14, 2010. 8 pages.
GenBank Accession No. NP_036370, Apr. 25, 2010. 6 pages.
GenBank Accession No. NP_501912, Nov. 13, 2008. 4 pages.
GenBank Accession No. P53685, Apr. 20, 2010. 8 pages.

Geng et al., "A Specific Antagonist of the p110σ Catalytic Component of Phosphatidylinositol 3'-Kinase, IC486068, Enchances Radiation-Induced Tumor Vascular Destruction", Cancer Res., 64:4893-4899 (2004) 7 pages.

Ginis et al., "Hypoxia affects tumor cell invasiveness in vitro: the role of hypoxia-activated ligand HAL 1/13 (Ku 86 autoantigen)", Cancer Lett., 154:163-174 (2000) 12 pages.

Gladson, C.L., "Expression of integrin $\alpha\Box\beta3$ in Small Blood Vessels of Giioblastoma Tumors", J. Neurpath. Exp. Neurol., 55(11):1143-1149(1996) 7 pages.

Glinskii et al., "Modification of survival pathway gene expression in human breast cancer cells by tetraiodothyroacetic acid (tetrac)", Cell Cycle, 8(21):3562-3570 (2009) 9 pages.

Glinsky et al., "Classification of Human Breast Cancer Using Gene Expression Profiling as a Component of the Survival Predictor Algorithm", Clin. Cancer Res., 10:2272-2283 (2004) 12 pages.

Glinsky et al., "Gene expression prfiling predicts clinical outcome of prostate cancer", J. Clin. Invest., 113(6):913-923 (2004) 11 pages.

Glinsky et al., "Microarray analysis identifies a death-from-cancer signature predicting therapy failure in patients with multiple types of cancer", J. Clin. Invest., 115(6):1503-1521 (2005) 19 pages.

Glinsky et al., "Microarray Analysis of Xenograft-Derived Cancer Cells Lines Representing Multiple Experimental Models of Human Prostate Cancer", Mol. Carcinog., 37:209-221 (2003) 13 pages.

Goldstein et al., "Influence of Lesion Size and Location on Amphetamine-Facilitated Recovery of Beam-Walking in Rats", Behav. Neurosci., 104(2):320-327 (1990) 9 pages.

Goldstein, A., "Estimating the Error Variance and the Confidence Interval for a Regression Line", in Biostatistics, The MacMillan Co., New York, pp. 139-146 (1964) 10 pages.

Goodman, M.M., "Automated Synthesis of Radiotracers for PET Applications", in Clinical Positron Emission Tomography, Mosby Yearbook, K.F. Hubner et al., Chapter 14, pp. 110-122 (1992) 13 pages.

Grant, D.B., "Monitoring TSH concentrations during treatment for gongenital hypothyroidism", Arch. Disease Childhood, 66:669-670 (1991) 2 pages.

Gregoriadis, "Liposomes", in Drug Carriers in Biology and Medicine, Chapter 14, pp. 287-341, Academic Press (1979) 57 pages.

Guigon et al., "Regulation β-Catenin by a Novel Nongenomic Action of Thyroid Hormone β Receptor", Mol. Cell. Biol., 28(14):4598-4608 (2008) 11 pages.

Hahn et al., "Plateau-phase cultures of mammalian cells: An in vitro model for human cancer", Curr. Top. Radiat. Res. Q., 8:39-83 (1972) 45 pages.

Halks-Miller et al., "CCR1 Immunoreactivity in Alzheimer's Disease Brains", Society for Neuroscience Meeting, Abstract #787.6, vol. 24 (1998) Abstract Only. 1 page.

Hansebout, R.R., "A Comprehensive Review of Methods of Improving Cord Recovery After Acute Spinla Cord Injury", in Early Management of Acute Spinal Cord Injury, pp. 181-196 (1982) 16 pages.

Hartert, H., "Blutgerinnungsstud Mit Der Thrombelastogeraphie, Einem Neuen Untersuchungsverfahren", Klinische Wochenschrift 26(37138):577-583 (1948) German Language Only. 9 pages.

Hashimoto et al., "Matrix Metalloproteinases Cleave Connective Tissue Growth Factor Reactivate Angiogenic Activity of Vascular Endothelial Growth Factor 165", J. Biol. Chem. 277(39):36288-36295 (2002) 8 pages.

Heller et al., "Inhibition of potentially lethal damage recovery by altered pH, glucose utilization and proliferation in plateau growth phase human glioma cells", Int. J. Radiat. Biol., 66(1):41-47 (1994) 7 pages.

Hercbergs et al., "GL261 brain tumor cells: responses to signle or fractionated x-irradiation with the $\alpha\Box\beta3$ integrin tyroxine receptor antagonist tetrac (tetraiodothyroacetic acid)", 20th EORTC-NCI-AACR Symposium on Molecular Targets and Cancer Therapeutics, Geneva, Switzerland, Oct. 2008. 304 pages.

Hercbergs et al., "GL261 brain tumor cells: responses to single or fractionated x-irradiation with the $\alpha\Box\beta3$ integrin tyroxine receptor antagonist tetrac (tetraiodothyroacetic acid)", Euro. J. Cancer, 6(12):172 (Abstract Only) 4 pages.

Hercbergs et al., "Propylthiouracil-induced Chemical Hypothyroidism with High-Dose Tamoxifen Prolongs Survival in Recurrent High Grade Ciioma: A Phase I/II Study", Anticancer Res., 23:617-626 (2003) 10 pages.

Hercbergs, A., "The Thyroid Gland as an Intrinsic Biologic Response-Modifier in Advanced Neoplasia—A Novel Paradigm", in vivo, 10:245-247 (1996) 3 pages.

Hercbergs, et al., GL261 Brain Tumor Cells: In Vitro Single and Fractionated Dose Responses to X-Rays and Modification by Tetrac (Tetraiodothyroacetic Acid), The Cleveland Clinic Foundation, Department of Radiation Oncology 46 pages.

Hercbergs, et al., "Radiosensitization of GL261 glioma cells by tetraiodothyroacetic acid (tetrac)", Cell Cycle, 8 (16):2586-2591 (2009) 6 pages.

(56) References Cited

OTHER PUBLICATIONS

Hermanson, "Modification with Synthetic Polymers", in Bioconjugate Tech., Ch. 15, Academic Press, San Diego, CA, pp. 617-618 (1996) 4 pages.

Hoff et al., "Medullary Thyroid Carcinoma", Hematol. Oncol. Cin. North Am., 21(3):475-488 (2007) 14 pages.

Horuk et al., "Expression of Chemokine Receptors by Subsets of Neurons in the Central Nervous System", J. Immunol., 158:2882-2890 (1997) 9 pages.

Hubner, K.F., "University of Tennessee Biomedical Imaging Center and Transfer of Technology to the Clinical Floor", in Clinical Positron Emission Tomography, Mosby Yearbook, K.F. Hubner et al., Chapter 2, pp. 4-16(1992) 13 pages.

Hudlicka et al., "Factors involved in capillary growth in the heart", Mol. Cell. Biochem, 147:57-68 (1995) 12 pages.

Igarashi et al., "Techniques Supporting Angiogenesis Therapy 2: DDS Technique Supporting Regenerative Medicine." Inflamm. Immun. 10.6(2002):652-658 7 pages.

Illario et al., "Fibronectin-Induced Proliferation in Thyroid Cells is Mediated by α□β3 Integrin through Ras/Raf-1/MEK/ERK and Calcium/CaMKII Signals", J. Clin. Endocrinol. Metab., 90(5):2865-2873 (2005) 9 pages.

Ingerman-Wojenski et al., "Evaluation of electrical aggregometry: comparison with optial aggregometry, secretion of ATP, and accumulation of radiolabeled platelets", J. Lab. Clin. Med., 101(1):44-52 (1983) 10 pages.

Iwata et al., "A new, convenient method for the preparation of 4-[18F]fluorobenzyl halides", Applied Radiation and Isotopes, 52(1):87-92 (2000) 7 pages.

Jain, K.K., "Strategies and technologies for drug delivery systems", TIPS, 19:155-157 (1998) 5 pages.

Janssen et al., "Pathogenesis of Spinal Cord Injury and Newer Treatments—A Review", Spine, 14(1):23-32 (1989) 11 pages.

Jeffrey et al., "The preparation and characterisation of poly(lactide-co-glycolide) microparticles. 1. Oil-in-water emulsion solvent evaporation", Int. J. Pharm., 77:169-175 (1991) 7 pages.

Jonker et al., "Cetuximab for the Treatment of Colorectal Cancer", N. Engl. J. Med., 357(20):2040-2048 (2007) 9 pages.

Jordan et al., "Thyroid Status is a Key Modulator of Tumor Oxygenation: Implication for Radiation Therapy", Radiat. Res., 168:428-432 (2007) 5 pages.

Kalofonos et al., "Monoclonal Antibodies in the Management of Solid Tumors", Curr. Top. Med. Chem., 6:1687-1705 (2006) 19 pages.

Kapiszewska et al., "The Effects of Reduced Temperature and/or Starvation Conditions on the Radiosensitivity and Repair of Potentially Lethal Damage and Sublethal Damage in L5178Y-R and L5178Y-S Cells", Radiat. Res., 113:458-472 (1988) 15 pages.

Kastan et al., "A Mammalian Cell Cycle Checkpoint Pathway Utliziing P53 and GADD45 is Defective in Ataxia-Telangiectasia", Cell. 71:587-597 (1992) 11 pages.

Kawasuji et al., Jap. Circ. J., 63(Suppl. 1):65 (1999) Japanese Abstract Only. 3 pages.

Kerr et al., "Novel Small Molecule α□ Integrin Antagonists: Comparative Anti-Cancer Efficacy With Known Angiogenesis Inhibitors", Anticancer Res., 19:959-968 (1999).

Kerr et al., "Small molecule α□ integrin antagonists: novel anti-cancer agents", Exp. Opin. Invest. Drugs, 9 (6):1271-1279 (2000) 9 pages.

Kim et al., "Regulation of Antiogenesis in Vivo, by Ligation of Integrin α5 β1 with the Central Cell-Binding Domaing of Fibronectin", Am. J. Pathol., 156(4): 1345-1362 (2000) 18 pages.

Kim et al., "Soluble Flt-1 gene delivery using PEI-g-PEG-RGD conjugate for anti-angiogenesis", J. Control Release, 106:224-234 (2005) 11 pages.

Kimelberg, H.K., "Astrocytic Edema in CNS Trauma", J. Neurotrauma, 9(Suppl. 1):S71-S81 (1992) 12 pages.

Kitevska et al., "Caspase-2: controversial killer or checkpoint controller?", Apoptosis, 14:829-848(2009) 20 pages.

Kleczkowska et al., "Differntial poly(ADP-ribose) metabolism in repair-proficient and repair-deficient murine lymphoma cells", Mut. Res., 235:93-99 (1990) 7 pages.

Klunk et al., "Development of Small Molecule Probes for the Beta-Amyloid Protein of Alzheimer's Disease", Neurobiol. Aging, 15(6):691-698 (1994) 8 pages.

Kobayashi et al., "Drug Delivery Catheter." Surg. Front. 9.1(2002):55-57 3 pages.

Konno et al., "Antiogenetic therapy for carcinoma", Igaku No Ayumi, 194(10): 824-828 (2000) 5 pages.

Koutras et al., "Antiproliferative effect of exemestane in lung cancer cells", Mol. Cancer, 8(1):109 (2009) 12 pages.

Koyama et al., "Recent Status and Future Perspectives in Therapeutic Angiogenesis", Prog. Med., 22(12):3070-3076 (2002) (English Abstract) 7 pages.

Kramer et al., "Human Microvascular Endothelial Cells Use α1 and α3 Integrin Receptor Complexes to Attach to Laminin", J. Cell Biol., 111:1233-1343 (1990) 11 pages.

Kumar et al., "Enhancing Effect of Thyroxine on Tumor Growth and Metastases in Syngeneic Mouse Tumor Systems", Cancer Res., 39:3515-3518 (1979) 4 pages.

Kuroki et al., "Diabetic retinopathy—The mechanisms of the ocular neovascularization of the development of anti-angiogenic drugs—", Nippon Rinsho, 57(3):584-589 (1999) (English Abstract Only) 6 pages.

Kwok et al., "Differences in EGF rated radiosensitisation of human squamous carcinoma cells with high and low Numbers of EGF receptors", Br. J. Cancer, 64:251-254 (1991) 4 pages.

Lameloise et al., "Differences between the effects of thyroxine and tetraiodothyroacetic acid on TSH suppression and cardiac hypertrophy", Eur. J. Endocrinol., 144:145-154 (2001) 10 pages.

Lawler et al., "Cell Attachment to Thombospondin: The Role of ARG-GLY-ASP, Calcium and Integrn Receptors", J. Cell Biol., 107(6 Pt. 1): 2351-2361 (1988) 11 pages.

Letterio et al., "Maternal Rescue of Transforming Growth Facotr-β1 Null Mice", Science, 264:1936-1938 (1994) 4 pages.

Office Action (Mail Date May 23, 2012) for U.S. Appl. No. 12/816,287, filed Jun. 15, 2010.

Office Action (Mail Date Oct. 16, 2014) for U.S. Appl. No. 12/644,493, filed Dec. 22, 2009.

Newcomb et al., "Radiation Sensitivity of GL261 Murine Glioma Model and Enhanced Radiation Response by Flavopiridol", Cell Cycle., 5(1):93-99 (2006) 7 pages.

Nickoloff et al., "Aberrant Production of Interleukin-8 and Thrombospondin-1 by Psoriatic Keratinocytes Mediates Angiogenesis." Am. J. Pathol. 144.4(1994):820-828 9 pages.

Nilsson et al., "Evidence for Multiple Thyroxine-binding Sites in Human Prealbumin", J. Biol. Chem., 246(19): 6098-6105 (1971) 8 pages.

Ning et al., "Anti-integrin monoclonal antibody CNTO 95 enhances the therapeutic efficacy of fractionated radiation therapy in vivo", Mol. Cancer Ther., 7(6):1569-1578 (2008) 10 pages.

Oak et al., "Antiangiogenic properties of natural polyphenols from red wine and green tea", J. Nutr. Biochem., 16:1-8 (2005) 8 pages.

Okada et al., "A Quantitative in vivo Method of Analyzing Human Tumor-induced Angiogenesis in Mice Using Agarose Microencapsulation and Hemoglobin Enzyme-linked Immunosorbent Assay", Jpn. J. Cancer Res., 86(12):1182-1188 (1995) 7 pages.

Pages et al., "Signaling Angiogenesis via p42/p44 MAP Kinase Cascade", Ann. N.Y. Acad., Sci., 902:187-200 (2000) 14 pages.

Painter et al., "Membrane initiation of DNA synthesis", Nature, 270:543 (1977) 1 page.

Panter et al., "Pretreatment with NMDA antagonists limits release of excitatory amino acids following traumatic brain injury", Neurosci. Lett., 136(2):165-168 (1992) 4 pages.

Panyam, et al., "Biodegradable nanoparticles for drug and gene delivery to cells and tissues", Advanced Drug Delivery Reviews, 55: 329-347 (2009) 19 pages.

Pardridge, W.M., "Receptor-Mediated Peptide Transport through the Blood-Brain Barrier", Endocrine Rev., 7 (3):314-330 (1986) 18 pages.

(56) References Cited

OTHER PUBLICATIONS

Park et al., "Effects of Tetramethoxystilbene on Hormone-Resistant Breast Cancer Cells: Biological and Biochemical Mechanisms of Action", Cancer Res., 67:5717-5726 (2007) 10 pages.
Parveen, et al., "Polymeric nanoparticles for cancer therapy", Journal of Drug Targeting, 16(2): 108-123, Feb. 2008. 16 pages.
Patel, D.K., "Clinical Use of Anti-Epidermal Growth Factor Receptor Monoclonal Antibodies in Metastatic Colorectal Cancer", Pharacotherapy, 28(11 Pt.2):31S-41S (2008) 12 pages.
Penno et al., "Rapid and quantitative in vitro measurement of cellular chemotaxis and invasion", Meth. Cell Sci., 19:189-195 (1997) 7 pages.
Pirola, et al., "Resveratrol: One Molecule, Many Targets", IUBMB Life, vol. 60, Issue 5, pp. 323-332. 10 pages.
Plow et al., "Ligand Binding to Integrins", J. Biol. Chem., 275(29):21785-21788 (2000) 4 pages.
Powell, J., "The Serial Analysis of Gene Expression", in Meth. Mol. Biol., Chapter 20, 99:297-319 (2000) 23 pages.
Prichard et al., "Concurrent Cetuximab and Bevacizumab Therapy in a Murine Orthotopic Model of Anaplastic Thyroid Carcinoma", Laryngoscope, 117:674-679 (2007) 7 pages.
Pujol et al., "Letter to the editors: Preventioon of thyroid neoplasm recurrence with Triac and levothyroxine", Clin. Endocrinol., 46(1):121-122 (1997) 2 pages.
Raue et al., "Multiple Endocrine Neoplasia Type 2", Horm. Res., 68(Suppl.5): 101-104 (2007) 4 pages.
Rayalam et al., "Resveratrol induces apoptosis and inhibits adipogenesis in 3T3-L1 adipocytes", Phytother. Res., 22:1367-1371 (2008) 5 pages.
Rebbaa et al., "Novel function of the thyroid hormone analog tetraiodothyroacetic acide: a cancer chemosensitizing and anti-cancer agent", Angiogenesis, 11(3):269-276 (2008) 8 pages.
Reinholt et al., "Osteopontin—a possible anchor of osteoclasts to bone", Proc. Natl. Acad. Sci. U.S.A., 87:4473-4475 (1990) 3 pages.
Remsen et al., "Antibodies to the Neural Cell Adhesion Molecule Disrupt Functional Recovery in Injured Nerves", Exp. Neurol., 110:268-273 (1990) 6 pages.
Ren et al., "Regulation of tumor angiogenesis by thrombospondin-1", Biochim. Biophys. Acta. 1765: 178-188 (2006) 11 pages.
Risau, W., "Mechanisims of angiogenesis", Nature, 386:671-674 (1997) 4 pages.
Sahni et al., "Stimulation of endothelial cell proliferation by FGF-2 in the presence of fibrinogen requires $\alpha\beta3$", Blood, 104(12):3635-3641 (2004) 7 pages.
Saito et al., "Vector-mediated delivery of 125I-labeled β-amyloid peptide Aβ1-40 through the blood-brain barrier and binding to Alzheimer disease of the Aβ1-40/vector complex", Proc. Natl. Acad. Sci. US, 92:10227-10231 (1995) 5 pages.
Samuels et al., "Depletion of L-3-5-3'-Triiodothyronine and L-Thyroxine in Euthyroid Calf Serum for Use in Cell Culture Studies of the Action of Thyroid Hormone", Endo., 105(1):80-85 (1979) 6 pages.
SAS/STAT Guide for Personal Computers, Version 6 Edition, p. 717 (1987) 3 pages.
Sato et al., "Neovascularization: General Remarks", Biotherapy, 15(6):631-636 (2001) (English Abstract) 6 pages.
Scanlan et al., "3-Iodothyronamine is an endogenous and rapid-acting derivative of thyroid hormone", Nat. Med., 10 (6):638-642 (2004) 5 pages.
Scanlan et al., "Selective thyrmimetics: Tissue-selective thyroid hormone analogs", Curr. Opin. Drug Discov. Dev., 4 (5):614-622 (2001) 9 pages.
Schlange et al., "Autocrine WNT signaling contributes to breast cancer cell proliferation via the canonical WNT pathway and EGFR transactivation", Breast Cancer Res., 9:R63 (2007) 15 pages.
Schlumberger et al., "New therapeutic approaches to treat meduliary thyroid carcinoma", Nat. Clin. Prac. Endocrinol. Metab., 4(10):22-32 (2008) 11 pages.

Schnell et al., "Expression of alpha v beta 3 integrin in patients with high and low grade glioma", Proc. Amer. Assoc. Cancer Res., 47:226 (2006) Abstract Only. 5 pages.
Schnell et al., "Expression of Integrin $\alpha\beta3$ in Gliomas Correlates with Tumor Grade and Is not Restricted to Tumor Vasculature", Brain Pathol., 18:378-386 (2008) 9 pages.
Schreiber et al., "Hormone delivery systems to the brain-transhyretin", Exp. Clin. Endocrinol Diabetes, 103(2): 75-80 (1995) 7 pages.
Schueneman et al., "SU11248 Maintenance Therapy Prevents Tumor Regrowth after Fractionated Irradiation of Murine Tumor Models", Cancer Res., 63:4009-4016 (2003) 8 pages.
Shih et al., "Thyroid Hormone Promotes Serine Phosphorylation of p53 by Mitogen-Activated Protein Kinase", Biochem., 40:2870-2878 (2001) 10 pages.
Shih et al., "Disparate Effects of Thyroid Hormone on Actions of Epidermal Growth Factor and Transforming Growth Factor-α Are Mediated by 3,5'-Cyclic Adenosine 5'-Monophosphate-Dependent Protein Kinase II", Endo., 145(4): 1708-1717 (2004) 10 pages.
Shih et al., "Inhibitory effect of epidermal growth factor on resveratrol-induced apoptosis in prostate cancer cells is mediated by protein kinase C-α", Mol. Cancer Ther., 3:1355-1363 (2004) 9 pages.
Shinohara et al., "Enhanced radiation damage of tumor vasculature by mTOR inhibitors", Oncogene, 24:5414-5422 (2005) 9 pages.
Skrovronsky et al., "In vivo detection of amyloid plaques in a mouse model of Alzheimer's disease", Proc. Natl. Acad. Sci US, 97(13):7609-7614 (2000) 6 pages.
Skuli et al., "$\alpha\beta3/\alpha\beta5$ integrins-FAK-RhoB: A Novel Pathway for Hypoxia Regulation in Glioblastoma", Cancer Res., 69*8):3308-3316 (2009) 9 pages.
Song et al., "Formulation and characterization of biodegradable nanoparticles for intravascular local drug delivery", J. Controlled Rel., 43:197-212 (1997) 16 pages.
Stefani et al., "The Effect of Resveratrol on a Cell Model of Human Aging", Ann. NY Acad. Sci., 1114:407-418 (2007) 12 pages.
Strieth, et al., "Antiangiogenic combination tumor therapy blocking $\alpha$-integrins and VEGF-receptor-2 increases therapeutic effects in vivo", Int. J. Cancer, 119:423-431 (2006) 9 pages.
Sumi et al., "Wound healing using regenerative medicine", Surg. Front., 10(2):162-165 (2003) 4 pages.
Sunwoo et al., "Novel Proteasome Inhibitor PS-341 Inhibits Activation of Nuclear Factor-κB, Cell Survival, Tumor Growth, and Angiogenesis in Squamous Cell Carcinoma", Clin. Cancer Res., 7:1419-1428 (2001) 10 pages.
Szatmari et al., "Detailed characterization of the mouse glioma 261 tumor model for experimental glioblastoma therapy", Cancer Sci., 97(6):546-553 (2006) 8 pages.
Szumiel, I., "Ca2+, Mg2+ and (Adenosine Diphosphate Ribose)n in Cellular Response to Irradiation", J. Theor. Biol., 101:441-451 (1983) 11 pages.
Takemaru et al., "Chibby, a nuclear β-catenin-associated antagonist of the Wnt/Wingless pathway", Nature, 422:905-909 (2003) 5 pages.
Tanaka et al., J. Soc. Gastroenterological Surgery, 27(2):360 (1996) 3 pages.
Tang et al., "Resveratrol-induced Cyclooxygenase-2 facilitates p53-dependent apoptosis in human breast cancer cells", Mol. Cancer Ther., 5(8):2034-2042 (2006) 9 pages.
Tang et al., "Thyroid Hormone Causes Mitogen-Activated Protein Kinase-Dependent Phosphorylation of the Nuclear Estrogen Receptor", Endocrinol., 145(7):3265-3272 (2004) 8 pages.
Tator et al., "Review of the secondary injury theory of acute spinal cord trauma with emphasis on vascular mechanisms", J. Neurosurg., 75(1):15-26 (1991) 13 pages.
Theodossiou et al., "Propylthiouracil-induced Hypothyroidism Reduces Xenograft Tumor Growth in Athymic Nude Mice", Cancer, 86:1596-1601 (1999) 6 pages.
Thompson et al., "The Clinical Manipulation of Angiogenesis: Pathology, Side-Effects, Surprises, and Opportunites with Novel Human Therapies." J. Pathol. 190(2000):330-337 8 pages.

(56) References Cited

OTHER PUBLICATIONS

Thraves et al., "Radiosensitization of Human Fibroblasts by 3-Aminobenzamide: An Inhibitor of Poly(ADP-Ribosylation)", Radiat Res., 104:119-127 (1985) 9 pages.
Tol et al., "Chemotherapy, Bevacizumab, and Cetuximab in Metastatic Colorectal Cancer", N. Engl. J. Med., 360 (6):563-572 (2009) 10 pages.
Tomanek et al., "A Thyroid Hormone Analog Stimulates Angiogenesis in the Post-infarcted Rat Heart", J. Mol. Cell Cardiol., 30(5):923-932 (1998) 10 pages.
Tomanek et al., "Angiogenesis: New Insights and Therapeutic Potential", Anatomical Record (New Anat.), 261:126-135 (2000) 10 pages.
Tomanek et al., "Early Coronary Angiogenesis in Resposne to Thyroxine: Growth Characteristics and Upregulation of Basic Fibroblast Growth Factor", Circ. Res., 82(5):587-593 (1998) 8 pages.
Tomanek et al., "Growth of the Coronary Vasculature in Hypertrophy: Mechanisms and Model Dependence", Cell. Mol. Bio. Res., 40(2):129-136 (1994) 8 pages.
Toms et al., "Thyroid Hormone Depletion Inhibits Astrocytoma Proliferation via a p53-Independent Induction of p21 (WAF/1CIP1)", Anticancer Res., 18:289-293 (1998) 5 pages.
Tuttle et al., "Recombinant Human TSH-Assisted Radioactive Iodine Remnant Ablation Achieves Short-Term Clinical Recurrence Rates Similar to Those of Traditional Thyroid Hormone Withdrawal", J. Nucl. Med., 49(5):764-770 (2008) 7 pages.
Tzirogiannis et al., "Enhanced Proliferation of Human Lung Adenocarcinoma and Small Cell Lung Carcinoma Cells Directed from the Cell Surface by Thyroid Hormone", in 89th Annual Meeting, The Endocrine Society (2007) Abstract Only 3 pages.
Utsumi et al., "Potentially Lethal Damage Versus Sublethal Damage: Independent Repair Processes in Actively Growing Chinese Hamster Cells", Radiat. Res., 77:346-360 (1979) 9 pages.
Van Waes et al., "Effects of the novel an integrin antagonist SM256 and cis-platinum on growth of murine squamos cell carcinoma PAM LY8", Int. J. Oncol., 16(6):1189-1195 (2000) 8 pages.
VanCutsem et al., "Cetuximab and Chemotherapy as Initial Treatment for Metastatic Colorectal Cancer", N. Engl. J. Med., 360:1408-1417 (2009) 10 pages.
Varnes et al., "The Effect of pH on Potentially Lethal Damage Recovery in A549 Cells", Radiat. Res., 108:80-90 (1986) 11 pages.
Velasco et al., "Dermatological Aspects of Angiogenesis." Brit. J. Dermatol. 147(2002):841-852 12 pages.
Wang et al., "DITPA stimulated bFGF, VEGF, angiopoietin, and Tie-2 and facilates coronary arteriolar growth", Am. J. Physiol. Heart Circ. Physiol., 284(2):H613-H618 (2003) 6 pages.
Wang et al., "Integrin-associated Protein Stimulates $\alpha 2\beta 1$-dependent Chemotaxis via Gi-mediated inhibition of Adenylate Cyclase and Extracelular-regulated Kinases", J. Cell. Biol., 147:389-399 (1999) 11 pages.
Wen et al., "Prognostic Value of EGFR and TGF-$\alpha$ in Early Laryngeal Cancer Treated With Radiotherapy", Laryngoscope, 106(7):884-888 (1996) 6 pages.
Werdelin et al., "Neuropeptides and neural cell adhesion molecule (NCAM) in CSF from patients with ALS", Acta Neurol. Scand., 79(3):177-181 (1989).
Wilkinson, J.H., "Synthesis of some Possible Metabolites of Thyroxine and Triiodothyronine", Biochem. J., 63:601-605 (1956) 5 pages.
Xia et al., "Chemokines/chemokine receptors in the central nervous system and Alzheimer's disease", J. NeuroVirol., 5:32-41 (1999) 11 pages.
Yalcin et al., "Tetraidothyroacetic Acid (Tetrac) and Tetrac Nanoparticles Inhibit Growth of Human Renal Cell Carcinoma Xenografts", Anticancer Res., 29:3825-3832 (2009) 7 pages.
Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 7 pages.
Yalcin et al., "Tetraiodothyroacetic Acid (Tetrac) and Nanoparticulate Tetrac Arrest Growth of Medullary Carcinoma of the Thyroid", J. Clin. Endocrinol. Metab., 95(4):1972-1980 (2010) 9 pages.
Yalcin et al., "Tetraiodothyroacetic Acid and Tetraiodothyroacetic Acid Nanoparticle Effectively Inhibit the Growth of Human Follicular Thyroid Cell Carcinoma", Thyroid, 20(3):281-286 (2010) 6 pages.
Yanase et al., "Role of N-methyl-D-aspartate receptor in acute spinal cord injury", J. Neurosurg., 83:884-888 (1995) 6 pages.
Yang et al., "Rab7b, a novel lysosome-associated small GTPase, is involved in monocytic differentiation of human acute promyelocytic leukemia cells", Biochem. Biophys. Res. Commun., 318:792-799 (2004) 8 pages.
Yang, et al., "Enhanced inhibition of adipogenesis and induction of apoptosis in 3T3-L1 adipocytes with combinations of resveratrol and quercetin", Life Sci., 82:1032-1039 (2008) 8 pages.
Yonkers et al., "Sensory Neuron Sodium Current Requires Nongenomic Actions of Thyroid Hormone During Development", J. Neurophysiol., 100:2719-2725 (2008) 7 pages.
Young, W., "Role of Calcium in Central Nervous System Injuries", J. Neurotrauma, 9(Suppl. 1): S9-S25 (1992) 18 pages.
Young, W., "Secondary injury mechanisms in acute spinal cord injury", J. Emerg. Med., 11:13-22 (1993) 11 pages.
Yu et al., "Osteopontin Gene is Expressed in the Dermal Papilla of Pelage Follicles in a Hair-Cycle-Dependent Manner", J. Invest. Dermatol., 117:1554-1558 (2001) 5 pages.
Yu, et al., "The Compressor Silencing Mediator for Retinoid and Thyroid Hormone Receptor Facilitates Cellular Recovery from DNA Double-Strand Breaks", Cancer Res., 66(18):9316-9322 (2006) 7 pages.
Zhang et al., "Oestrogen inhibits resveratrol-induced post-translational modification of p53 and apoptosis in breast cancer cells", Br. J. Cancer, 91:178-185 (2004) 8 pages.
Zhang et al., "Quantitative PET Imaging of Tumor Integrin $\alpha v\beta 3$ Expression with 18F-FRGD2", J. Nucl. Med., 47:113-121 (2006) 9 pages.
Zhen et al., "Synthesis and Amyloid Binding Properties of Rhenium Compleses: Preliminary Progress Toward a Reagent for SPECT Imaging of Alzheimer's Disease Brain", J. Med. Chem., 42:2805-2815 (1999) 11 pages.
Zhuang et al., "99mTc-Labeled MIBG Derivatives: Novel 99m Tc Complexes as Myocardial Imaging Agents for Sympathetic Neurons", Bioconjugate Chem., 10:159-168 (1999) 10 pages.
Office Action (Mail Date Apr. 11, 2013) for U.S. Appl. No. 12/816,287, filed Jun. 15, 2010.
Office Action (Mail Date Apr. 8, 2013) for U.S. Appl. No. 11/786,723, filed Apr. 11, 2007.
Office Action (Mail Date Apr. 12, 2013) for U.S. Appl. No. 12/751,375, filed Mar. 31, 2010.
Office Action (Mail Date Apr. 29, 2013) for U.S. Appl. No. 13/345,194, filed Jan. 6, 2012.
Office Action (Mail Date Oct. 24, 2013) for U.S. Appl. No. 12/816,287, filed Jun. 15, 2010.
Notice of Allowance (Mail Date Oct. 4, 2013) for U.S. Appl. No. 11/786,723, filed Apr. 11, 2007.
Office Action (Mail Date Oct. 15, 2013) for U.S. Appl. No. 13/345,194, filed Jan. 6, 2012.
Office Action (Mail Date Apr. 2, 2013) for U.S. Appl. No. 13/156,047, filed Jun. 8, 2011.
Office Action (Mail Date Feb. 25, 2014) for U.S. Appl. No. 13/156,047, filed Jun. 8, 2011.
U.S. Appl. No. 14/184,889, filed Feb. 20, 2014; Confirmation No. 3033; Customer No. 5409.
U.S. Appl. No. 14/185,010, filed Feb. 20, 2014; Confirmation No. 4595; Customer No. 5409.
U.S. Appl. No. 14/078,713, filed Nov. 13, 2013; Confirmation No. 1006; Customer No. 5409.
U.S. Appl. No. 13/975,725, filed Aug. 26, 2013; Confirmation No. 7136; Customer No. 5409.
U.S. Appl. No. 12/751,375, filed Mar. 31, 2010; Confirmation No. 1512; Customer No. 5409.

(56) References Cited

OTHER PUBLICATIONS

U.S. Appl. No. 13/345,194, filed Jan. 6, 2012; Confirmation No. 5479; Customer No. 5409.
U.S. Appl. No. 13/156,047, filed Jun. 8, 2011; Confirmation No. 4235; Customer No. 5409.
U.S. Appl. No. 12/644,493, filed Dec. 22, 2009; Confirmation No. 6460; Customer No. 5409.
U.S. Appl. No. 11/786,723, filed Apr. 11, 2007; Confirmation No. 2124; Customer No. 5409.
U.S. Appl. No. 12/816,287, filed Jun. 15, 2010; Confirmation No. 2994; Customer No. 5409.
U.S. Appl. No. 12/947,389, filed Nov. 16, 2010; Confirmation No. 1791; Customer No. 5409.
Office Action (Mail Date Mar. 12, 2014) for U.S. Appl. No. 12/947,389, filed Nov. 16, 2010.
Notice of Allowance (Mail Date Feb. 6, 2014) for U.S. Appl. No. 13/345,194, filed Jan. 6, 2012.
Offce Action (Mail Date Mar. 24, 2016) for U.S. Appl. No. 14/546,440, filed Nov. 18, 2014.
Advisory Action (Mail Date Jan. 21, 2016) for U.S. Appl. No. 14/242,041, filed Apr. 1, 2014.
Office Action (Mail Date May 12, 2015) for U.S. Appl. No. 14/078,713, filed Nov. 13, 2013.
Office Action (Mail Date Apr. 24, 2015) for U.S. Appl. No. 13/975,725, filed Aug. 26, 2013.
Office Action (Mail Date Apr. 16, 2015) for U.S. Appl. No. 12/751,375, filed Mar. 31, 2010.
Office Action (Mail Date Jan. 12, 2015) for U.S. Appl. No. 12/751,375, filed Mar. 31, 2010.
Office Action (Mail Date Oct. 17, 2012) for U.S. Appl. No. 12/947,389, filed Jun. 21, 2011.
Office Action (Mail Date Apr. 4, 2014) for U.S. Appl. No. 12/947,389, filed Nov. 16, 2010.
NCI Cancer Drug Information, Cetuximab, 2006,http://www.cancer.gov/cancertopics/druginfo/cetuximab,downloaded Jul. 18, 2014.
Gu et al. 2007, Nanotoday 2:14-21.
Application No. PCT/US2010/038700, Supplemental European Search Report dated Apr. 20, 2015. 7 pages.
Surks, Martin I. et al. "Subclinical Thyroid Disease; Scientific Review and Guidelines for Diagnosis and Management." Journal of the American Medical Association, Jan. 14, 2004, vol. 291, No. 2, pp. 228-238; especially p. 230-231.
J Wood, K Bonjean, S Ruetz, A Bellahcene, L Devy, JM Foidart, V Castronovo, JR Green. "Novel Antiangiogenic Effects of the u Bisphosphonate Compound Zoledronic Acid." The Journal of Pharmacology and Experimental Therapeutics, vol. 302, No. 3, 2002, pp. 1 055-1 061.
M Yalcin, DJ Bharali, L Lansing, E Dyskin, SS Mousa, A Hercbergs, FB Davis, PJ Davis, SA Mousa. "Tetraidothyroacetic Acid v (Tetrac) and Tetrac Nanoparticles Inhibit Growth of Human Renal Cell Carcinoma Xenografts." Anticancer Research, vol. 29, 2009, pp. 3825-3832.
Office Action (Mail Date Jun. 21, 2011) for U.S. Appl. No. 12/947,389, filed Nov. 16, 2010.
Office Action (Mail Date Apr. 4, 2012) for U.S. Appl. No. 12/947,389, filed Nov. 16, 2010.
Notice of Allowance (Mail Date May 12, 2015) for U.S. Appl. No. 12/816,287.
Office Action (Mail Date Oct. 5, 2012) for U.S. Appl. No. 12/644,493, filed Dec. 22, 2009.
Office Action (Mail Date Apr. 16, 2015) for U.S. Appl. No. 13/156,047, filed Jun. 8, 2011.
Office Action (Mail Date Jun. 3, 2015) for U.S. Appl. No. 12/751,375, filed Mar. 31, 2010.
Office Action (Mail Date Oct. 14, 2014) for U.S. Appl. No. 14/242,041, filed Apr. 1, 2014.
Avgoustakis, et al., "PLGA-mPEG nanoparticles of cisplatin: in vitro nanoparticle degradation, in vitro drug release and in vino drug residence in blood properties" J. Contr. Rel. 2002, 79, 123-135. 13 pages.
Office Action (Mail Date Sep. 4, 2014) for U.S. Appl. No. 12/947,389, filed Nov. 16, 2010.
Office Action (Mail Date May 8, 2014) for U.S. Appl. No. 12/816,287, filed Jun. 15, 2010.
Office Action (Mail Date Jul. 13, 2012) for U.S. Appl. No. 12/751,375, filed Mar. 31, 2010.
European Office Action for EP Application No. 07867073.4, mailed on Jul. 16, 2015.
Notice of Allowance (Mail Date Jul. 7, 2015) for U.S. Appl. No. 12/751,375, filed Mar. 31, 2010.
Notice of Allowance (Mail Date Aug. 3, 2015) for U.S. Appl. No. 14/078,713, filed Nov. 13, 2013.
Li et al., "Requirement of hypoxia-inducible factor-1$\alpha$ down-regulation in mediating the anti-tumor activity of the anit-epidermal growth factor receptor monoclonal antibody cetuximab", Mol. Cancer Ther., 7(5):1207-1217 (2008) 11 pages.
Lin et al., "Androgen-induced human breast cancer cell proliferation is mediated by discrete mechanisms in estrogen receptor-$\alpha$-positive and -negative breast cancer cells", J. Steroid Biochem. Mol. Biol., 113:182-188 (2009) 7 pages.
Lin et al., "Identification of the Putative MAP Kinase Docking Site in the Thyroid Hormone Receptor-$\beta$1 DNA-Binding Domain: Functional Consequences of Mutations at the Docking Site", Biochem., 42:7571-7579 (2003) 9 pages.
Lin et al., "Integrin $\alpha\beta$3 contains a receptor site for resveratrol", FASEB J., 20(10): 1742-1744 (2006) 3 pages.
Lin et al., "L-Thyroxine vs. 3,5,3'-triiodo-L-thyronine and cell proliferation: activation of mitogen-activated protein kinase and phosphatidylinositol 3-kinase", Am. J. Physiol. Cell Physiol., 296:C980-C991 (2009) 12 pages.
Lin et al., "Resveratrol Causes COX-2- and p53-Dependent Apoptosis in Head and Neck Squamos Cell Cancer Cells", J. Cell Biochem., 104:2131-2142 (2008) 12 pages.
Lin et al., "Resveratrol Induced Serine Phosphorylation of p53 Causes Apoptosis in a Mutant p53 Prostate Cancer Cell Line", J. Urol., 168:748-755 (2002) 8 pages.
Lin et al., "Resveratrol is pro-apoptotic and thyroid hormone is anti-apoptotic in glioma cells: both actions are integrin and ERK mediated", Carcinogenesis, 29(1):62-69 (2008) 8 pages.
Lin et al., "The pro-apoptotic action of stilbene-induced COX-2 in cancer cells: Convergence with the anti-apoptotic effect of thyroid hormone", Cell Cycle, 8(12):1877-1882 (2009) 6 pages.
Lin et al., "Thyroid hormone is a MAPK-dependent growth factor for thyroid cancer cells and is anti-apoptotic", Steriods, 72:180-187 (2007) 8 pages.
Liu et al., "Calcineurin Is a Common Target of Cyclophilin-Cyclosporin A and FKBP-FK506 Complexes", Cell, 66:807-815 (1991) 9 pages.
Lorger et al., "Activation of tumor cell integrin $\alpha\beta$3 controls angiogenesis and metastatic growth in the brain", Proc. Natl. Acad. Sci. U.S.A., 106 (26):10666-10671 (2009) 7 pages.
Louie et al., "Pharmacodynamics of Levofloxacin in a Murine Pneumonia Model of Pseudomonas aeruginosa Infection: Determination of Epithelial Lining Fluid Targets", Antimicrob Agents Chemother., 53(8):3325-3330 (2009) 6 pages.
Luidens et al., "Thyroid hormone and angiogenesis", Vascular Pharmacology, 52(3-4):142-145 (2010) 4 pages.
Lyons et al., "The Expression of an N-CAM Serum Fragment is Positively Correlated with Severity of Negative Featues in Type II Schizophrenia", Biol. Psychiatry, 23:769-775 (1988) 7 pages.
Ma, et al., "Use of Encapsulated Single Chain Antibodies for Induction of Anti-Idiotypic Humoral and Cellular Immune Responses", J. Pharm. Sci., 87:1375-1378 (1998). 4 pages.
Mahmood et al., "An N2S2 Teradentate Chelate for Solid-Phase Synthesis: Evaluation in Solution and Solid Phase and Characterization of Technetium-99 Complexes", Technetium, Rhenium and Other Metals in Chemistry and Nuclear Medicine, 5:71-76 (1999) 6 pages.

(56) References Cited

OTHER PUBLICATIONS

Mandelin et al., "Extracellular and Intracellular Mechanisms That Mediate the Metastatic Activity of Exogenous Osteopontin", Cancer, 115:1753-1764 (2009) 12 pages.

Mangale et al., "Identification of genes regulated by an interaction between α☐β3 integrin and vitronectin in murine decidua", Reprod. Fertil. Dev., 20:311-319 (2008) 10 pages.

Markgraf et al., "Sensorimotor and cognitive consequences of middle cerebral artery occlusion in rates", Brain Res., 575(2):238-246 (1992) 10 pages.

Martens et al., "Inhibition of Glioblastoma Growth in a Highly Invasive Nude Mouse Model Can Be Achieved by Targeting Epidermal Growth Factor Receptor but not Vascular Endothelial Growth Factor Receptor-2", Clin. Cancer Res., 14(17):5447-5458 (2008) 12 pages.

Masson-Gadais et al., "Integrin α☐β3 requirement for VEGFR2-mediated activation of SAPK2/p38 and Hsp90-dependent phosphorylation of focal adhesion kinase in endothelial cells activated by VEGF", Cell Stress Chaperones, 8(1):37-52 (2003) 16 pages.

McCarty et al., "Promises and Pitfalls of Anti-Angiogenic Therapy in Clinical Trials." Trends Mol. Med. 9.2(2003):53-58 6 pages.

Meneses et al., "Recombinant angiostatin prevents retinal neovascularization in a murine proliferative retinopathy model", Gene Therapy, 8(8):646-648 (2011) 3 pages.

Mezosi et al., "Nongenomic effect of thyroid hormone on free-radical production in human polymorphonuclear leukocytes", J. Endocrinol., 185:121-129 (2005) 9 pages.

Mishkin et al., "Increased Survival of Rats Bearing Morris Hepatoma 7800 after Induction of Hypothroidism", Cancer Res., 39:2371-2375 (1979) 5 pages.

Miyaguchi et al., "Correlation of Epidermal Growth Factor Receptor and Radiosensitivity in Human Maxillary Carcinoma Cell Lines", ActaOtolaryngol., 118:428-431 (1998) 4 pages.

Moeller et al., "Cytosolic Action of Thyroid Hormone Leads to Induction of Hypoxia-inducible Factor-1α and Glycolytic Genes", Molec. Endo., 19(12):2955-2963 (2005) 9 pages.

Moeller et al., "Thyroid hormone mediated changes in gene expression can be initiated by cytosolic action of the thyroid hormone receptor beta through the phosphatidylinositol 3-kinase pathway", Nuclear Receptor Signaling, 4: E020 (2006) 4 pages.

Mohamed et al., "Wound healing properties of cimetidine in vitro", Drug Intell. Clin. Pharm., 20(12):973-975 (1986) 4 pages.

Monferran et al., "α☐β3 and α☐β3 integrins control glioma cell response to ionising radiation through ILK and RhoB", Int. J. Cancer, 123:357-364 (2008) 8 pages.

Morand et al., "Effect of Iodide on Nicotinamide Adenine Dinucleotide Phosphate Oxidase Activity and Duox2 Protein Expression in Isolated Porcine Thyroid Follicles", Endo., 144(4):1241-1248 (2003) 8 pages.

Moreno et al., "Metabolic Effects of Thyroid Hormone Derivatives", Thyroid, 18(2):239-253 (2008) 15 pages.

Moreno et al., "Thyroid Economy—Regulation, Cell Biology, Thyroid Hormone Metabolism and Action: The Special Edition: Metabolic Effects of Thyroid Hormones. Metabolic Effects of Thyroid Hormone Derivatives", Thyroid, 18 (2):239-253 (2008) 15 pages.

Mousa et al., "Cellular and Molecular Mechanisms of Nicotine's Pro-Angiogenesis Activity and Its Potential Impact on Cancer", J. Cell. Biochem., 97:1370-1378 (2006) 9 pages.

Mousa et al., "Discovery of Pro-Angiogenic Effects of Nicotine's Pro-Angiogenesis Activity and Its Potential Impact on Cancer", J. Cell. Biochem., 97:1370-1378 (2006) Abstract Only. 3 pages.

Mousa et al., "Proangiogenesis Action of the Thyroid Hormone Analog 3,5-Diiodothyropropionic Acid (DITPA) Is Initiated at the Cell Surface and is Integrin Mediated", Endocrinol., 147(4):1602-1607 (2006) 6 pages.

Mousa et al., "Pro-angiogenesis action of thyroid hormone and analogs in a three-dimensional in vitro microvascular endothelial sprouting model", Int. Angiol., 25(4):407-413 (2006) 7 pages.

Mousa et al., "Tetraiodothyroacetic (tetrac) inhibits angiogenesis", In: Program of the 77th Annual Meeting of the American Thyroid Association, Phoenix, AZ, 2006: Abstract 108. 4 pages.

Mousa et al., "Tetraiodothyroacetic acid, a small molecule integrin ligand, blocks angiogenesis induced by vascular endothelial growth factor and basic fibroblast growth factor", Angiogenesis, 11:183-190 (2008) 8 pages.

Mousa et al., "The Proangiogenic Action of Thyroid Hormone Analogue GC-1 Is Initiated at an Integrin", J. Cardiovasc. Pharmacol., 46(3):356-360 (2005) 6 pages.

Mousa, S.A., "Mechanisms of Angiogenesis: Potential Therapeutic Targets", in Angiogenesis Inhibotors and Stimulators: Potential Therapeutic Implications, Landes Bioscience, Georgetown, Texas, Chapter I, pp. 1-12 (2000) 14 pages.

Mousa, S.A., et al., "Effect of Resveratrol on Angiogenesis and Platelet/Fibrin-Accelerated Tumor Growth in the Chick Chorioallantoic Membrane Model," Nutr. Cancer, 52(1):59-65 (2005) 7 pages.

Muller et al., "The Double Life of the Ku Protein: Facing the DNA Breaks and the Extracellular Environment", Cell Cycle, 4(30:438-441 (2005) 4 pages.

Ndiaye et al., "Red wine polyphenol-induced, endothelium-dependent NO-mediated relaxation is due to the redox-sensitive PI3-kinase / Akt-dependent phosphorylation of endothelial NO-synthase in the isolated porcine coronary artery", FASEB J., 19(3):455-457 (2005) 3 pages.

Nehls et al., "A microcarrier-based concultivation system for the investigation of factors and cells involved in angiogenesis in three-dimensional fibrin matrices in vitro", Histochem. Cell Biol., 104(6):459-466 (1995) 8 pages.

Nehls et al., "A Novel Micrcarrier-Based in Vitro Assay for Rapid and Reliable Quantification of Three-Domensional Cell Migration and Angiogenesis", Microvasc. Res., 50(3):311-322 (1995) 12 pages.

Neises et al., "Esterification of Carboxylic Acids with Dicyclohexylcarbodiimide/4-Dimethylaminopyridine: tert-Butyl Ethyl Fumarate", Org. Synth., 7:93 (1990); 63:183 (1985) 3 pages.

Restriction Requirement (Mail Date: May 5, 2016) for U.S. Appl. No. 14/977,776.

Office Action (Mail Date Sep. 9, 2016) for U.S. Appl. No. 14/185,010, filed Feb. 20, 2014.

Office Action (Mail Date Jun. 17, 2016) for U.S. Appl. No. 13/975,725, filed Aug. 26, 2013.

Notice of Allowance (Mail Date Jul. 19, 2016) for U.S. Appl. No. 14/242,041, filed Apr. 1, 2014.

Restriction Requirement (Mail Date Dec. 3, 2015) for U.S. Appl. No. 14/184,889, filed Feb. 20, 2014.

Office Action (Mail Date May 6, 2016) for U.S. Appl. No. 14/184,889, filed Feb. 20, 2014.

T4 and T3 stimulate angiogenesis in the chorioallantoic membrane model

| Treatment | Angiogenesis Index |
|---|---|
| PBS | 63 10 |
| $T_3$ (1 nM) | 121 18** |
| $T_4$ (0.1 µM) | 155 11** |

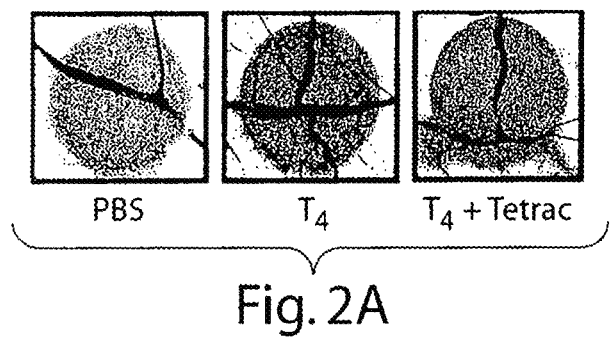
Fig. 2A
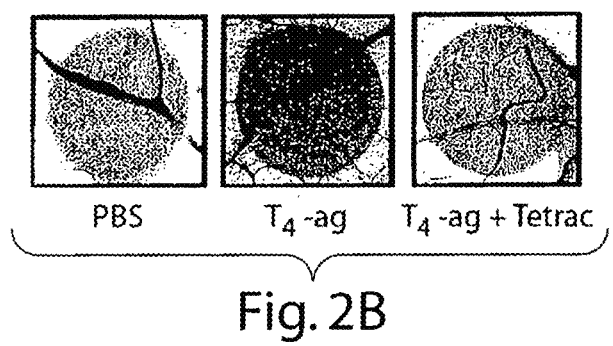
Fig. 2B
Summary of effects of $T_4$ and $T_3$ -agarose and tetrac on angiogenesis
| Treatment | Angiogenesis Index |
|---|---|
| PBS | 67 9 |
| $T_4$ (0.1 μM) | 156 16** |
| Tetrac (0.1 μM) | 76 9 |
| $T_4$ + tetrac | 66 6 |
| $T_4$ -agarose (0.1 μM) | 194 28** |
| $T_4$ -agarose + tetrac | 74 7 |
Fig. 2C Effects of FGF2 and $T_4$ on angiogenesis

| Treatment | Angiogenesis Index |
|---|---|
| PBS | 86 11 |
| FGF2 (0.5 µg/ml) | 126 17* |
| FGF2 (1.0 µg/ml) | 172 9** |
| $T_4$ (0.5 µM) | 115 4* |
| $T_4$ + FGF2 (0.5 µg/ml) | 167 10** |

Effects of FGF2 antibody on angiogenesis stimulated by $T_4$ and FGF2

| Treatment | Angiogenesis Index | |
|---|---|---|
| PBS | 92 | 10 |
| FGF2 (1.0 μg/ml) | 187 | 17* |
| FGF2 + FGF2-ab | 118 | 7 |
| $T_4$ (0.1 μM) | 142 | 12* |
| $T_4$ + FGF2-ab | 96 | 10 |

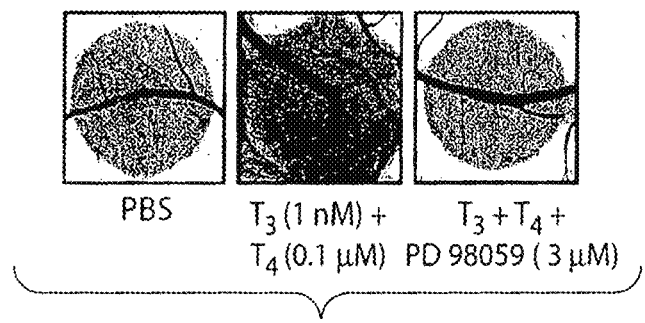
Fig. 5A
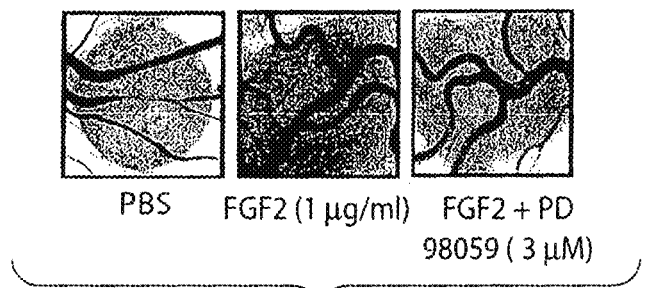
Fig. 5B
Effects of PD 98059 on angiogenesis stimulated by $T_4$ and FGF2
| Treatment | Angiogenesis Index | |
|---|---|---|
| PBS | 63 | 10 |
| $T_3$ (1 nM) + $T_4$ (0.1 μM) | 153 | 15* |
| $T_3$ + $T_4$ + PD 98059 (3 μM) | 50 | 10 |
| PBS | 86 | 11 |
| FGF2 (1 μg/ml) | 191 | 15** |
| FGF2 + PD 98059 (3 μM) | 110 | 16 |
Fig. 5C

| CAM treatment | # of Branches SEM | % Inhibition SEM |
|---|---|---|
| PBS | 73  8 | |
| $T_4$ (0.1 µM) | 170  16 | 0 |
| $T_4$ + LM609 (10 µg) | 109  9 | 64  9 |

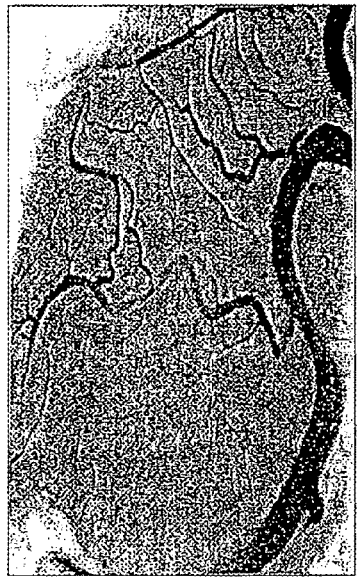
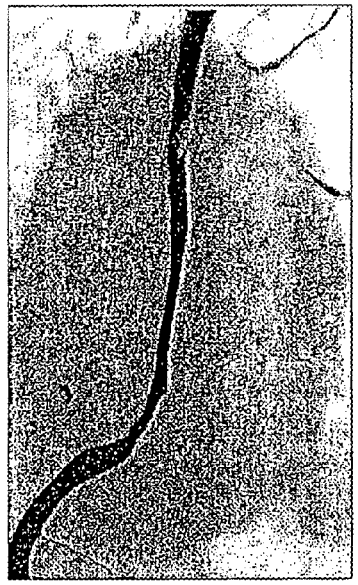
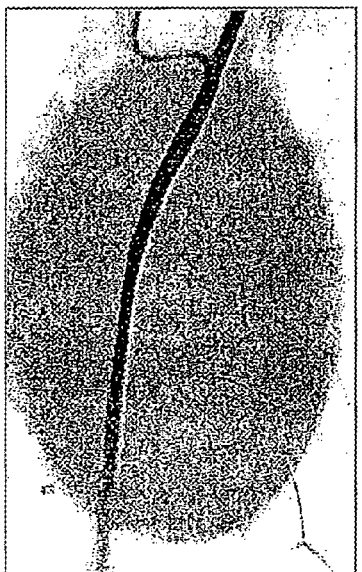
Fig. 16C
Inhibitory Effect of αvβ3 MAB (LM609) and XT 199 on T4-induced angiogenesis in the CAM Model Table A

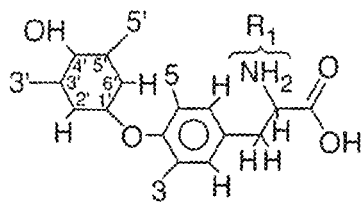

| 3' | 5' | 3 | 5 | $R_1$ | Analogue |
|---|---|---|---|---|---|
| I | I | I | I | $NH_2$ | $L\text{-}T_4$ |
| I | H | I | I | $NH_2$ | $L\text{-}T_3$ |
| I | I | I | H | $NH_2$ | $rT_3$ |
| H | H | I | I | $NH_2$ | $3,5\text{-}L\text{-}T_2$ |
| I | I | H | H | $NH_2$ | $3',5'\text{-}L\text{-}T_2$ |
| I | H | I | H | $NH_2$ | $3,3'\text{-}L\text{-}T_2$ |
| I | H | H | H | $NH_2$ | $3'\text{-}L\text{-}T_3$ |
| Br | Br | Br | Br | $NH_2$ | 3,5,3'-tetra-bromo-L-thyronine |
| H | H | Br | Br | $NH_2$ | 3,5,3',-dibromo-L-thyronine |
| Isop[a] | H | Me[b] | Me | $NH_2$ | DIMIT |
| Isop | H | Me | Me | $NH\text{-}COCH_3$ | N-acetyl DIMIT |

[a] Isop, isopropyl
[b] Me, methyl

Fig. 20A

Table B

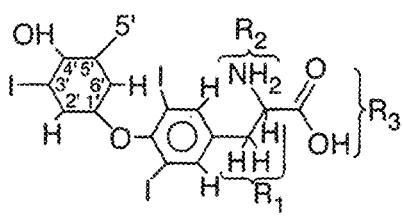

| $R_1$ | $R_2$ | $R_3$ | 5' | Analogue |
|---|---|---|---|---|
| $CH_2CH$ | H | $CO_2H$ | I | 3,5,3',5'-tetraiodo-thyropropionic acid |
| $CH_2$ | H | $CO_2H$ | I | 3,5,3',5'-tetraiodo-thyroacetic acid |
| $CH_2$ | H | $CO_2H$ | H | 3,5,3'-triiodothyroa-cetic acid |
| $CH_2CH$ | $NH_2$ | $COC_2H_5$ | I | $L\text{-}T_4$ ethylester |
| $CH_2CH$ | $NH_2$ | H | H | 3,5,3'-triiodothyrona-mine |

Fig. 20B

Table C

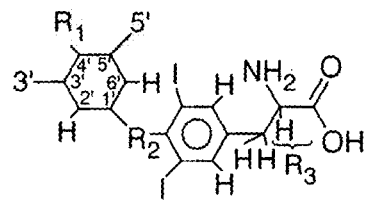

| $R_1$ | $R_2$ | $R_3$ | 3' | 5' | 3 | 5 | Analogue |
|---|---|---|---|---|---|---|---|
| H | O | L | H | H | I | I | 4'-deoxy $T_2$ |
| OH | S | L | I | H | I | I | S-bridged $T_3$ |
| OH | O | D | I | I | I | I | D-$T_4$ |
| OH | O | D | I | H | I | I | D-$T_3$ |

Fig. 20C

Table D

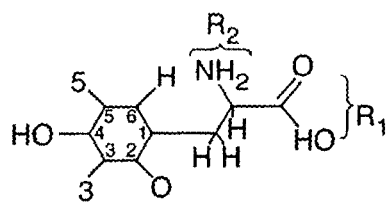

| 3 | 5 | $R_1$ | $R_3$ | Analogue |
|---|---|---|---|---|
| I | I | COOH | $NH_2$ | 3,5-diiodo-L-tyrosine |
| Br | Br | COOH | $NH_2$ | 3,5-dibromo-L-tyrosine |
| Me | Me | COOH | $NH_2$ | 3,5-dimethyl-DL-tyrosine |
| $NO_2$ | $NO_2$ | COOH | $NH_2$ | 3,5-dinitro-L-tyrosine |
| I | H | COOH | $NH_2$ | 3-iodo-L-tyrosine |
| $NO_2$ | H | COOH | $NH_2$ | 3-nitro-L-tyrosine |
| H | H | COOH | $NH_2$ | L-tyrosine |
| I | I | H | $NH_2$ | 3,5-diiodotyramine |
| H | H | H | $NH_2$ | tyramine |
| I | I | COOH | H | 3-(3,5-diiodo-4-hydroxy-phenyl) propionic acid |
| H | H | COOH | H | 3-(p-hydroxy-phenyl) propionic acid |

Fig. 20D

PBS     T₄ (0.1 μM)     T₄ + LM609 (10 μg)

| CAM Treatment | # of Branches ± SEM | % Inhibition ± SEM |
|---|---|---|
| PBS | 73 ± 8 | - |
| T₄ (0.1 μM) | 170 ± 16 | 0 |
| T₄ + LM609 (10 μg) | 109 ± 9 | 64 ± 9*** |

— Record 68: PLGA-Tween 80-Final-zeta-average585960

| TREATMENT | BRANCH Pts± SEM | % INHIBITION± SEM |
|---|---|---|
| PBS | 75.6 ± 7.3 | |
| VEGF (75ng) | 68.2 ± 8.5 | |
| FGF2 (1μg/ml) | 184.6 ± 18.5 | |
| FGF2 (1μg/ml) +TETRAC (75ng) | 122.2 ± 10.3 | 57.3 ± 9.4 |

NIPAAM: N-isopropylacrylamide (thermosensitive polymer)
APMAH: N-3-aminopropylmethacrylamide hydrochloride (manipulation of surface charge)
AA: Acrylic Acid (to induce mucoadhesive properties)

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 1
tggtatgtgg cactgaaacg                                          20

<210> SEQ ID NO 2
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 2
ctcaatgacc tggcgaagac                                          20

<210> SEQ ID NO 3

```
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 3
aaggtcatcc ctgagctgaa cg                                        22

<210> SEQ ID NO 4
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 4
gggtgtcgct gttgaagtca ga                                        22
```

NANOPARTICLE AND POLYMER FORMULATIONS FOR THYROID HORMONE ANALOGS, ANTAGONISTS, AND FORMULATIONS THEREOF

RELATED APPLICATIONS

This application is a continuation application of U.S. patent application Ser. No. 11/786,723 filed Apr. 11, 2007. U.S. patent application Ser. No. 11/786,723 is a continuation-in-part of U.S. patent application Ser. No. 11/663,047 filed Oct. 9, 2007 which issued on Dec. 6, 2011 as U.S. Pat. No. 8,071,134. U.S. patent application Ser. No. 11/786,723 also claims the benefit of U.S. Provisional Patent No. 60/856,450 filed Nov. 2, 2006, U.S. Provisional Patent Application No. 60/831,740 filed Jul. 17, 2006 and U.S. Provisional Patent Application No. 60/791,235 filed Apr. 11, 2006. U.S. patent application Ser. No. 11/663,047 is a continuation-in-part of U.S. patent application Ser. No. 10/943,072 filed Sep. 15, 2004 which issued on Aug. 31, 2010 as U.S. Pat. No. 7,785,632. U.S. patent application Ser. No. 10/943,072 claimed the benefit of U.S. Provisional Patent Application No. 60/502,721 filed Sep. 15, 2003. U.S. patent application Ser. No. 11/663,047 is a U.S. National Phase of PCT US 05/32813, filed on Sep. 15, 2005, which claims the benefit of U.S. Provisional Patent Application No. 60/670,534 filed Apr. 13, 2005. Each of these documents are incorporated herein by reference in its entirety.

FIELD OF THE INVENTION

This invention relates to nanoparticle and polymer conjugate forms of thyroid hormone, thyroid hormone analogs and derivatives thereof. Methods of using such compounds and pharmaceutical compositions containing same are also disclosed. The invention also relates to methods of preparing such compounds and to a sustained release and long residing ophthalmic formulation and the process of preparing the same.

BACKGROUND OF THE INVENTION

Thyroid hormones, such as L-thyroxine (T4) and 3,5,3'-triiodo-L-thyronine (T3), and their analogs such as GC-1, DITPA, Tetrac and Triac, regulate many different physiological processes in different tissues in vertebrates. It was previously known that many of the actions of thyroid hormones are mediated by the thyroid hormone receptor ("TR"). A novel cell surface receptor for thyroid hormone (L-thyroxine, T4, T3) has been described on integrin $\alpha V\beta 3$. The receptor is at or near the Arg-Gly-Asp (RGD) recognition site on the integrin. The $\alpha V\beta 3$ receptor is not a homologue of the nuclear thyroid hormone receptor (TR), but activation of the cell surface receptor results in a number of nucleus-mediated events, including the recently-reported pro-angiogenic action of the hormone and fibroblast migration in vitro in the human dermal fibroblast monolayer model of wound-healing.

Tetraiodothyroacetic acid (tetrac) is a deaminated analogue of $T_4$ that has no agonist activity at the integrin, but inhibits binding of $T_4$ and $T_3$ by the integrin and the pro-angiogenic action of agonist thyroid hormone analogues at $\alpha V\beta 3$. Inhibition of the angiogenic action of thyroid hormone has been shown in the chick chorioallantoic membrane (CAM) model and in the vessel sprouting model involving human dermal microvascular endothelial cells (HDMEC). In the absence of thyroid hormone, tetrac blocks the angiogenic activity of basic fibroblast growth factor (bFGF, FGF2), vascular endothelial growth factor (VEGF) and other pro-angiogenic peptides. Tetrac is effective in the CAM and HDMEC models. This inhibitory action of tetrac is thought to reflect its influence on the RGD recognition site that is relevant to pro-angiogenic peptide action.

Evidence that thyroid hormone can act primarily outside the cell nucleus has come from studies of mitochondrial responses to T3 or T2, from rapid onset effects of the hormone at the cell membrane and from actions on cytoplasmic proteins. The recent description of a plasma membrane receptor for thyroid hormone on integrin $\alpha V\beta 3$ has provided some insight into effects of the hormone on membrane ion pumps, such as the Na+/H+ antiporter, and has led to the description of interfaces between the membrane thyroid hormone receptor and nuclear events that underlie important cellular or tissue processes, such as angiogenesis and proliferation of certain tumor cells.

Circulating levels of thyroid hormone are relatively stable; therefore, membrane-initiated actions of thyroid hormone on neovascularization or on cell proliferation or on membrane ion channels—as well, of course, as gene expression effects of the hormone mediated by TR mentioned above—may be assumed to contribute to 'basal activity' or setpoints of these processes in intact organisms. The possible clinical utility of cellular events that are mediated by the membrane receptor for thyroid hormone may reside in inhibition of such effect(s) in the contexts of neovascularization or tumor cell growth. Indeed, we have shown that blocking the membrane receptor for iodothyronines with tetraiodothyroacetic acid (tetrac), a hormone-binding inhibitory analogue that has no agonist activity at the receptor, can arrest growth of glioma cells and of human breast cancer cells in vitro. Tetrac is a useful probe to screen for participation of the integrin receptor in actions of thyroid hormone.

Integrin $\alpha V\beta 3$ binds thyroid hormone near the Arg-Gly-Asp (RGD) recognition site of the protein; the RGD site is involved in the protein-protein interactions linking the integrin to extracellular matrix (ECM) proteins such as vitronectin, fibronectin and laminin.

Also initiated at the cell surface integrin receptor is the complex process of angiogenesis, monitored in either a standard chick blood vessel assay or with human endothelial cells in a sprouting assay. This hormone-dependent process requires MAPK activation and elaboration of basic fibroblast growth factor (bFGF; FGF2) that is the downstream mediator of thyroid hormone's effect on angiogenesis. Tetrac blocks this action of T4 and T3, as does RGD peptide and small molecules that mimic RGD peptide. It is possible that desirable neovascularization can be promoted with local application of thyroid hormone analogues, e.g., in wound-healing, or that undesirable angiogenesis, such as that which supports tumor growth, can be antagonized in part with tetrac.

Thyroid hormone can also stimulate the proliferation in vitro of certain tumor cell lines. Murine glioma cell lines have been shown to proliferate in response to physiological concentrations of T4 by a mechanism initiated at the integrin receptor and that is MAPK-dependent. In what may be a clinical corollary, a prospective study of patients with far advanced glioblastoma multiforme (GBM) in whom mild hypothyroidism was induced by propylthiouracil showed an important survival benefit over euthyroid control patients. We reported in 2004 that human breast cancer MCF-7 cells proliferated in response to T4 by a mechanism that was inhibited by tetrac. A recent retrospective clinical analysis by Cristofanilli et al. showed that hypothyroid women who developed breast cancer did so later in life than matched euthyroid controls and had less aggressive, smaller lesions at the time of diagnosis than controls. Thus, the trophic action of thyroid hormone on in vitro models of both brain tumor and breast cancer appears to have clinical support.

The cellular or tissue actions of thyroid hormone that are known to be initiated at integrin αVβ3 and that require transduction of the hormone signal via MAPK are summarized below. The integrin is a signal transducing protein connecting signals from extracellular matrix (ECM) proteins to the cell interior (outside-in) or from cytoplasm and intracellular organelles to ECM (inside-out). Binding of L-thyroxine (T4) or 3,5,3'-triiodo-L-thyronine (T3) to heterodimeric αVβ3 results in activation of mitogen-activated protein kinase (MAPK; ERK1/2). Activated MAPK (phosphoMAPK, pMAPK) translocates to the cell nucleus where it phosphorylates transactivator proteins such as thyroid hormone receptor-β1 (TRβ1), estrogen receptor-α (ERα) or signal transducer and activator of transcription-1α (STAT1α). Among the genes consequently transcribed are basic fibroblast growth factor (bFGF), that mediates thyroid hormone-induced angiogenesis) and other proliferation factors important to cell division of tumor cells.

There is thus a need in the art for thyroid hormone analogs that can bind to the cell surface receptor while not being able to enter the cell. Such reformulated hormone analogues would not express intracellular actions of the hormone and thus if absorbed into the circulation would not have systemic thyroid hormone analog actions.

SUMMARY OF THE INVENTION

The invention is based, in part, on the discovery that thyroid hormone, thyroid hormone analogs, their polymeric and nanoparticle forms, act at the cell membrane level and have pro-angiogenic properties that are independent of the nuclear thyroid hormone effects. Accordingly, these thyroid hormone analogs, polymeric forms, and nanoparticles can be used to treat a variety of disorders. Similarly, the invention is also based on the discovery that thyroid hormone analog antagonists inhibit the pro-angiogenic effect of such analogs, and can also be used to treat a variety of disorders.

Accordingly, in one aspect the invention features methods for treating a condition amenable to treatment by promoting angiogenesis by administering to a subject in need thereof an amount of a polymeric form of thyroid hormone, or an analog thereof, effective for promoting angiogenesis. Examples of such conditions amenable to treatment by promoting angiogenesis are provided herein and can include occlusive vascular disease, coronary disease, erectile dysfunction, myocardial infarction, ischemia, stroke, peripheral artery vascular disorders, cerebrovascular, limb ischemia, and wounds.

Examples of thyroid hormone analogs are also provided herein and can include triiodothyronine (T3), levothyroxine (T4), T4 or T3 N-Methyl, T4 or T3 N-Ethyl, T4 or T3 N-Triphenyl, T4 or T3 N-Propyl, T4 or T3 N-Isopropyl, T4 or T3 N-tertiary butyl, 3,5-dimethyl-4-(4'-hydroxy-3'-isopropylbenzyl)-phenoxy acetic acid (GC-1), or 3,5-diiodo-thyropropionic acid (DITPA), tetraiodothyroacetic acid (TETRAC), and triiodothyroacetic acid (TRIAC). Additional analogs are in FIG. 20 Tables A-D. These analogs can be conjugated to polyvinyl alcohol, acrylic acid ethylene co-polymer, polylactic acid, or agarose. The conjugation is via covalent or non-covalent bonds depending on the polymer used.

In one embodiment the thyroid hormone, thyroid hormone analogs, or polymeric forms thereof are administered by parenteral, oral, rectal, or topical means, or combinations thereof. Parenteral modes of administration include, for example, subcutaneous, intraperitoneal, intramuscular, or intravenous modes, such as by catheter. Topical modes of administration can include, for example, a band-aid.

In another embodiment, the thyroid hormone, thyroid hormone analogs, or polymeric forms thereof can be encapsulated or incorporated in a microparticle, liposome, or polymer. The polymer can include, for example, polyglycolide, polylactide, or co-polymers thereof. The liposome or microparticle has a size of about less than 200 nanometers, and can be administered via one or more parenteral routes, or another mode of administration. In another embodiment the liposome or microparticle can be lodged in capillary beds surrounding ischemic tissue, or applied to the inside of a blood vessel via a catheter.

Thyroid hormone, thyroid hormone analogs, or polymeric forms thereof according to the invention can also be co-administered with one or more biologically active substances that can include, for example, growth factors, vasodilators, anti-coagulants, anti-virals, anti-bacterials, anti-inflammatories, immuno-suppressants, analgesics, vascularizing agents, or cell adhesion molecules, or combinations thereof. In one embodiment, the thyroid hormone analog or polymeric form is administered as a bolus injection prior to or post-administering one or more biologically active substance.

Growth factors can include, for example, transforming growth factor alpha ("TGFα"), transforming growth factor beta ("TGFβ"), basic fibroblast growth factor, vascular endothelial growth factor, epithelial growth factor, nerve growth factor, platelet-derived growth factor, and vascular permeability factor. Vasodilators can include, for example, adenosine, adenosine derivatives, or combinations thereof. Anticoagulants include, but are not limited to, heparin, heparin derivatives, anti-factor Xa, anti-thrombin, aspirin, clopidgrel, or combinations thereof.

In another aspect of the invention, methods are provided for promoting angiogenesis along or around a medical device by coating the device with a thyroid hormone, thyroid hormone analog, or polymeric form thereof according to the invention prior to inserting the device into a patient. The coating step can further include coating the device with one or more biologically active substance, such as, but not limited to, a growth factor, a vasodilator, an anti-coagulant, or combinations thereof. Examples of medical devices that can be coated with thyroid hormone analogs or polymeric forms according to the invention include stents, catheters, cannulas or electrodes.

In a further aspect, the invention provides methods for treating a condition amenable to treatment by inhibiting angiogenesis by administering to a subject in need thereof an amount of an anti-angiogenesis agent effective for inhibiting angiogenesis. Examples of the conditions amenable to treatment by inhibiting angiogenesis include, but are not limited to, primary or metastatic tumors, diabetic retinopathy, and related conditions. Examples of the anti-angiogenesis agents used for inhibiting angiogenesis are also provided by the invention and include, but are not limited to, tetraiodothyroacetic acid (TETRAC), triiodothyroacetic acid (TRIAC), monoclonal antibody LM609, XT 199 or combinations thereof. Such anti-angiogenesis agents can act at the cell surface to inhibit the pro-angiogenesis agents.

In another aspect, the invention provides for primary or adjunctive anti-proliferative treatment of certain cancers.

Examples of the cancerous conditions amenable to this treatment include, but are not limited to, glioblastoma multiforme, lung cancer, nonthyroidal head-and-neck cancer, thyroid cancer, breast cancer and ovarian cancer. Examples of the agents used for anti-proliferative action are provided by the invention and include, but are limited to, tetraiodothyroacetic acid (TETRAC), triiodothyroacetic acid (TRIAC), monoclonal antibody LM609, XT 1999 or combinations thereof. These agents act at the cell surface integrin receptor for thyroid hormone to inhibit cancer cell proliferation.

In one embodiment, the anti-angiogenesis agent is administered by a parenteral, oral, rectal, or topical mode, or combination thereof. In another embodiment, the anti-angiogenesis agent can be co-administered with one or more anti-angiogenesis therapies or chemotherapeutic agents.

In yet a further aspect, the invention provides compositions (i.e., angiogenic agents) that include thyroid hormone, and analogs conjugated to a polymer. The conjugation can be through a covalent or non-covalent bond, depending on the polymer. A covalent bond can occur through an ester or anhydride linkage, for example. Examples of the thyroid hormone analogs are also provided by the instant invention and include levothyroxine (T4), triiodothyronine (T3), 3,5-dimethyl-4-(4'-hydroxy-3'-isopropylbenzyl)-phenoxy acetic acid (GC-1), or 3,5-diiodothyropropionic acid (DITPA). In one embodiment, the polymer can include, but is not limited to, polyvinyl alcohol, acrylic acid ethylene co-polymer, polylactic acid, or agarose.

In another aspect, the invention provides for pharmaceutical formulations including the angiogenic agents according to the present invention in a pharmaceutically acceptable carrier. In one embodiment, the pharmaceutical formulations can also include one or more pharmaceutically acceptable excipients.

The pharmaceutical formulations according to the present invention can be encapsulated or incorporated in a liposome, microparticle, or polymer. The liposome or microparticle has a size of less than about 200 nanometers. Any of the pharmaceutical formulations according to the present invention can be administered via parenteral, oral, rectal, or topical means, or combinations thereof. In another embodiment, the pharmaceutical formulations can be co-administered to a subject in need thereof with one or more biologically active substances including, but not limited to, growth factors, vasodilators, anti-coagulants, or combinations thereof.

In other aspects, the present invention concerns the use of the polymeric thyroid hormone analogs and pharmaceutical formulations containing said hormone, for the restoration of neuronal functions and enhancing survival of neural cells. For the purpose of the present invention, neuronal function is taken to mean the collective physiological, biochemical and anatomic mechanisms that allow development of the nervous system during the embryonic and postnatal periods and that, in the adult animal, is the basis of regenerative mechanisms for damaged neurons and of the adaptive capability of the central nervous system when some parts of it degenerate and cannot regenerate.

Therefore, the following processes occur in order to achieve neuronal function: denervation, reinnervation, synaptogenesis, synaptic repression, synaptic expansion, the sprouting of axons, neural regeneration, development and organisation of neural paths and circuits to replace the damaged ones. Therefore, the suitable patients to be treated with the polymeric thyroid hormone analogs or combinations thereof according to the present invention are patients afflicted with degenerative pathologies of the central nervous system (senile dementia like Alzheimer's disease, Parkinsonism, Huntington's chorea, cerebellar-spinal adrenoleucodystrophy), trauma and cerebral ischemia.

In a preferred embodiment, methods of the invention for treating motor neuron defects, including amyotrophic lateral sclerosis, multiple sclerosis, and spinal cord injury comprise administering a polymeric thyroid hormone analog, or combinations thereof, and in combination with growth factors, nerve growth factors, or other pro-angiogenesis or neurogenesis factors. Spinal cord injuries include injuries resulting from a tumor, mechanical trauma, and chemical trauma. The same or similar methods are contemplated to restore motor function in a mammal having amyotrophic lateral sclerosis, multiple sclerosis, or a spinal cord injury. Administering one of the aforementioned polymeric thyroid hormone analogs alone or in combination with nerve growth factors or other neurogenesis factors also provides a prophylactic function. Such administration has the effect of preserving motor function in a mammal having, or at risk of having, amyotrophic lateral sclerosis, multiple sclerosis, or a spinal cord injury. Also according to the invention, polymeric thyroid hormone analogs alone or in combination with nerve growth factors or other neurogenesis factors administration preserves the integrity of the nigrostriatal pathway.

Specifically, methods of the invention for treating (pre- or post-symptomatically) amyotrophic lateral sclerosis, multiple sclerosis, or a spinal cord injury comprise administering a polymeric thyroid hormone analog alone or in combination with nerve growth factors or other neurogenesis factors. In a particularly-preferred embodiment, the polymeric thyroid hormone analog alone or in combination with nerve growth factors or other neurogenesis factors is a soluble complex, comprising at least one polymeric thyroid hormone analog alone or in combination with nerve growth factors or other neurogenesis factors.

In one aspect, the invention features compositions and therapeutic treatment methods comprising administering to a mammal a therapeutically effective amount of a morphogenic protein ("polymeric thyroid hormone analog alone or in combination with nerve growth factors or other neurogenesis factors"), as defined herein, upon injury to a neural pathway, or in anticipation of such injury, for a time and at a concentration sufficient to maintain the neural pathway, including repairing damaged pathways, or inhibiting additional damage thereto.

In another aspect, the invention features compositions and therapeutic treatment methods for maintaining neural pathways. Such treatment methods include administering to the mammal, upon injury to a neural pathway or in anticipation of such injury, a compound that stimulates a therapeutically effective concentration of an endogenous polymeric thyroid hormone analog. These compounds are referred to herein as polymeric thyroid hormone analogs alone or in combination with nerve growth factors or other neurogenesis factors-stimulating agents, and are understood to include substances which, when administered to a mammal, act on tissue(s) or organ(s) that normally are responsible for, or capable of, producing a polymeric thyroid hormone analog alone or in combination with nerve growth factors or other neurogenesis factors and/or secreting a polymeric thyroid hormone analog alone or in combination with nerve growth factors or other neurogenesis factors, and which cause endogenous level of the polymeric thyroid hormone analogs alone or in combination with nerve growth factor or other neurogenesis factors to be altered.

In particular, the invention provides methods for protecting neurons from the tissue destructive effects associated with the body's immune and inflammatory response to nerve injury. The invention also provides methods for stimulating neurons to maintain their differentiated phenotype, including inducing the redifferentiation of transformed cells of neuronal origin to a morphology characteristic of untransformed neurons. In one embodiment, the invention provides means for stimulating production of cell adhesion molecules, particularly nerve cell adhesion molecules ("N-CAM"). The invention also provides methods, compositions and devices for stimulating cellular repair of damaged neurons and neural pathways, including regenerating damaged dendrites or axons. In addition, the invention also provides means for evaluating the status of nerve tissue, and for detecting and monitoring neuropathies by monitoring fluctuations in polymeric thyroid hormone analogs alone or in combination with nerve growth factors or other neurogenesis factors levels.

In one aspect of the invention, the polymeric thyroid hormone analogs alone or in combination with nerve growth factors or other neurogenesis factors described herein are useful in repairing damaged neural pathways of the peripheral nervous system. In particular, polymeric thyroid hormone analogs alone or in combination with nerve growth factors or other neurogenesis factors are useful for repairing damaged neural pathways, including transected or otherwise damaged nerve fibers. Specifically, the polymeric thyroid hormone analogs alone or in combination with nerve growth factor or other neurogenesis factors described herein are capable of stimulating complete axonal nerve regeneration, including vascularization and reformation of the myelin sheath. Preferably, the polymeric thyroid hormone analogs alone or in combination with nerve growth factors or other neurogenesis factors are provided to the site of injury in a biocompatible, bioresorbable carrier capable of maintaining the polymeric thyroid hormone analogs alone or in combination with nerve growth factors or other neurogenesis factors at the site and, where necessary, means for directing axonal growth from the proximal to the distal ends of a severed neuron. For example, means for directing axonal growth may be required where nerve regeneration is to be induced over an extended distance, such as greater than 10 mm. Many carriers capable of providing these functions are envisioned. For example, useful carriers include substantially insoluble materials or viscous solutions prepared as disclosed herein comprising laminin, hyaluronic acid or collagen, or other suitable synthetic, biocompatible polymeric materials such as polylactic, polyglycolic or polybutyric acids and/or copolymers thereof. A preferred carrier comprises an extracellular matrix composition derived, for example, from mouse sarcoma cells.

In a particularly preferred embodiment, a polymeric thyroid hormone analog alone or in combination with nerve growth factors or other neurogenesis factors is disposed in a nerve guidance channel which spans the distance of the damaged pathway. The channel acts both as a protective covering and a physical means for guiding growth of a neurite. Useful channels comprise a biocompatible membrane, which may be tubular in structure, having a dimension sufficient to span the gap in the nerve to be repaired, and having openings adapted to receive severed nerve ends. The membrane may be made of any biocompatible, nonirritating material, such as silicone or a biocompatible polymer, such as polyethylene or polyethylene vinyl acetate. The casing also may be composed of biocompatible, bioresorbable polymers, including, for example, collagen, hyaluronic acid, polylactic, polybutyric, and polyglycolic acids. In a preferred embodiment, the outer surface of the channel is substantially impermeable.

The polymeric thyroid hormone analogs alone or in combination with nerve growth factors or other neurogenesis factors may be disposed in the channel in association with a biocompatible carrier material, or it may be adsorbed to or otherwise associated with the inner surface of the casing, such as is described in U.S. Pat. No. 5,011,486, provided that the polymeric thyroid hormone analogs alone or in combination with nerve growth factors or other neurogenesis factors is accessible to the severed nerve ends.

In another aspect of the invention, polymeric thyroid hormone analogs alone or in combination with nerve growth factors or other neurogenesis factors described herein are useful to protect against damage associated with the body's immune/inflammatory response to an initial injury to nerve tissue. Such a response may follow trauma to nerve tissue, caused, for example, by an autoimmune dysfunction, neoplastic lesion, infection, chemical or mechanical trauma, disease, by interruption of blood flow to the neurons or glial cells, or by other trauma to the nerve or surrounding material. For example, the primary damage resulting from hypoxia or ischemia-reperfusion following occlusion of a neural blood supply, as in an embolic stroke, is believed to be immunologically associated. In addition, at least part of the damage associated with a number of primary brain tumors also appears to be immunologically related. Application of a polymeric thyroid hormone analog alone or in combination with nerve growth factors or other neurogenesis factors, either directly or systemically alleviates and/or inhibits the immunologically related response to a neural injury. Alternatively, administration of an agent capable of stimulating the expression and/or secretion in vivo of polymeric thyroid hormone analogs alone or in combination with nerve growth factors or other neurogenesis factors expression, preferably at the site of injury, may also be used. Where the injury is to be induced, as during surgery or other aggressive clinical treatment, the polymeric thyroid hormone analogs alone or in combination with nerve growth factors or other neurogenesis factors or agent may be provided prior to induction of the injury to provide a neuroprotective effect to the nerve tissue at risk.

Generally, polymeric thyroid hormone analogs alone or in combination with nerve growth factors or other neurogenesis factors useful in methods and compositions of the invention are dimeric proteins that induce morphogenesis of one or more eukaryotic (e.g., mammalian) cells, tissues or organs. Tissue morphogenesis includes de novo or regenerative tissue formation, such as occurs in a vertebrate embryo during development. Of particular interest are polymeric thyroid hormone analogs alone or in combination with nerve growth factors or other neurogenesis factors that induce tissue-specific morphogenesis at least of bone or neural tissue. As defined herein, a polymeric thyroid hormone analog alone or in combination with nerve growth factor or other neurogenesis factors comprises a pair of polypeptides that, when folded, form a dimeric protein that elicits morphogenetic responses in cells and tissues displaying thyroid receptors. That is, the polymeric thyroid hormone analogs alone or in combination with nerve growth factors or other neurogenesis factors generally induce a cascade of events including all of the following in a morphogenically permissive environment: stimulating proliferation of progenitor cells; stimulating the differentiation of progenitor cells; stimulating the proliferation of differentiated cells; and, supporting the growth and maintenance of differentiated cells. "Progenitor" cells are uncommitted cells that are competent to differentiate into one or more specific types of differentiated cells, depending on their genomic repertoire and the tissue specificity of the permissive environment in which morphogenesis is induced. An exemplary progenitor cell is a hematopoeitic stem cell, a mesenchymal stem cell, a basement epithelium cell, a neural crest cell, or the like. Further, polymeric thyroid hormone analogs alone or in combination with nerve growth factors or other neurogenesis factors can delay or mitigate the onset of senescence- or quiescence-associated loss of phenotype and/or tissue function. Still further, polymeric thyroid hormone analogs alone or in combination with nerve growth factors or other neurogenesis factors can stimulate phenotypic expression of a differentiated cell type, including expression of metabolic and/or functional, e.g., secretory, properties thereof. In addition, polymeric thyroid hormone analogs alone or in combination with nerve growth factor or other neurogenesis factors can induce redifferentiation of committed cells (e.g., osteoblasts, neuroblasts, or the like) under appropriate conditions. As noted above, polymeric thyroid hormone analogs alone or in combination with nerve growth factors or other neurogenesis factors that induce proliferation and/or differentiation at least of bone or neural tissue, and/or support the growth, maintenance and/or functional properties of neural tissue, are of particular interest herein.

Of particular interest are polymeric thyroid hormone analogs alone or in combination with nerve growth factors or other neurogenesis factors which, when provided to a specific tissue of a mammal, induce tissue-specific morphogenesis or maintain the normal state of differentiation and growth of that tissue. In preferred embodiments, the present polymeric thyroid hormone analog alone or in combination with nerve growth factors or other neurogenesis factors induce the formation of vertebrate (e.g., avian or mammalian) body tissues, such as but not limited to nerve, eye, bone, cartilage, bone marrow, ligament, tooth dentin, periodontium, liver, kidney, lung, heart, or gastrointestinal lining. Preferred methods may be carried out in the context of developing embryonic tissue, or at an aseptic, unscarred wound site in post-embryonic tissue.

Other aspects of the invention include compositions and methods of using thyroid hormone analogs and polymers thereof for imaging and diagnosis of neurodegenerative disorders, such as, for example, Alzheimer's disease. For example, in one aspect, the invention features T4 analogs that have a high specificity for target sites when administered to a subject in vivo. Preferred T4 analogs show a target to non-target ratio of at least 4:1, are stable in vivo and substantially localized to target within 1 hour after administration. In another aspect, the invention features pharmaceutical compositions comprised of a linker attached to the T4 analogs for Technetium, indium for gamma imaging using single photon emission ("SPECT") and with contrast agents for MRI imaging. Additionally, halogenated analogs that bind TTR can inhibit the formation of amyloid fibrils and thus can be utilized for the prevention and treatment of Alzheimer's disease. Such compounds can also be used with positron emission tomography ("PET") imaging methods.

In other aspects, the invention also includes compositions and methods for modulating actions of growth factors and other polypeptides whose cell surface receptors are clustered around integrin αVβ3, or other cell surface receptors containing the amino acid sequence Arg-Gly-Asp ("RGD"). Polypeptides that can be modulated include, for example, insulin, insulin-like growth factors, epidermal growth factors, and interferon-γ.

The details of one or more embodiments of the invention have been set forth in the accompanying description below. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural references unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference in their entirety.

BRIEF DESCRIPTION OF THE DRAWINGS

FIG. 2A. Tetrac inhibits stimulation of angiogenesis by T4 and agarose-linked T4 (T4-ag). A 2.5-fold increase in blood vessel branch formation is seen in a representative CAM preparation exposed to 0.1 µmol/L T4 for 3 days. In 3 similar experiments, there was a 2.3-fold increase. This effect of the hormone is inhibited by tetrac (0.1 µmol/L), a T4 analogue shown previously to inhibit plasma membrane actions of T4.13 Tetrac alone does not stimulate angiogenesis (C).

FIG. 2B. T4-ag (0.1 µmol/L) stimulates angiogenesis 2.3-fold (2.9-fold in 3 experiments), an effect also blocked by tetrac.

FIG. 2C. Summary of the results of 3 experiments that examine the actions of tetrac, T4-ag, and T4 in the CAM assay. Data (means±SEM) were obtained from 10 images for each experimental condition in each of 3 experiments. **$P<0.001$ by ANOVA, comparing T4-treated and T4-agarose-treated samples with PBS-treated control samples.

Figures 4A, 4B:
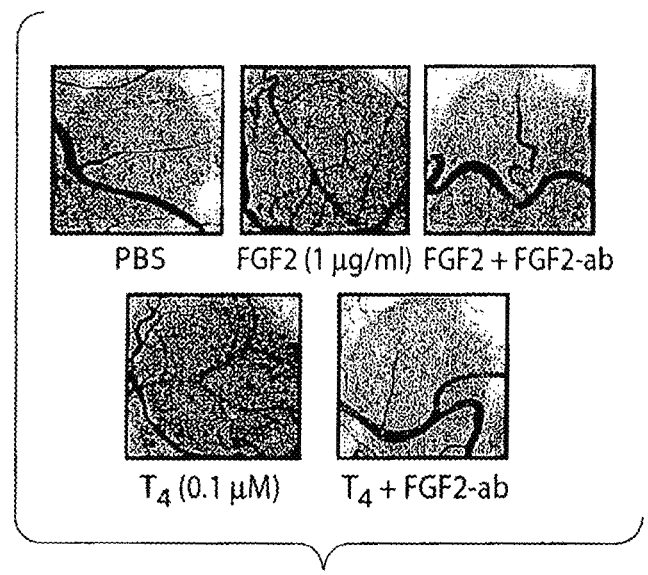
FIG. 4A. Effect of anti-FGF2 on angiogenesis caused by T4 or exogenous FGF2. FGF2 caused a 2-fold increase in angiogenesis in the CAM model in 3 experiments, an effect inhibited by antibody (ab) to FGF2 (8 µg). T4 also stimulated angiogenesis 1.5-fold, and this effect was also blocked by FGF2 antibody, indicating that the action of thyroid hormone in the CAM model is mediated by an autocrine/paracrine effect of FGF2 because T4 and T3 cause FGF2 release from cells in the CAM model (Table 1). We have shown previously that a nonspecific IgG antibody has no effect on angiogenesis in the CAM assay.

FIG. 4B. Summary of results from 3 CAM experiments that studied the action of FGF2-ab in the presence of FGF2 or T4. *P<0.01; **P<0.001, indicating significant effects in 3 experiments studying the effects of thyroid hormone and FGF2 on angiogenesis and loss of these effects in the presence of antibody to FGF2.

FIG. 5A. Effect of PD 98059, a MAPK (ERK1/2) signal transduction cascade inhibitor, on angiogenesis induced by T4, T3, and FGF2. Angiogenesis stimulated by T4 (0.1 µmol/L) and T3 (1 nmol/L) together is fully inhibited by PD 98059 (3 µmol/L).

FIG. 5B. Angiogenesis induced by FGF2 (1 µg/mL) is also inhibited by PD 98059, indicating that the action of the growth factor is also dependent on activation of the ERK1/2 pathway. In the context of the experiments involving T4-agarose (T4-ag) and tetrac (FIG. 2) indicating that T4 initiates its proangiogenic effect at the cell membrane, results shown in A and B are consistent with 2 roles played by MAPK in the proangiogenic action of thyroid hormone: ERK1/2 transduces the early signal of the hormone that leads to FGF2 elaboration and transduces the subsequent action of FGF2 on angiogenesis.

FIG. 5C, Summary of results of 3 experiments, represented by A and B, showing the effect of PD98059 on the actions of T4 and FGF2 in the CAM model. *P<0.01; **P<0.001, indicating results of ANOVA on data from 3 experiments.

Figure 6A:
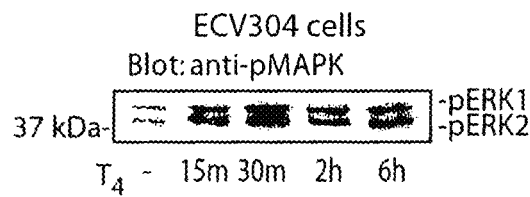

FIG. 6A. T4 and FGF2 activate MAPK in ECV304 endothelial cells. Cells were prepared in M199 medium with 0.25% hormone-depleted serum and treated with T4 (0.1 µmol/L) for 15 minutes to 6 hours. Cells were harvested and nuclear fractions prepared as described previously. Nucleoproteins, separated by gel electrophoresis, were immunoblotted with antibody to phosphorylated MAPK (pERK1 and pERK2, 44 and 42 kDa, respectively), followed by a second antibody linked to a luminescence-detection system. A β-actin immunoblot of nuclear fractions serves as a control for gel loading in each part of this figure. Each immunoblot is representative of 3 experiments. T4 causes increased phosphorylation and nuclear translocation of ERK1/2 in ECV304 cells. The effect is maximal in 30 minutes, although the effect remains for ≥6 hours.

Figure 6B:
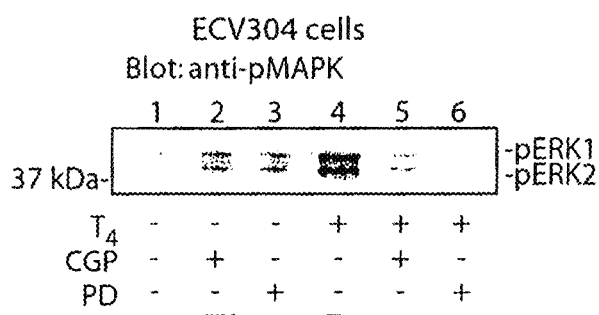

FIG. 6B, ECV304 cells were treated with the ERK1/2 activation inhibitor PD 98059 (PD; 30 µmol/L) or the PKC inhibitor CGP41251 (CGP; 100 nmol/L) for 30 minutes, after which $10^{-7}$ M T4 was added for 15 minutes to cell samples as shown. Nuclei were harvested, and this representative experiment shows increased phosphorylation (activation) of ERK1/2 by T4 (lane 4), which is blocked by both inhibitors (lanes 5 and 6), suggesting that PKC activity is a requisite for MAPK activation by T4 in endothelial cells.

Figure 6C:
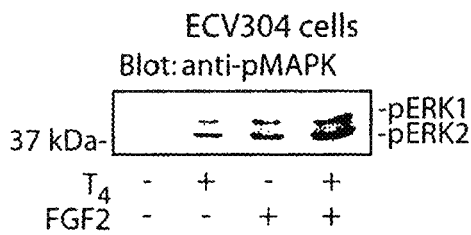

FIG. 6C, ECV304 cells were treated with either T4 ($10^{-7}$ mol/L), FGF2 (10 ng/mL), or both agents for 15 minutes. The figure shows pERK1/2 accumulation in nuclei with either hormone or growth factor treatment and enhanced nuclear pERK1/2 accumulation with both agents together.

Figure 7:
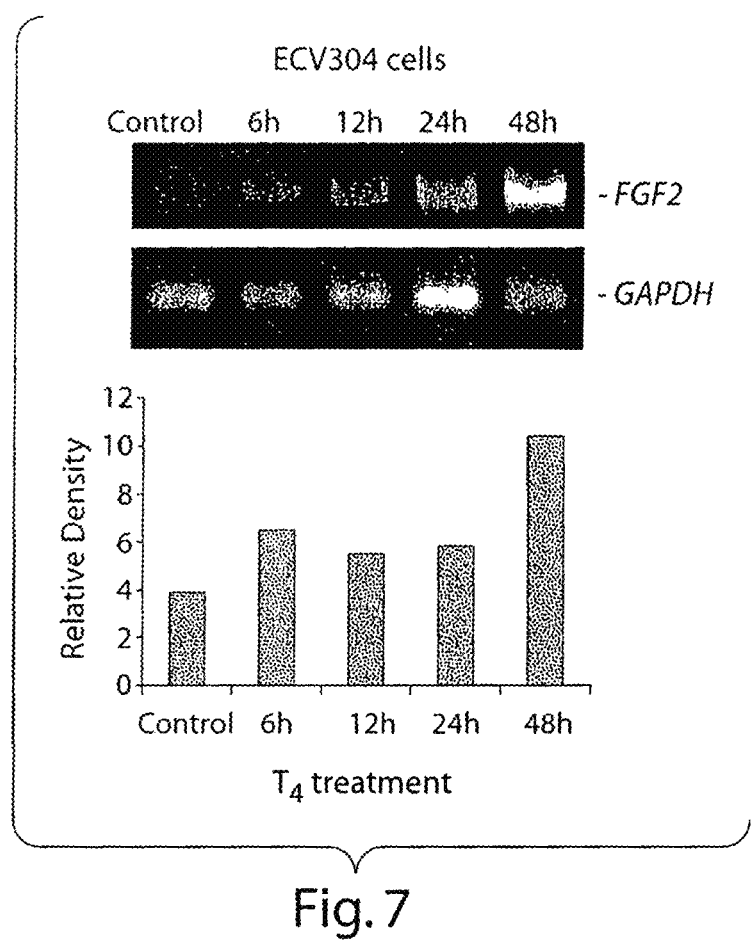

FIG. 7. T4 increases accumulation of FGF2 cDNA in ECV304 endothelial cells. Cells were treated for 6 to 48 hours with T4 ($10^{-7}$ mol/L) and FGF2 and GAPDH cDNAs isolated from each cell aliquot. The levels of FGF2 cDNA, shown in the top blot, were corrected for variations in GAPDH cDNA content, shown in the bottom blot, and the corrected levels of FGF2 are illustrated below in the graph (mean±SE of mean; n=2 experiments). There was increased abundance of FGF2 transcript in RNA extracted from cells treated with T4 at all time points. *P<0.05; **P<0.01, indicating comparison by ANOVA of values at each time point to control value.

Figure 8:
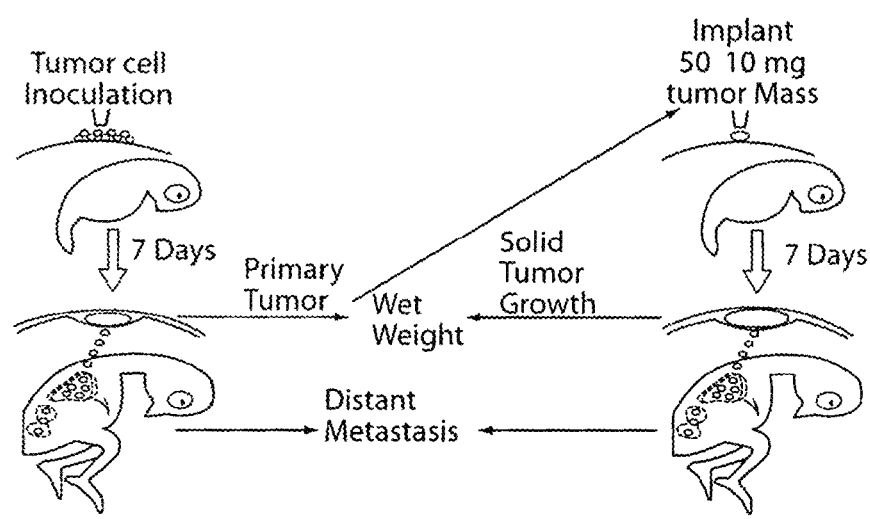

FIG. 8. 7 Day Chick Embryo Tumor Growth Model. Illustration of the Chick Chorioallantoic Membrane (CAM) model of tumor implant.

Figure 9:
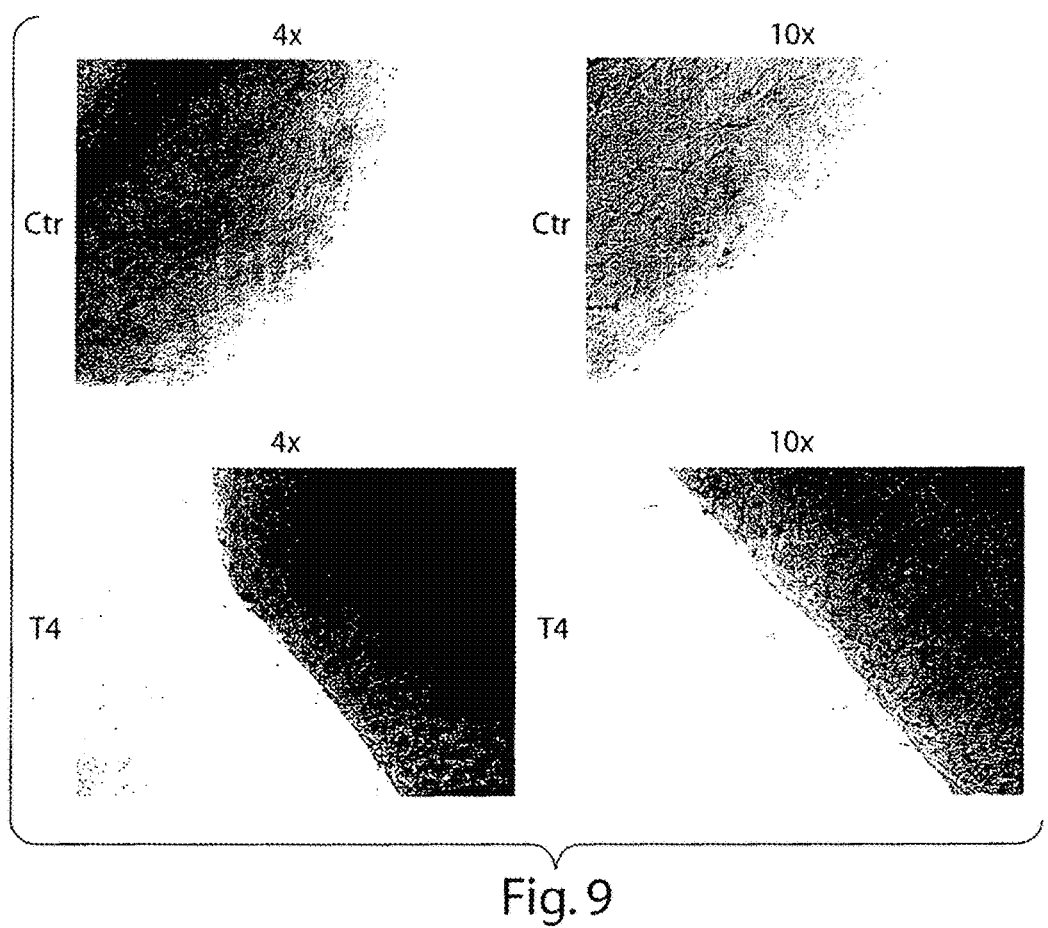

FIG. 9. T4 Stimulates 3D Wound Healing. Photographs of human dermal fibroblast cells exposed to T4 and control, according to the 3D Wound Healing Assay described herein.

Figure 10:
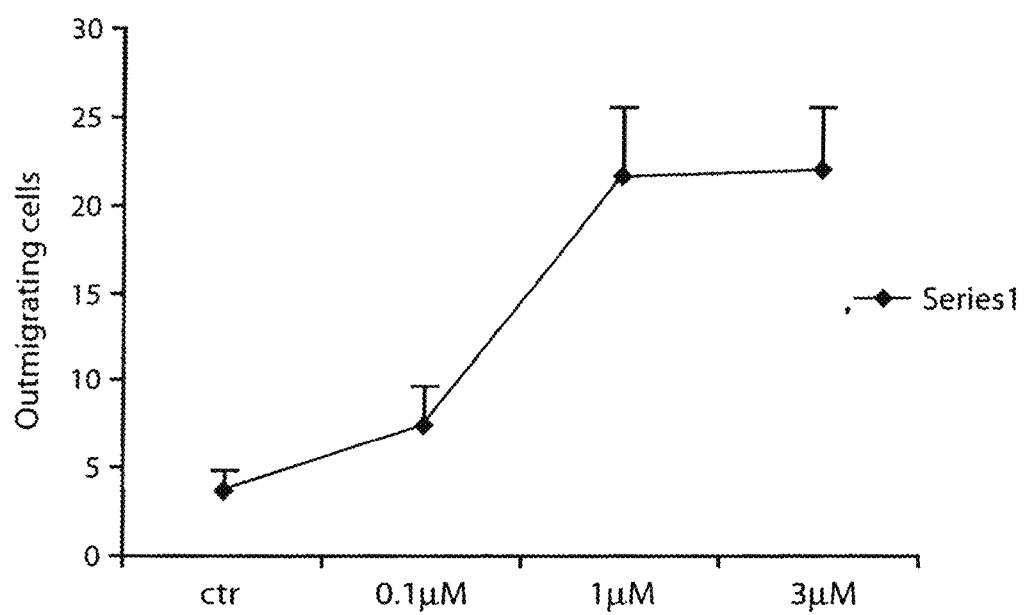

FIG. 10. T4 Dose-Dependently Increases Wound Healing, Day 3. As indicated by the graph, T4 increases wound healing (measured by outmigrating cells) in a dose-dependent manner between concentrations of 0.1 µM and 1.0 µM. This same increase is not seen in concentrations of T4 between 1.0 µM and 3.0 µM.

Figure 11A:
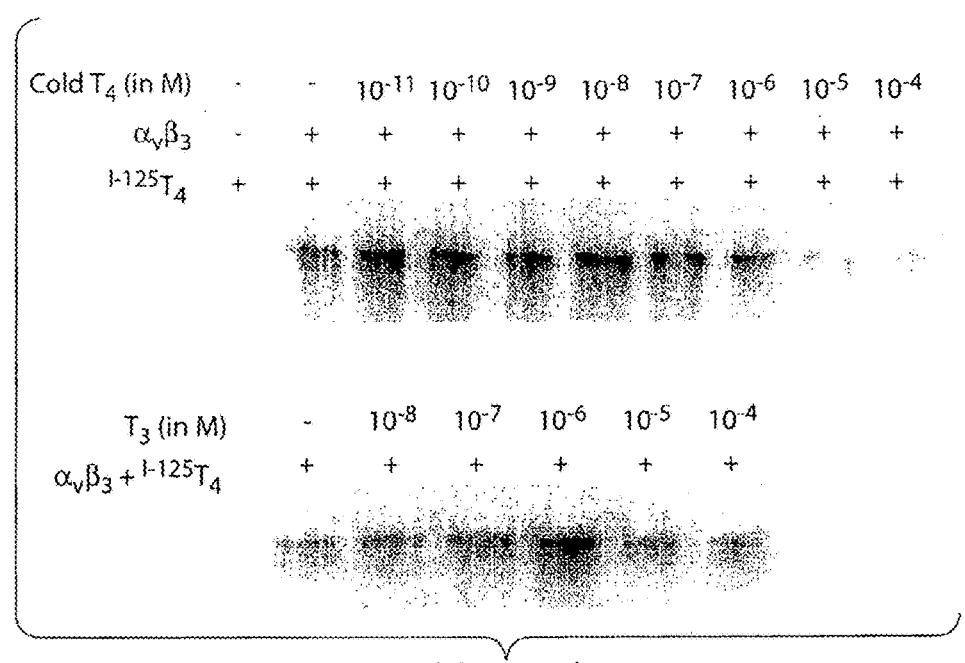

FIG. 11a. Effect of unlabeled $T_4$ and $T_3$ on $I^{-125}$-$T_4$ binding to purified integrin. Unlabeled $T_4$ ($10^{-4}$M to $10^{-11}$ M) or $T_3$ ($10^{-4}$M to $10^{-8}$M) were added to purified αVβ3 integrin (2 µg/sample) and allowed to incubate for 30 min. at room temperature. Two microcuries of I-125 labeled $T_4$ was added to each sample. The samples were incubated for 20 min. at room temperature, mixed with loading dye, and run on a 5% Native gel for 24 hrs. at 4° C. at 45 mA. Following electrophoresis, the gels were wrapped in plastic wrap and exposed to film. $I^{-125}$-$T_4$ binding to purified αVβ3 is unaffected by unlabeled $T_4$ in the range of $10^{-11}$ M to $10^{-7}$M, but is competed out in a dose-dependent manner by unlabeled $T_4$ at a concentration of $10^{-6}$M. Hot $T_4$ binding to the integrin is almost completely displaced by $10^{-4}$M unlabeled $T_4$. $T_3$ is less effective at competing out $T_4$ binding to αVβ3, reducing the signal by 11%, 16%, and 28% at $10^{-6}$M, $10^{-5}$M, and $10^{-4}$M $T_3$, respectively.

Figure 11B:
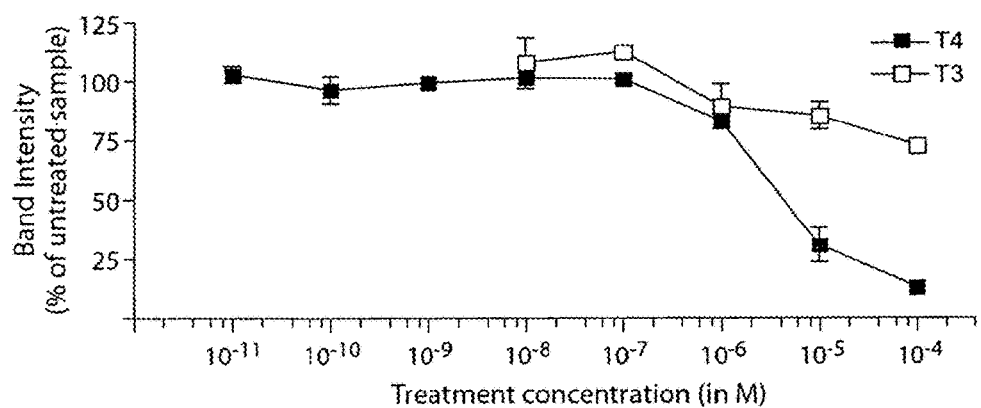

FIG. 11b depicts a graphical representation of FIG. 11a.

Figure 12A:
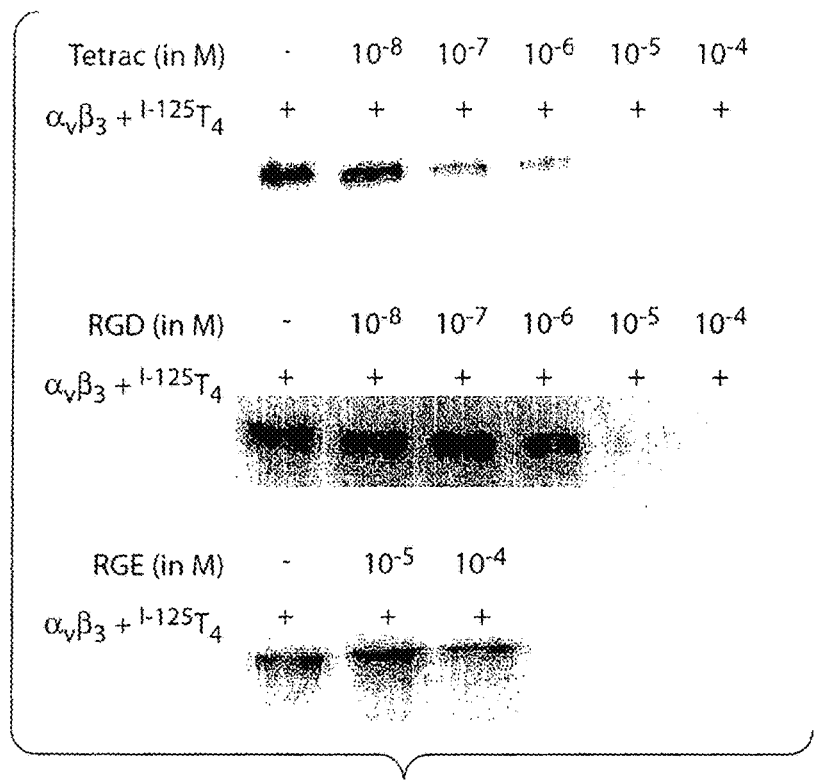

FIG. 12A. Tetrac and an RGD containing peptide, but not an RGE containing peptide compete out $T_4$ binding to purified αVβ3. Tetrac addition to purified αVβ3 reduces $^{I-125}$-labeled $T_4$ binding to the integrin in a dose dependent manner. $10^{-8}$M tetrac is ineffective at competing out hot $T_4$ binding to the integrin. The association of $T_4$ and αVβ3 was reduced by 38% in the presence of $10^{-7}$M tetrac and by 90% with $10^{-5}$M tetrac. Addition of an RGD peptide at $10^{-5}$M competes out $T_4$ binding to αVβ3. Application of $10^{-5}$M and $10^{-4}$M RGE peptide, as a control for the RGD peptide, was unable to diminish hot $T_4$ binding to purified αVβ3.

Figure 12B:
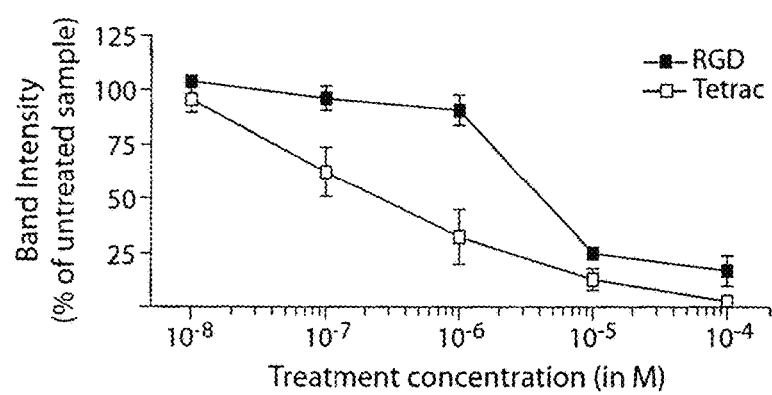

FIG. 12B. Graphical representation of the tetrac and RGD data from panel A. Data points are shown as the mean±S.D. for 3 independent experiments.

Figure 13A:
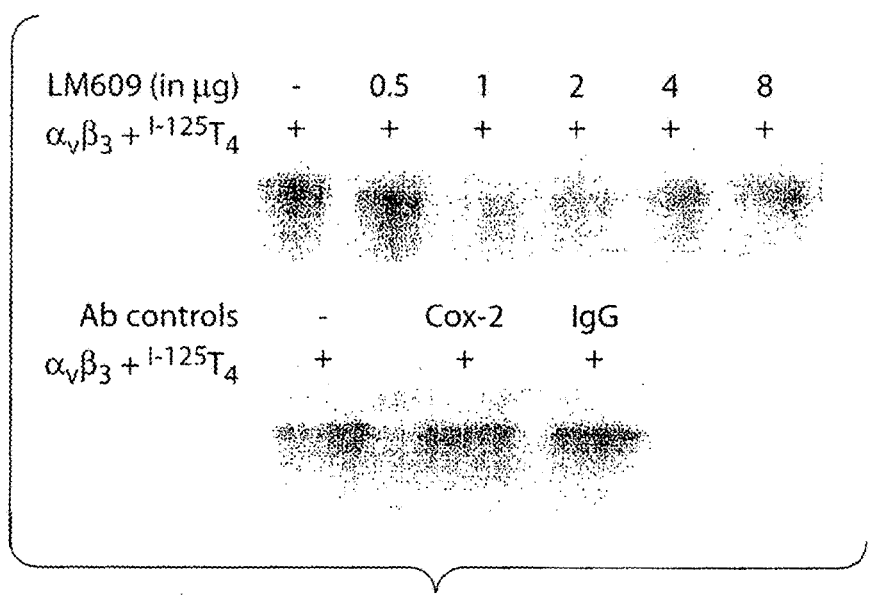

FIG. 13A. Effects of the monoclonal antibody LM609 on $T_4$ binding to αVβ3. LM609 was added to αVβ3 at the indicated concentrations. One µg of LM609 per sample reduces $^{I-125}$-labeled $T_4$ binding to the integrin by 52%. Maximal inhibition of $T_4$ binding to the integrin is reached when concentrations of LM609 are 2 µg per sample and is maintained with antibody concentrations as high as 8 µg. As a control for antibody specificity, 10 µg/sample Cox-2 mAB and 10 µg/sample mouse IgG were added to αVβ3 prior to incubation with $T_4$.

Figure 13B:
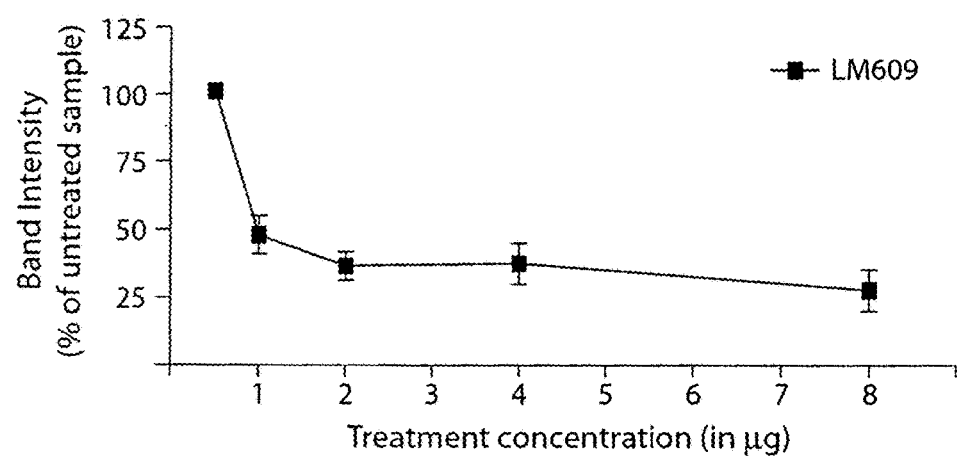

FIG. 13B. Graphical representation of data from panel A. Data points are shown as the mean±S.D. for 3 independent experiments.

Figure 14A:
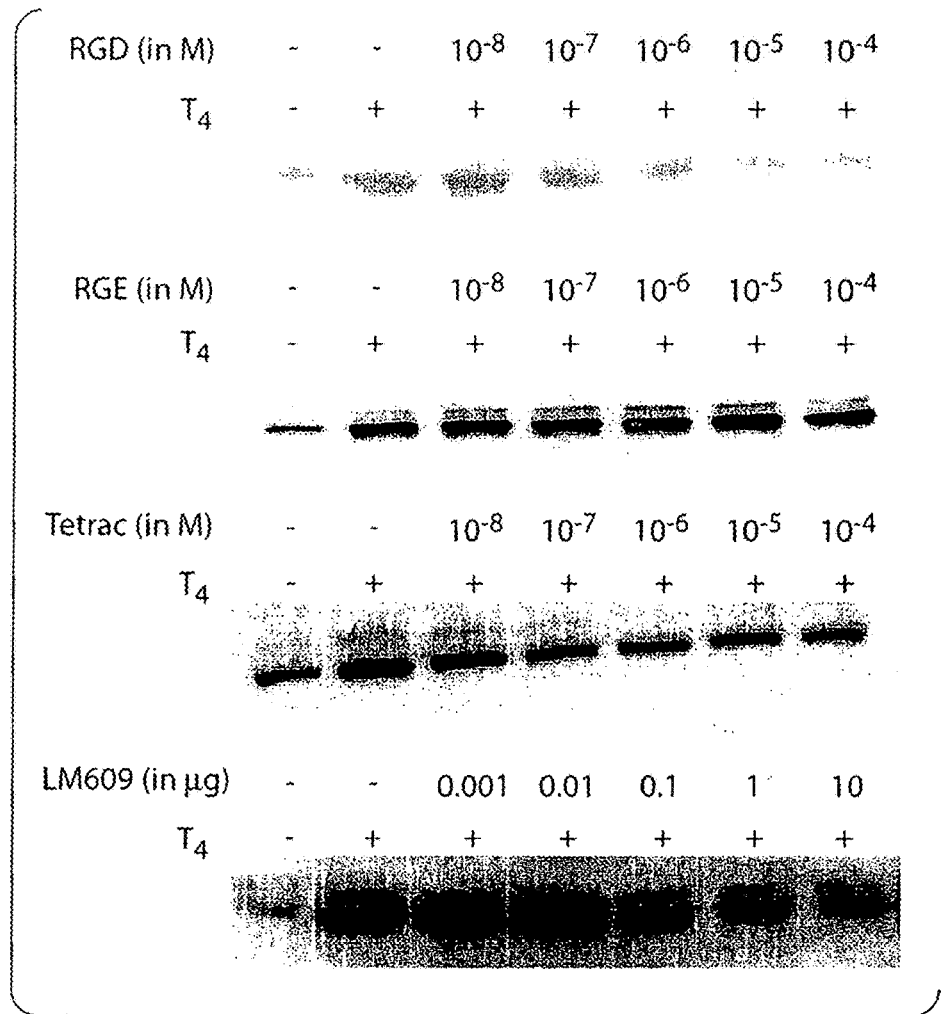

FIG. 14A. Effect of RGD, RGE, tetrac, and the mAB LM609 on $T_4$-induced MAPK activation. CV-1 cells (50-70% confluency) were treated for 30 min. with $10^{-7}$ M $T_4$ ($10^{-7}$ M total concentration, $10^{-10}$M free concentration). Selected samples were treated for 16 hrs with the indicated concentrations of either an RGD containing peptide, an RGE containing peptide, tetrac, or LM609 prior to the addition of $T_4$. Nuclear proteins are separated by SDS-PAGE and immunoblotted with anti-phospho-MAPK (pERK1/2) antibody. Nuclear accumulation of pERK1/2 is diminished in samples treated with $10^{-6}$ M RGD peptide or higher, but not significantly altered in samples treated with $10^{-4}$ M RGE. pERK1/2 accumulation is decreased 76% in CV1 cells treated with $10^{-6}$M tetrac, while $10^{-5}$M and higher concentrations of tetrac reduce nuclear accumulation of pERK1/2 to levels similar to the untreated control samples. The monoclonal antibody to $\alpha V\beta 3$ LM609 decrease accumulation of activated MAPK in the nucleus when it is applied to CV1 cultures a concentration of 1 μg/ml.

Figure 14B:
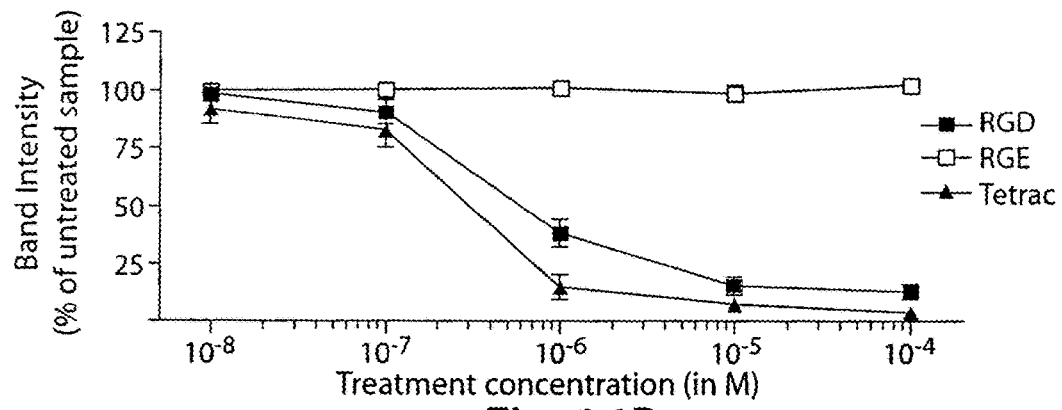

FIG. 14B Graphical representation of the data for RGD, RGE, and tetrac shown in panel A. Data points represent the mean±S.D. for 3 separate experiments.

Figure 15A:
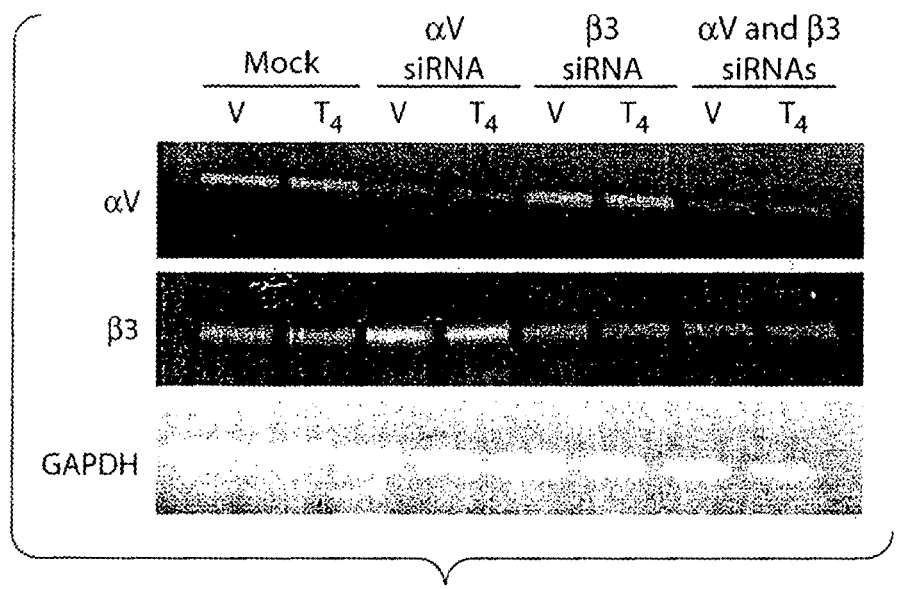

FIG. 15A. Effects of siRNA to αV and β3 on $T_4$ induced MAPK activation. CV1 cells were transfected with siRNA (100 nM final concentration) to αV, β3, or αV and β3 together. Two days after transfection, the cells were treated with $10^{-7}$M $T_4$. RT-PCR was performed from RNA isolated from each transfection group to verify the specificity and functionality of each siRNA.

Figure 15B:
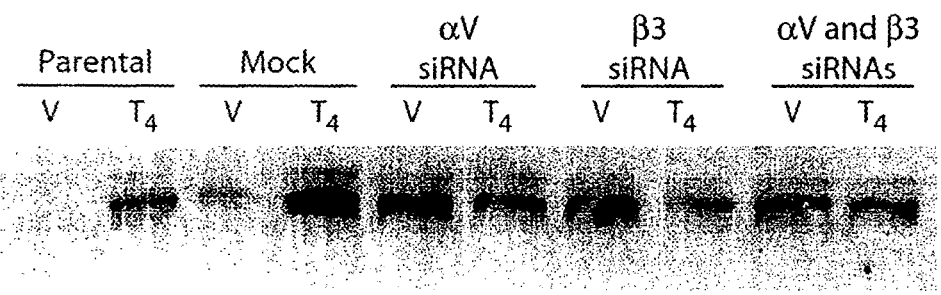

FIG. 15B. Nuclear proteins from each transfection were isolated and subjected to SDS-PAGE.

Figures 16A, 16B:
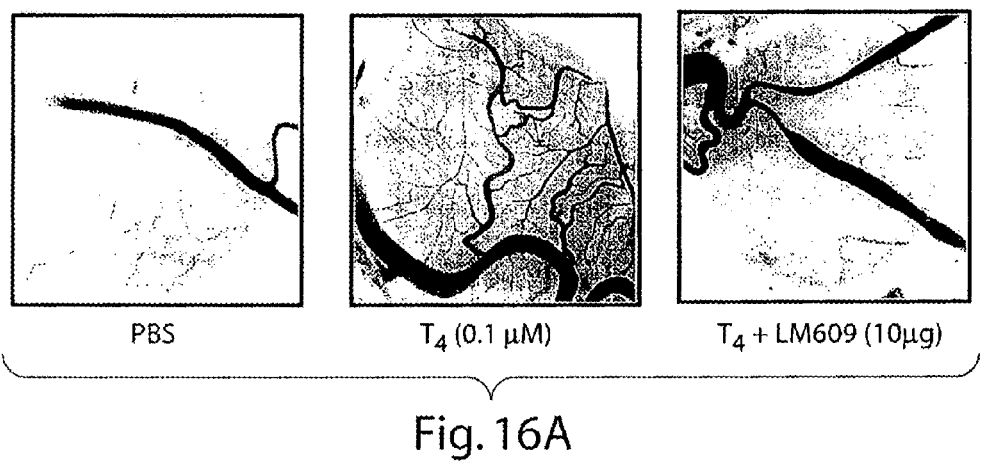

FIG. 16A. Inhibitory Effect of αVβ3 mAB (LM609) on $T_4$-stimulated Angiogenesis in the CAM Model. Samples were exposed to PBS, $T_4$ (0.1 μM), or $T_4$ plus 10 mg/ml LM609 for 3 days. Angiogenesis stimulated by $T_4$ is substantially inhibited by the addition of the αVβ3 monoclonal antibody LM609.

FIG. 16B. Tabulation of the mean±SEM of new branches formed from existing blood vessels during the experimental period. Data was drawn from 3 separate experiments, each containing 9 samples in each treatment group.

Figure 16D:
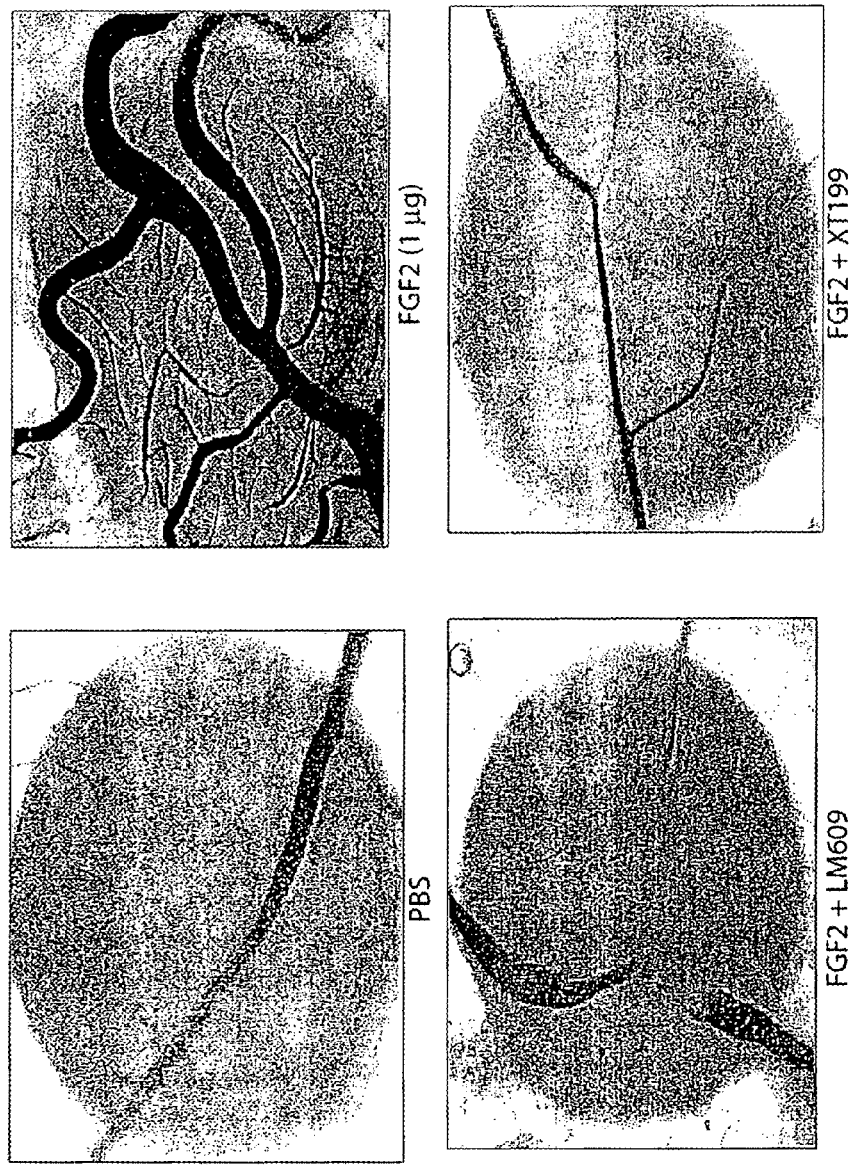

FIG. 16C and FIG. 16D. Angiogenesis stimulated by T4 or FGF2 is also inhibited by the addition of the αVβ3 monoclonal antibody LM609 or XT 199.

Figure 17:
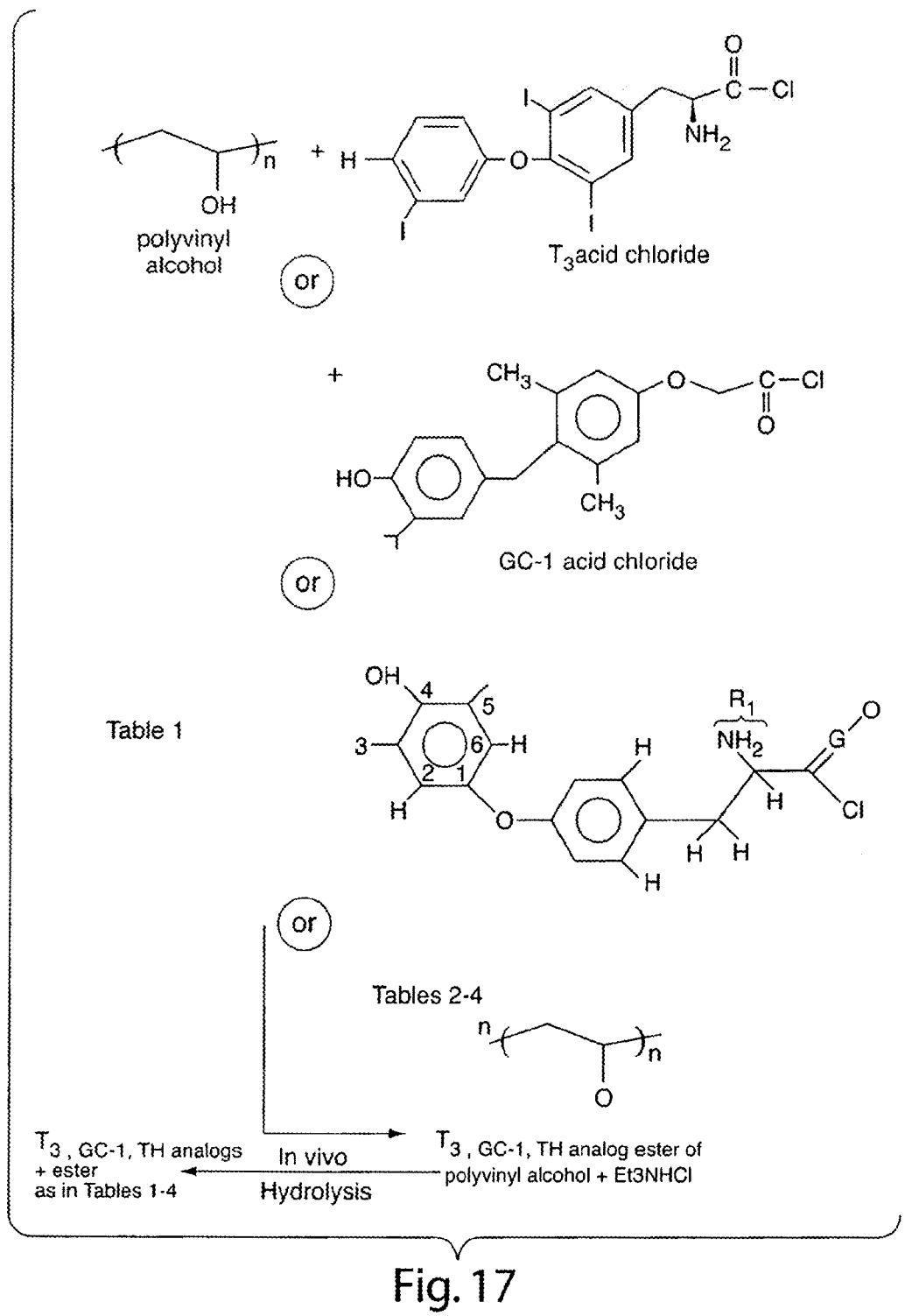

FIG. 17. Polymer Compositions of Thyroid Hormone Analogs—Polymer Conjugation Through an Ester Linkage Using Polyvinyl Alcohol. In this preparation commercially available polyvinyl alcohol (or related co-polymers) can be esterified by treatment with the acid chloride of thyroid hormone analogs, namely the acid chloride form. The hydrochloride salt is neutralized by the addition of triethylamine to afford triethylamine hydrochloride which can be washed away with water upon precipitation of the thyroid hormone ester polymer form for different analogs. The ester linkage to the polymer may undergo hydrolysis in vivo to release the active pro-angiogenesis thyroid hormone analog.

Figure 18:
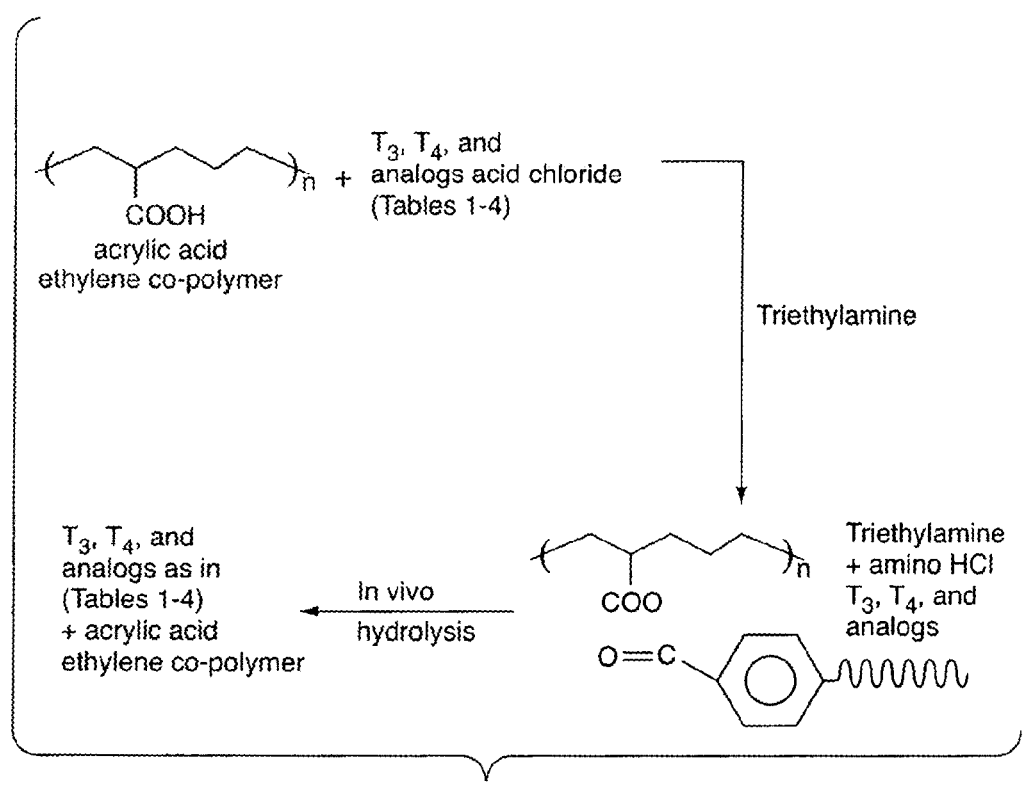

FIG. 18. Polymer Compositions of Thyroid Hormone Analogs—Polymer Conjugation Through an Anhydride Linkage Using Acrylic Acid Ethylene Co-polymer. This is similar to the previous polymer covalent conjugation however this time it is through an anhydride linkage that is derived from reaction of an acrylic acid co-polymer. This anhydride linkage is also susceptible to hydrolysis in vivo to release thyroid hormone analog. Neutralization of the hydrochloric acid is accomplished by treatment with triethylamine and subsequent washing of the precipitated polyanhydride polymer with water removes the triethylamine hydrochloride byproduct. This reaction will lead to the formation of Thyroid hormone analog acrylic acid co-polymer+triethylamine. Upon in vivo hydrolysis, the thyroid hormone analog will be released over time that can be controlled plus acrylic acid ethylene Co-polymer.

Figure 19:
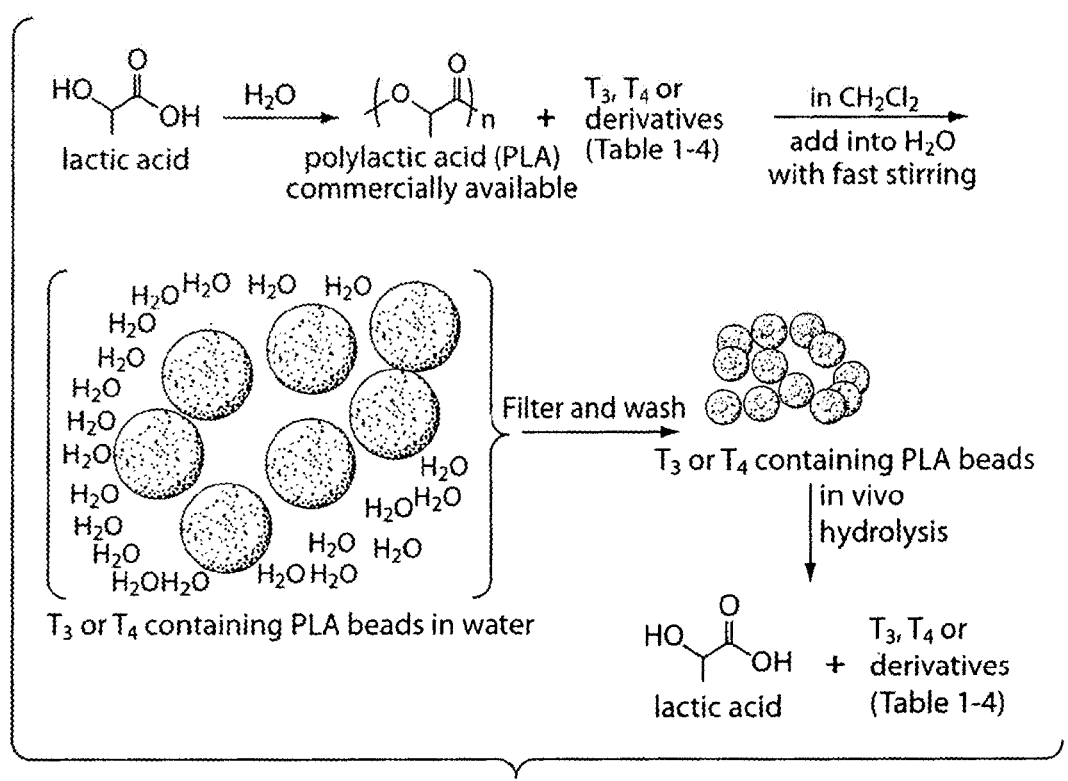

FIG. 19. Polymer Compositions of Thyroid Hormone Analogs—Entrapment in a Polylactic Acid Polymer. Polylactic acid polyester polymers (PLA) undergo hydrolysis in vivo to the lactic acid monomer and this has been exploited as a vehicle for drug delivery systems in humans. Unlike the prior two covalent methods where the thyroid hormone analog is linked by a chemical bond to the polymer, this would be a non-covalent method that would encapsulate the thyroid hormone analog into PLA polymer beads. This reaction will lead to the formation of Thyroid hormone analog containing PLA beads in water. Filter and washing will result in the formation of thyroid hormone analog containing PLA beads, which upon in vivo hydrolysis will lead to the generation of controlled levels of thyroid hormone plus lactic acid.

FIG. 20A-FIG. 20D. Thyroid Hormone Analogs Capable of Conjugation with Various Polymers. A-D show substitutions required to achieve various thyroid hormone analogs which can be conjugated to create polymeric forms of thyroid hormone analogs of the invention.

Figure 21:
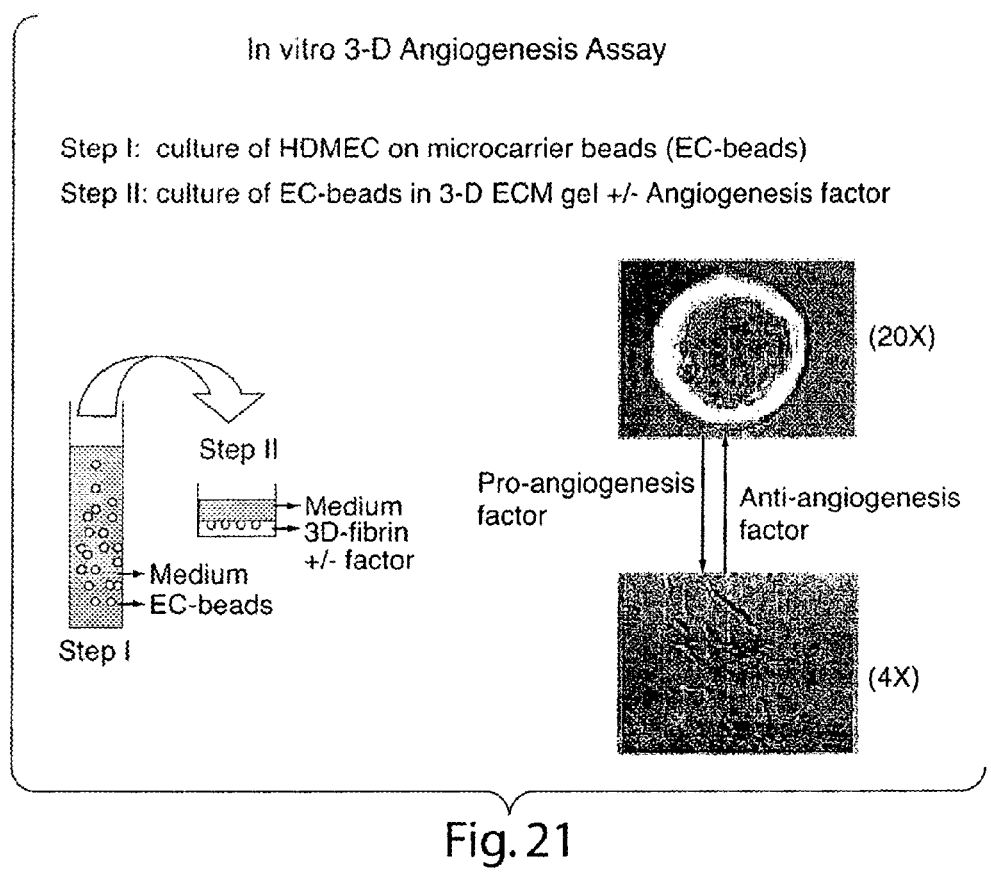

FIG. 21. In vitro 3-D Angiogenesis Assay FIG. 21 is a protocol and illustration of the three-dimensional in vitro sprouting assay for human micro-vascular endothelial on fibrin-coated beads.

Figure 22:
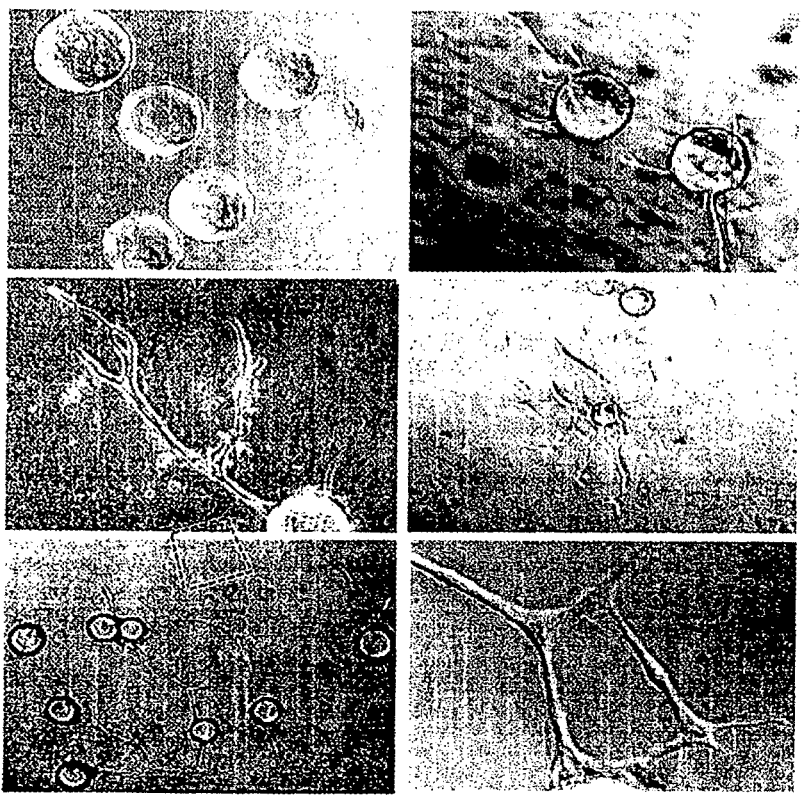
Figure 23A:
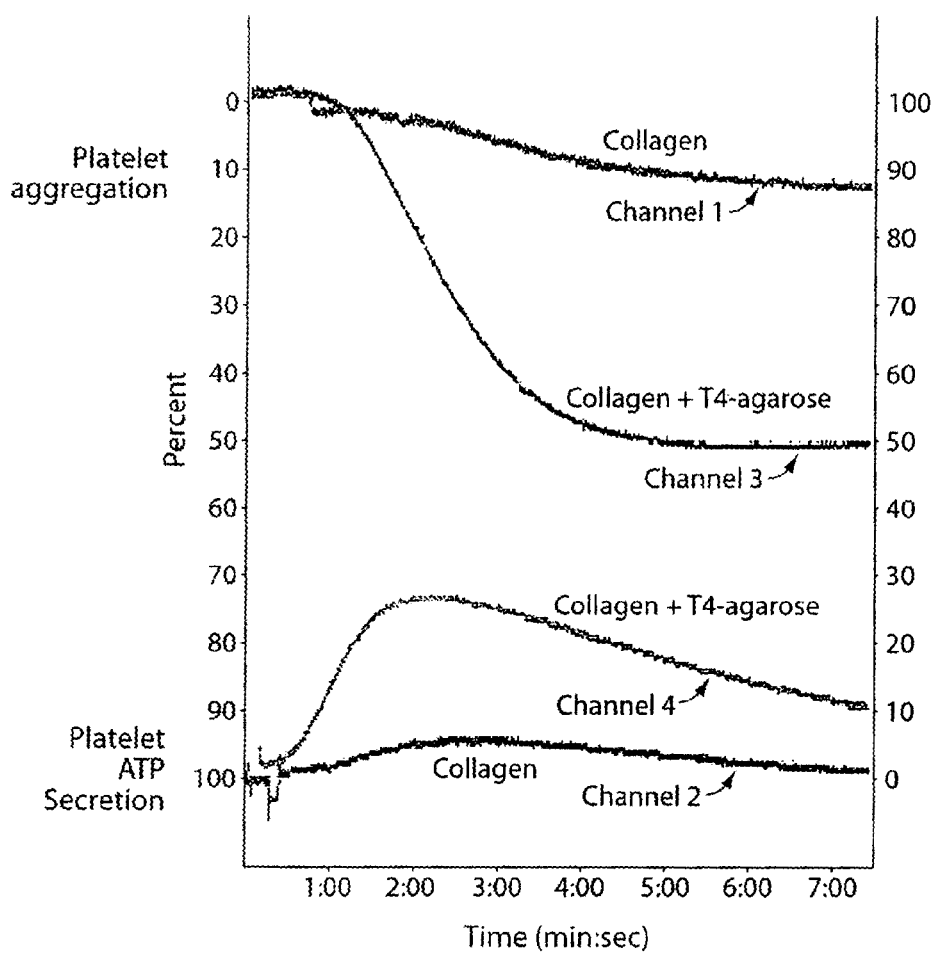
Figure 23B:
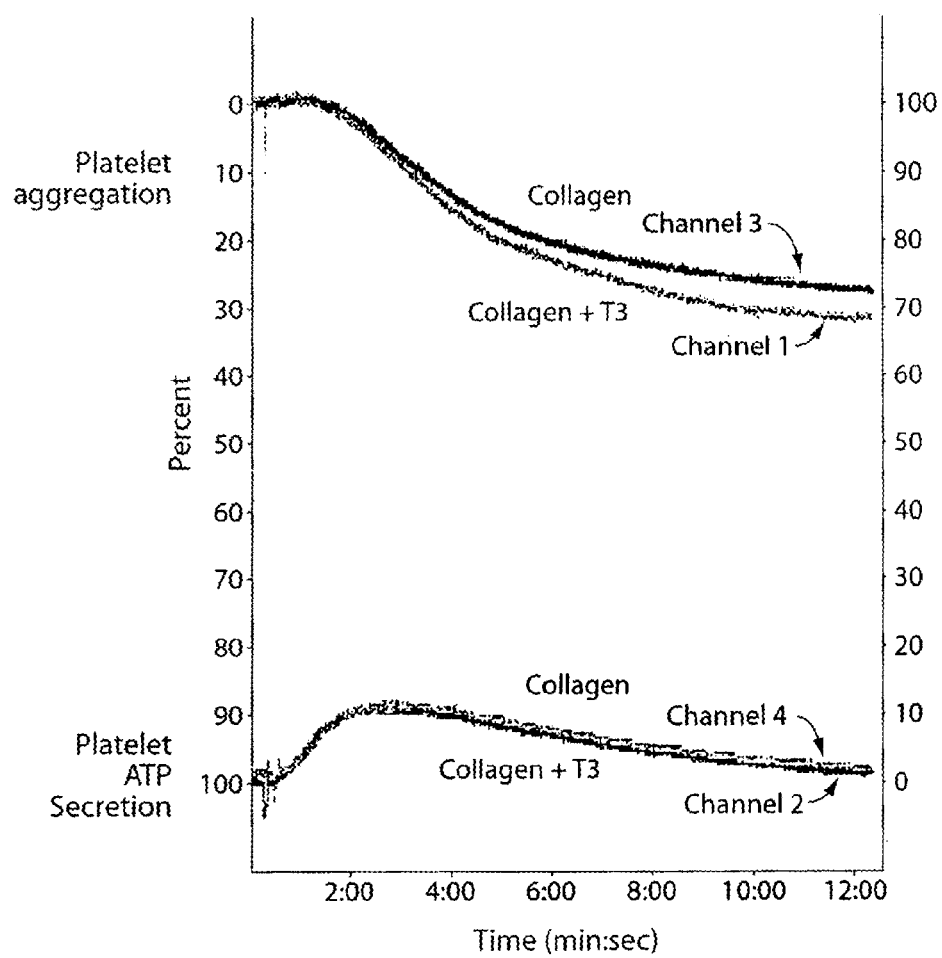
Figure 23C:
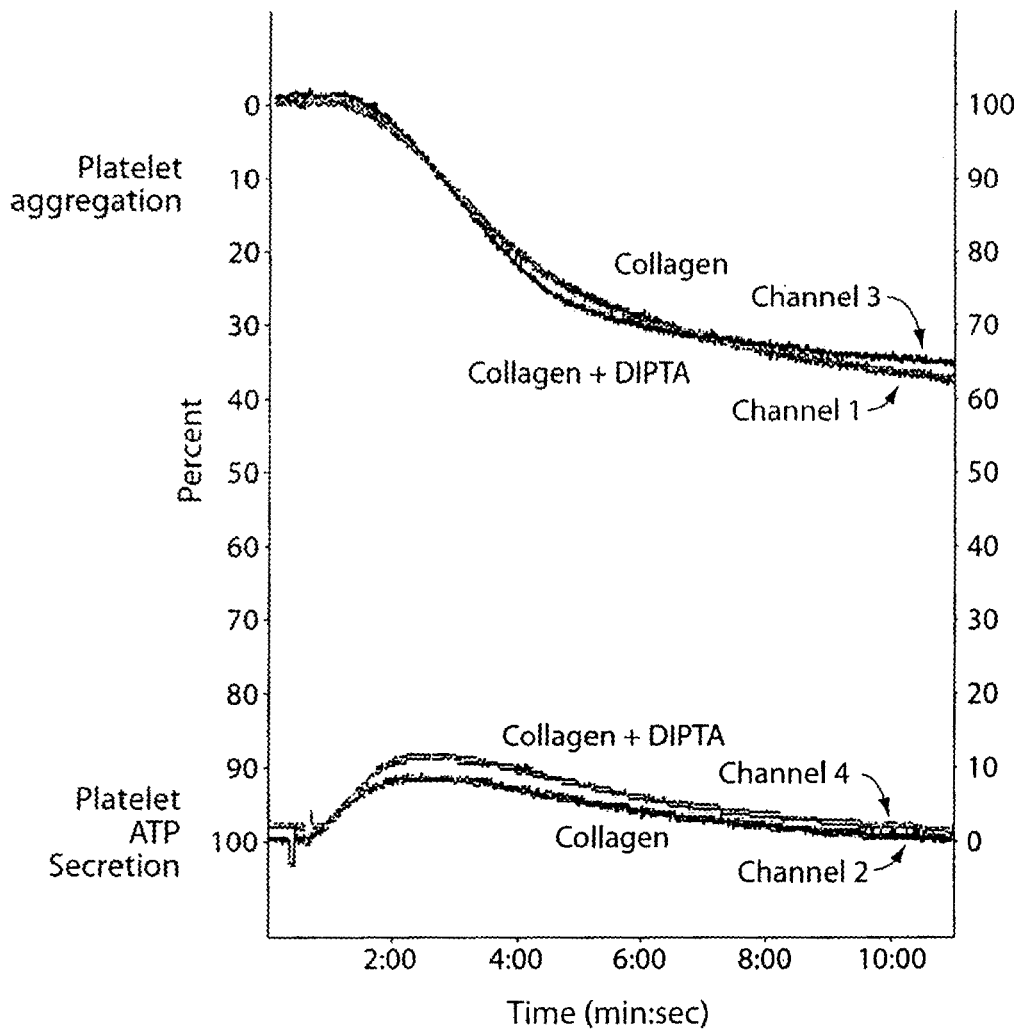
Figure 23D:
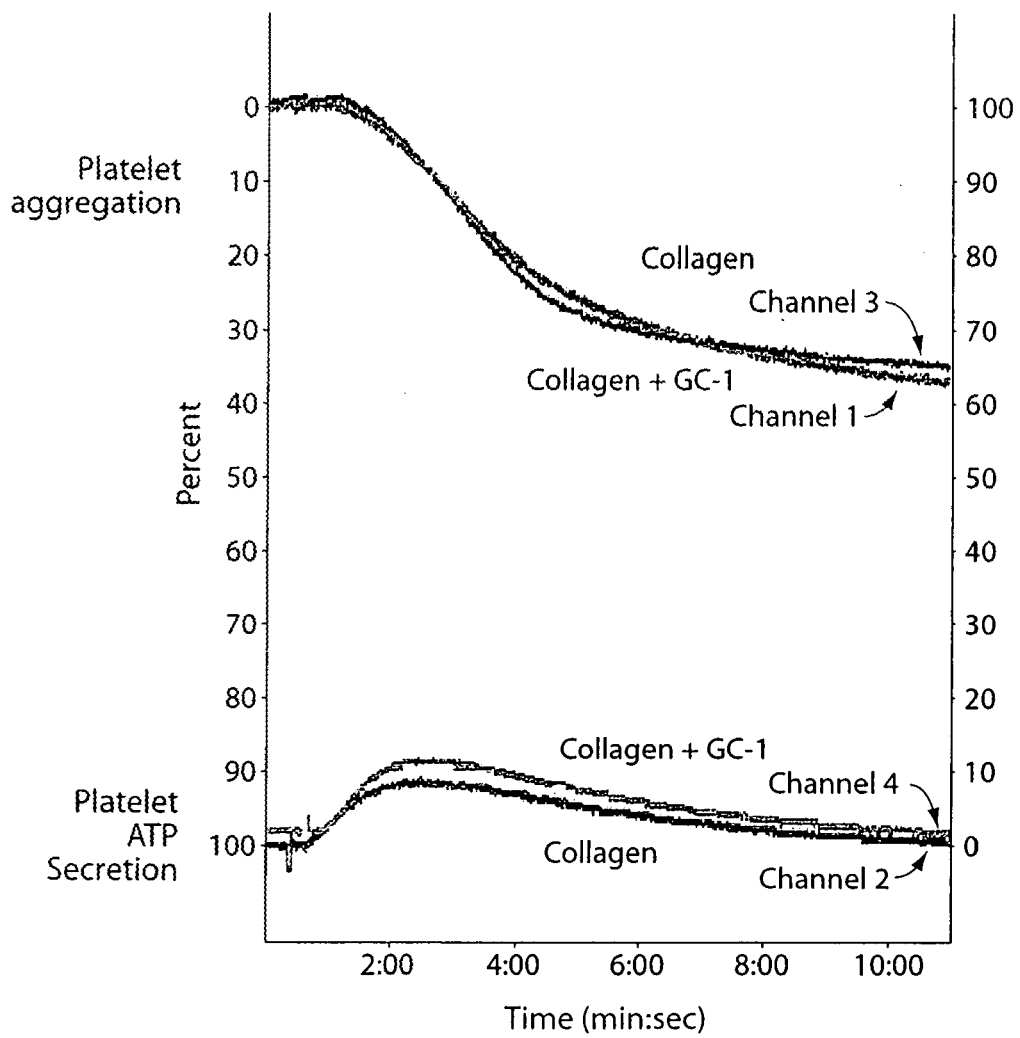
Figure 23E:
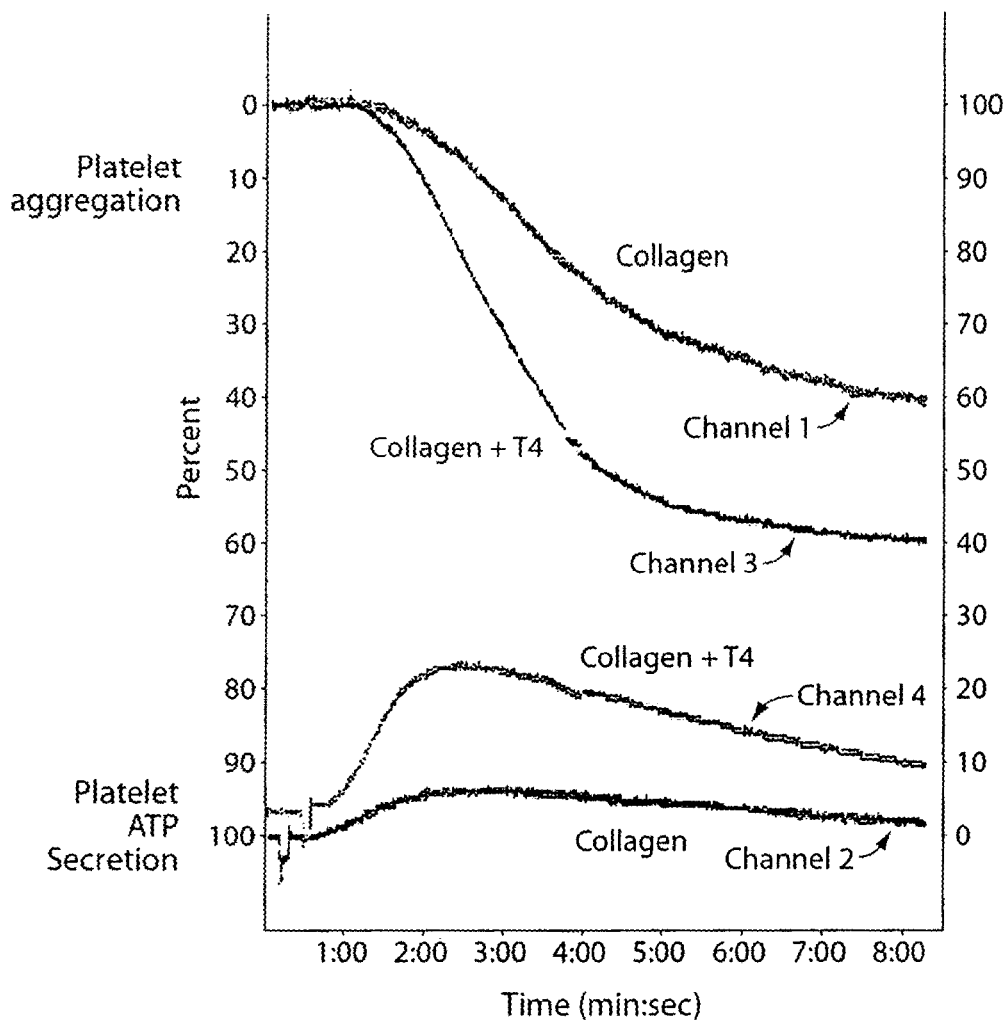
Figure 24A:
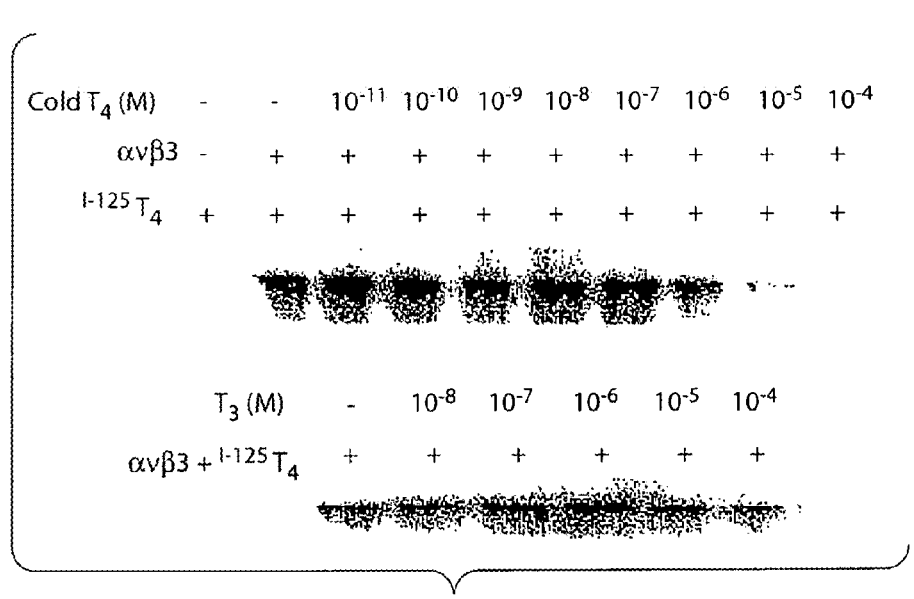

FIG. 22. In Vitro Sprout Angiogenesis of HOMEC in 3-D Fibrin FIG. 22 is an illustration of human micro-vascular endothelial cell sprouting in three dimensions under different magnifications FIGS. 23A-E. Release of platelet-derived wound healing factors in the presence of low level collagen FIG. 24A. Unlabeled T4 and T3 displace [$^{125}$I]-T4 from purified integrin. Unlabeled T4 ($10^{-11}$ M to $10^{-4}$ M) or T3 ($10^{-8}$ to $10^{-4}$ M) were added to purified αVβ3 integrin (2 μg/sample) prior to the addition of [$^{125}$I]-T4 (a) [$^{125}$I]-T4 binding to purified αVβ3 was unaffected by unlabeled T4 in the range of $10^{-11}$ M to $10^{-7}$ M, but was displaced in a concentration-dependent manner by unlabeled T4 at concentrations $\geq 10^{-6}$ M. T3 was less effective at displacing T4 binding to αVβ3.

Figure 24B:
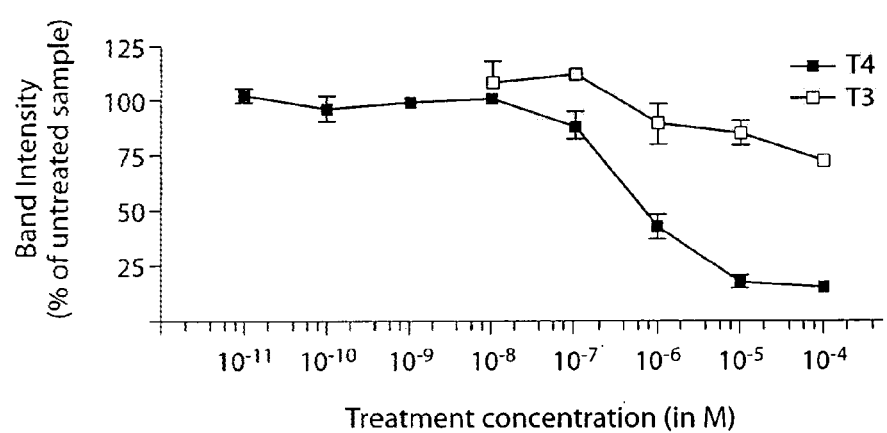

FIG. 24B. Graphic presentation of the T4 and T3 data shows the mean±S.D. of 3 independent experiments.

Figure 25A:
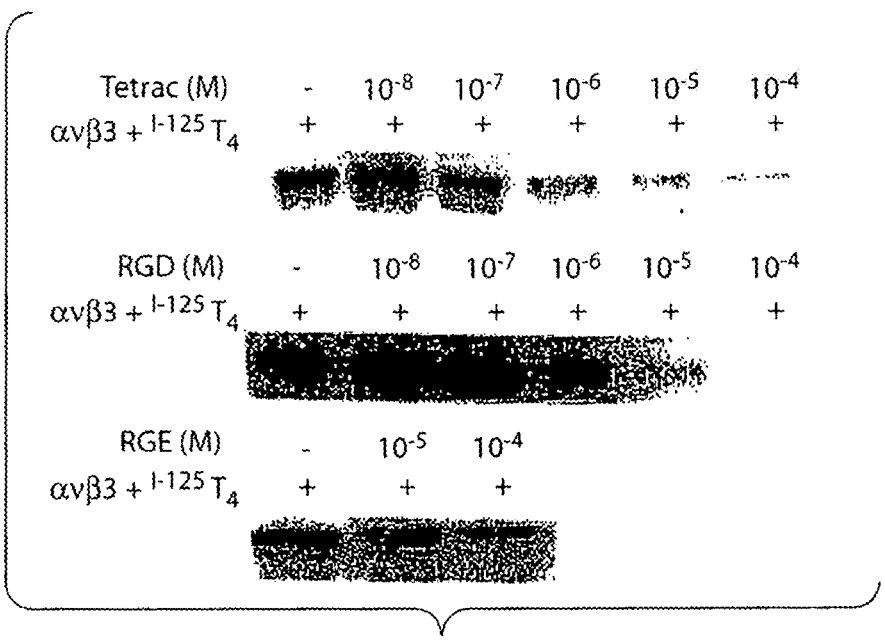

FIG. 25A. Tetrac and an RGD-containing peptide, but not an RGE-containing peptide, displace T4 binding to purified αVβ3. Pre-incubation of purified αVβ3 with tetrac or an RGD-containing peptide reduced the interaction between the integrin and [$^{125}$I]-T4 in a dose-dependent manner. Application of $10^{-5}$ M and $10^{-4}$ M RGE peptide, as controls for the RGD peptide, did not diminish labeled T4 binding to purified αVβ3.

Figure 25B:
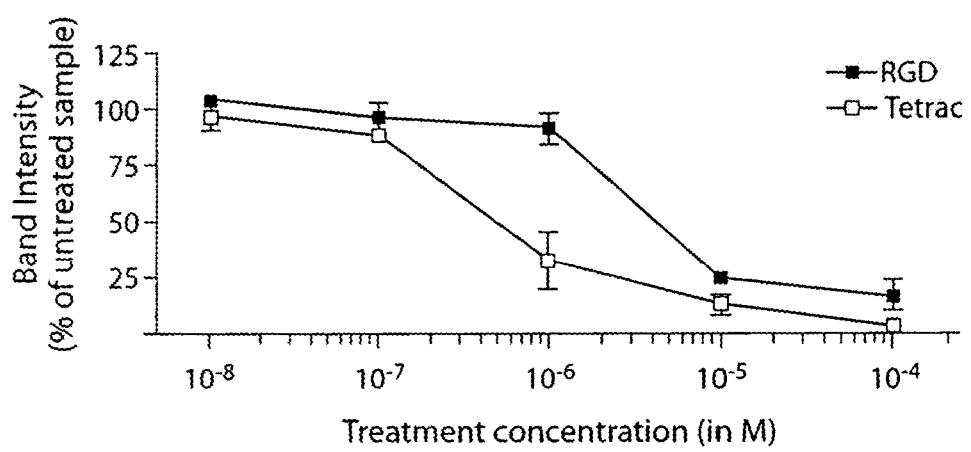

FIG. 25B Graphic presentation of the tetrac and RGD data indicates the mean±S.D. of results from 3 independent experiments.

Figure 26A:
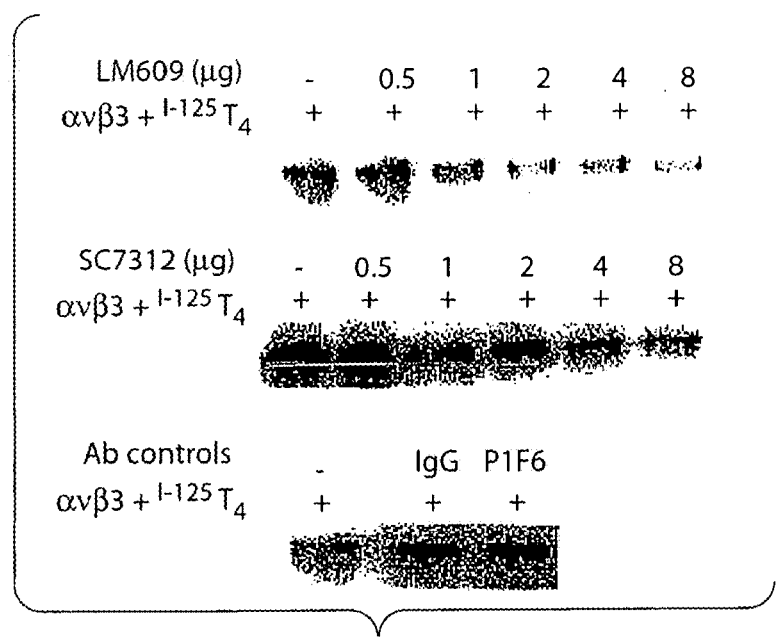

FIG. 26A. Integrin antibodies inhibit T4 binding to αVβ3. The antibodies LM609 and SC7312 were added to αVβ3 at the indicated concentrations (μg/ml) 30 min prior to the addition of [$^{125}$I]-T4 Maximal inhibition of T4 binding to the integrin was reached when the concentration of LM609 was 2 μg/ml and was maintained with antibody concentrations as high as 8 μg/ml. SC7312 reduced T4 binding to αVβ3 by 46% at 2 μg/ml antibody/sample and by 58% when 8 μg/ml of antibody were present. As a control for antibody specificity, 10 μg/ml of anti-αVβ3 mAb (PIF6) and 10 μg/ml mouse IgG were added to αVβ3 prior to incubation with T4.

Figure 26B:
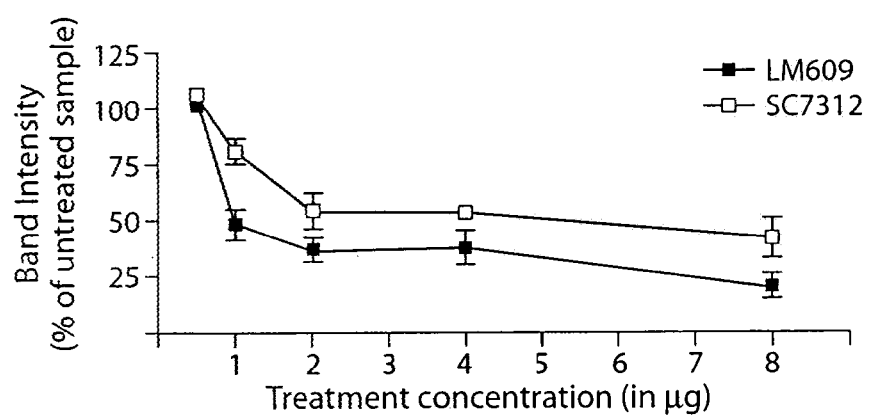

FIG. 26B. The graph shows the mean±S.D. of data from 3 independent experiments.

Figure 27A:
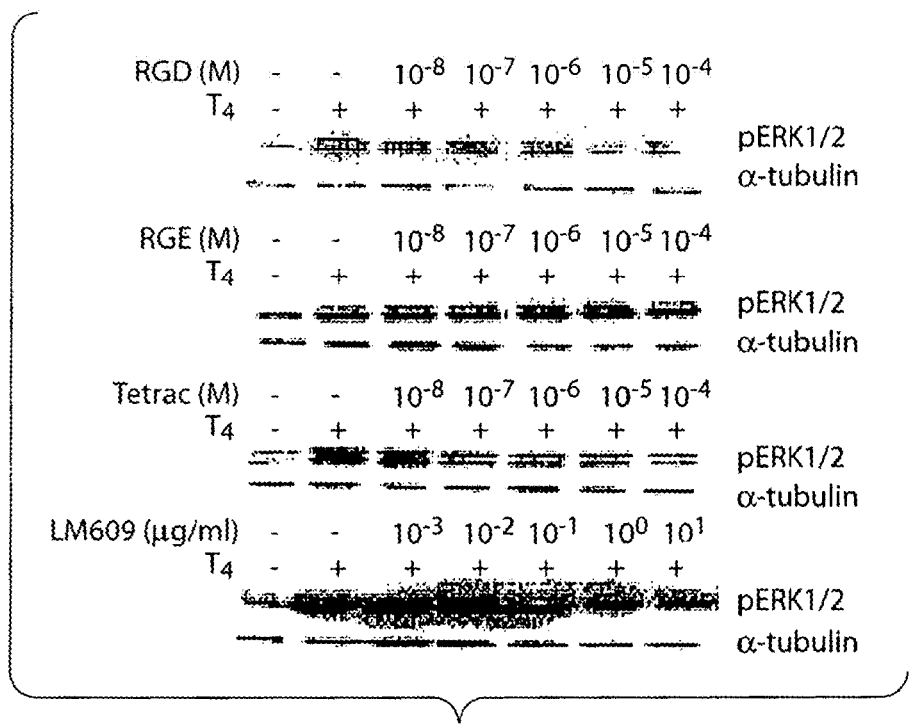

FIG. 27A. Effect of RGD and RGE peptides, tetrac, and the mAb LM609 on T4-induced MAPK activation. Nuclear accumulation of pERK1/2 was diminished in samples treated with $10^{-6}$ M RGD peptide or higher, but not significantly altered in samples treated with up to $10^{-4}$ M RGE. pERK1/2 accumulation in CV-1 cells treated with $10^{-5}$ M tetrac and T4 were similar to levels observed in the untreated control samples. LM609, a monoclonal antibody to $\alpha V\beta 3$, decreased accumulation of activated MAPK in the nucleus when it was applied to CV-1 cultures in a concentration of 1 µg/ml.

Figure 27B:
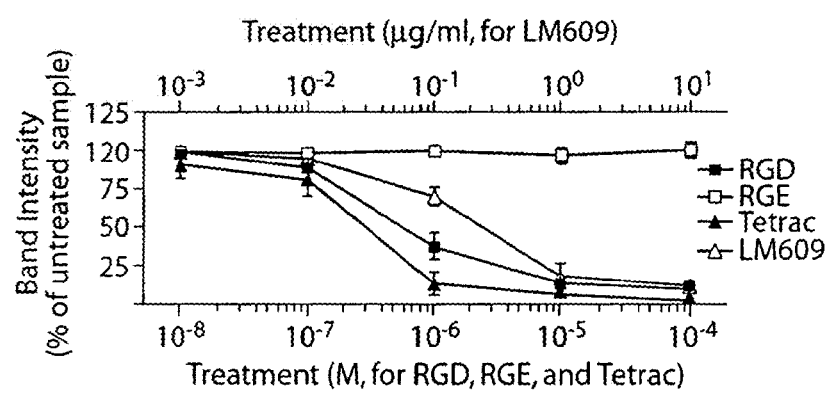

FIG. 27B. The graph shows the mean±S.D. of data from 3 separate experiments. Immunoblots with $\alpha$-tubulin antibody are included as gel-loading controls.

Figure 28A:
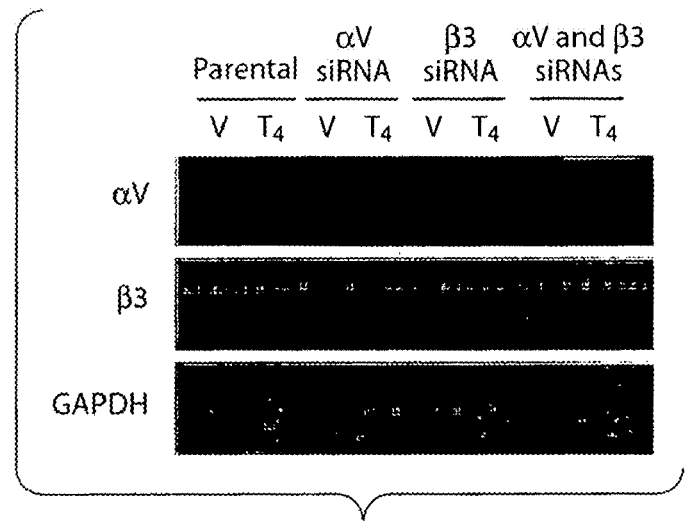

FIG. 28A. Effects of siRNA to $\alpha V$ and $\beta 3$ on T4-induced MAPK activation. CV-1 cells were transfected with siRNA (100 nM final concentration) to $\alpha V$, $\beta 3$, or $\alpha V$ and $\beta 3$ together. Two days after transfection, the cells were treated with 10–7 M T4 or the vehicle control for 30 min. RT-PCR was performed with RNA isolated from each transfection group to verify the specificity and functionality of each siRNA.

Figure 28B:
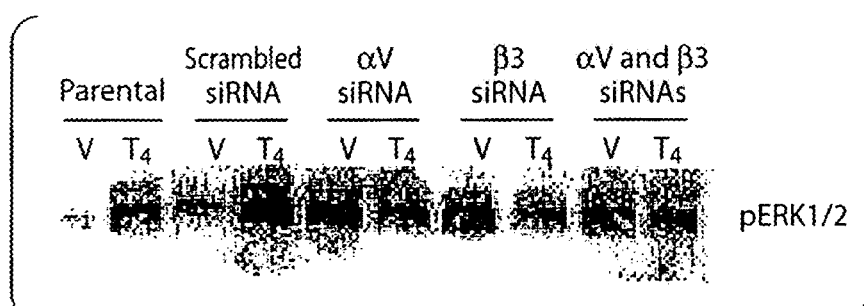

FIG. 28B Nuclear proteins from each set of transfected cells were isolated, subjected to SDS-PAGE, and probed for pERK1/2 in the presence or absence of treatment with T4. In the parental cells and in those treated with scrambled siRNA, nuclear accumulation of pERK1/2 with T4 was evident. Cells treated with siRNA to $\alpha V$ or $\beta 3$ showed an increase in pERK1/2 in the absence of T4, and a decrease with T4 treatment. Cells containing $\alpha V$ and $\beta 3$ siRNAs did not respond to T4 treatment.

Figures 29A, 29B:
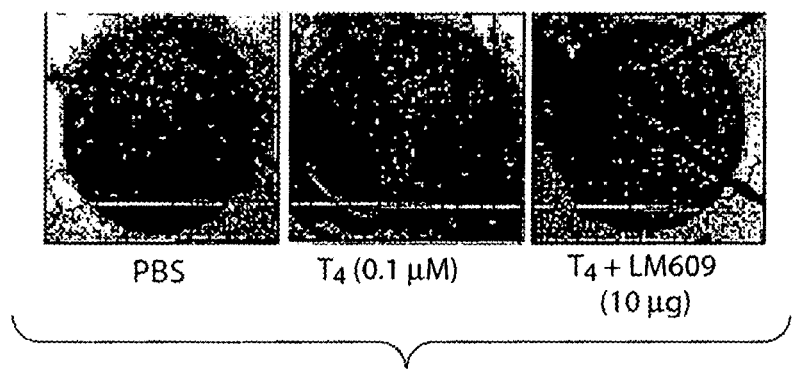

FIG. 29A. Inhibitory effect of $\alpha V\beta 3$ mAb (LM609) on T4-stimulated angiogenesis in the CAM model. CAMS were exposed to filter disks treated with PBS, T4 (10–7 M), or T4 plus 10 µg/ml LM609 for 3 days. Angiogenesis stimulated by T4 was substantially inhibited by the addition of the $\alpha V\beta 3$ monoclonal antibody LM609.

FIG. 29B. Tabulation of the mean±SEM of new branches formed from existing blood vessels during the experimental period is shown. ***P<0.001, comparing results of T4/LM609-treated samples with T4-treated samples in 3 separate experiments, each containing 9 images per treatment group. Statistical analysis was performed by 1-way ANOVA.

Figure 30A:
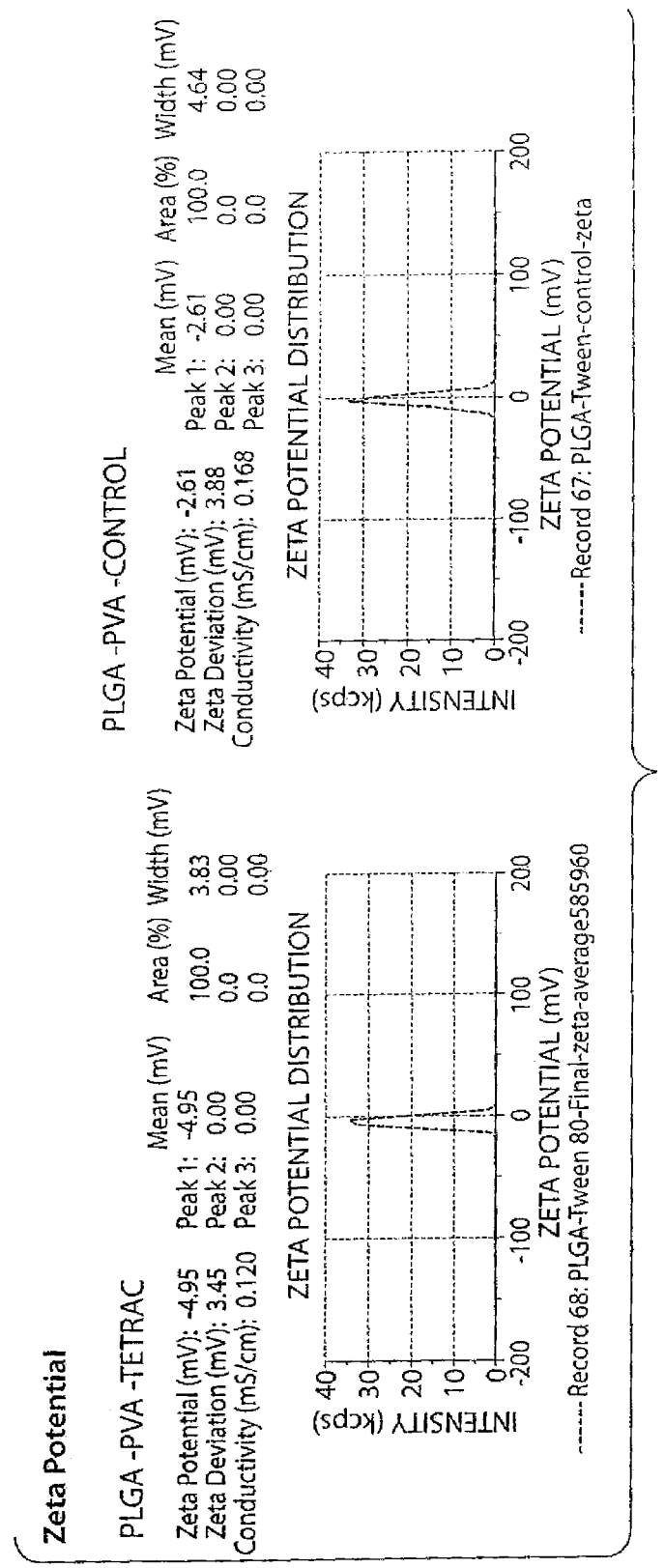

FIG. 30A. Tectrac doped PLGA nanoparticles coated with PVA were synthesized and characterized. Several sets of nanoparticles were examined for the optimum loading of Tetrac. Also the size and the zeta potential of the void and tetrac doped nanoparticles were examined. There was no significant difference in the size and zeta potential between tetrac doped and void nanoparticles coated with Tween-80 were found. The average size of the nanoparticles slightly increased (void-193 nm) in case tetrac doped nanoparticles. It is determined that the amount of Tetrac inside the nanoparticles by HPLC. It was found that the concentration of tetrac is 540 ug/ml of the nanoparticles. FIG. 30A depicts the Zeta potential.

Figure 30B:
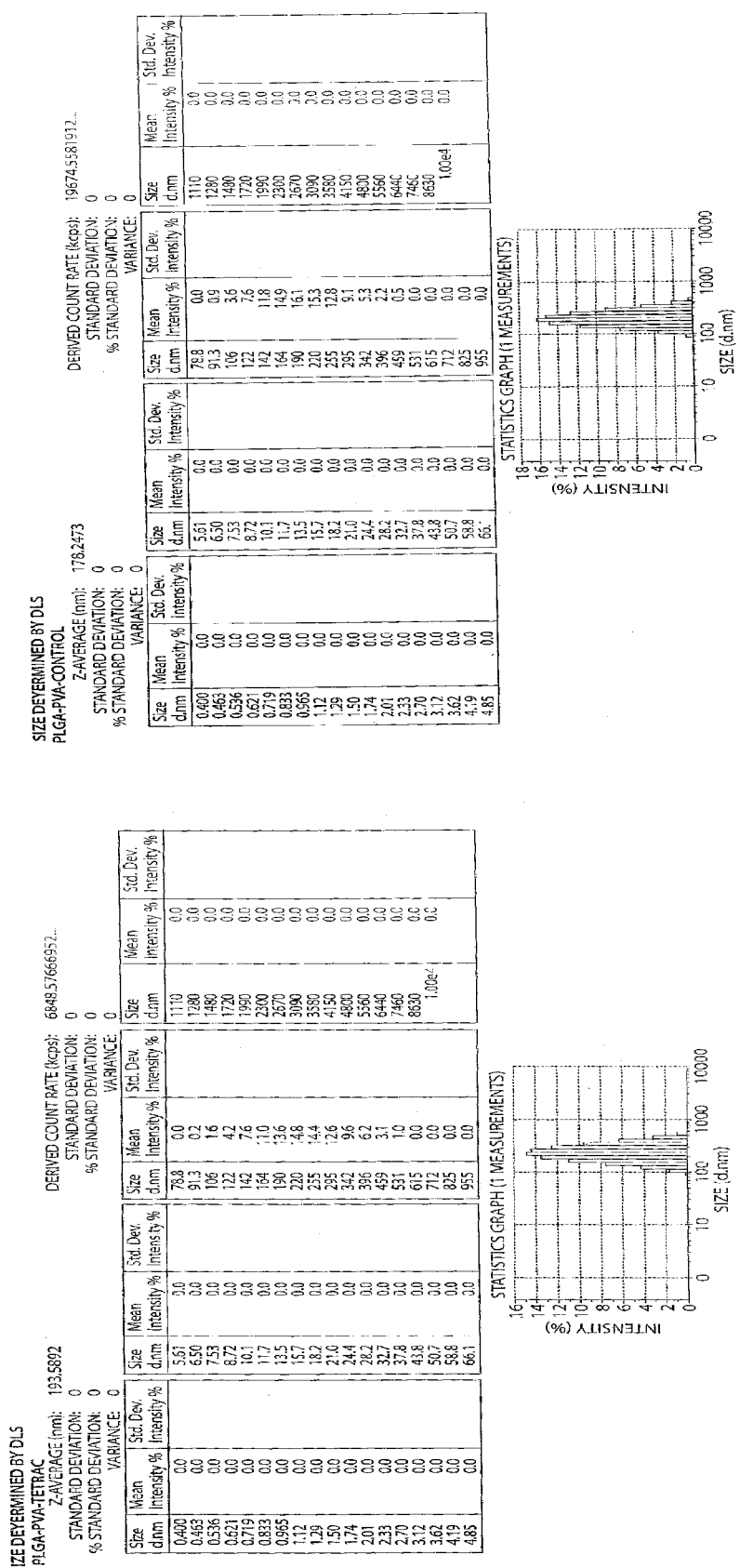

FIG. 30B depicts the size determination by DLS of tetrac doped PLGA nanoparticles of FIG. 30A.

Figure 31A:
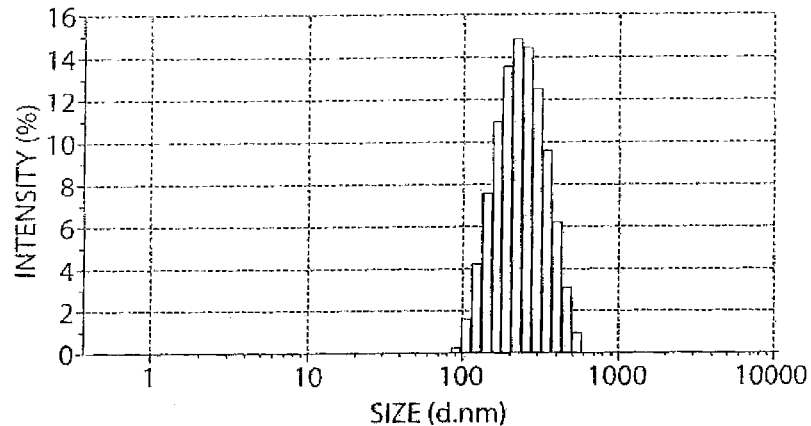

FIG. 31A. PLGA/PVA-Tetrac Nanoparticles. PLGA nanoparticles coated with Tween-80 were prepared by a single emulsion method using polyvinyl alcohol (PV A) as a stabilizer. The sizes of the nanoparticles were determined by using dynamic light scattering. The amount of the Tetrac encapsulated in the nanoparticles was determined by using an HPLC. FIG. 31A depicts size statistics report by intensity.

Figure 31B:
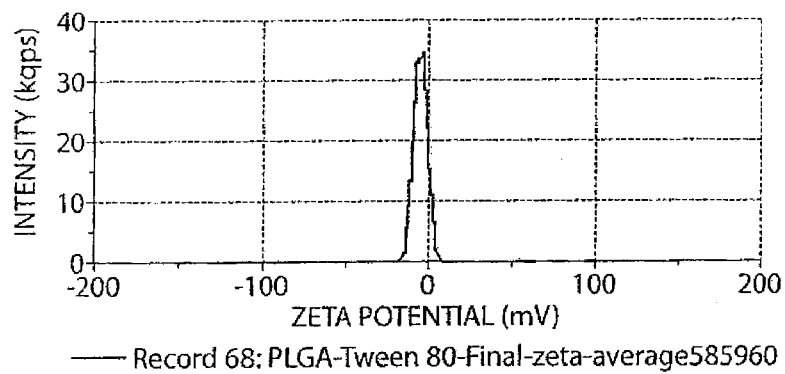

FIG. 31B depicts the zeta potential report of the PLGA/PVA-Tetrac nanoparticles of FIG. 31A.

Figure 32:
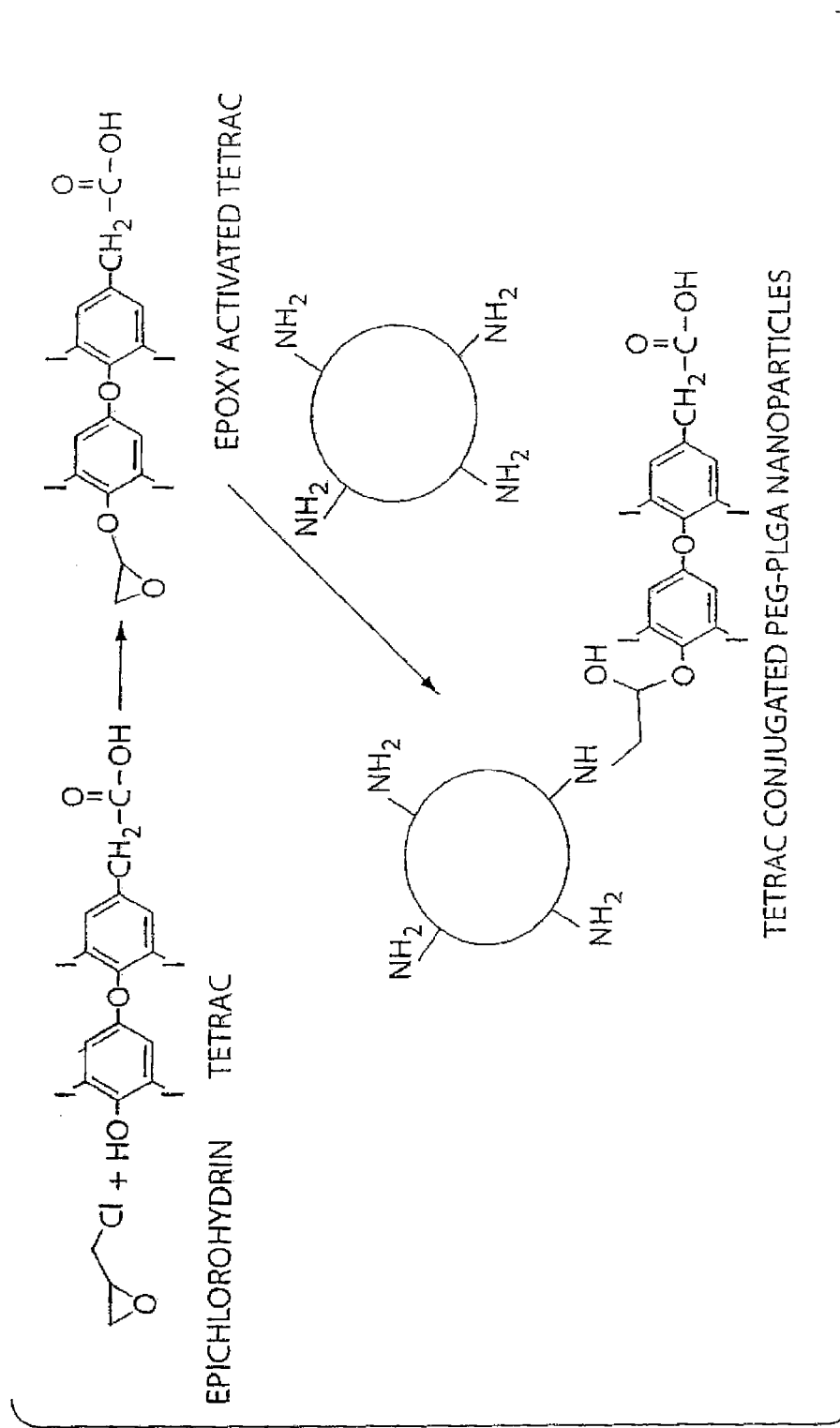

FIG. 32 is an illustration of tetrac nanoparticles within the scope of the present invention are shown below.

Figure 33A:
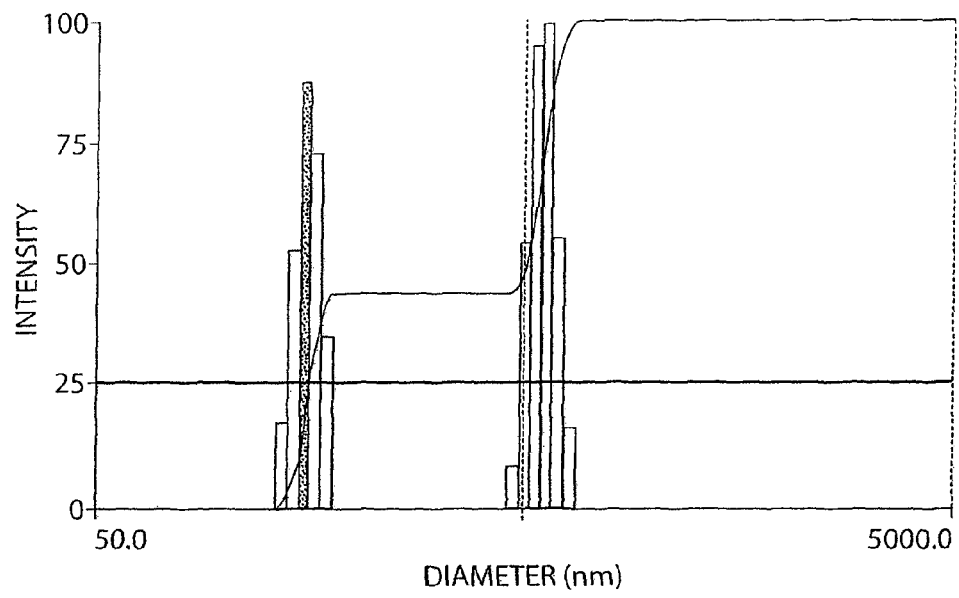

FIG. 33A. Size distribution spectra of PLGA nanoparticles encapsulating Tetrac when no stabilizer was used.

Figure 33B:
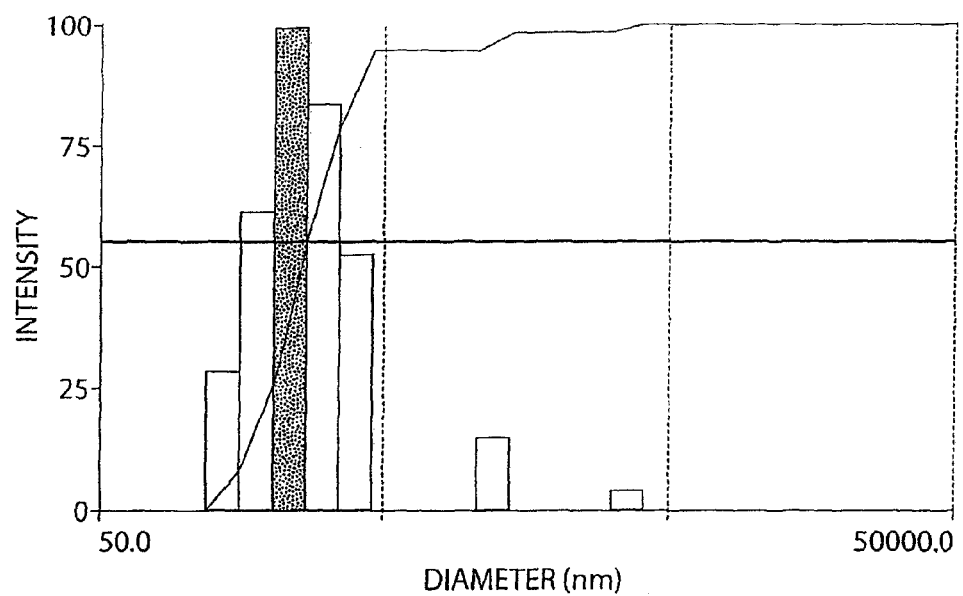

FIG. 33B. Size distribution spectra of PLGA nanoparticles encapsulating Tetrac when 1% PVA solution was used as a stabilizer.

Figure 34:
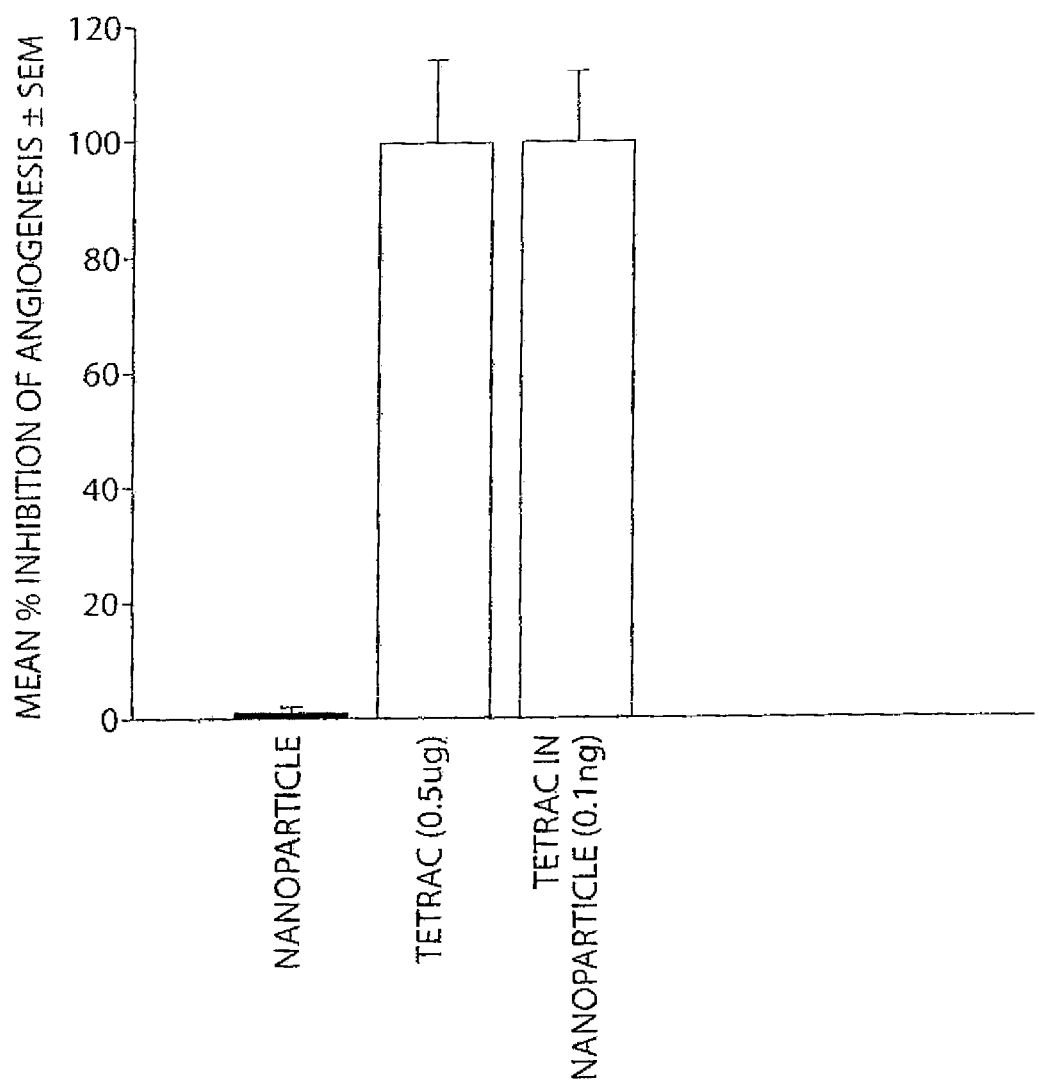

FIG. 34. Depicts a bar graph showing the anti-angiogenesis of Tetrac and Tetrac PLGA nanoparticles in the CAM model.

Figure 35:
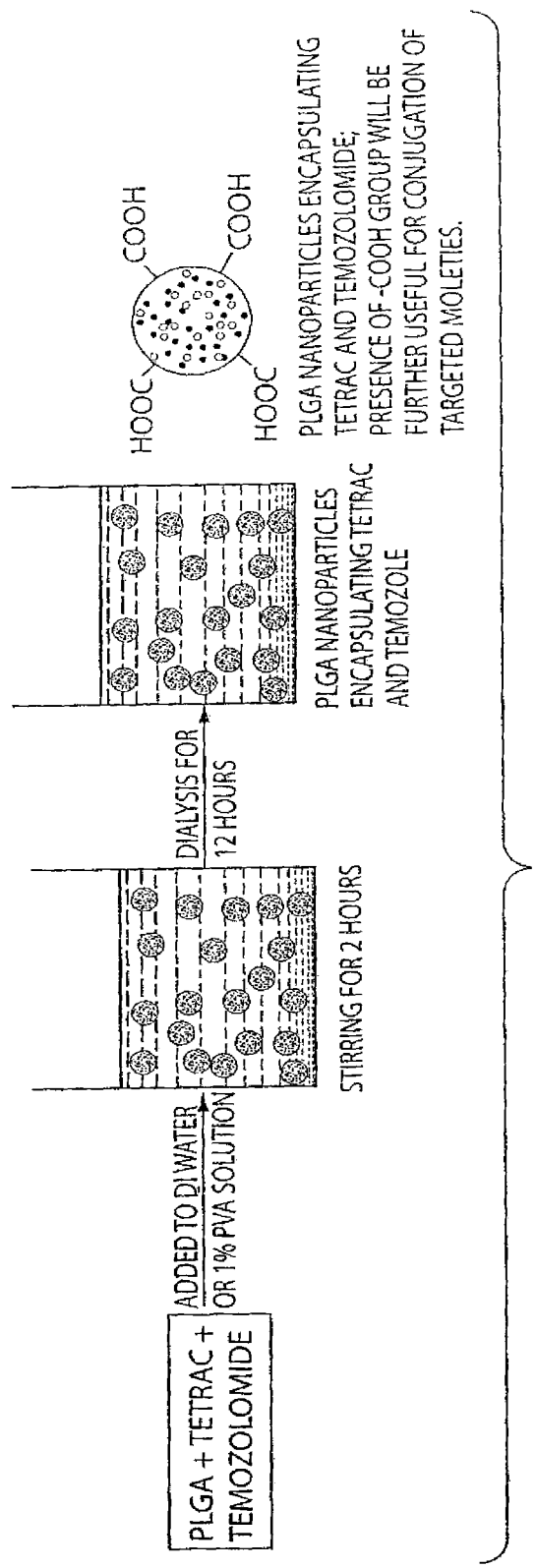

FIG. 35. Depicts schematic diagram for the preparation of PLGA nanoparticles co-encapsulating tetrac and Temozolomide.

Figure 36A:
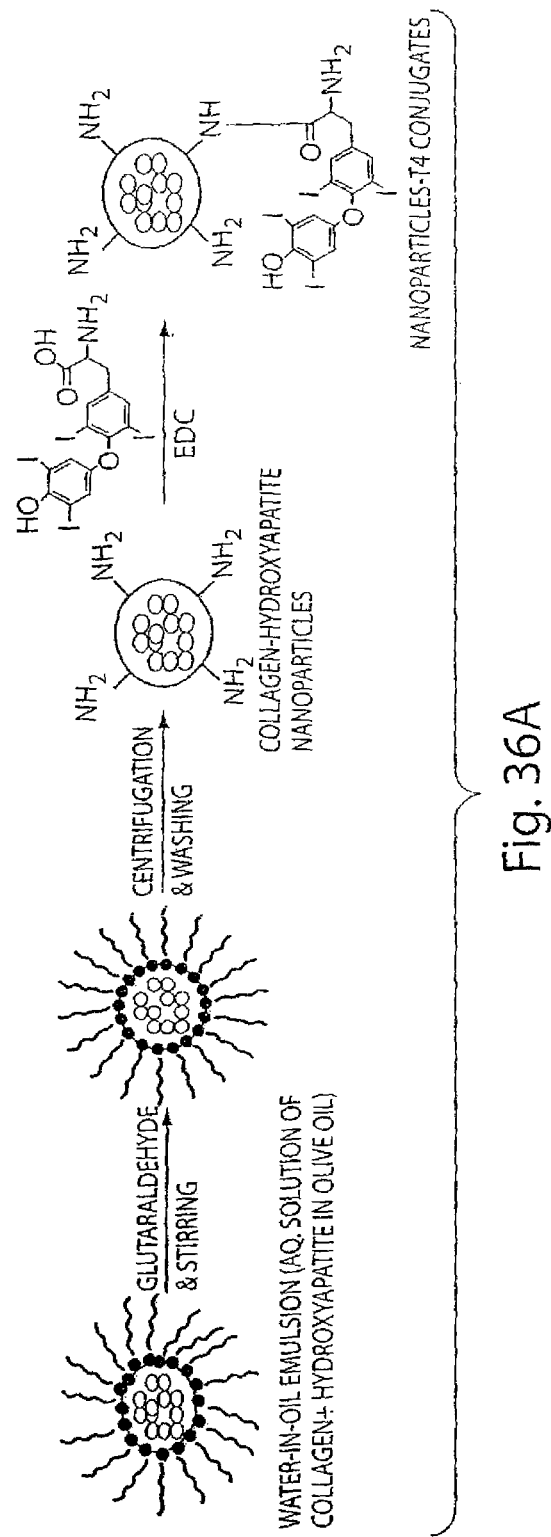

FIG. 36A. Depicts an illustration show ling how collegen-hydrocapatite nanospheres can be prepared by using a water-in-oil emulsion method, then the nanoparticles can be conjugated by T4 by using carbidiimide chemistry.

Figure 36B:
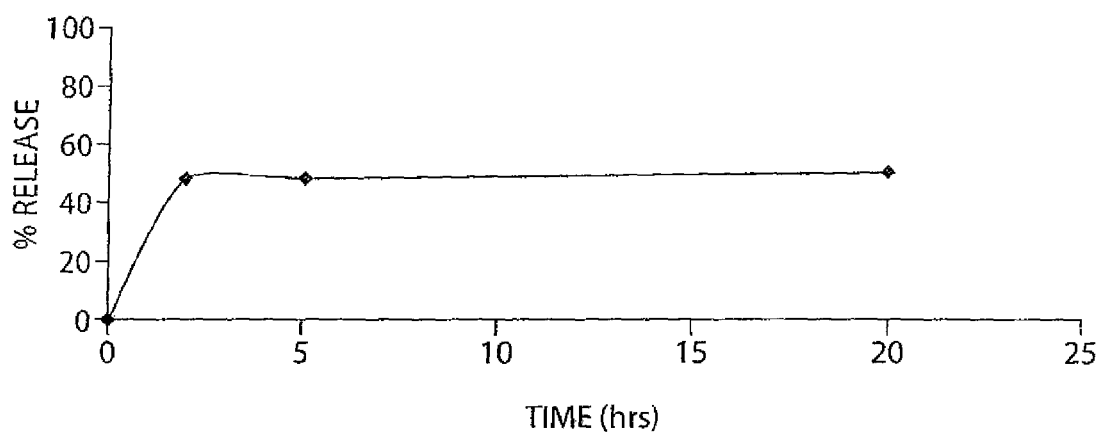

FIG. 36B. There is also a tremendous potential for encapsulation of T4 and its analogue in PLGA nanoparticles by using double emulsion methods. Also per the preliminary release kinetics experiments, the biodegradable nanoparticles are capable of releasing the encapsulating materials.

Figure 37A:
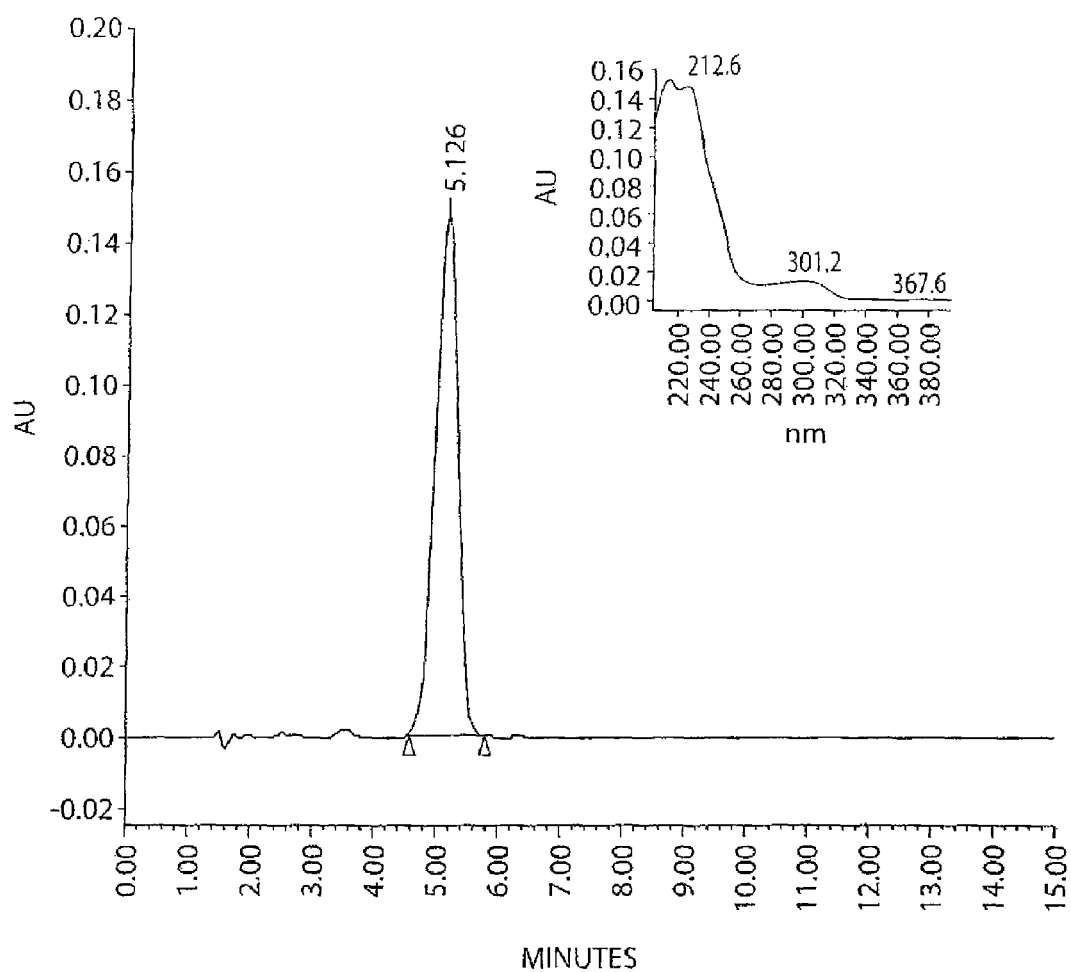

FIG. 37A. Depicts chromatograms and spectra of T4-collagen nanoparticles samples eluted on a C18 column, DWL: 225 nm, using a T4 standard 50 µM diluted with water.

Figure 37B:
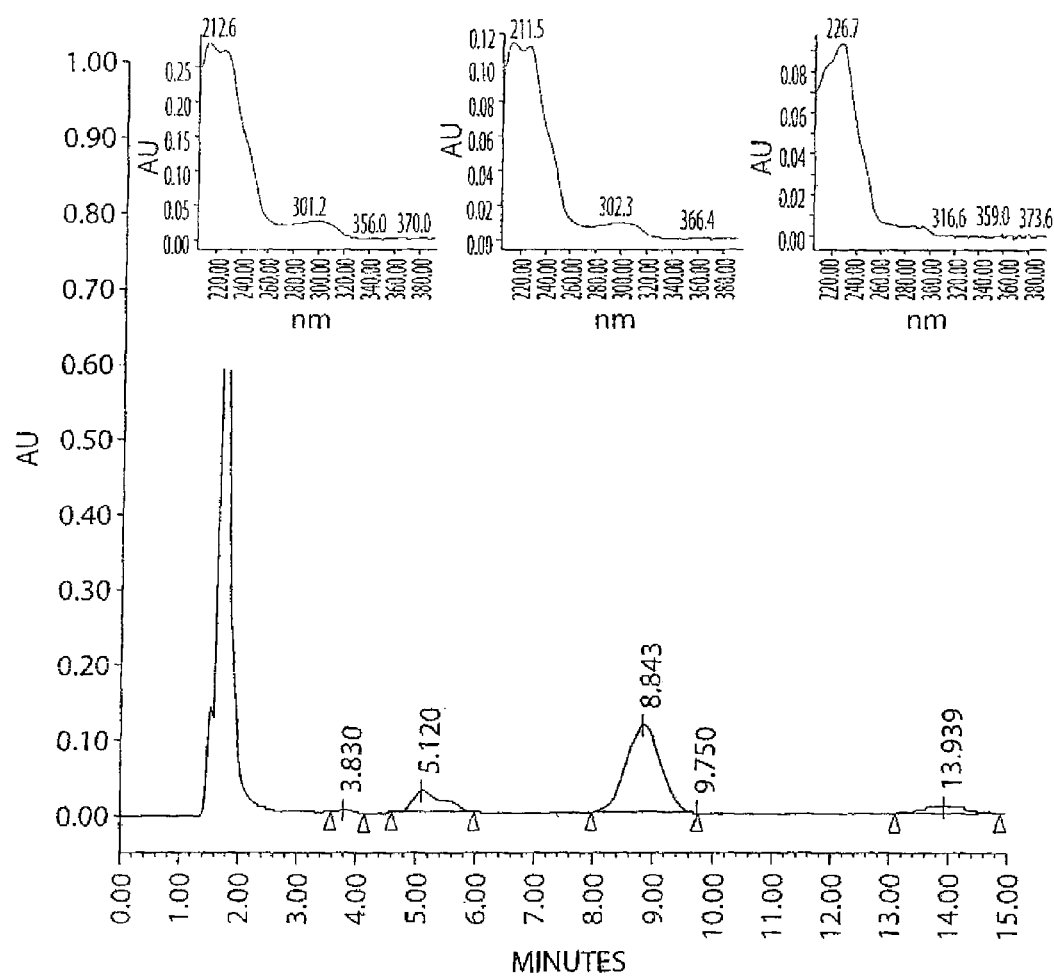

FIG. 37B. Depicts T4-collagen nanoparticle diluted with water and then filtrated through 300 KD membrane.

Figure 38A:
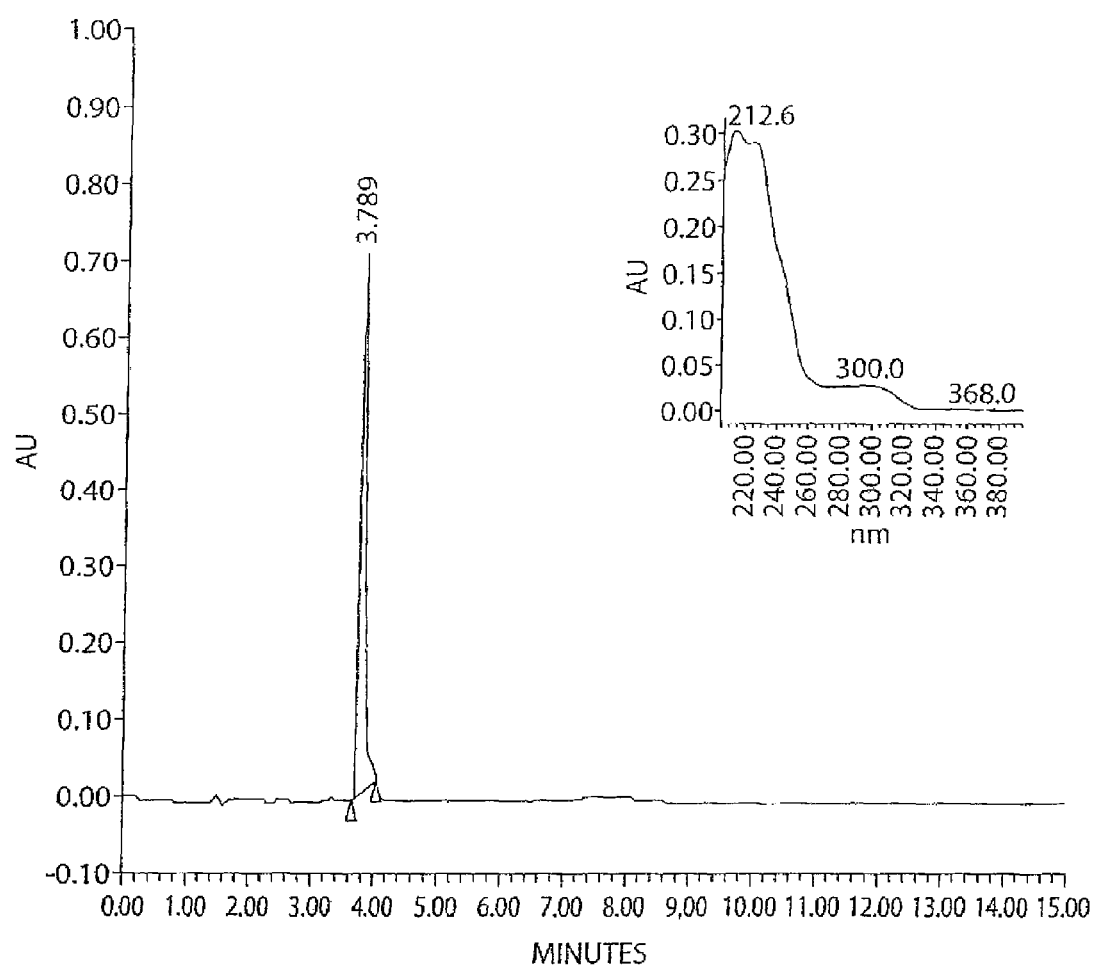

FIG. 38A. Depicts chromatograms and spectra of T4-collagen nanoparticle samples eluted on a C18 column, DWL: 225 nm using a T4 standard 50 µM diluted with 0.5M NaOH.

Figure 38B:
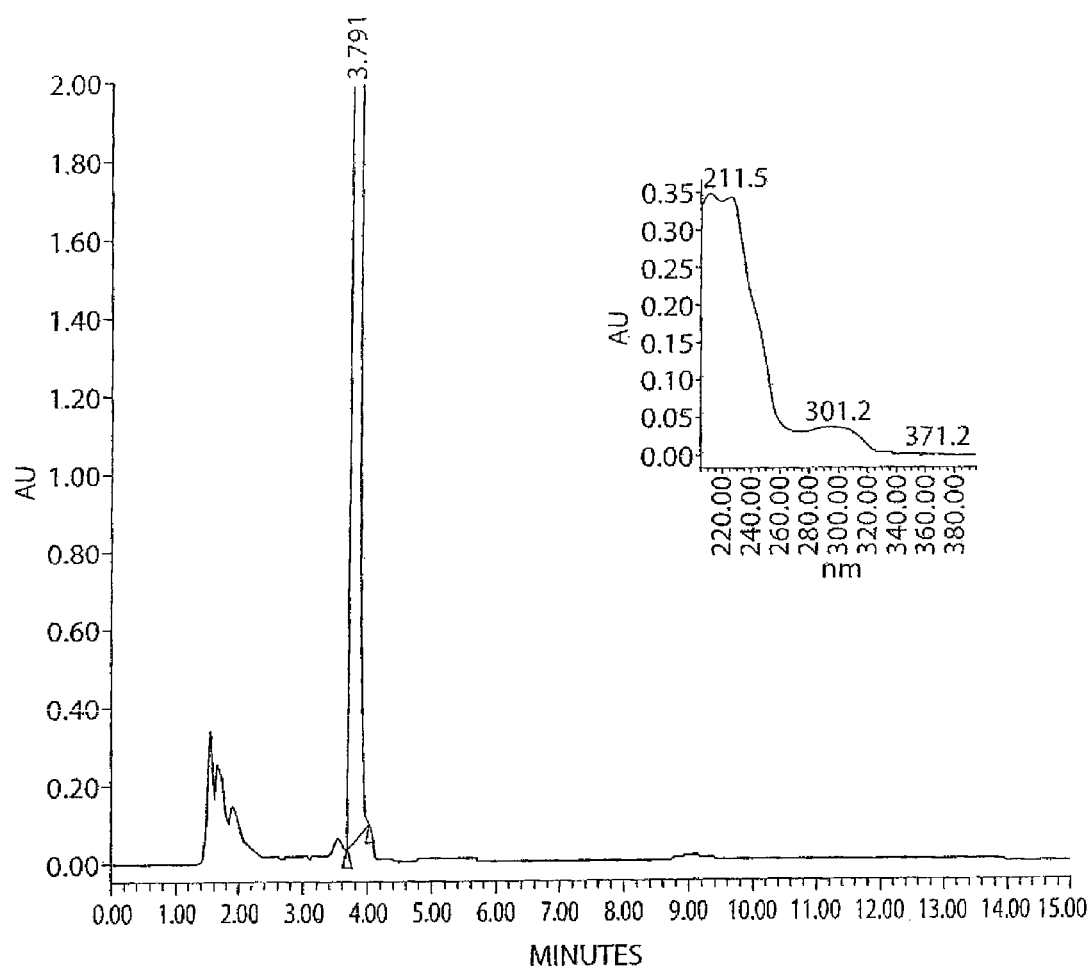

FIG. 38B. Depicts T4-collagen nanoparticles incubated with 0.5M NaOH for 2 hours and then filtrated through a 300 KD membrane.

Figure 39:
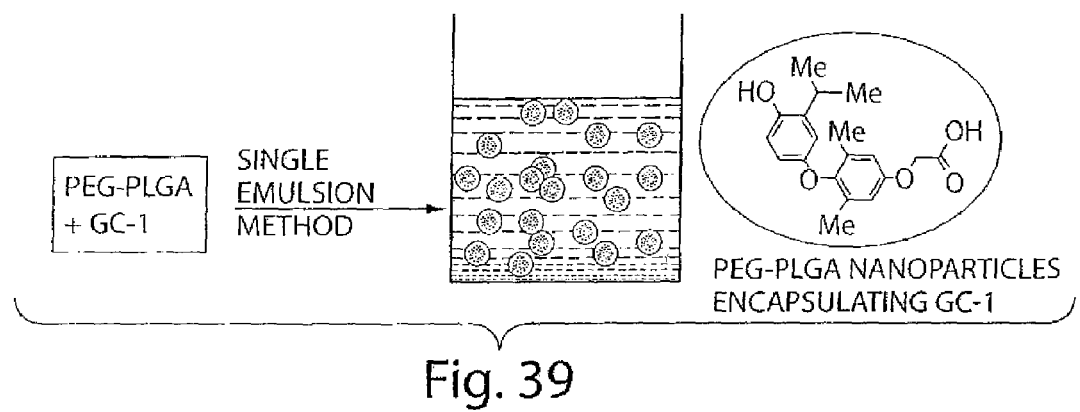

FIG. 39 is a schematic of PEG-PLGA nanoparticles encapsulating GC-1.

Figure 40:
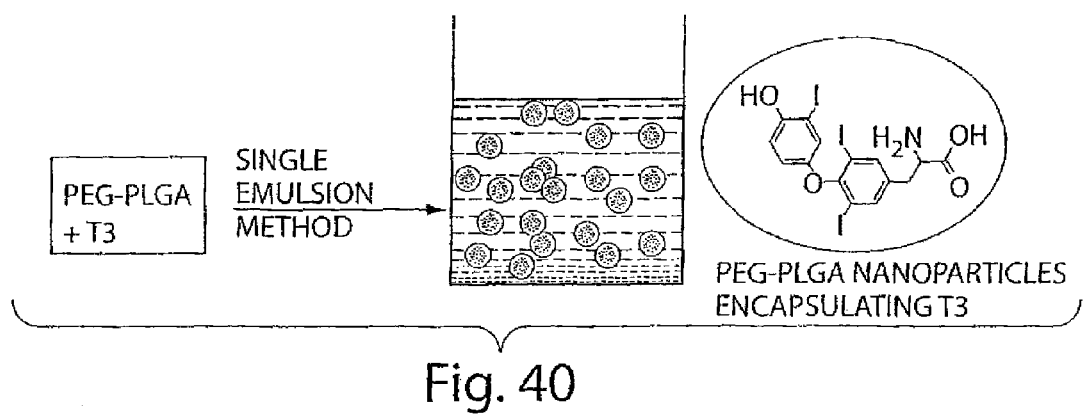

FIG. 40 is a schematic of PEG PLGA nanoparticles encapsulating T3.

Figure 41A:
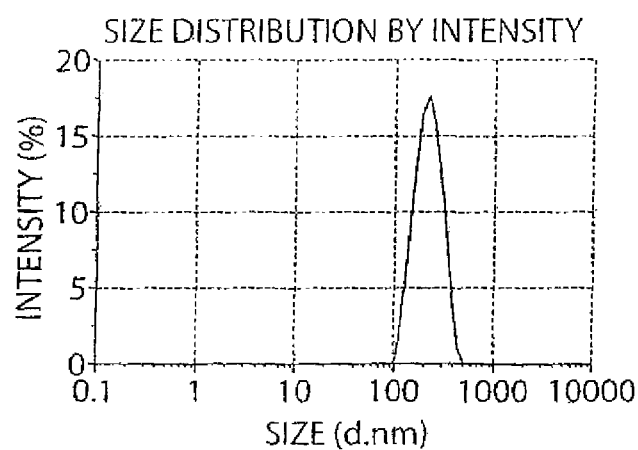

FIG. 41A show the results of the synthesis of a big batch of PLGA nanoparticles conjugating tetrac. Shows the size distribution by intensity.

Figure 41B:
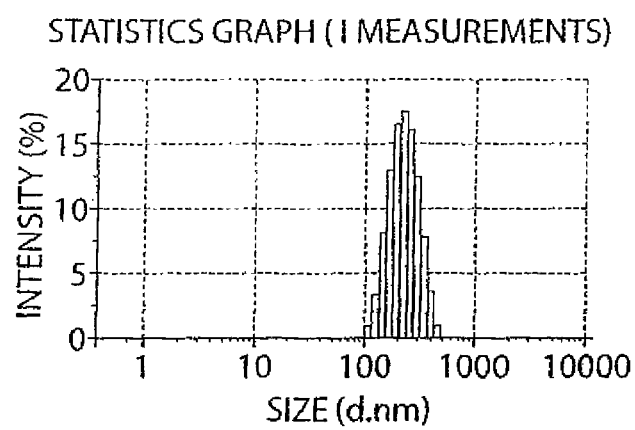

FIG. 41B shows the statistics graph with I measurement of results of the synthesis of a big batch of PLGA nanoparticles conjugating tetrac.

Figure 42:
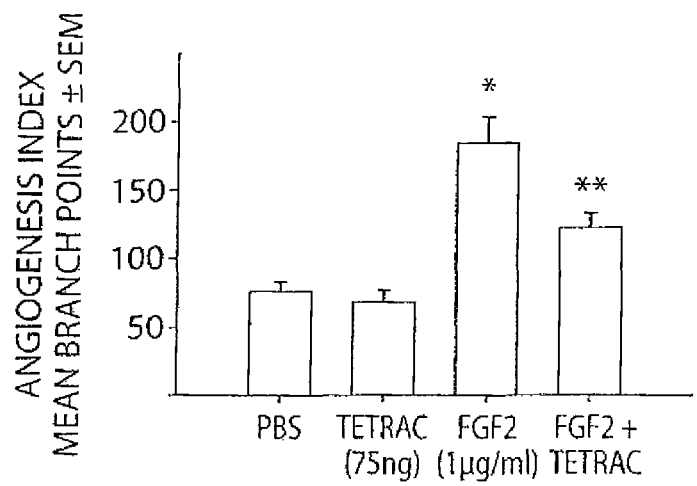

FIG. 42 shows that angiogenesis is stimulated in the CAM assay by application of physiological concentrations of FGF2, VEGF, and T3. FGF2 (lJlg/ml) placed on the CAM filter disk induced blood vessel branch formation by 2.4-fold (P<0.001) compared with PBS treated membranes. The addition of tetrac (75 nglfilter disc) inhibited the proangiogenic response to FGF2, while tetrac alone had no effect on angiogenesis.

Figure 43:
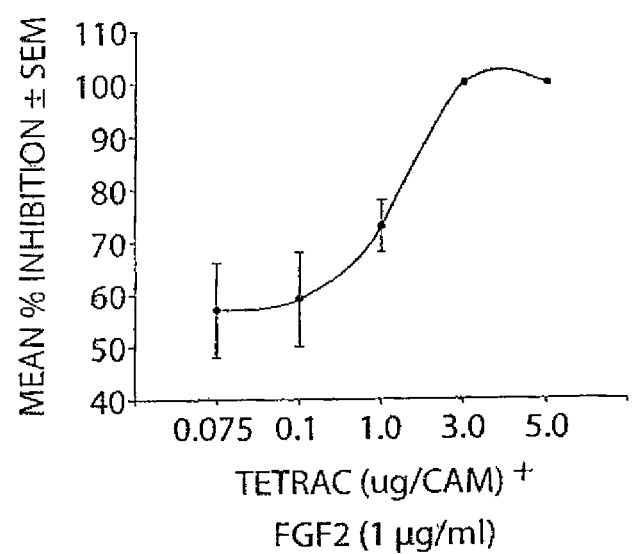

FIG. 43 is a line graph showing a tetrac dose response curve was performed to find maximum inhibition of FGF2 stimulated angiogenesis.

Figure 44:
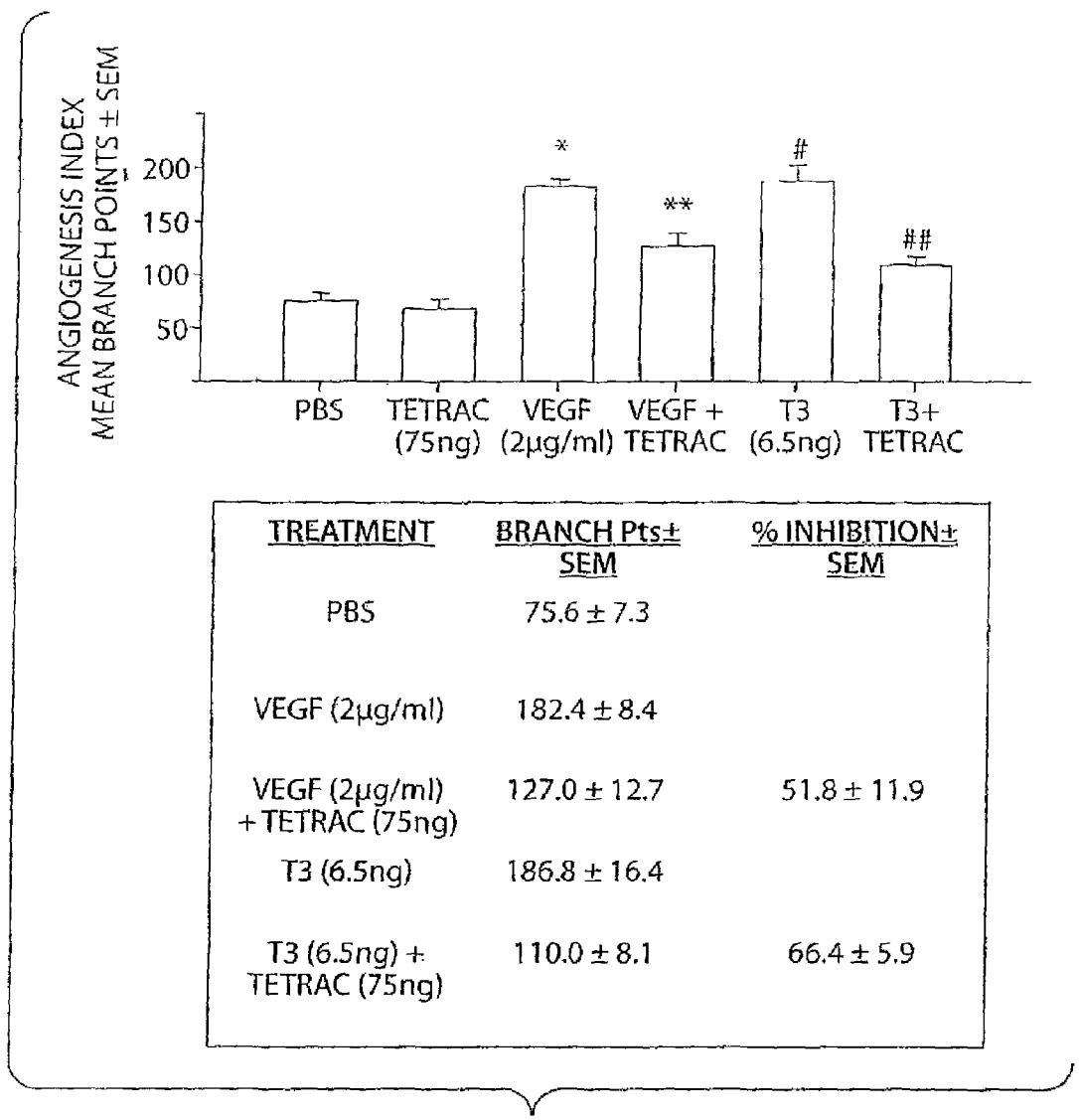

FIG. 44 is a bar graph showing that Tetrac similarly inhibits the pro-angiogenic effect of VEGF and T3 by 52% and 66% respectively.

Figure 45:
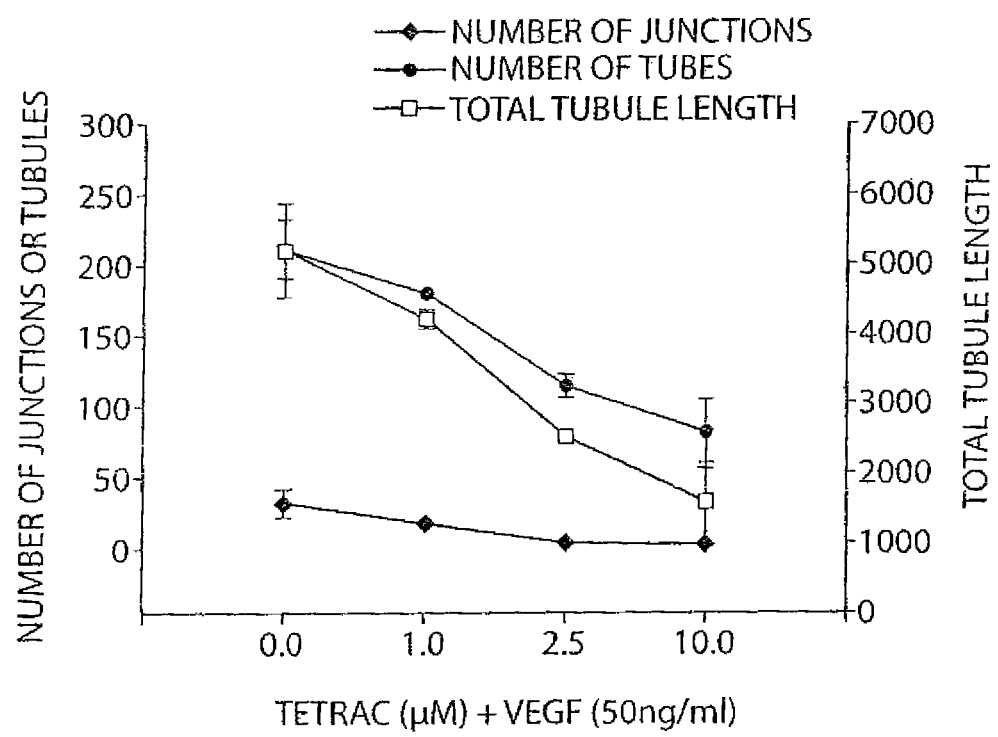

FIG. 45 is a line graph showing the results of HMVEC-d cells cultured on matrigel for 24 hrs and stimulated with VEGF (50 nglml) in the presence or absence of increasing amounts of tetrac. Tetrac inhibited the tube formation induced by VEGF as demonstrated by a reduction in the number of junctions, and number of tubes and a decrease in total tubule length.

Figure 46:
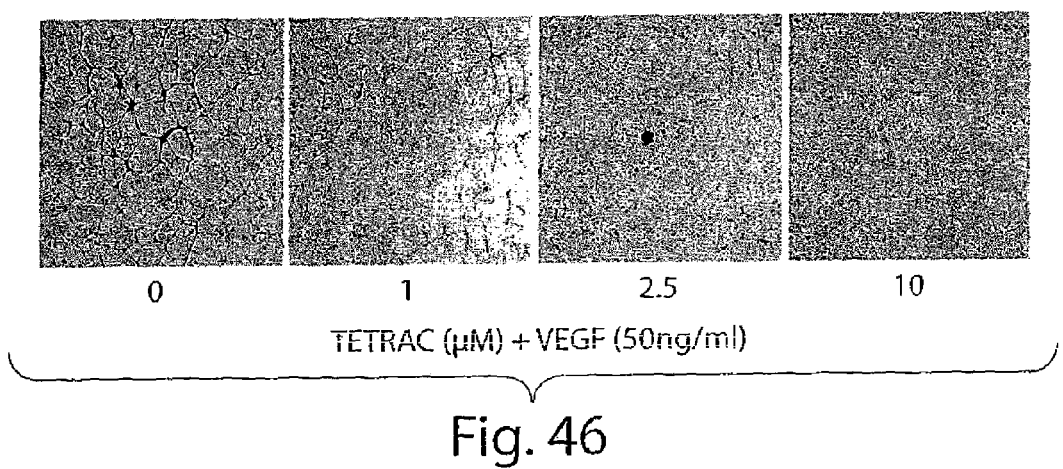

FIG. 46 are photographs showing the effect of Tetrac inhibiting the tube formation induced by VEGF.

Figure 47A:
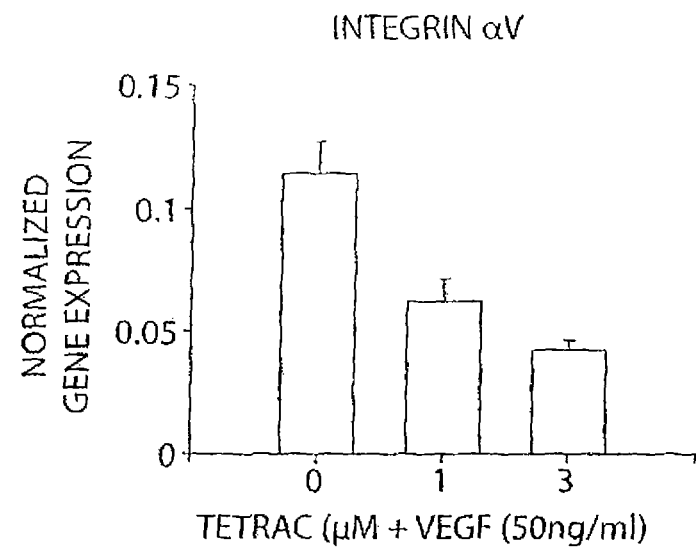

FIG. 47A is a graph of the mRNA expression of integrin αV and angiopoietin-2 Decreased by Tetrac. HMVEC-d cells were grown on matrigel and stimulated with VEGF (50 ng/ml) with and without Tetrac for 2 hours. Messenger RNA was isolated and real-time RT-PCR was performed for integrin αV.

Figure 47B:
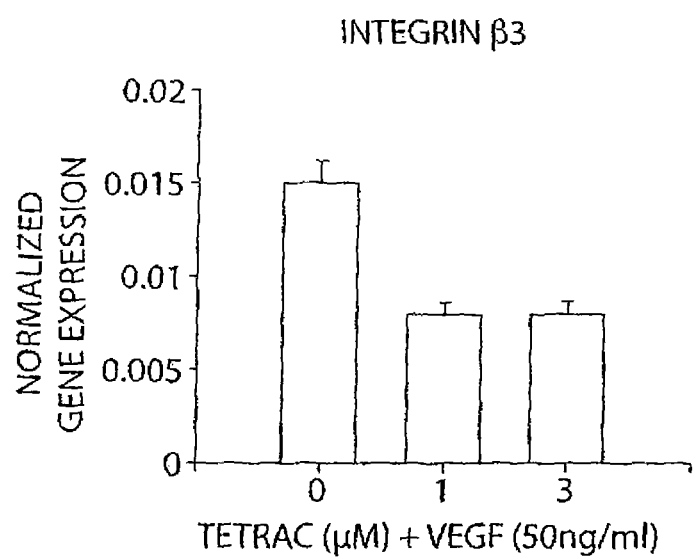

FIG. 47B is a graph of the mRNA expression of integrin β3, and angiopoietin-2 Decreased by Tetrac. HMVEC-d cells were grown on matrigel and stimulated with VEGF (50 ng/ml) with and without Tetrac for 2 hours. Messenger RNA was isolated and real-time RT-PCR was performed for integrin β3.

Figure 48A:
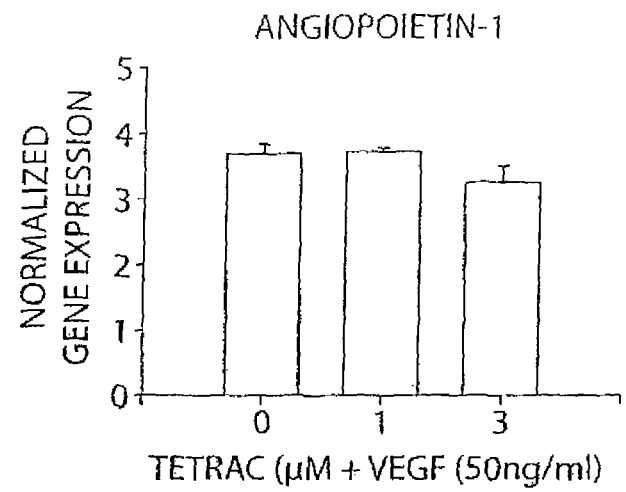

FIG. 48A is a bar graph showing real-time RT-PCR for angiopoietin-1 was performed and it was found that tetrac did not affect the mRNA levels of angiopoietin-1.

Figure 48B:
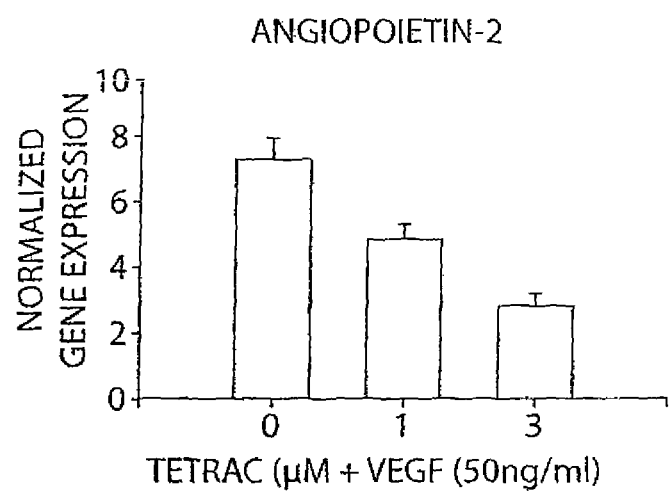

FIG. 48B is a bar graph showing real-time RT-PCR for angiopoietin-2 was performed and it was found that tetrac inhibited mRNA expression of angiopoietin-2 in a dose response fashion.

Figure 49A:
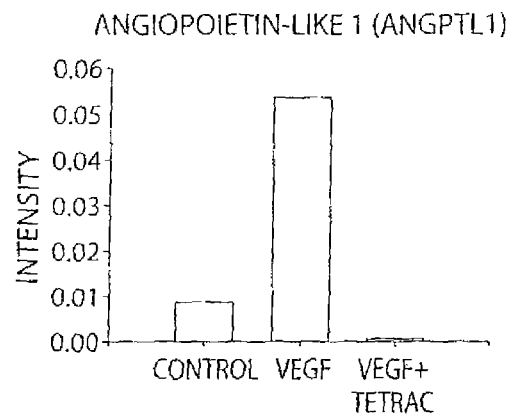
Figure 49B:
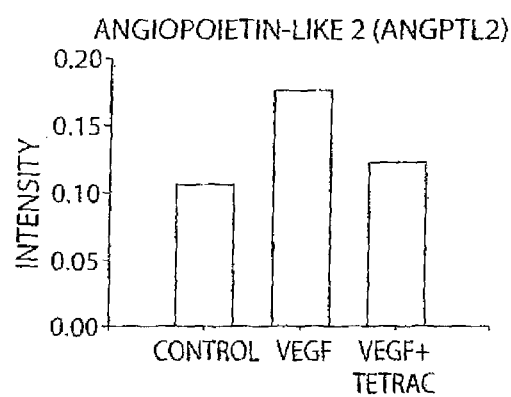
Figure 49C:
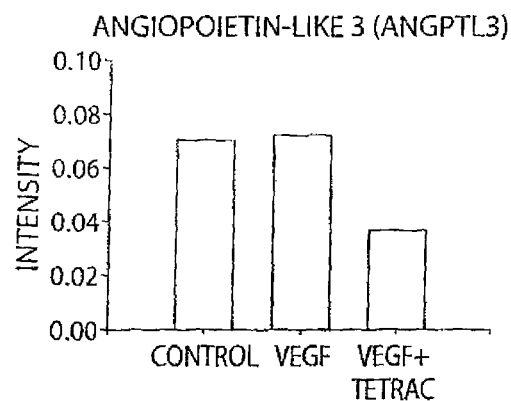

FIG. 49A, FIG. 49B and FIG. 49C are bar graphs showing microarray analysis performed using the Human U133 Plus 2.0 array from Affymetrix. HDMEC cells were incubated with VEGF at 50 ng/ml for 24 hours with and without Tetrac (3 uM). The results of the Affymetrix GeneChip analysis indicated that three different angiopoietin-like transcripts were differentially expressed in the HMVEC-d cells suggesting that tetrac can inhibit the expression of target genes that are necessary for the stimulation of angiogenesis.

Figure 50A:
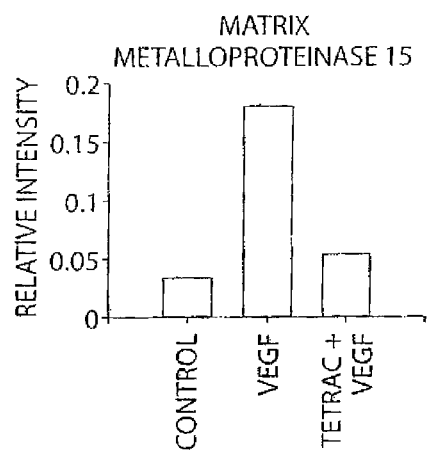
Figure 50B:
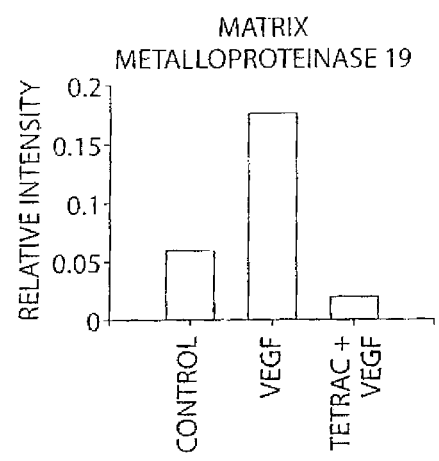
Figure 50C:
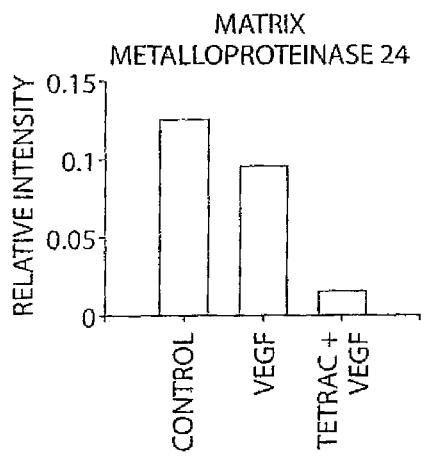
Figure 50D:
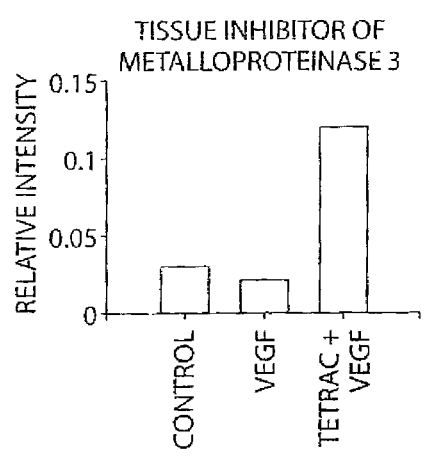

FIG. 50A, FIG. 50B, Fig. C and FIG. 50D are bar graphs showing the small molecule, tetrac, directed at the plasma membrane receptor for thyroid hormone has potent anti-angiogenic activity. While tetrac is an antagonist of the cell surface-initiated actions of thyroid hormone, tetrac in the absence of thyroid hormone is now shown to inhibit angiogenic activity of VEGF and FGF2 in chick and human endothelial cell assays.

Figure 51:
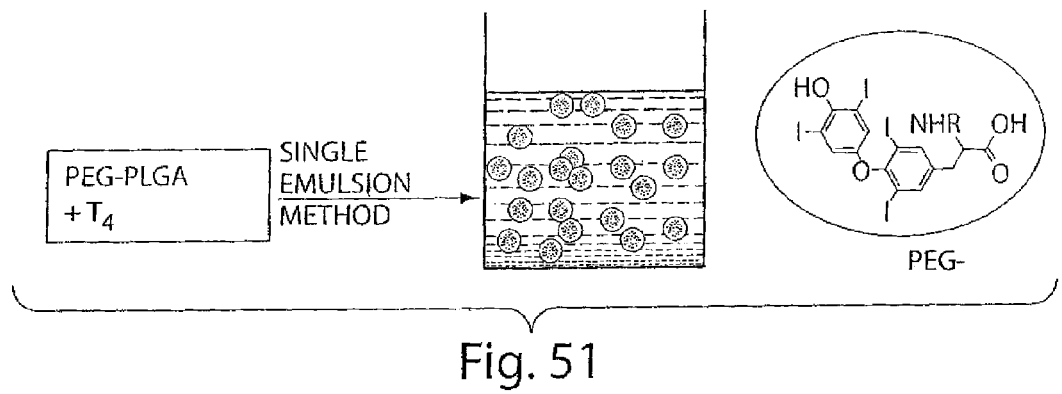

FIG. 51 is a schematic of showing the method of making T4 conjugated PEG-PLGA nanoparticles.

Figure 52:
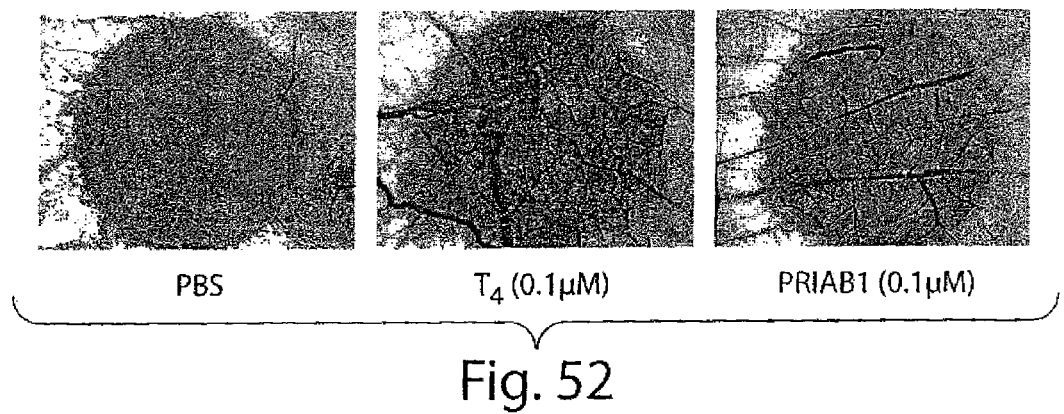

FIG. 52 depicts photographs showing the test results of PRIAB 1, PRIAB4 and PRIAB5, and the chick chlorioallantoic membrane (CAM) assay before conjugation which results in clear pro-angiogenesis action by the protected T4 analogs and the bulkiest protective group showed the merest activity.

Figure 53:
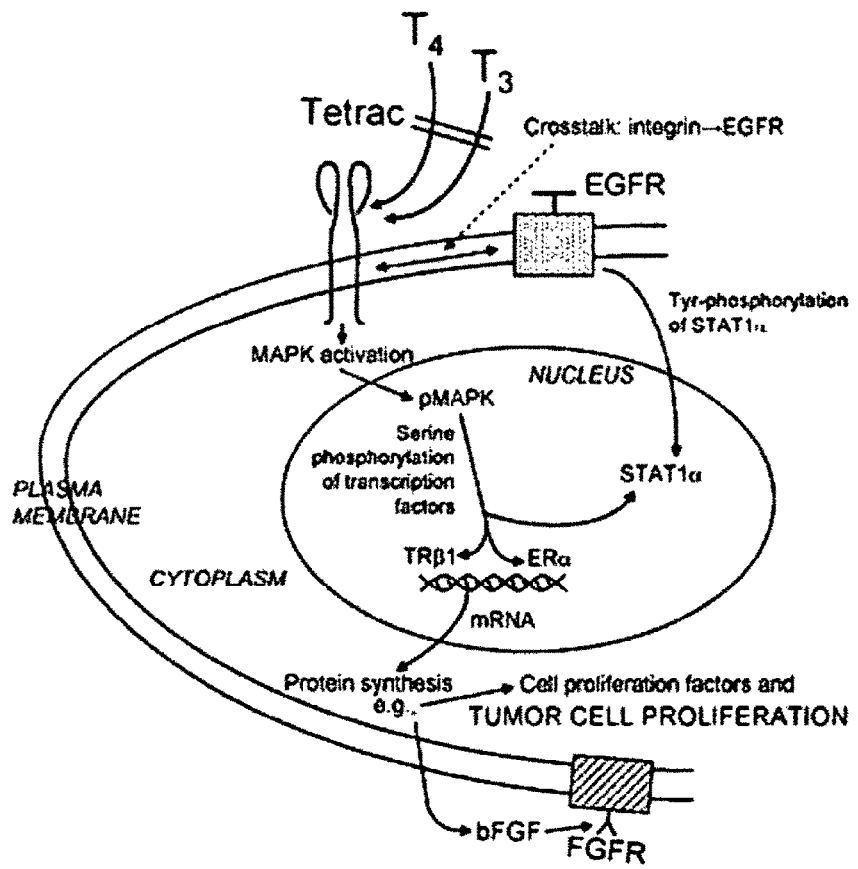

FIG. 53 depicts the ability of tetraiodothyroacetic acid (tetrac) to inhibit the action of T4 and T3 at the integrin; tetrac blocks the binding of iodothyronines to the integrin receptor. Also shown is crosstalk between the integrin and epidermal growth factor receptor (EGFR). Here, the presence of thyroid hormone at the cell surface alters the function of EGFR to allow the latter to distinguish EGF from TGF-α, another growth factor that binds to EGFR.

Figure 54:
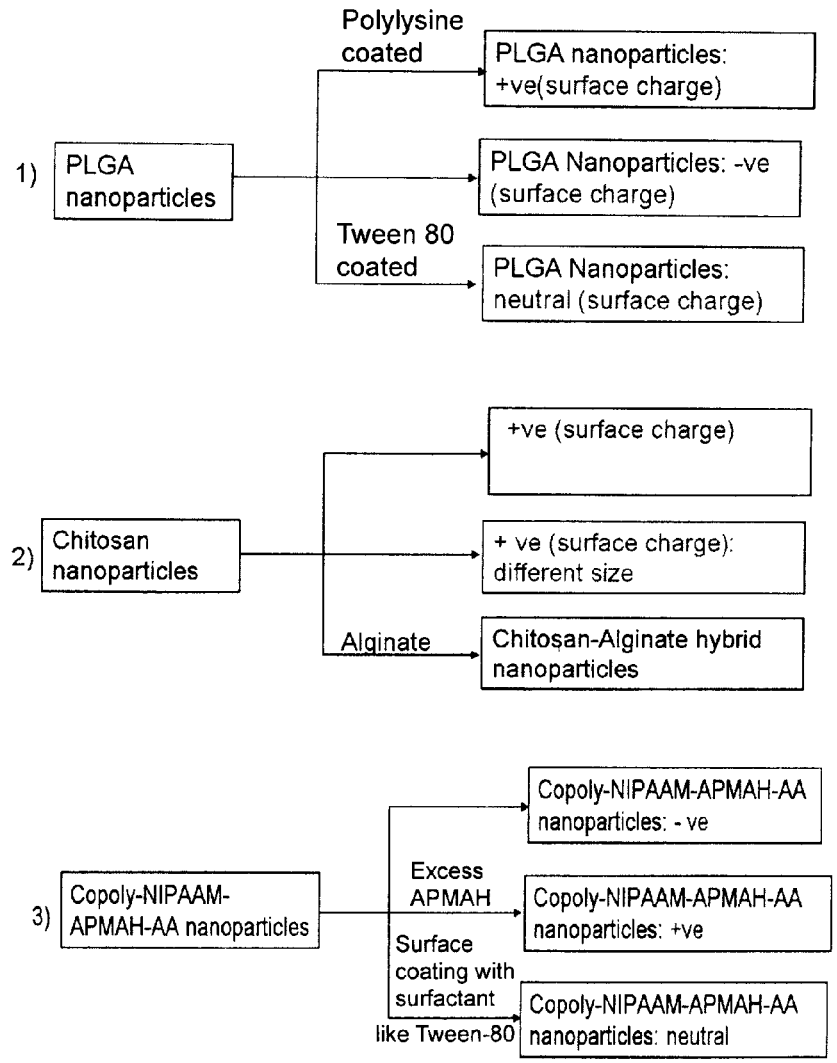

FIG. 54 depicts a schematic representation showing synthesis of different kinds of TETRAC encapsulated Nanoparticles and their surface modification.

DETAILED DESCRIPTION OF THE INVENTION

Disclosed herein are a new class of thyroid hormone molecules that act on the cell-surface, termed "Thyrointegrin molecules." These molecules selectively activate the receptor on the cell surface. Thyroid hormone is pro-angiogenic, acting via a mechanism that is mitogen-activated protein kinase (MAPK/ERK1/2)- and fibroblast growth factor (FGF2)-dependent.

Effects of the hormone on tumor cells are mediated by a novel cell surface receptor on integrin aVb3. Our recent discovery that thyroid hormone acts by means of this receptor located at the plasma membrane of cells has led to the discovery that polymer-conjugated thyroid hormone analogs and nanoparticulate thyroid hormone analogs can bind to the cell surface receptor while not being able to enter the cell.

Within the scope of the present invention are nanoparticulate thyroid hormone analogs and polymer conjugates thereof that cannot gain access to the cell interior and whose activities must therefore be limited to the integrin receptor. The nanoparticulate hormone analogs are polylysyl glycolic acid (PLGA) derivatives, either esters or the more stable ether-bond formulations. Agarose-T4 is a model of the nanoparticulate that we have shown to be fully active at the integrin receptor. The reformulated hormone analogs will not express intracellular actions of the hormone and thus if absorbed into the circulation will not have systemic thyroid hormone analog actions.

The molecules of the present invention can thus selectively activate the receptor. When this receptor is activated, a cascade of changes in protein mediators takes place, culminating in a signal which can modify the activity of nuclear transactivator proteins, such as STAT proteins, p53 and members of the superfamily of nuclear hormone receptors.

Nongenomic actions of thyroid hormone are those which are independent of intranuclear binding of hormone by the nuclear T3 receptor (TR). These actions are initiated largely at the cell surface. By conjugating known thyroid hormone analogs to synthetic polymers, a new family of hormones is created that acts exclusively at the cell surface receptor, but allows endogenous hormone to continue to enter the cell and act on mitochondria or directly on nuclear TR. Depending upon the hormone analogue that is conjugated, angiogenesis or wound-healing can be supported or actions on tumor cell growth and angiogenesis can be antagonized.

Described in detail below are formulations and uses of the thyroid hormone polymer conjugates and nanoparticles within the scope of the present invention.

Definitions

For convenience, certain terms used in the specification, examples and claims are collected here. Unless otherwise defined, all technical and scientific terms used herein have the same meaning as commonly understood by one of ordinary skill in the art to which this invention pertains.

As used herein, the term "angiogenic agent" includes any compound or substance that promotes or encourages angiogenesis, whether alone or in combination with another substance. Examples include, but are not limited to, T3, T4, T3 or T4-agarose, polymeric analogs of T3, T4, 3,5-dimethyl-4-(4'-hydroxy-3'-isopropylbenzyl)-phenoxy acetic acid (GC-1), or DITPA. In contrast, the terms "anti-angiogenesis agent" or anti-angiogenic agent" refer to any compound or substance that inhibits or discourages angiogenesis, whether alone or in combination with another substance. Examples include, but are not limited to, TETRAC, TRIAC, XT 199, and mAb LM609.

As used herein, the term "myocardial ischemia" is defined as an insufficient blood supply to the heart muscle caused by a decreased capacity of the heart vessels. As used herein, the term "coronary disease" is defined as diseases/disorders of cardiac function due to an imbalance between myocardial function and the capacity of coronary vessels to supply sufficient blood flow for normal function. Specific coronary diseases/disorders associated with coronary disease which can be treated with the compositions and methods described herein include myocardial ischemia, angina pectoris, coronary aneurysm, coronary thrombosis, coronary vasospasm, coronary artery disease, coronary heart disease, coronary occlusion and coronary stenosis.

As used herein the term "occlusive peripheral vascular disease" (also known as peripheral arterial occlusive disorder) is a vascular disorder-involving blockage in the carotid or femoral arteries, including the iliac artery. Blockage in the femoral arteries causes pain and restricted movement. A specific disorder associated with occlusive peripheral vascular disease is diabetic foot, which affects diabetic patients, often resulting in amputation of the foot.

As used herein the terms "regeneration of blood vessels," "angiogenesis," "revascularization," and "increased collateral circulation" (or words to that effect) are considered as synonymous. The term "pharmaceutically acceptable" when referring to a natural or synthetic substance means that the substance has an acceptable toxic effect in view of its much greater beneficial effect, while the related term, "physiologically acceptable," means the substance has relatively low toxicity. The term, "co-administered" means two or more drugs are given to a patient at approximately the same time or in close sequence so that their effects run approximately concurrently or substantially overlap. This term includes sequential as well as simultaneous drug administration.

"Pharmaceutically acceptable salts" refers to pharmaceutically acceptable salts of thyroid hormone analogs, polymeric forms, and derivatives, which salts are derived from a variety of organic and inorganic counter ions well known in the art and include, by way of example only, sodium, potassium, calcium, magnesium, ammonium, tetra-alkyl ammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt. The term also includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, and the like. Particularly preferred salts of compounds of the invention are the monochloride salts and the dichloride salts.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, zinc, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Ureido" refers to a radical of the formula —N(H)—C(O)—NH$_2$.

It is understood from the above definitions and examples that for radicals containing a substituted alkyl group any substitution thereon can occur on any carbon of the alkyl group. The compounds of the invention, or their pharmaceutically acceptable salts, may have asymmetric carbon atoms in their structure. The compounds of the invention and their pharmaceutically acceptable salts may therefore exist as single enantiomers, diastereoisomers, racemates, and mixtures of enantiomers and diastereomers. All such single enantiomers, diastereoisomers, racemates and mixtures thereof are intended to be within the scope of this invention. Absolute configuration of certain carbon atoms within the compounds, if known, are indicated by the appropriate absolute descriptor R or S.

Separate enantiomers can be prepared through the use of optically active starting materials and/or intermediates or through the use of conventional resolution techniques, e.g., enzymatic resolution or chiral HPLC.

As used herein, the phrase "growth factors" or "neurogenesis factors" refers to proteins, peptides or other molecules having a growth, proliferative, differentiative, or trophic effect on cells of the CNS or PNS. Such factors may be used for inducing proliferation or differentiation and can include, for example, any trophic factor that allows cells of the CNS or PNS to proliferate, including any molecule which binds to a receptor on the surface of the cell to exert a trophic, or growth-inducing effect on the cell. Preferred factors include, but are not limited to, nerve growth factor ("NGF"), epidermal growth factor ("EGF"), platelet-derived growth factor ("PDGF"), insulin-like growth factor ("IGF"), acidic fibroblast growth factor ("aFGF" or "FGF-1"), basic fibroblast growth factor ("bFGF" or "FGF-2"), and transforming growth factor-alpha and -beta ("TGF-α" and "TGF-β").

"Subject" includes living organisms such as humans, monkeys, cows, sheep, horses, pigs, cattle, goats, dogs, cats, mice, rats, cultured cells therefrom, and transgenic species thereof. In a preferred embodiment, the subject is a human. Administration of the compositions of the present invention to a subject to be treated can be carried out using known procedures, at dosages and for periods of time effective to treat the condition in the subject. An effective amount of the therapeutic compound necessary to achieve a therapeutic effect may vary according to factors such as the age, sex, and weight of the subject, and the ability of the therapeutic compound to treat the foreign agents in the subject. Dosage regimens can be adjusted to provide the optimum therapeutic response. For example, several divided doses may be administered daily or the dose may be proportionally reduced as indicated by the exigencies of the therapeutic situation.

"Administering" includes routes of administration which allow the compositions of the invention to perform their intended function, e.g., promoting angiogenesis. A variety of routes of administration are possible including, but not necessarily limited to parenteral (e.g., intravenous, intra-arterial, intramuscular, subcutaneous injection), oral (e.g., dietary), topical, nasal, rectal, or via slow releasing microcarriers depending on the disease or condition to be treated. Oral, parenteral and intravenous administration are preferred modes of administration. Formulation of the compound to be administered will vary according to the route of administration selected (e.g., solution, emulsion, gels, aerosols, capsule). An appropriate composition comprising the compound to be administered can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See generally, *Remington's Pharmaceutical Science,* 16th Edition, Mack, Ed. (1980)).

"Effective amount" includes those amounts of pro-angiogenic or anti-angiogenic compounds which allow it to perform its intended function, e.g., promoting or inhibiting angiogenesis in angiogenesis-related disorders as described herein. The effective amount will depend upon a number of factors, including biological activity, age, body weight, sex, general health, severity of the condition to be treated, as well as appropriate pharmacokinetic properties. For example, dosages of the active substance may be from about 0.01 mg/kg/day to about 500 mg/kg/day, advantageously from about 0.1 mg/kg/day to about 100 mg/kg/day. A therapeutically effective amount of the active substance can be administered by an appropriate route in a single dose or multiple doses. Further, the dosages of the active substance can be proportionally increased or decreased as indicated by the exigencies of the therapeutic or prophylactic situation.

"Pharmaceutically acceptable carrier" includes any and all solvents, dispersion media, coatings, antibacterial and antifungal agents, isotonic and absorption delaying agents, and the like which are compatible with the activity of the compound and are physiologically acceptable to the subject. An example of a pharmaceutically acceptable carrier is buffered normal saline (0.15M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

"Additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, e.g., in *Remington's Pharmaceutical Sciences.*

Thyro-Integrin Molecules

The Role of Thyroid Hormone, Analogs, and Polymeric Conjugations in Modulating the Actions of Polypeptides Whose Cell Surface Receptors are Clustered Around Integrin αVβ3, or Other RGD-Containing Compounds Disclosed herein are a new class of thyroid hormone molecule that work on the cell-surface, termed "Thyro-integrin molecules." These molecules selectively activate the cell surface receptor for thyroid hormone (L-thyroxine, T4; T3) that has been described on integrin αVβ3. The receptor is at or near the Arg-Gly-Asp (RGD) recognition site on the integrin. The αVβ3 receptor is not a homologue of the nuclear thyroid hormone receptor (TR), but activation of the cell surface receptor results in a number of nucleus-mediated events, including the recently-reported pro-angiogenic action of the hormone and fibroblast migration in vitro in the human dermal fibroblast monolayer model of wound-healing.

Integrin αVβ3 is a heterodimeric plasma membrane protein with several extracellular matrix protein ligands containing an amino acid sequence Arg-Gly-Asp ("RGD"). Using purified integrin, we discovered that integrin αVβ3 binds T4 and that this interaction is perturbed by αVβ3 antagonists. Radioligand-binding studies revealed that purified αVβ3 binds T4 with high affinity (EC50, 371 pM), and appears to bind T4 preferentially over T3. This is consistent with previous reports that show MAPK activation and nuclear translocation, as well as hormone-induced angiogenesis, by T4, compared to T3. Integrin αVβ3 antagonists inhibit binding of T4 to the integrin and, importantly, prevent activation by T4 of the MAPK signaling cascade. This functional consequence-MAPK activation—of hormone-binding to the integrin, together with inhibition of the MAPK-dependent pro-angiogenic action of thyroid hormone by integrin αVβ3 antagonists, allow us to describe the iodothyronamine-binding site on the integrin as a receptor. It should be noted that 3-iodothyronamine, a thyroid hormone derivative, has recently been shown by Scanlan et al. to bind to a trace amine receptor (TAR I), but the actions of this analog interestingly are antithetic to those of T4 and T3.

The traditional ligands of integrins are proteins. That a small molecule, thyroid hormone, is also a ligand of an integrin is a novel finding. The present invention also discloses that, resveratrol, a polyphenol with some estrogenic activity, binds to integrin αVβ3 with a functional cellular consequence, apoptosis, different from those that result from the binding of thyroid hormone. The site on the integrin at which T4 binds is at or near the RGD binding groove of the heterodimeric integrin. It is possible, however, that αVβ3 binds T4 elsewhere on the protein and that the occupation of the RGD recognition site by tetrac or by RGD-containing peptides allosterically blocks the T4 binding site or causes a conformational change within the integrin that renders the T4 site unavailable.

Accordingly, the modulation by T4 of the laminin-integrin interaction of astrocytes may be a consequence of binding of the hormone to the integrin. The possibility thus exists that at the cell exterior thyroid hormone may affect the liganding by integrin αVβ3 of extracellular matrix proteins in addition to laminin.

Actions of T4 that are nongenomic in mechanism have been well documented in recent years. A number of these activities are MAPK-mediated. We have shown that initial steps in activation of the MAPK cascade by thyroid hormone, including activation of protein kinase C, are sensitive to GTPγS and pertussis toxin, indicating that the plasma membrane receptor for thyroid hormone is G protein-sensitive. It should be noted that certain cellular functions mediated by integrin αVβ3 have been shown by others to be G protein-modulated. For example, site-directed mutagenesis of the RGD binding domain abolishes the ability of the nucleotide receptor P2Y2 to activate $G_0$, while the activation of $G_q$, was not affected. Wang et al. demonstrated that an integrin-associated protein, IAP/CD47, induced smooth muscle cell migration via $G_i$-mediated inhibition of MAPK activation.

In addition to linking the binding of T4 and other analogs by integrin αVβ3 to activation of a specific intracellular signal transduction pathway, the present invention also discloses that the liganding of the hormone by the integrin is critical to induction by T4 of MAPK-dependent angiogenesis. In the CAM model, significant vessel growth occurs after 48-72 h of T4 treatment, indicating that the plasma membrane effects of T4 can result in complex transcriptional changes. Thus, what is initiated as a nongenomic action of the hormone—transduction of the cell surface T4 signal—interfaces with genomic effects of the hormone that culminate in neovascularization. Interfaces of nongenomic and genomic actions of thyroid hormone have previously been described, e.g., MAPK-dependent phosphorylation at Ser-142 of TRβ1 that is initiated at the cell surface by T4 and that results in shedding by TR of corepressor proteins and recruitment of coactivators. The instant invention also discloses that T4 stimulates growth of C-6 glial cells by a MAPK-dependent mechanism that is inhibited by RGD peptide, and that thyroid hormone causes MAPK-mediated serine-phosphorylation of the nuclear estrogen receptor (ERα) in MCF-7 cells by a process we now know to be inhibitable by an RGD peptide. These findings in several cell lines all support the participation of the integrin in functional responses of cells to thyroid hormone.

Identification of αVβ3 as a membrane receptor for thyroid hormone indicates clinical significance of the interaction of the integrin and the hormone and the downstream consequence of angiogenesis. For example, αVβ3 is overexpressed in many tumors and this overexpression appears to play a role in tumor invasion and growth. Relatively constant circulating levels of thyroid hormone can facilitate tumor-associated angiogenesis. In addition to demonstrating the pro-angiogenic action of T4 in the CAM model here and elsewhere, the present invention also discloses that human dermal microvascular endothelial cells also form new blood vessels when exposed to thyroid hormone. Local delivery of αVβ3 antagonists or tetrac around tumor cells might inhibit thyroid hormone-stimulated angiogenesis. Although tetrac lacks many of the biologic activities of thyroid hormone, it does gain access to the interior of certain cells. Anchoring of tetrac, or specific RGD antagonists, to non-immunogenic substrates (agarose or polymers) would exclude the possibility that the compounds could cross the plasma membrane, yet retain as shown here the ability to prevent T4-induced angiogenesis. The agarose-T4 used in the present studies is thus a prototype for a new family of thyroid hormone analogues that have specific cellular effects, but do not gain access to the cell interior.

Accordingly, the Examples herein identify integrin αVβ3 as a cell surface receptor for thyroid hormone (L-thyroxine, T4) and as the initiation site for T4-induced activation of intracellular signaling cascades. αVβ3 dissociably binds radiolabeled T4 with high affinity; radioligand-binding is displaced by tetraiodothyroacetic acid (tetrac), αVβ3 antibodies and by an integrin RGD recognition site peptide. CV-1 cells lack nuclear thyroid hormone receptor but bear plasma membrane αVβ3; treatment of these cells with physiological concentrations of T4 activates the MAPK pathway, an effect inhibited by tetrac, RGD peptide and αVβ3 antibodies. Inhibitors of T4-binding to the integrin also block the MAPK-mediated pro-angiogenic action of T4. T4-induced phosphorylation of MAPK is blocked by siRNA knockdown of αV and β3. These findings indicate that T4 binds to αVβ3 near the RGD recognition site and show that hormone-binding to αVβ3 has physiologic consequences.

The compositions of the present invention are based, in part, on the discovery that thyroid hormone, thyroid hormone analogs, and their polymeric forms, act at the cell membrane level and have pro-angiogenic properties that are independent of the nuclear thyroid hormone effects. Accordingly, these thyroid hormone analogs and polymeric forms (i.e., angiogenic agents) can be used to treat a variety of disorders. Similarly, the invention is also based on the discovery that thyroid hormone analog antagonists inhibit the pro-angiogenic effect of such analogs, and can also be used to treat a variety of disorders. These compositions and methods of use therefore are described in detail below.

Compositions

Disclosed herein are angiogenic and anti-angiogenic agents comprising thyroid hormones, analogs thereof, polymer conjugations, and nanoparticles of the hormones and their analogs. The disclosed compositions can be used for promoting angiogenesis to treat disorders wherein angiogenesis is beneficial. Additionally, the inhibition of these thyroid hormones, analogs and polymer conjugations can be used to inhibit angiogenesis to treat disorders associated with such undesired angiogenesis. As used herein, the term "angiogenic agent" includes any compound or substance that promotes or encourages angiogenesis, whether alone or in combination with another substance.

Pro-angiogenic agents of the present invention are thyroid hormone agonists and include thyroid hormone, analogs, and derivatives either alone or in covalent or non-covalent conjugation with polymers. Examples include, but are not limited to, T3, T4, T3 or T4-agarose, polymeric analogs of T3, T4, 3,5-dimethyl-4-(4'-hydroxy-3'-isopropylbenzyl)-phenoxy acetic acid (GC-1), or DITPA. Anti-angiogenic agents of the present invention include thyroid hormone antagonists, analogs, and derivatives either alone or in covalent or non-covalent conjugation with polymers. Examples of such anti-angiogenic thyroid hormone antagonists include, but are not limited to, TETRAC, TRIAC, XT 199, and mAb LM609.

Examples of representative thyroid hormone agonists, antagonists, analogs and derivatives are shown below, and are also shown in FIG. 20, Tables A-D. Table A shows T2, T3, T4, and bromo-derivatives. Table B shows alanyl side chain modifications. Table C shows hydroxy groups, diphenyl ester linkages, and D-configurations. Table D shows tyrosine analogs. The formulae of some of the representative compounds are illustrated below.

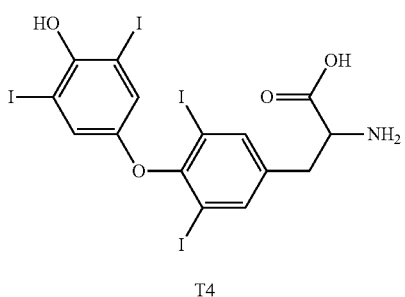

T4

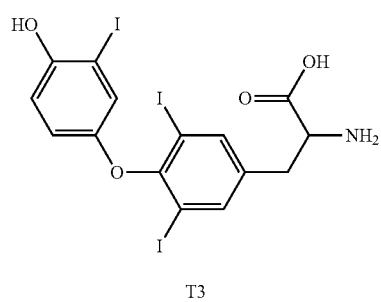

T3

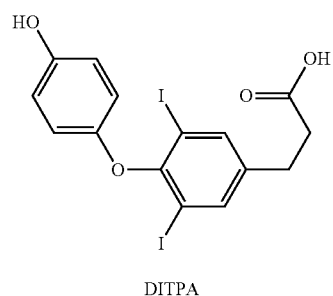

DITPA

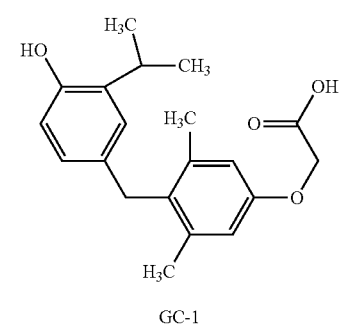

GC-1

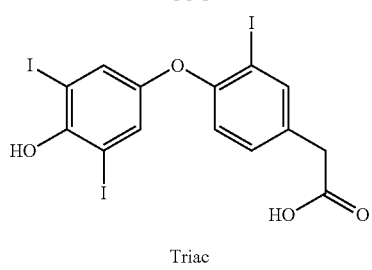

Triac

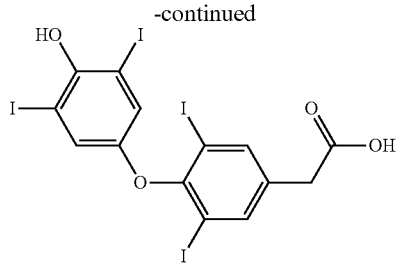

Tetrac

Polymer Conjugations

Polymer conjugations are used to improve drug viability. While many old and new therapeutics are well-tolerated, many compounds need advanced drug discovery technologies to decrease toxicity, increase circulatory time, or modify biodistribution. One strategy for improving drug viability is the utilization of water-soluble polymers. Various water-soluble polymers have been shown to modify biodistribution, improve the mode of cellular uptake, change the permeability through physiological barriers, and modify the rate of clearance through the body. To achieve either a targeting or sustained-release effect, water-soluble polymers have been synthesized that contain drug moieties as terminal groups, as part of the backbone, or as pendent groups on the polymer chain.

Representative compositions of the present invention include thyroid hormone or analogs thereof conjugated to polymers. Conjugation with polymers can be either through covalent or non-covalent linkages. In preferred embodiments, the polymer conjugation can occur through an ester linkage or an anhydride linkage. An example of a polymer conjugation through an ester linkage using polyvinyl alcohol is shown in FIG. 17. In this preparation commercially available polyvinyl alcohol (or related co-polymers) can be esterified by treatment with the acid chloride of thyroid hormone analogs, including the acid chloride form. The hydrochloride salt is neutralized by the addition of triethylamine to afford triethylamine hydrochloride which can be washed away with water upon precipitation of the thyroid hormone ester polymer form for different analogs. The ester linkage to the polymer may undergo hydrolysis in vivo to release the active pro-angiogenesis thyroid hormone analog.

An example of a polymer conjugation through an anhydride linkage using acrylic acid ethylene co-polymer is shown in FIG. 18. This is similar to the previous polymer covalent conjugation, however, this time it is through an anhydride linkage that is derived from reaction of an acrylic acid co-polymer. This anhydride linkage is also susceptible to hydrolysis in vivo to release thyroid hormone analog. Neutralization of the hydrochloric acid is accomplished by treatment with triethylamine and subsequent washing of the precipitated polyanhydride polymer with water removes the triethylamine hydrochloride byproduct. This reaction will lead to the formation of Thyroid hormone analog acrylic acid co-polymer+triethylamine. Upon in vivo hydrolysis, the thyroid hormone analog will be released over time that can be controlled plus acrylic acid ethylene Co-polymer.

Another representative polymer conjugation includes thyroid hormone or its analogs conjugated to polyethylene glycol (PEG). Attachment of PEG to various drugs, proteins and liposomes has been shown to improve residence time and decrease toxicity. PEG can be coupled to active agents through the hydroxyl groups at the ends of the chains and via other chemical methods. PEG itself, however, is limited to two active agents per molecule. In a different approach, copolymers of PEG and amino acids were explored as novel biomaterials which would retain the biocompatibility properties of PEG, but which would have the added advantage of numerous attachment points per molecule and which could be synthetically designed to suit a variety of applications.

A variety of synthetic, natural and biopolymeric origin side groups with efficient biodegradable backbone polymers can be conjugated to thyroid hormone analogs. Poly alkyl glycols, polyesters, poly anhydride, poly saccharide, and poly amino acids are available for conjugation. Below are representative examples of conjugated thyroid hormone analogs.

Polymer Conjugate Structures from Natural, Synthetic and Polypeptide Polymer Chain.

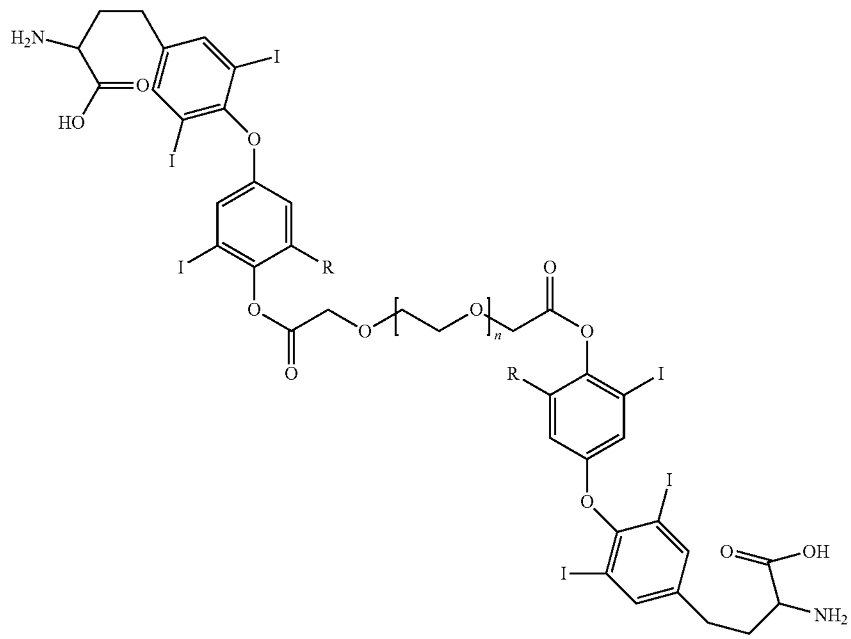

n=chain length

R=H, Bifunctional PEG-linked-T3

R=I, Bifunctional PEG-linked-T4

PEG Based Thyroid Compounds Polymer Conjugated Delivery Systems

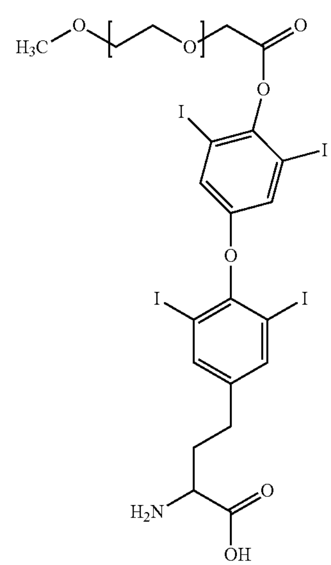

Methoxy-PEG-Linked-T4 Thyroid Product's Polymer Conjugate

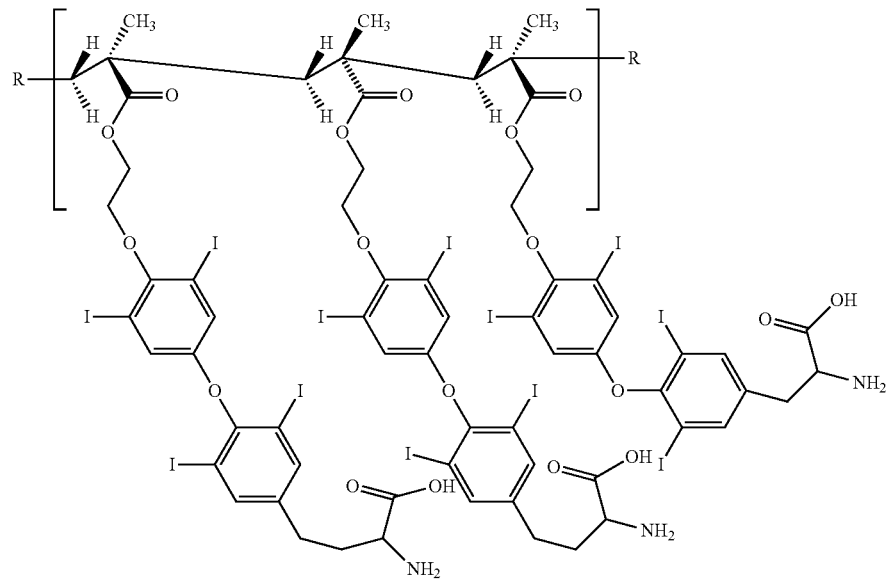

R=Repeating unit of HEMA chain
Poly-(HEMA)-Linked-T4-Conjugate

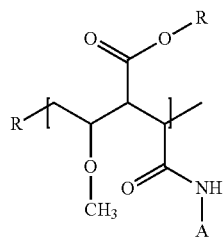

Poly-(vinyl-co-maleic anhydride) immobilized conjugate
A=Thyroid Constituent (conjugated through amine end)

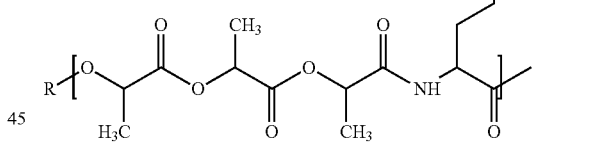

R=Repeating Chain Unit
A=Thyroid Constituent (conjugated through carboxyl end)
Poly-(lactide-co-lysine) immobilized conjugate

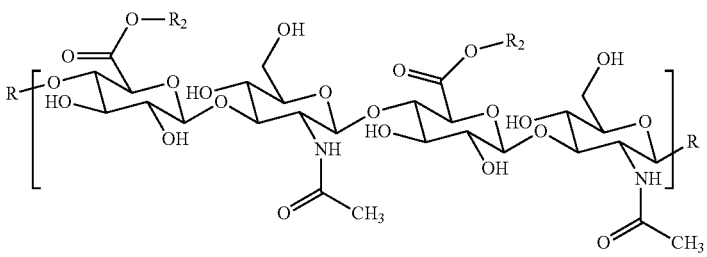

R1=Monomers of saccharide chain
R2=Thyroid Constituents

Hyaluronic Acid Bound Conjugates

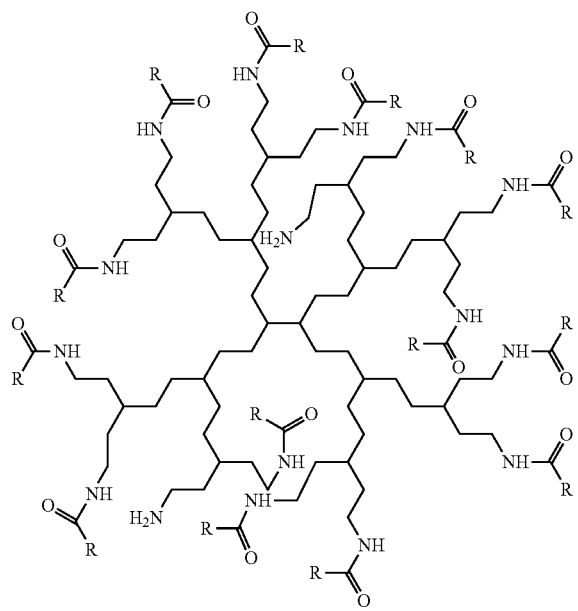

R=Thyroid Constituents T3/T4/DITPA/GC-1
Immobilized Thyroid Constituents on Multifunctional Polyamidoamine

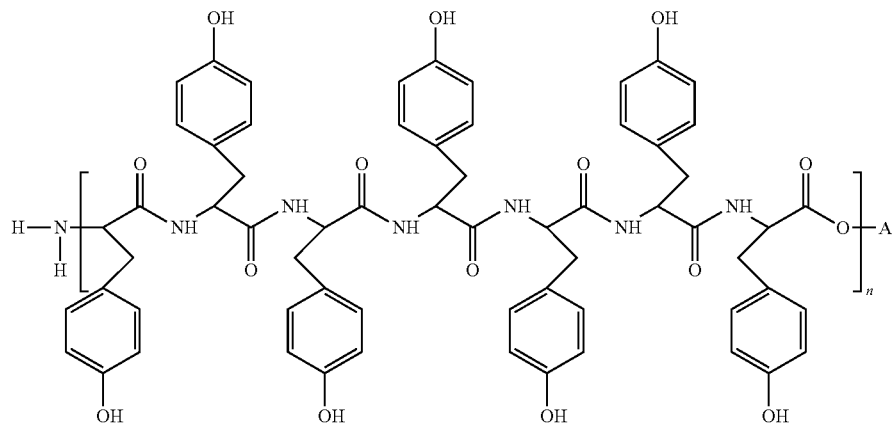

A=Conjugated Selected Thyroid Constituent
Mobilized Thyroid Polypeptide Conjugate Biodegradable and biocompatible polymers have been designated as probable carriers for long term and short time delivery vehicles including non hydrolysable polymeric conjugates. PEGs and PEOs are the most common hydroxyl end polymers with a wide range of molecular weights to choose for the purpose of solubility (easy carrier mode), degradation times and ease of conjugation. One end protected Methoxy-PEGs will also be employed as a straight chain carrier capable of swelling and thereby reducing the chances of getting protein attached or stuck during the subcellular transportation. Certain copolymers of ethylene and vinyl acetate, i.e. EVAc which have exceptionally good biocompatibility, low crystallinity and hydrophobic in nature are ideal candidate for encapsulation mediated drug delivery carrier.

Polymers with demonstrated high half-life and in-system retention properties will be undertaken for conjugation purpose. Among the most common and recommended biodegradable polymers from lactic and glycolic acids will be used. The copolymers of L-lactide, and L-lysine is useful because of its availability of amine functional groups for amide bond formation and this serves as a long of hydrophilic and hydrophobic nature. Following is a list of polymer conjugates within the scope of the present invention (Table 9).

TABLE 9

Library of Designated Polymer Conjugates for Possible Preparation based on Chemical Class Reactivities & Stability Data.

| Sr. No. | Polymer | Properties (H Hydrolysable, NH Non Hydrolysable, RR Retarded Release) |
|---|---|---|
| 1 | PEG | H |
| 2 | m-PEG | H |
| 3 | PVA | Hydrophilic, H |
| 4 | PLLA | Hydrophilic, H |
| 5 | PGA | Hydrophilic, H |
| 6 | Poly L-Lysine | NH |
| 7 | Human Serum Albumin | Protein, NH |
| 8 | Cellulose Derivative (Carbomethoxy/ethyl/hydroxypropyl) | Polysaccharide, RR |
| 9 | Hyaluronic Acid | Polysaccharide, RR |
| 10 | Folate Linked Cyclodextrin/Dextran | RR |
| 11 | Sarcosine/Amino Acid spaced Polymer | RR |
| 12 | Alginate/Carrageenan | Polysaccharide, RR |
| 13 | Pectin/Chitosan | Polysaccharide, RR |
| 14 | Dextran | Polysaccharide, RR |
| 15 | Collagen | Protein, NH |
| 16 | Poly amine | Aminic, NH |
| 17 | Poly aniline | Aminic, NH |
| 18 | Poly alanine | Peptidic, RR |
| 19 | Polytryptophan | Peptidic, NH/RR |
| 20 | Polytyrosine | Peptidic, NH/RR |

Another representative polymer conjugation includes thyroid hormone or its analogs in non-covalent conjugation with polymers. This is shown in detail in FIG. 19. A preferred non-covalent conjugation is entrapment of thyroid hormone or analogs thereof in a polylactic acid polymer. Polylactic acid polyester polymers (PLA) undergo hydrolysis in vivo to the lactic acid monomer and this has been exploited as a vehicle for drug delivery systems in humans. Unlike the prior two covalent methods where the thyroid hormone analog is linked by a chemical bond to the polymer, this would be a non-covalent method that would encapsulate the thyroid hormone analog into PLA polymer beads. This reaction will lead to the formation of Thyroid hormone analog containing PLA beads in water. Filter and washing will result in the formation of thyroid hormone analog containing PLA beads, which upon in vivo hydrolysis hydrolysis will lead to the generation of controlled levels of thyroid hormone plus lactic acid.

A. Polymer Conjugate Synthesis of TRs Agonist or Antagonist and Nanoparticles

There are two functional groups in the TRs agonist or antagonist molecules: a carboxylic acid and a hydroxyl group. To synthesize the TRs agonist or antagonist/polymer conjugates, the reaction site can be either of the two. Possible agonists and antagonists within the scope of the present invention are shown in the tables below. Two possible synthesis routes are described below:

1) With the carboxylic acid group located on the α, β or γ position relative to the inner phenyl ring. The acid group can be activated and then reacted with hydroxyl and amino groups to form ester and amide. The candidate polymers include PVA, PEG-NH$_2$, poly(lysine) and related polymers. The schematic synthesis route is shown in Sketch 1A.

2) The hydroxyl group located on the outer phenyl is shown in Sketch 2A.

Sketch 1A: Schematic Route of TRs agonist or antagonist/Polymer Conjugates Synthesis via the Carboxylic acid Group

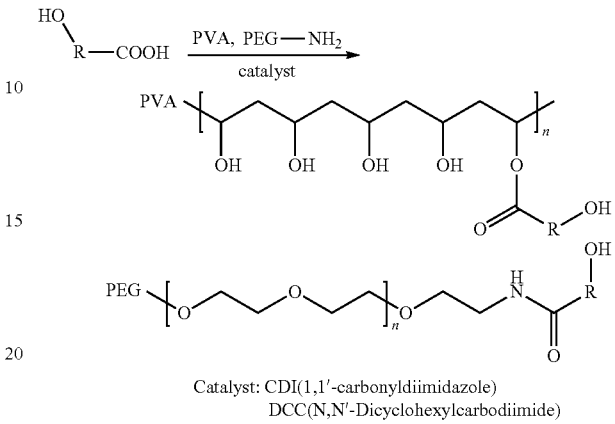

Catalyst: CDI(1,1'-carbonyldiimidazole)
DCC(N,N'-Dicyclohexylcarbodiimide)

Sketch 2A: Schematic Route of TRs agonist or antagonist/Polymer Conjugates Synthesis via Hydroxyl Group

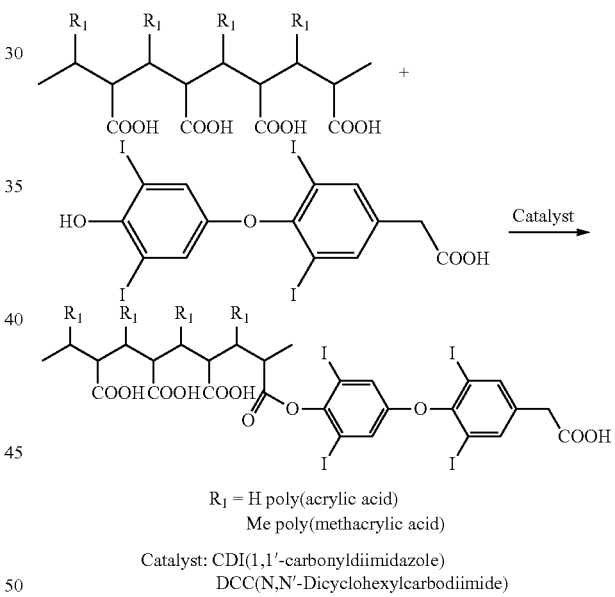

R$_1$ = H poly(acrylic acid)
Me poly(methacrylic acid)

Catalyst: CDI(1,1'-carbonyldiimidazole)
DCC(N,N'-Dicyclohexylcarbodiimide)

Representative thyroid agonists (Pro-angiogenic) within the scope of the present invention include T3, T4, DITPA, GC-1 and analogs and derivatives thereof. Illustrative embodiments are shown below.

| Number | R |
|---|---|
| 1 | 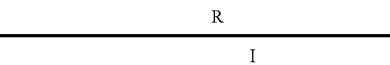 |

| Number | R |
|---|---|
| 2 | 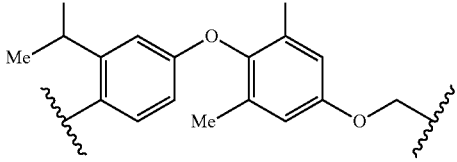 |
| 3 | 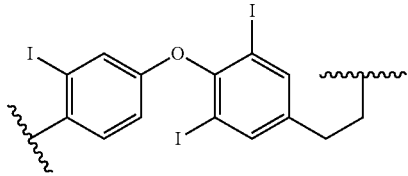 [SMILES: *CCc1cc(I)c(Oc2ccc(*)c(I)c2)c(I)c1] |
| 4 | 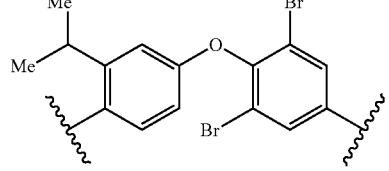 |
| 5 | 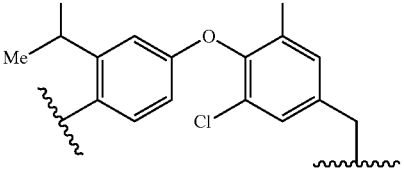 |
| 6 | 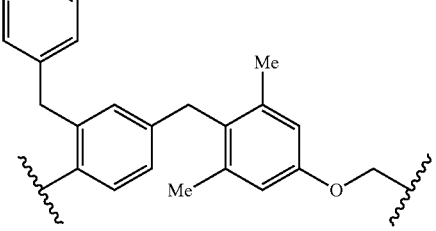 |
Representative thyroid antagonists (anti-angiogenic) within the scope of the present invention are shown below.
| Number | Structure | Code |
|---|---|---|
| A | 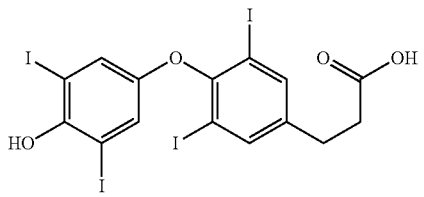 [SMILES: O=C(O)CCc1cc(I)c(Oc2cc(I)c(O)c(I)c2)c(I)c1] | Tetrac |
| B | 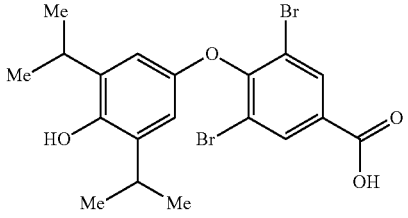 [SMILES: CC(C)c1cc(Oc2c(Br)cc(C(=O)O)cc2Br)cc(C(C)C)c1O] | DIBRT |
| C | 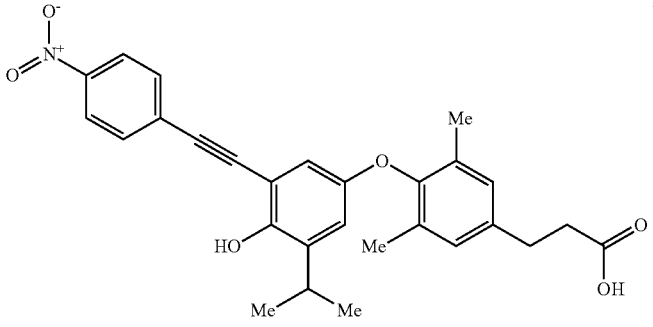 [SMILES: Cc1cc(CCC(=O)O)cc(C)c1Oc1cc(C#Cc2ccc([N+](=O)[O-])cc2)c(O)c(C(C)C)c1] | NH-3 |

-continued

| Number | Structure | Code |
|---|---|---|
| D | 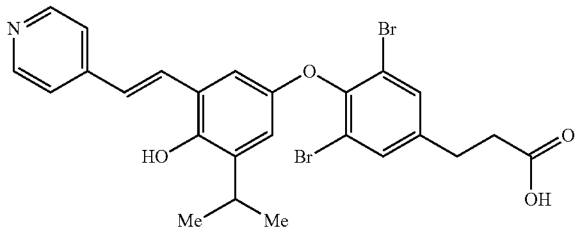 [SMILES: CC(C)c1cc(Oc2c(Br)cc(CCC(=O)O)cc2Br)cc(/C=C/c2ccncc2)c1O] | |
| E | 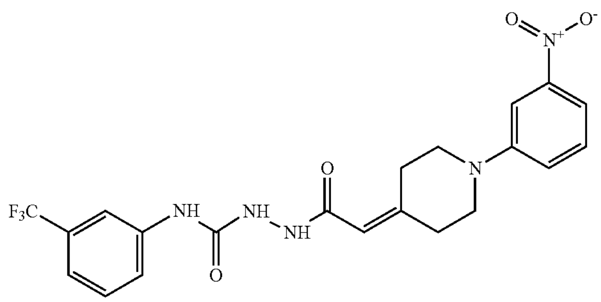 [SMILES: O=C(C=C1CCN(c2cccc([N+](=O)[O-])c2)CC1)NNC(=O)Nc1cccc(C(F)(F)F)c1] | 1-850 |
| F | 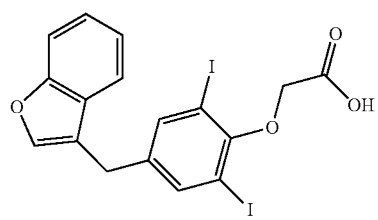 [SMILES: O=C(O)COc1c(I)cc(Cc2coc3ccccc23)cc1I] | |
| G | 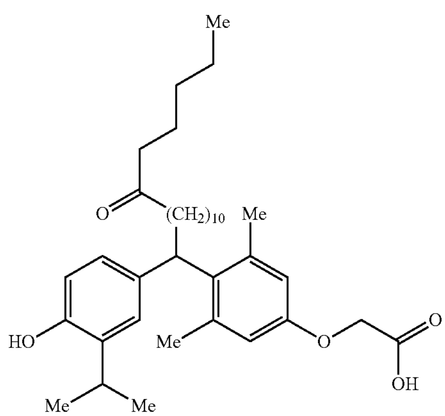 | |
| H | 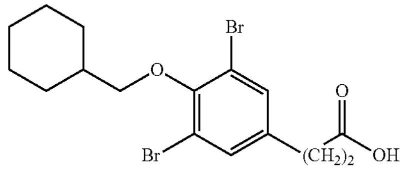 | |

B. Polymer Conjugate Synthesis of T4 and Nanoparticles Thereof

There are three functional groups in T4 molecules: one carboxylic acid group, one amine group and one hydroxyl group.

To synthesize the T4/polymer conjugates, the reaction site can be any one of the three.

1) With carboxylic acid group. Acid group can be activated and reaction with hydroxyl and amine group to form ester and amide. Due to the high reactivity of amine group in the T4, the amine group should be protected before the conjugating reaction, and then de-protected reaction. Otherwise, the self polymerization will form the T4 oligomers. The candidate polymers include PVA, PEG-NH$_2$, poly (lysine) and related polymers. The Schematic synthesis route is shown in Sketch 1B.

2) With the amine group. The amine group can reacted with polymer with activated carboxylic acid or with halogen group. If the polymer has a large amount of excess of activated acid group, the reaction can go through directly. Poly (methylacrylic acid) and poly (acrylic acid) can be used in this way. The scheme is shown in Sketch 2B.

3) With the hydroxyl group. Due to the existence of a higher reactive amine group, the direct reaction of T4 with a polymer with carboxylic acid is difficult. This amine group must be protected before the reaction and de-protected after the conjugating reaction. The common protected group can be acetate (Ac) or BOC group. The scheme is shown in Sketch 3B.

Sketch 1B: Schematic Route of T4/Polymer Conjugates Synthesis via Carboxylic Acid Group

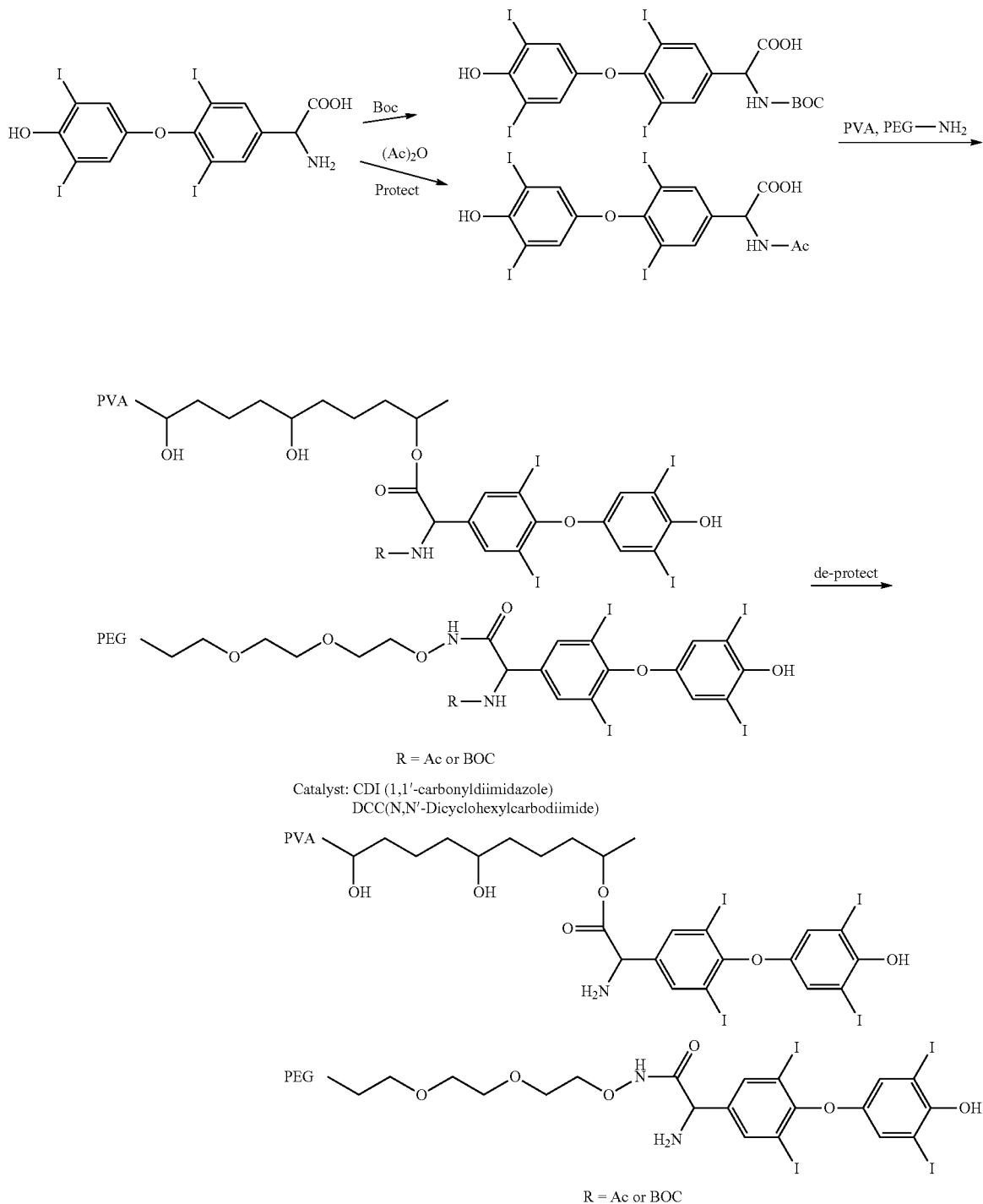

Sketch 2B: Schematic Route of T4/Polymer Conjugates Synthesis via Amine Group

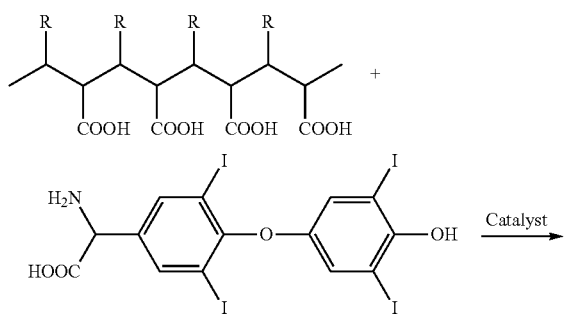

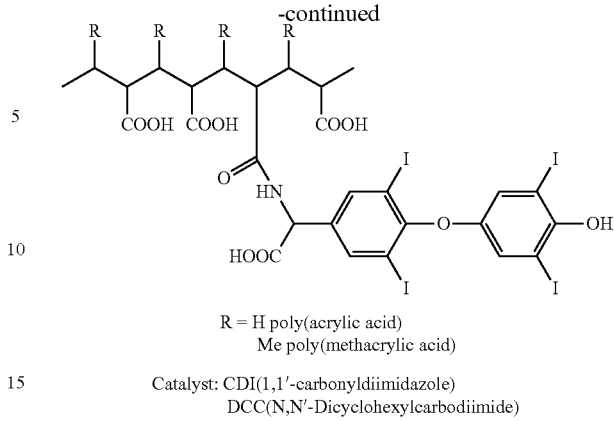

R = H poly(acrylic acid)
Me poly(methacrylic acid)

Catalyst: CDI(1,1'-carbonyldiimidazole)
DCC(N,N'-Dicyclohexylcarbodiimide)

Sketch 3B: Schematic Route of T4/Polymer Conjugates Synthesis via Hydroxyl Group

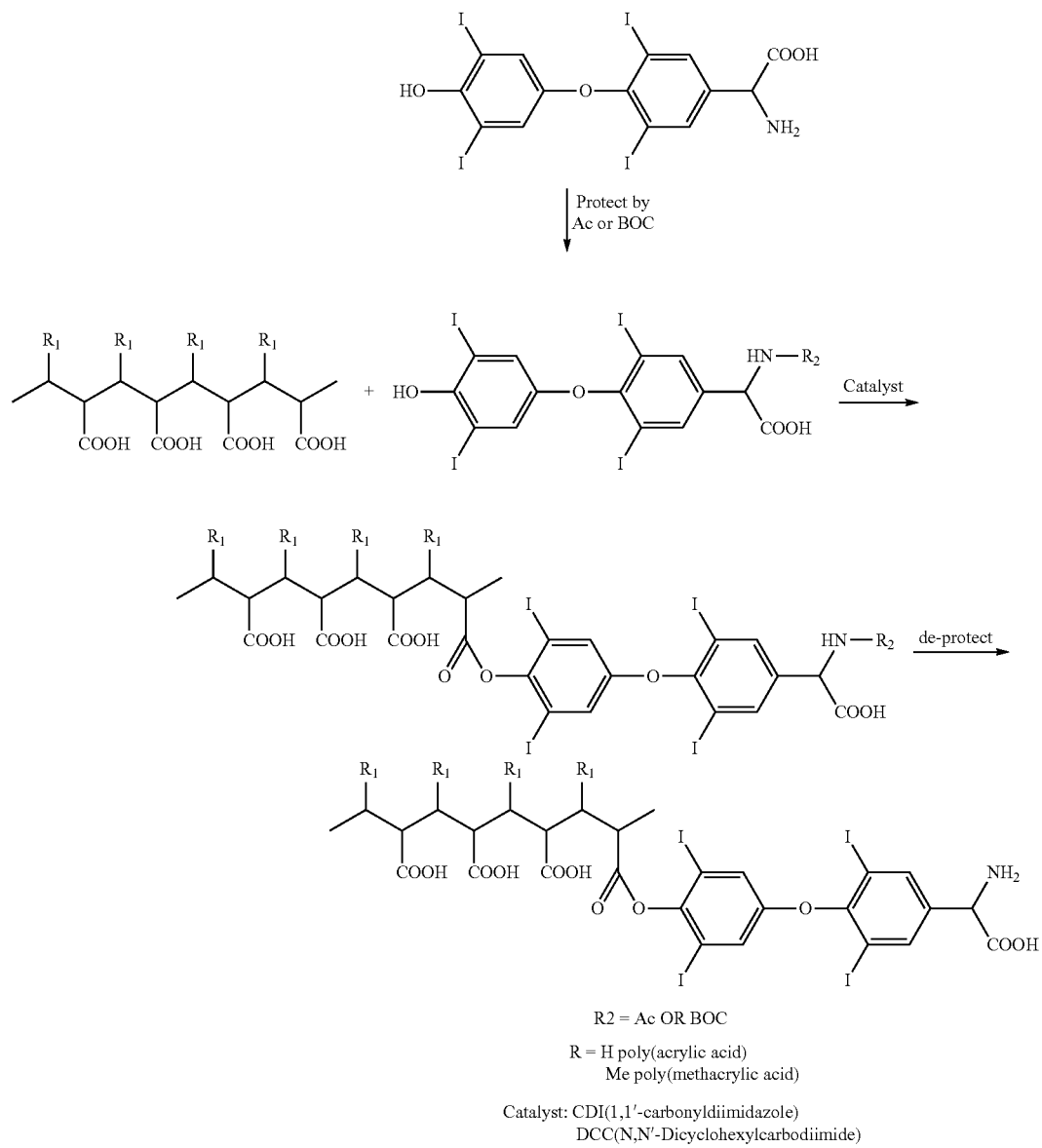

R2 = Ac OR BOC

R = H poly(acrylic acid)
Me poly(methacrylic acid)

Catalyst: CDI(1,1'-carbonyldiimidazole)
DCC(N,N'-Dicyclohexylcarbodiimide)

It is contemplated that the T4 polymer conjugates, nanopolymers and nanoparticles described herein can be used in a variety of indications including, but not limited to, aneurism, surgery (including dental, vascular, or general), heart attack (e.g., acute myocardial infarction) to be delivered using devices such as a defibrillator and other means, topical applications such as ointments, cream, spray, or sheets (such as for skin applications), or immobilized on a stent or other medical device and implanted at the tissue site for sustained size the GC-1/polymer conjugates, the reaction site can be anyone of the two.

1) With carboxylic acid group. Acid group can be activated and react with hydroxyl and amine group to form ester and amide. The candidate polymers include PVA, PEG-NH$_2$, poly (lysine), poly (arginine) and related polymers. The Schematic synthesis route is shown in Sketch 1C.

2) With the hydroxyl group. The scheme is shown in Sketch 2C.

Sketch 1C: Schematic Route of GC-1/Polymer Conjugates Synthesis via Carboxylic acid Group.

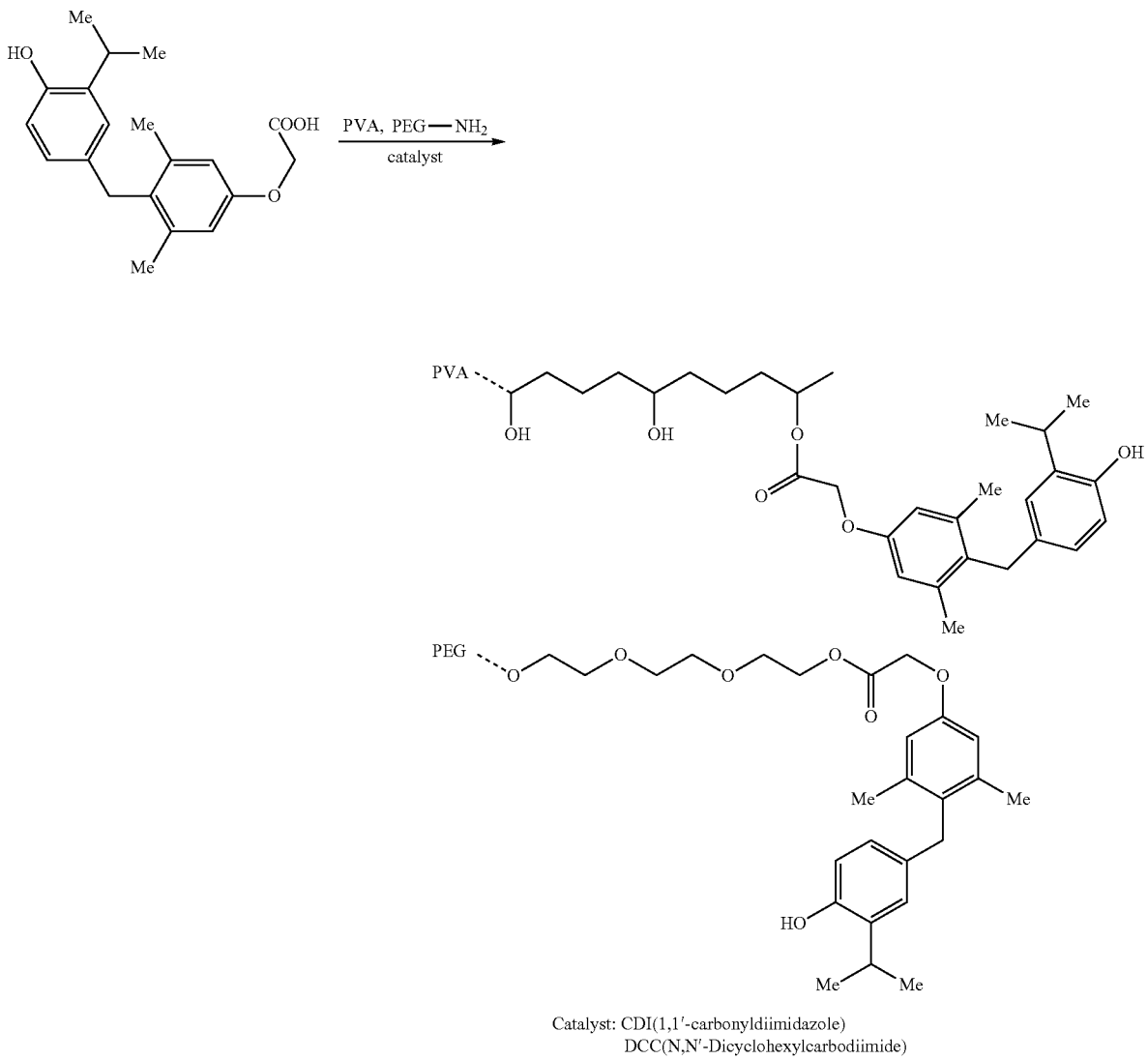

Catalyst: CDI(1,1'-carbonyldiimidazole)
DCC(N,N'-Dicyclohexylcarbodiimide)

local delivery in myocardial infarction, stroke, or peripheral artery disease patients to achieve collateral artery formation over an extended period of time ranging from weeks to months.

C. Polymer Conjugate Synthesis of GC-1 and Nanoparticles Thereof

There are two functional groups in GC-1 molecules: one carboxylic acid group, and one hydroxyl group. To synthe- Sketch 2C: Schematic Route of GC-1/Polymer Conjugates Synthesis via Hydroxyl Group

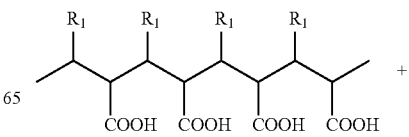

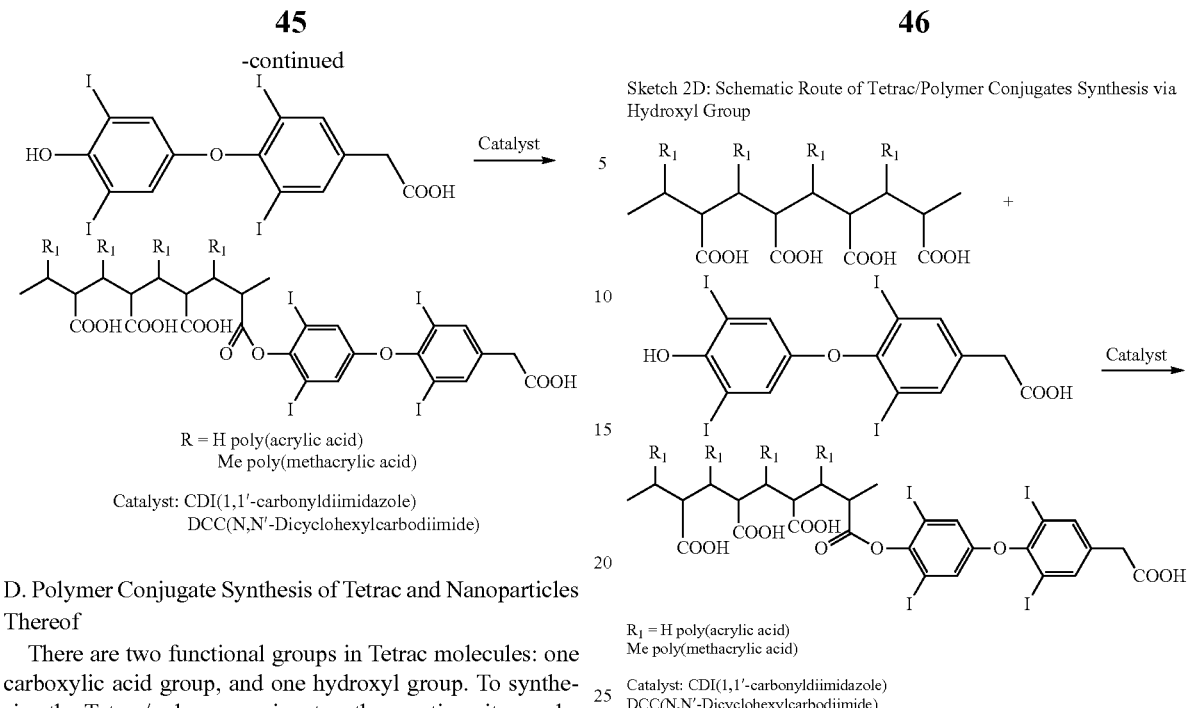

R = H poly(acrylic acid)
Me poly(methacrylic acid)

Catalyst: CDI(1,1'-carbonyldiimidazole)
DCC(N,N'-Dicyclohexylcarbodiimide)

D. Polymer Conjugate Synthesis of Tetrac and Nanoparticles Thereof

There are two functional groups in Tetrac molecules: one carboxylic acid group, and one hydroxyl group. To synthesize the Tetrac/polymer conjugates, the reaction site can be any one of the three.

1) With carboxylic acid group. Acid group can be activated and reaction with hydroxyl and amine group to form ester and amide. The candidate polymers include PVA, PEG-NH$_2$ poly (lysine) and related polymers. The Schematic synthesis route is shown in Sketch 1D.

2) The scheme with the hydroxyl group is shown in Sketch 2D.

Sketch 2D: Schematic Route of Tetrac/Polymer Conjugates Synthesis via Hydroxyl Group $R_1$ = H poly(acrylic acid)
Me poly(methacrylic acid)

Catalyst: CDI(1,1'-carbonyldiimidazole)
DCC(N,N'-Dicyclohexylcarbodiimide)

Still further, compositions of the present invention include thyroid hormone analogs conjugated to retinols (e.g., retinoic acid (i.e., Vitamin A), which bind to the thyroid hormone binding protein transthyretin ("TTR") and retinoic binding protein ("RBP"). Thyroid hormone analogs can also be conjugated with halogenated stilbesterols, alone or in combination with retinoic acid, for use in detecting and Sketch 1D: Schematic Route of Tetrac/Polymer Conjugates Synthesis via Carboxylic acid Group

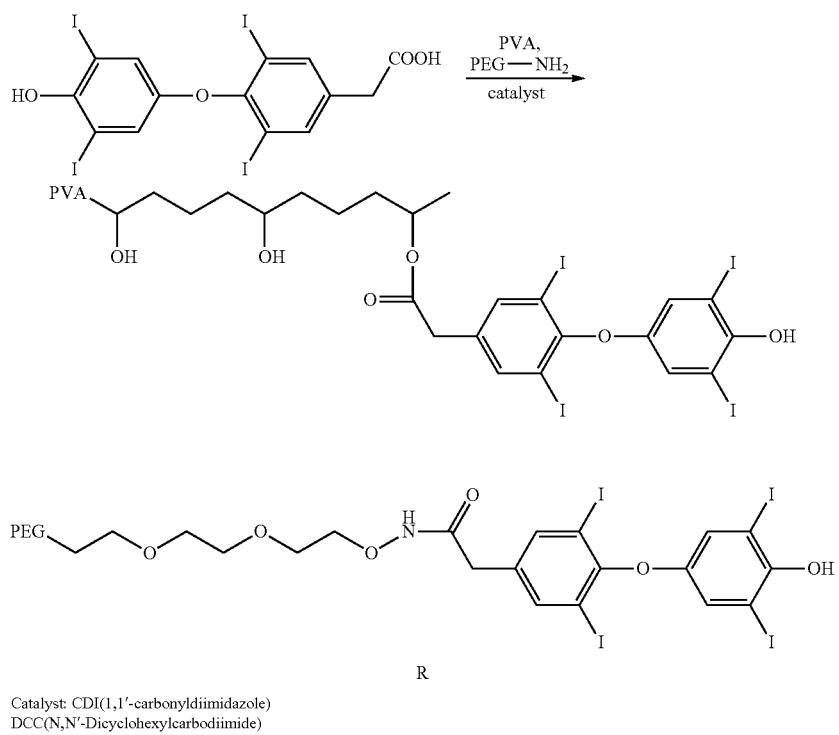

Catalyst: CDI(1,1'-carbonyldiimidazole)
DCC(N,N'-Dicyclohexylcarbodiimide)

suppressing amyloid plaque. These analogs combine the advantageous properties of T4-TTR, namely, their rapid uptake and prolonged retention in brain and amyloids, with the properties of halogen substituents, including certain useful halogen isotopes for PET imaging including fluorine-18, iodine-123, iodine-124, iodine-131, bromine-75, bromine-76, bromine-77 and bromine-82. Below are representative examples of thyroid hormone analogs conjugated to retinols and halogenated stilbestrols.

E. Retinoic Acid Analogs

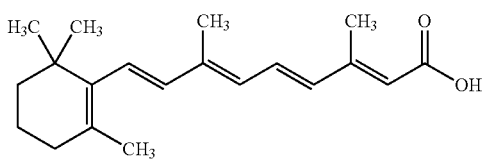 [SMILES: CC1=C(/C=C/C(C)=C/C=C/C(C)=C/C(=O)O)C(C)(C)CCC1]

Thyroid Hormone Analog Conjugated with Retinoic Acid

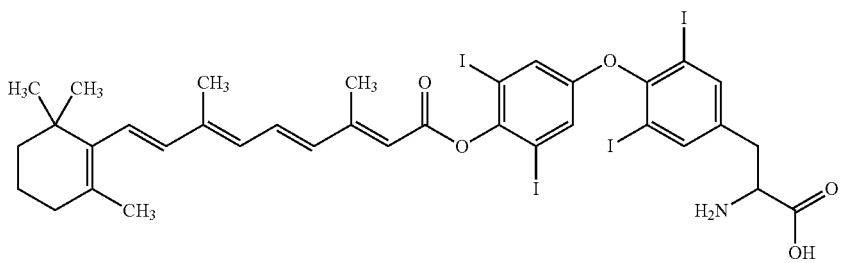

T4-Retinoic Acid

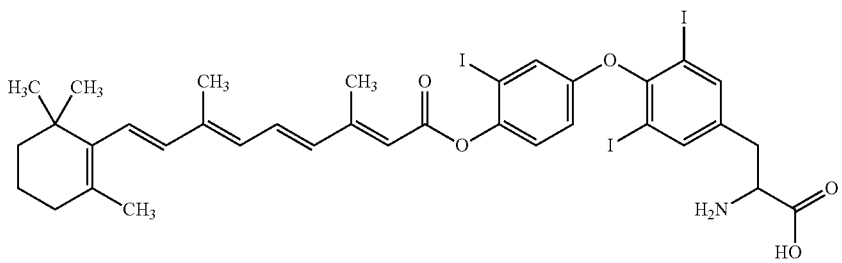

T3-Retinoic Acid

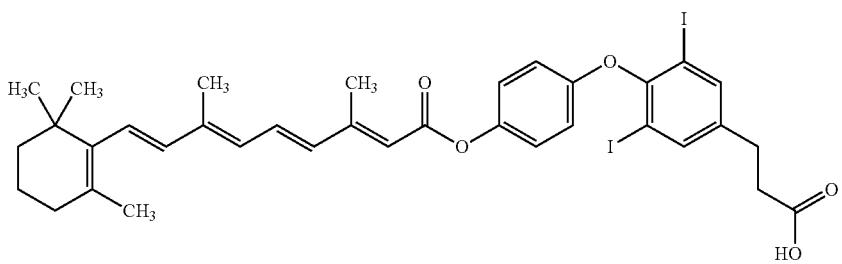

DITPA-Retinoic Acid

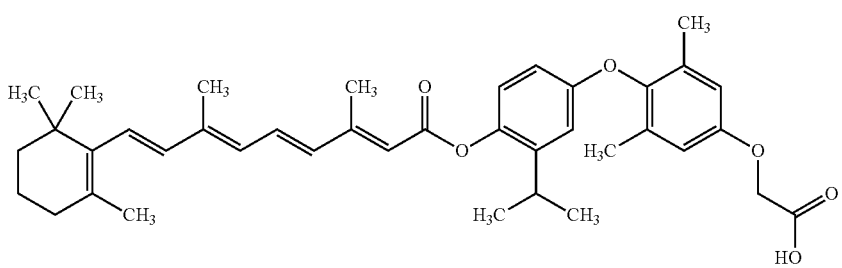

GC-1-Retinoic Acid

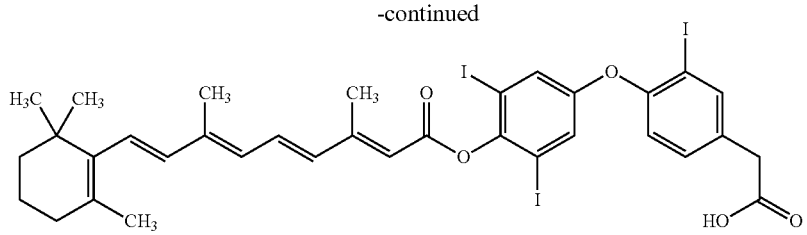

TRIAC-Retinoic Acid

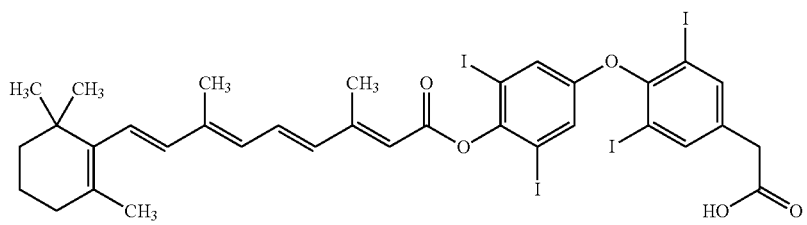

TETRAC-Retinoic Acid

Halogenated Stilbestrol Analogs

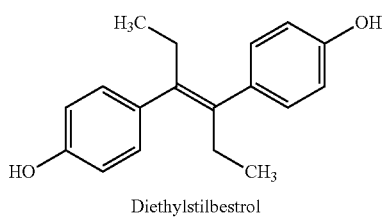 [SMILES: CC/C(=C(/CC)c1ccc(O)cc1)c1ccc(O)cc1]

Diethylstilbestrol

T4 Analogs, Halogenated Stilbesterols, and Retinoic Acid

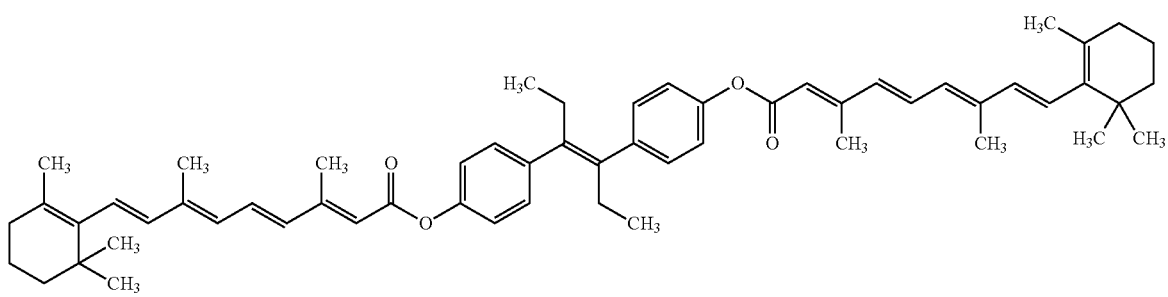

Retinoic Acid-Diethylstilbestrol-Retinoic Acid

Nanoparticles

Furthermore, nanotechnology can be used for the creation of useful materials and structures sized at the nanometer scale. One drawback with biologically active substances is fragility. Nanoscale materials can be combined with such biologically active substances to dramatically improve the durability of the substance, create localized high concentrations of the substance and reduce costs by minimizing losses. Therefore, additional polymeric conjugations include nano-particle formulations of thyroid hormones and analogs thereof. In such an embodiment, nano-polymers and nano-particles can be used as a matrix for local delivery of thyroid hormone and its analogs. This will aid in time controlled delivery into the cellular and tissue target.

The present invention provides nanoparticle formulations of thyroid hormone analogs containing hydrophobic anti-oxidant, anti-inflammatory, and anti-angiogenesis compounds. This invention also provides sustained release and long residing ophthalmic formulation, so that the release of the entrapped drug can be controlled and the process of preparing the same.

Within the scope of the present invention are nanoparticulate thyroid hormone analogues ($T_4$, T3, GC-1, DITPA, and tetrac) that cannot gain access to the cell interior and whose activities must therefore be limited to the integrin receptor. The nanoparticulate hormone analogues are polylysyl glycolic acid (PLGA) derivatives, either esters or the more stable ether-bond formulations. Agarose-$T_4$ is a model of the nanoparticulate that we have shown to be fully active at the integrin receptor. The reformulated hormone analogues will not express intracellular actions of the hormone and thus if absorbed into the circulation will not have systemic thyroid hormone analogues actions.

As used herein, the term "nanoparticle" refers to particles between about 1 nm and less than 1000 nm in diameter. In suitable embodiments, the diameter of the nanoparticles of the present invention will be less than 500 nm in diameter, and more suitably less than about 250 nm in diameter. In certain such embodiments, the nanoparticles of the present invention will be between about 10 nm and about 200 nm, between about 30 nm and about 100 nm, or between about 40 nm and about 80 nm in diameter. As used herein, when referring to any numerical value, "about" means a value of ±10% of the stated value (e.g. "about 100 nm" encompasses a range of diameters from 90 nm to 110 nm, inclusive).

In accordance with the present invention, there is provided a nanoparticle conjugate comprising a nanoparticle conjugated to a plurality of thyroid hormone analogs or polymer conjugates. Thyroid hormone analogs which can be the basis of nanoparticles include, but are not limited to, T3, T4, DITPA, GC-1, and Tetrac. A key element in the nanoparticle formation is the linkage bridge between the thyroid hormone molecule and the nanoparticles. The thyroid hormone analog is conjugated to the nanoparticle by means of an ether (—O—) or sulfhydryl linkage (sulfur (—S—) through the alcohol moiety of the thyroid hormone analog molecule. Conjugations through the alcohol moiety have more activity than conjugations through the COOH moiety of the thyroid hormone analog molecule. The NH2 group of thyroid hormone analogs, such as T3 and T4, can also be blocked with a protecting group (R group). Suitable R groups within the scope of the present invention include BOC, acetyl, methyl, ethyl, or isopropyl. For T4 unmodified, R═H. Additionally, when the thyroid hormone is T4 or T3 with a protecting group at the NH2, the suitable protecting group at the $NH_2$ of T4 or T3 can include N-Methyl, N-Ethyl, N-Triphenyl, N-Propyl, N-Isopropyl, N-tertiary butyl and other functional groups.

The nanoparticle may have a diameter in the range of about 1 to <1000 nm. Nanoparticles within the present invention may have up to approximately 100 molecules of thyroid hormone analogs per nanoparticle. The ratio of thyroid hormone molecules per nanoparticle ranges from a ratio of 1 thyroid hormone molecule per 1 nanoparticle (shown also as 1:1) up to 100 thyroid hormone molecules per nanoparticle (shown also as 100:1). More preferably, the range is from 15:1-30:1 thyroid hormone analog molecules per nanoparticle, and more preferably from 20:1-25:1 thyroid hormone analog molecules per nanoparticle.

Suitable nanoparticles within the scope of the present invention include PEG-PLGA nanoparticles conjugated with T4, T3, DITPA, GC-1, or tetrac. Additionally, temozolomide can be encapsulated in PLGA nanoparticles. One of the major advantages of nanoparticles is its ability to co-encapsulate multiple numbers of encapsulating materials in it altogether. So, these PLGA nanoparticles also have the tremendous potential to co-encapsulate T4, T3, DITPA, GC-1, or Tetrac and temozolomide altogether. Furthermore, due to the presence of free —COOH group on the surface of the nanoparticles these nanoparticles can be conjugated to different targeting moieties and can be delivered to a desired site. In a preliminary study we were able to target few cell lines by using specific antibody attached to the Nanoparticles for tumor specific site directed delivery. Additional embodiments of nanoparticles within the resent invention include T4, T3, DITPA, GC-1, or tetrac collagen conjugated nanoparticles containing calcium phosphate; T4, T3, DITPA, GC-1, or tetrac conjugated with mono- or di-PEGOH via a stable ether linkage.

Furthermore, the Nanoparticles encapsulate the thyroid hormone agonists, partial agonists or antagonists inside the Nanoparticles or immobilized on the cell surface of the Nanoparticles via a chemical linkage. Representative embodiments of nanoparticles within the scope of the present invention are illustrated below.

A. Nanoparticles of TR Agonists and Antagonists
TRs Agonist or Antagonist Conjugated Nanopolymer Via an Ester Linkage

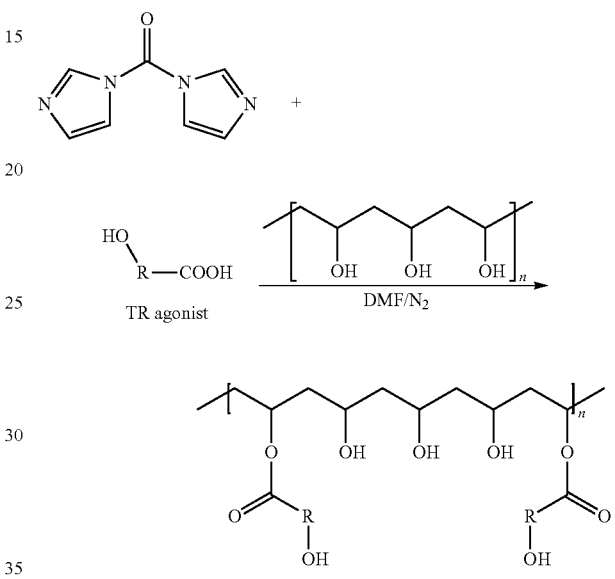

TRs Agonist or Antagonist Conjugated with Mono- or Di-PEGOH Via a Stable Ether Linkage

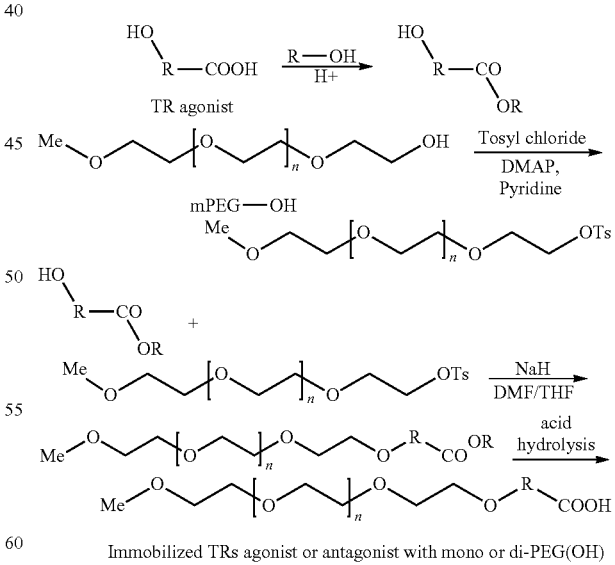

Immobilized TRs agonist or antagonist with mono or di-PEG(OH)

Another suitable nanoparticle embodiment is the preparation of TR agonists conjugated PEG-PLGA nanoparticles. Void nanoparticles will be prepared first. Amino-PEG-PLGA polymer will be chose to prepare the nanoparticles. The TH analog will be activated by using epichlorohydrin.

This epoxy activated TH agonist will react readily with amino terminated PEG-PLGA nanoparticles.

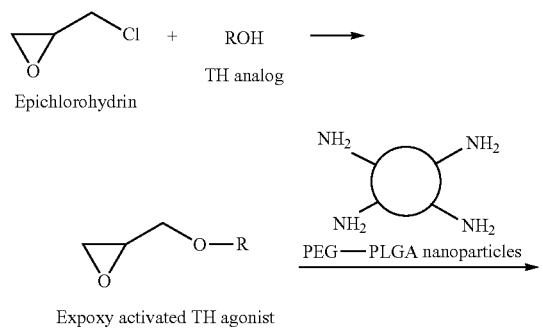

Epichlorohydrin / TH analog / Expoxy activated TH agonist / PEG—PLGA nanoparticles

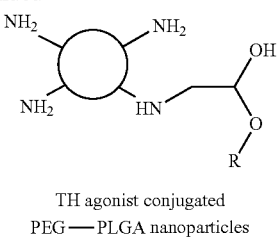

TH agonist conjugated PEG—PLGA nanoparticles

B. T4 Nanoparticles

Another suitable embodiment of a nanoparticle within the present invention includes T4 immobilized to mono or di-PEG-OH through a stable ether linkage, as shown below.

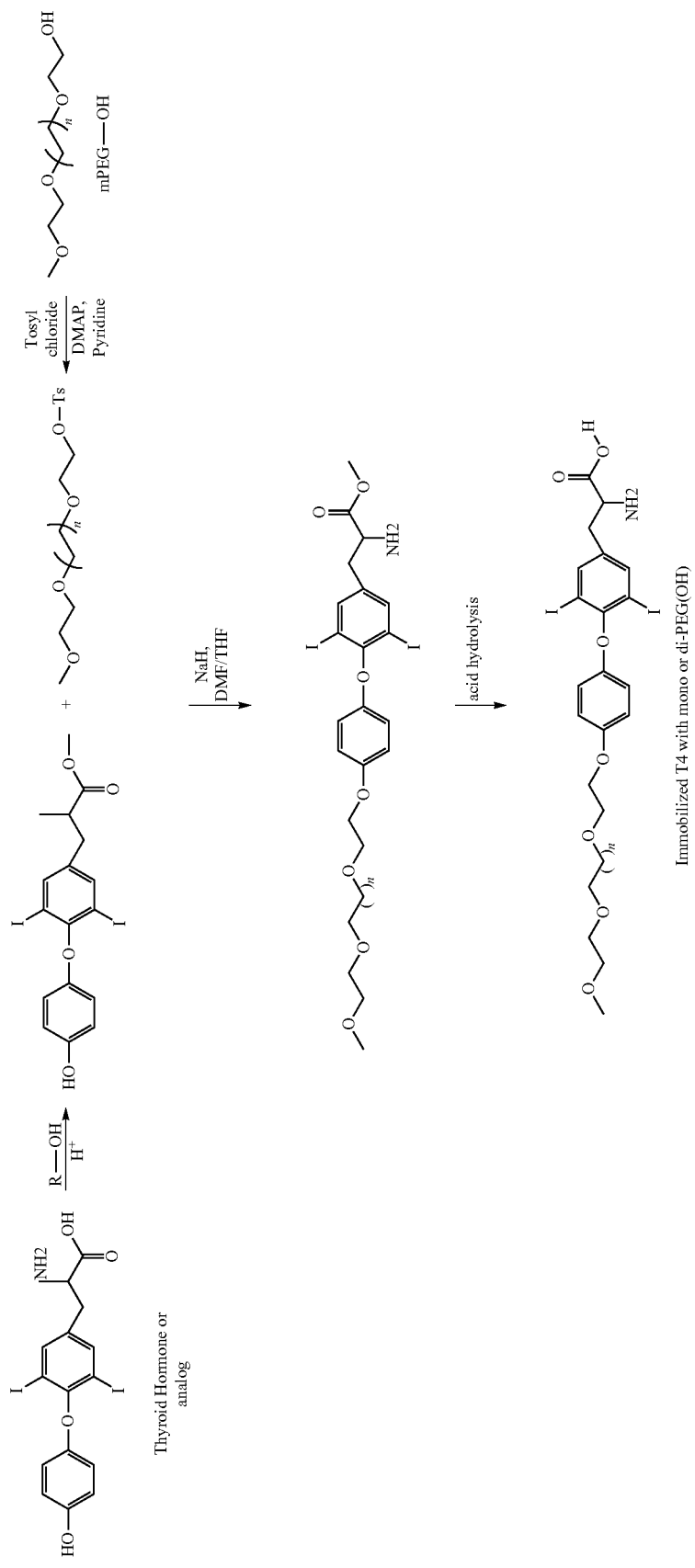

C. GC-1 Nanoparticles

A representative embodiment of a nanoparticle within the present invention includes also the encapsulation of GC-1 in PEG-PLGA Nanoparticles, conjugated via an ester linkage, as shown below.

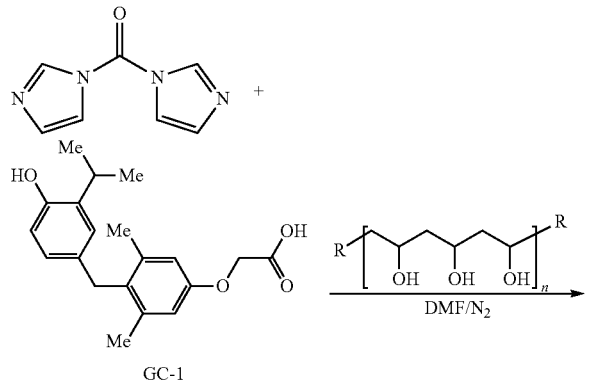

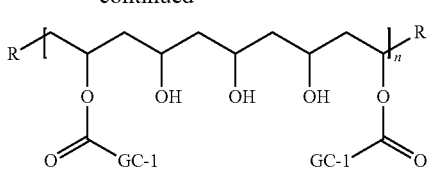

Another suitable embodiment of a nanoparticle within the present invention includes a GC-1 conjugate with mono- or di-PEGOH via a stable ether linkage, as shown below.

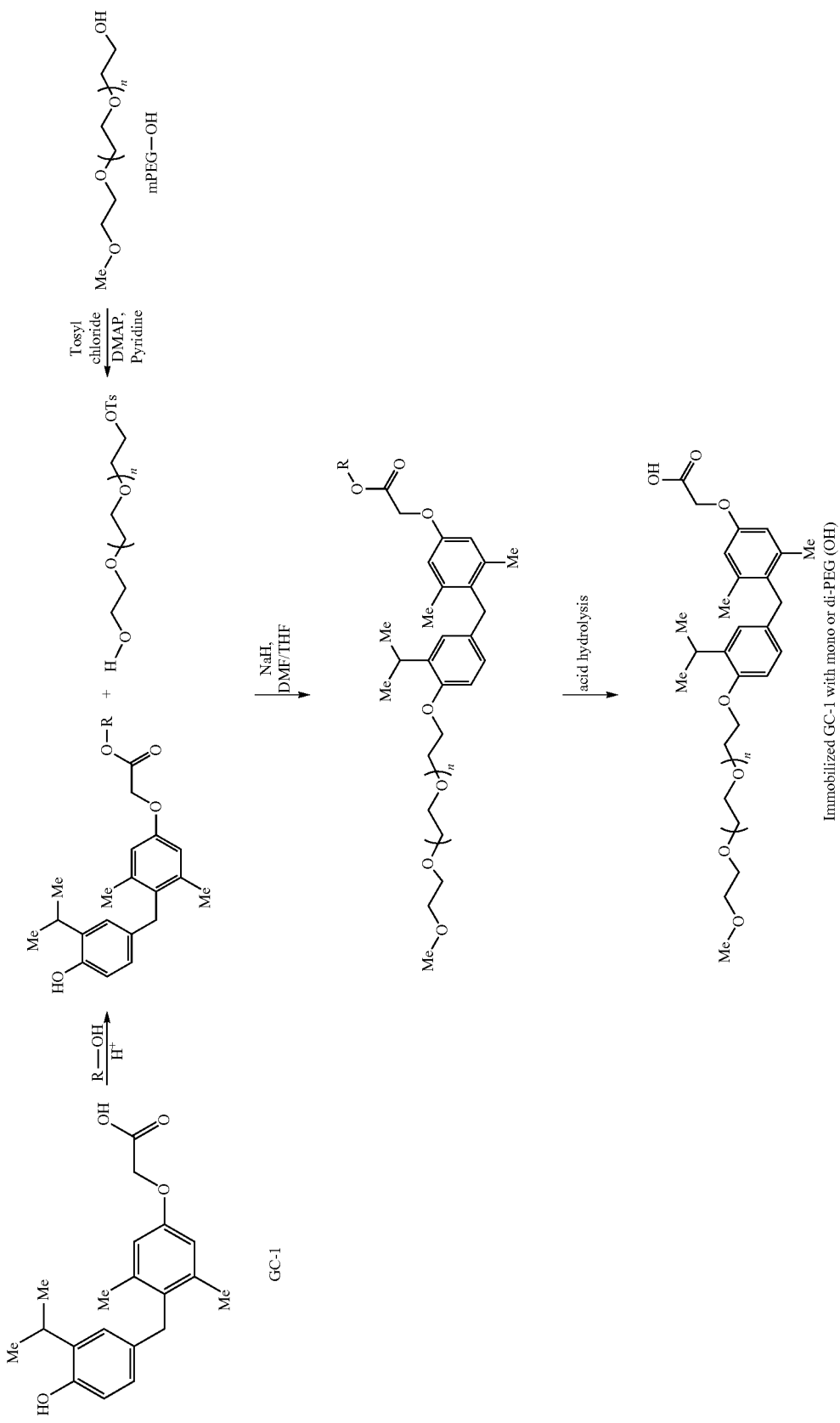

Another suitable embodiment of a nanoparticle within the present invention includes GC-1 conjugated PEG-PLGA nanoparticles. In this case void nanoparticles will be prepared first. Amino-PEG-PLGA polymer will be chosen to prepare the nanoparticles. GC-1 will be activated by using epichlorohydrin. This activated GC-1 will react readily with amino terminated PEG-PLGA nanoparticles, as shown below.

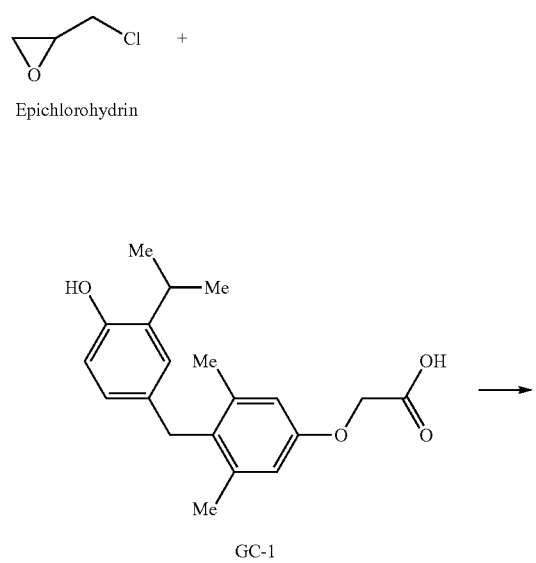

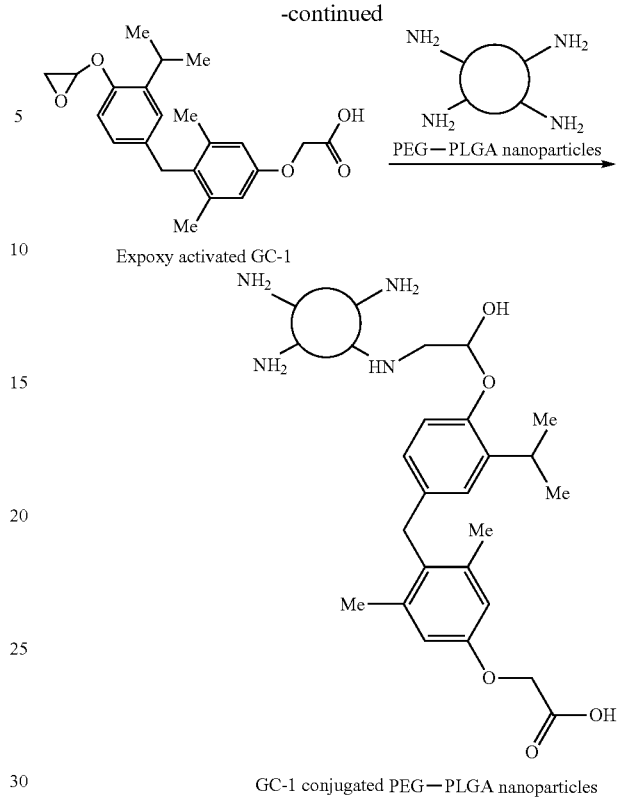

Additional GC-1 analogs Nanoparticles encapsulated or immobilized are shown below.

New Analogs of GC-1

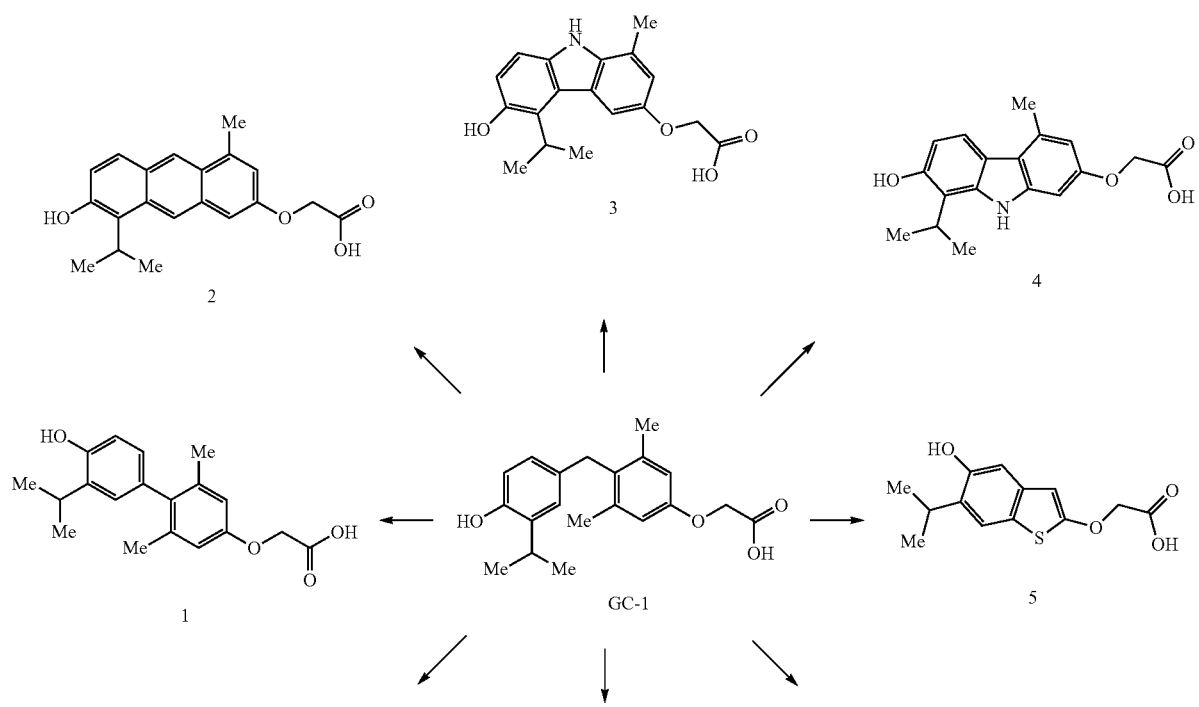

-continued

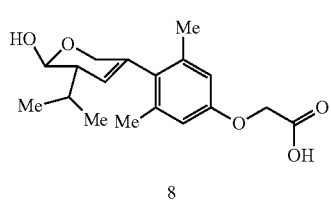

8

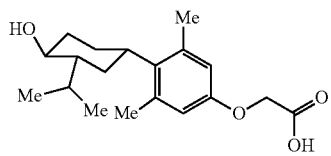

7

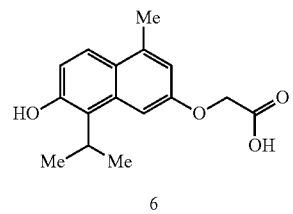

6

D. Tetrac Nanoparticles

Representative tetrac nanoparticles within the scope of the present invention are shown in FIGS. 30A-B, FIGS. 31A-B and FIG. 32.

Below is an additional representation of a Tetrac conjugated Nanopolymer via an ester linkage.

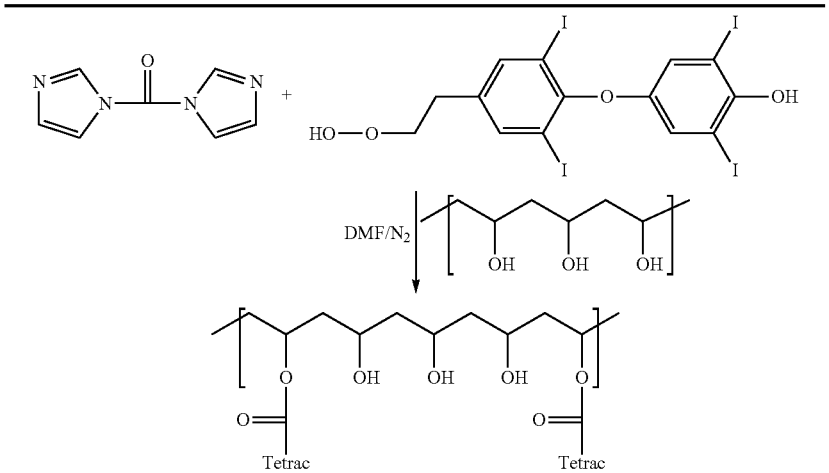

| Design of Experiments | | | | | | | |
|---|---|---|---|---|---|---|---|
| Chemicals | Formula | Mol. Wt | Amount (mg) | mmol | Volume (ml) | Loading % | Conc. |
| N,N'-carbonyldiimidazole | $C_7H_6N_4O$ | 162.15 | 131.0 | 0.808 | 2.50 | | |
| Tetrac | $C_{14}H_8I_4O_4$ | 747.83 | 189.6 | 0.254 | 2.50 | | 16.49 (mg/ml) |
| Poly (vinyl alcohol) Dimethylformamide | $C_2H_4O$ | 44.05 | 136.5 | 3.099 | 6.50 | 58.14 | 0.021 (g/ml) |

Below is a suitable embodiment of a Tetrac conjugate with mono- or di-PEGOH via a stable ether linkage.

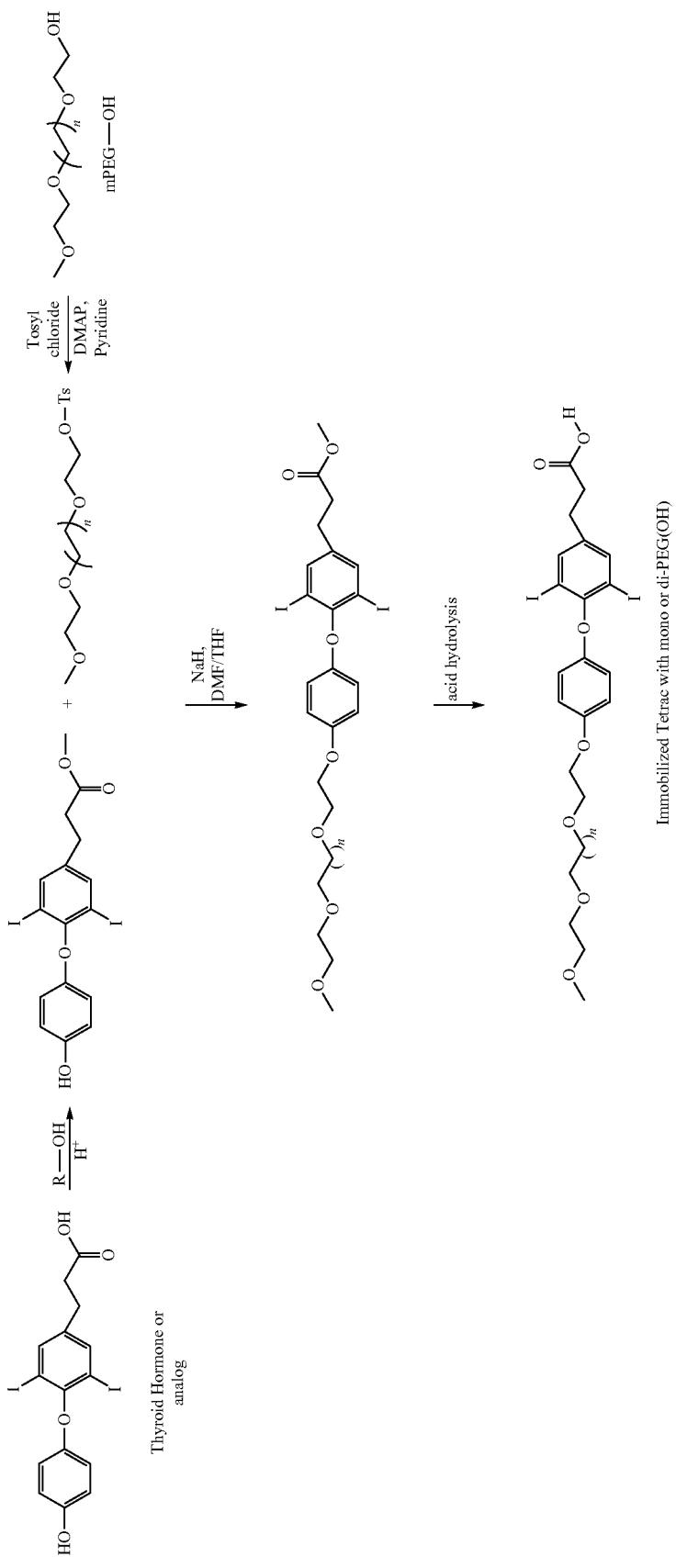

E. T3 Nanoparticles

Another suitable embodiment is a preparation of T3 conjugated PEG-PLGA nanoparticles. The conjugation of is similar to the conjugation of GC-1. Only in this case, the highly reactive amine group present in T3 will be blocked first by using either acetate (Ac) or BOC group. Then, it will be activated with epicholorohydrin. Finally, after conjugation to T3 it will be deprotected, as shown below.

Protection of Amine Group with Acetate (Ac) or BOC.

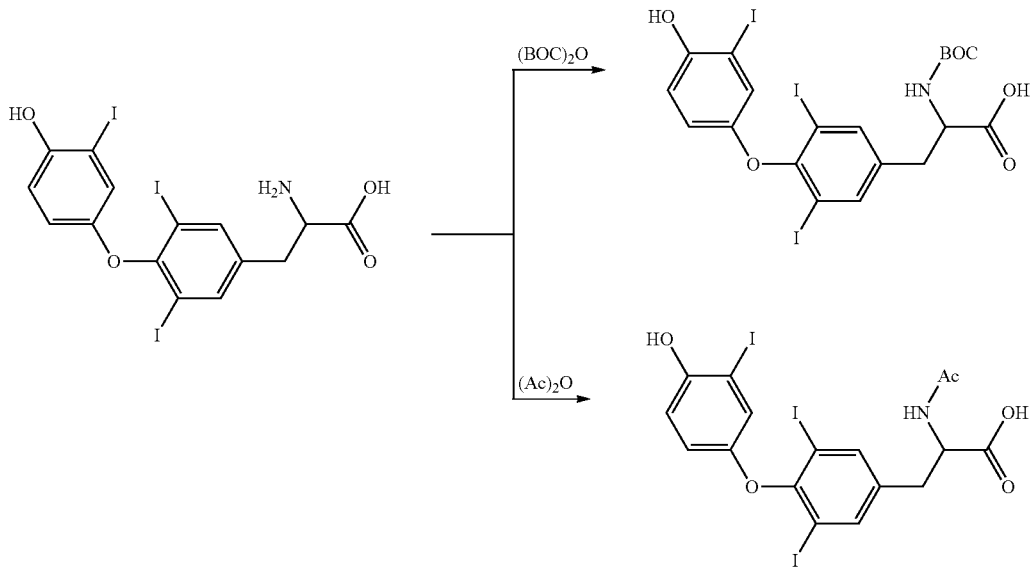

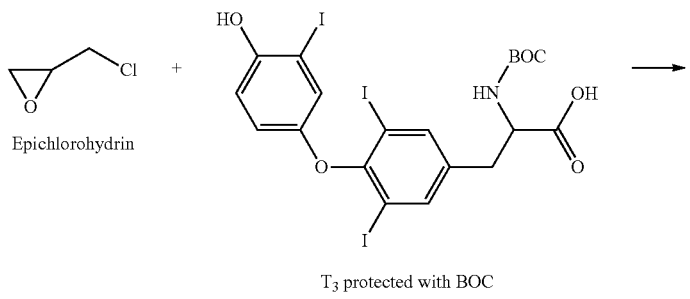

T3 protected with BOC

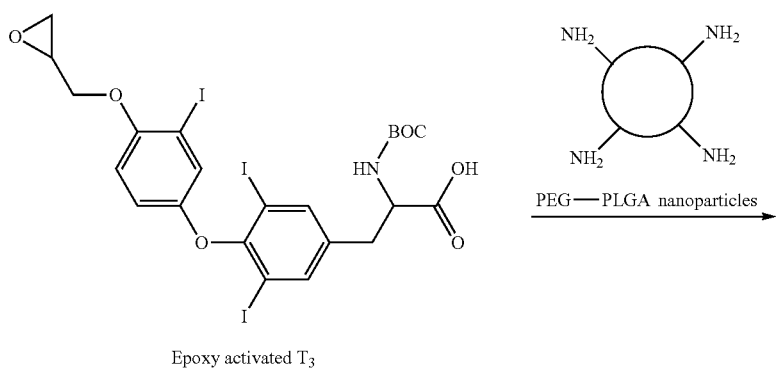

Epoxy activated T3

-continued

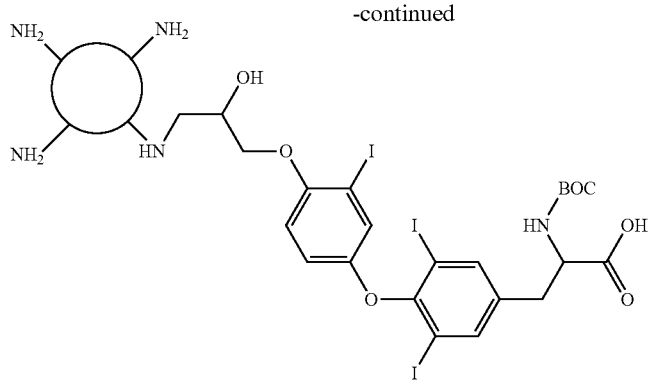

PEG—PLGA nanoparticles conjugated with $T_3$

F. DITPA

Additional suitable nanoparticle embodiments include DITPA analogs, as shown below.

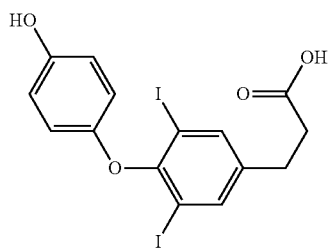 [SMILES: O=C(O)CCc1cc(I)c(Oc2ccc(O)cc2)c(I)c1]

DITPA—3, 5 Iodine could be Replaced by Methyl or Halogen Group

Uses of Thyroid Hormone Analogs

The thyroid hormone analogs of the present invention are T3, T4, GC-1, DITPA, tetrac, triac and polymer conjugates and nanoparticles thereof. T3, T4, GC-1 and DITPA and their conjugates and as nanoparticles are pro-angiogenic, and are also referred to herein as thyroid hormone agonists. Tetrac and triac and their conjugates and as nanoparticles are anti-angiogenic and anti-proliferative, and are also referred to herein as thyroid hormone antagonists.

Thyroid hormone analogs of the present invention can be used to treat disorders of the skin. These disorders include wound healing, noncancer skin conditions and cancerous skin conditions. Wound healing encompasses surgical incisions and traumatic injury. T4, T3, GC-1 and DITPA, both unmodified and as nanoparticles, can be used for wound healing. These thyroid hormone analogs work by angiogenesis and by enhancing fibroblast and white blood cell migration into the area of the wound. T4, modified and as a nanoparticle, has, in addition, platelet aggregating activity that is relevant to early wound healing. The actions of T4, T3, GC-1 and DITPA nanoparticles are limited to the cell surface. Because they do not enter the cell, they avoid systemic side effects when they escape the local application site. Examples of these intracellular systemic side effects include the mild hyperthyroid state and, specifically at pituitary thyrotrophic cells, suppression of thyrotropin (TSH) release. Noncancer skin disorders that can be treated by compositions of the present invention, specifically tetrac, triac and other anti-angiogenic and anti-proliferative thyroid hormone analogues, both unmodified and as nanoparticles or polymer conjugates, include, but are not limited to, rosacea, angiomas, telangiectasias, poikiloderma of Civatte and psoriasis. Examples of cancerous skin disorders that can be treated by compositions of the present invention are basal cell carcinoma, squamous cell carcinoma of the skin and melanoma. Compositions to be used for such purposes are tetrac, triac and other anti-angiogenic and anti-proliferative thyroid hormone analogues, both unmodified and as nanoparticles or polymer conjugates. For skin disorders, the compositions of the present invention can be administered as topical cutaneous applications, such as solutions, sprays, incorporated into gauze pads or into synthetic sheets.

Non-cancer skin disorders that can be treated by compositions of the present invention, including tetrac, tetrac and analogs encapsulated or immobilized to Nanoparticles include, but are not limited to, rosacea, angiomas, telangiectasias, poikiladerma, psoriasis. For skin disorders, the compositions of the present invention can be administered as topical cutaneous (such as solutions, sprays, or incorporated into gauze pads or other synthetic sheets).

The thyroid hormone analogs of the present invention, including tetrac, triac and other anti-proliferative and anti-angiogenic thyroid hormone analogs, both unmodified and as nanoparticles or polymer conjugates can also be used to treat cancers of organs in addition to the skin. These cancers include, but are not limited to, glioma and glioblastoma, nonthyroidal head-and-neck tumors, thyroid cancer, lung, breast and ovary. Tetrac and triac nanoparticles or polymer conjugates, administered systemically or locally, do not gain access to the interior of cells and work exclusively at the cell surface integrin receptor for thyroid hormone. This attribute of the formulations eliminates undesired side thyromimetic effects of unmodified tetrac and triac, including hyperthyroidism and suppression of thyrotropin (TSH) release by pituitary thyrotrophic cells. Tetrac can be administered in doses from about 200-2000 ug/day or up to about 700 ug/m2.

The thyroid hormone analogs of the present invention, including tetrac, triac, analogs, other thyroid antagonists, and polymer conjugates and nanoparticles thereof, can also be used to treat cancer, including, but not limited to, glioma, head and neck, skin, lung, breast, and thyroid. In this embodiment, tetrac can be administered either with or without nanoparticles. Tetrac nanoparticles reduce the risk of hypothyroidism, as the nanoparticles will not be able to enter the call. For thyroid cancer, both tetrac and tetrac nanoparticles are co-administered or Tetrac encapsulated and/or immobilized on the Nanoparticles surface via stable chemical bonding are administered. Tetrac or tetrac Nanoparticles can be administered in a doses of from about 0.001 to 10 mg/Kg.

The thyroid hormone analogs of the present invention, including tetrac, triac, analogs, thyroid antagonists, and polymer conjugates and nanoparticles thereof, can also be used to treat eye disorders, including diabetic retinopathy and macular degeneration. Tetrac and analogs can be given unmodified, as a polymer conjugate, or as nanoparticles either systemically or as eye drops.

The thyroid hormone analogs of the present invention, including T3, T4, GC-1, DITPA, and polymer conjugates and nanoparticles thereof, can also be used to treat atherosclerosis, including coronary or carotid artery disease, ischemic limb disorders, ischemic bowel disorders. Preferred embodiments are T3, GC-1, DITPA polymeric forms with poly L-arginine or poly L-lysine or nanoparticles thereof. Additionally, the compositions of the present invention can be used in combination with biodegradable and non-biodegradable stents or other matrix.

The thyroid hormone analogs of the present invention can also be administered to treat disorders involving cell migration, such as those involving glia neurons, and potentiated NGFs. Such disorders to be treated include neurological diseases. Additionally, thyroid hormone analogs of the present invention can be used for hematopoietic and stem cell-related disorders. They can be administered at the time of bone marrow transplant for cells to reproduce faster. The present compositions can also be used for diagnostic imaging, including imaging for Alzheimer's by using 125 Iodine labeled tetrac nanoparticles. Since Alzheimer's plaques have transthyretin that bind tetrac, this can be used for early detection. The compositions of the present invention can also be used in conjunction with defibrillators and for treatment of viral agents, such as West Nile and HIV.

Details of the uses for the present compositions in both promoting and inhibiting angiogenesis are described in detail below.

Promoting Angiogenesis

The pro-angiogenic effect of thyroid hormone analogs, polymeric forms, or nanoparticles thereof depends upon a non-genomic initiation, as tested by the susceptibility of the hormonal effect to reduction by pharmacological inhibitors of the MAPK signal transduction pathway. Such results indicate that another consequence of activation of MAPK by thyroid hormone is new blood vessel growth. The latter is initiated nongenomically, but of course, requires a consequent complex gene transcription program. The ambient concentrations of thyroid hormone are relatively stable. The CAM model, at the time we tested it, was thyroprival and thus may be regarded as a system, which does not reproduce the intact organism.

The availability of a chick chorioallantoic membrane (CAM) assay for angiogenesis has provided a model in which to quantitate angiogenesis and to study possible mechanisms involved in the induction by thyroid hormone of new blood vessel growth. The present application discloses a pro-angiogenic effect of $T_4$ that approximates that in the CAM model of FGF2 and that can enhance the action of suboptimal doses of FGF2. It is further disclosed that the pro-angiogenic effect of the hormone is initiated at the plasma membrane and is dependent upon activation by $T_4$ of the MAPK signal transduction pathway. As provided above, methods for treatment of occlusive peripheral vascular disease and coronary diseases, in particular, the occlusion of coronary vessels, and disorders associated with the occlusion of the peripheral vasculature and/or coronary blood vessels are disclosed. Also disclosed are compositions and methods for promoting angiogenesis and/or recruiting collateral blood vessels in a patient in need thereof. The compositions include an effective amount of Thyroid hormone analogs, polymeric forms, and derivatives. The methods involve the co-administration of an effective amount of thyroid hormone analogs, polymeric forms, and derivatives in low, daily dosages for a week or more with other standard pro-angiogenesis growth factors, vasodilators, anticoagulants, thrombolytics or other vascular-related therapies.

The CAM assay has been used to validate angiogenic activity of a variety of growth factors and compounds believed to promote angiogenesis. For example, $T_4$ in physiological concentrations was shown to be pro-angiogenic in this in vitro model and on a molar basis to have the activity of FGF2. The presence of PTU did not reduce the effect of $T_4$, indicating that de-iodination of $T_4$ to generate $T_3$ was not a prerequisite in this model. A summary of the pro-angiogenesis effects of various thyroid hormone analogs is listed in Table below.

Pro-Angiogenesis Effects of Various Thyroid Hormone Analogs in the CAM Model

| TREATMENT | ANGIOGENESIS INDEX |
| --- | --- |
| PBS (Control) | 89.4 ± 9.3 |
| DITPA (0.01 uM) | 133.0 ± 11.6 |
| DITPA (0.1 uM) | 167.3 ± 12.7 |
| DITPA (0.2 mM) | 117.9 ± 5.6 |
| GC-1 (0.01 uM) | 169.6 ± 11.6 |
| GC-1 (0.1 uM) | 152.7 ± 9.0 |
| T4 agarose (0.1 uM) | 195.5 ± 8.5 |
| T4 (0.1 uM) | 143.8 ± 7.9 |
| FGF2 (1 ug) | 155 ± 9 | n = 8 per group

The appearance of new blood vessel growth in this model requires several days, indicating that the effect of thyroid hormone was wholly dependent upon the interaction of the nuclear receptor for thyroid hormone (TR) with the hormone. Actions of iodothyronines that require intranuclear complexing of TR with its natural ligand, $T_3$, are by definition, genomic, and culminate in gene expression. On the other hand, the preferential response of this model system to $T_4$-rather than $T_3$, the natural ligand of TR-raised the possibility that angiogenesis might be initiated nongenomically at the plasma membrane by $T_4$ and culminate in effects that require gene transcription. Non-genomic actions of $T_4$ have been widely described, are usually initiated at the plasma membrane and may be mediated by signal transduction pathways. They do not require intranuclear ligand of iodothyronine and TR, but may interface with or modulate gene transcription. Non-genomic actions of steroids have also been well described and are known to interface with genomic actions of steroids or of other compounds. Experiments carried out with $T_4$ and tetrac or with agarose-$T_4$ indicated that the pro-angiogenic effect of $T_4$ indeed very likely was initiated at the plasma membrane. Tetrac blocks membrane-initiated effects of $T_4$, but does not, itself, activate signal transduction. Thus, it is a probe for non-genomic actions of thyroid hormone. Agarose-$T_4$ is thought not to gain entry to the cell interior and has been used to examine models for possible cell surface-initiated actions of the hormone. Investigations of the pro-angiogenic effects of thyroid hormone in the chick chorioallantoic membrane ("CAM") model demonstrate that generation of new blood vessels from existing vessels was promoted two- to three-fold by either L-thyroxine ($T_4$) or 3,5,3'-triiodo-L-thyronine ($T_3$) at $10^{-7}$-$10^{-9}$ M. More interestingly, $T_4$-agarose, a thyroid hormone analog that does not cross the cell membrane, produced a potent pro-angiogenesis effect comparable to that obtained with $T_3$ or $T_4$.

In part, this invention provides compositions and methods for promoting angiogenesis in a subject in need thereof. Conditions amenable to treatment by promoting angiogenesis include, for example, occlusive peripheral vascular disease and coronary diseases, in particular, the occlusion of coronary vessels, and disorders associated with the occlusion of the peripheral vasculature and/or coronary blood vessels, erectile dysfunction, stroke, and wounds. Also disclosed are compositions and methods for promoting angiogenesis and/or recruiting collateral blood vessels in a patient in need thereof. The compositions include an effective amount of polymeric forms of thyroid hormone analogs and derivatives and an effective amount of an adenosine and/or nitric oxide donor. The compositions can be in the form of a sterile, injectable, pharmaceutical formulation that includes an angiogenically effective amount of thyroid hormone-like substance and adenosine derivatives in a physiologically and pharmaceutically acceptable carrier, optionally with one or more excipients.

Myocardial Infarction

A major reason for heart failure following acute myocardial infarction is an inadequate response of new blood vessel formation, i.e., angiogenesis. Thyroid hormone and its analogs are beneficial in heart failure and stimulate coronary angiogenesis. The methods of the invention include, in part, delivering a single treatment of a thyroid hormone analog at the time of infarction either by direct injection into the myocardium, or by simulation of coronary injection by intermittent aortic ligation to produce transient isovolumic contractions to achieve angiogenesis and/or ventricular remodeling.

Accordingly, in one aspect the invention features methods for treating occlusive vascular disease, coronary disease, myocardial infarction, ischemia, stroke, and/or peripheral artery vascular disorders by promoting angiogenesis by administering to a subject in need thereof an amount of a polymeric form of thyroid hormone, or an analog thereof, effective for promoting angiogenesis.

Examples of polymeric forms of thyroid hormone analogs are also provided herein and can include triiodothyronine (T3), levothyroxine (T4), (GC-1), or 3,5-diiodothyropropionic acid (DITPA) conjugated to polyvinyl alcohol, acrylic acid ethylene co-polymer, polylactic acid, Poly L-arginine, poly L-Lysine.

The methods also involve the co-administration of an effective amount of thyroid hormone-like substance and an effective amount of an adenosine and/or NO donor in low, daily dosages for a week or more. One or both components can be delivered locally via catheter. Thyroid hormone analogs, and derivatives in vivo can be delivered to capillary beds surrounding ischemic tissue by incorporation of the compounds in an appropriately sized Nanoparticles. Thyroid hormone analogs, polymeric forms and derivatives can be targeted to ischemic tissue by covalent linkage with a suitable antibody.

The method may be used as a treatment to restore cardiac function after a myocardial infarction. The method may also be used to improve blood flow in patients with coronary artery disease suffering from myocardial ischemia or inadequate blood flow to areas other than the heart including, for example, occlusive peripheral vascular disease (also known as peripheral arterial occlusive disease), or erectile dysfunction.

Wound Healing

The actions of thyroid hormone that are initiated at the integrin receptor and that are relevant to wound-healing in vivo are platelet aggregation, angiogenesis and fibroblast in-migration. Thyroid hormone can also enhance in-migration of white blood cells.

Wound angiogenesis is an important part of the proliferative phase of healing. Healing of any skin wound other than the most superficial cannot occur without angiogenesis. Not only does any damaged vasculature need to be repaired, but the increased local cell activity necessary for healing requires an increased supply of nutrients from the bloodstream. Moreover, the endothelial cells which form the lining of the blood vessels are important in themselves as organizers and regulators of healing.

Thus, angiogenesis provides a new microcirculation to support the healing wound. The new blood vessels become clinically visible within the wound space by four days after injury. Vascular endothelial cells, fibroblasts, and smooth muscle cells all proliferate in coordination to support wound granulation. Simultaneously, re-epithelialization occurs to reestablish the epithelial cover. Epithelial cells from the wound margin or from deep hair follicles migrate across the wound and establish themselves over the granulation tissue and provisional matrix. Growth factors such as keratinocyte growth factor (KGF) mediate this process. Several models (sliding versus rolling cells) of epithelialization exist.

As thyroid hormones regulate metabolic rate, when the metabolism slows down due to hypothyroidism, wound healing also slows down. The role of topically applied thyroid hormone analogs or polymeric forms in wound healing therefore represents a novel strategy to accelerate wound healing in diabetics and in non-diabetics with impaired wound healing abilities. Topical administration can be in the form of attachment to a band-aid. Additionally, nano-polymers and nano-particles can be used as a matrix for local delivery of thyroid hormone and its analogs. This will aid in time-controlled delivery into the cellular and tissue target.

Accordingly, another embodiment of the invention features methods for treating wounds by promoting angiogenesis by administering to a subject in need thereof an amount of a polymeric or nanoparticulate form of thyroid hormone, or an analog thereof, effective for promoting angiogenesis. For details, see Examples 9A and 9B.

For nanoparticles, $T_4$ as the PLGA formulation, when applied locally to surgical or traumatic wounds via gauze pads or adsorbed to synthetic films, will enhance wound-healing by the mechanisms described above. For small cutaneous wounds or abrasions, derivatized $T_4$ may be made available for clinical use in OTC gauze pads or films.

$T_4$ as the PLGA formulation, when applied locally to cutaneous ulcers via gauze pads or adsorbed to synthetic films, will enhance wound-healing by the mechanisms described above. Because it does not cause platelet aggregation, nanoparticulate $T_3$ is less desirable for these applications.

Additional wound healing uses include the use for mucus membrane related disorders, including post-biopsy radiation-induced inflammation, GI tract ulceration, to curb internal bleeding, post-tooth extraction for dental patients on anti-coagulant therapy. For these uses, nanoparticles or polymer conjugates may be used.

Ophthalmic

The present invention is also directed to sustained release and long residing ophthalmic formulation of thyroid hormone analogs having thermo-sensitivity, mucoadhesiveness, and small particle size (10<1000 nm). The said formulation comprises micelle solution of random block co-polymer having hydrophobic or hydrophilic thyroid hormone antagonists. The invention also provides a process of preparing said formulations with different particle size and different surface charges (positive, negative or neutral) in eye drops or ointment.

Most ocular diseases are treated with topical application of solutions administered as eye drops or ointment. One of the major problems encountered with the topical delivery of ophthalmic drugs is the rapid and extensive pre-corneal loss caused by drainage and high tear fluid turn over. After instillation of an eye-drop, typically less than 2-3% of the applied drug penetrates the cornea and reaches the intraocular tissue, while a major fraction of the instilled dose is often absorbed systematically via the conjunctiva and nasolacrimal duct. Another limitation is relatively impermeable corneal barrier that limits ocular absorption.

Because of the inherent problems associated with the conventional eye-drops there is a significant efforts directed towards new drug delivery systems for ophthalmic administration such as hydrogels, micro- and nanoparticles, liposomes and collagen shields. Ocular drug delivery is an approach to controlling and ultimately optimizing delivery of the drug to its target tissue in the eye. Most of the formulation efforts aim at maximizing ocular drug absorption through prolongation of the drug residence time in the cornea and conjunctival sac as well as to slow drug release from the delivery system and minimizing pre-corneal drug loss without the use of gel that has the blurring effect on the vision.

To overcome the problem of blurred vision and poor bio-availability of drug by using bulk gel in ophthalmic formulations, it has been suggested that colloidal carriers would have better effect. Nanoparticles as drug carriers for ocular delivery have been revealed to be more efficient than liposomes and in addition to all positive points of liposomes, these nanoparticles are exceptionally stable entity and the sustained release of drug can be modulated.

There have been studies on the use of co-polymeric materials for ophthalmic drugs and particularly noteworthy are the attempts to incorporate hydrophobic drugs into the hydrophobic core of the copolymer micelles. The pharmaceutical efficacy of these formulations depends on the specific nature and properties of the co-polymeric materials and the compound used. Moreover, the long residence time and sustained release of drug on cornea surface have not been achieved by other biocompatible formulations.

Neuronal

Contrary to traditional understanding of neural induction, the present invention is partly based on the unexpected finding that mechanisms that initiate and maintain angiogenesis are effective promoters and sustainers of neurogenesis. These methods and compositions are useful, for example, for the treatment of motor neuron injury and neuropathy in trauma, injury and neuronal disorders. This invention discloses the use of various pro-angiogenesis strategies alone or in combination with nerve growth factor or other neurogenesis factors. Pro-angiogenesis factors include polymeric thyroid hormone analogs as illustrated herein. The polymeric thyroid hormone analogs and its polymeric conjugates alone or in combination with other pro-angiogenesis growth factors known in the art and with nerve growth factors or other neurogenesis factors can be combined for optimal neurogenesis.

Disclosed are therapeutic treatment methods, compositions and devices for maintaining neural pathways in a mammal, including enhancing survival of neurons at risk of dying, inducing cellular repair of damaged neurons and neural pathways, and stimulating neurons to maintain their differentiated phenotype. Additionally, a composition containing polymeric thyroid hormone analogs, and combinations thereof, in the presence of anti-oxidants and/or anti-inflammatory agents demonstrate neuronal regeneration and protection.

The present invention also provides thyroid hormones, analogs, and polymeric conjugations, alone or in combination with nerve growth factors or other neurogenesis factors, to enhance survival of neurons and maintain neural pathways. As described herein, polymeric thyroid hormone analogs alone or in combination with nerve growth factors or other neurogenesis factors are capable of enhancing survival of neurons, stimulating neuronal CAM expression, maintaining the phenotypic expression of differentiated neurons, inducing the redifferentiation of transformed cells of neural origin, and stimulating axonal growth over breaks in neural processes, particularly large gaps in axons. Morphogens also protect against tissue destruction associated with immunologically-related nerve tissue damage. Finally, polymeric thyroid hormone analogs alone or in combination with nerve growth factors or other neurogenesis factors may be used as part of a method for monitoring the viability of nerve tissue in a mammal.

The present invention also provides effects of polymeric thyroid hormones on synapse formation between cultured rat cortical neurons, using a system to estimate functional synapse formation in vitro. Exposure to $10^{-9}$ M polymeric thyroid hormones, 3,5,3'-triiodothyronine or thyroxine, caused an increase in the frequency of spontaneous synchronous oscillatory changes in intracellular calcium concentration, which correlated with the number of synapses formed. The detection of synaptic vesicle-associated protein synapsin I by immunocytochemical and immunoblot analysis also confirmed that exposure to thyroxine facilitated synapse formation. The presence of amiodarone, an inhibitor of 5'-deiodinase, or amitrole, a herbicide, inhibited the synapse formation in the presence of thyroxine. Thus, the present invention also provides a useful in vitro assay system for screening of miscellaneous chemicals that might interfere with synapse formation in the developing CNS by disrupting the polymeric thyroid system.

As a general matter, methods of the present invention may be applied to the treatment of any mammalian subject at risk of or afflicted with a neural tissue insult or neuropathy. The invention is suitable for the treatment of any primate, preferably a higher primate such as a human. In addition, however, the invention may be employed in the treatment of domesticated mammals which are maintained as human companions (e.g., dogs, cats, horses), which have significant commercial value (e.g., goats, pigs, sheep, cattle, sporting or draft animals), which have significant scientific value (e.g., captive or free specimens of endangered species, or inbred or engineered animal strains), or which otherwise have value.

The polymeric thyroid hormone analogs alone or in combination with nerve growth factors or other neurogenesis factors described herein enhance cell survival, particularly of neuronal cells at risk of dying. For example, fully differentiated neurons are non-mitotic and die in vitro when cultured under standard mammalian cell culture conditions, using a chemically defined or low serum medium known in the art. See, for example, Charness, J. Biol. Chem. 26: 3164-3169 (1986) and Freese, et al., Brain Res. 521: 254-264 (1990). However, if a primary culture of non-mitotic neuronal cells is treated with polymeric thyroid analog alone or in combination with nerve growth factor or other neurogenesis factors, the survival of these cells is enhanced significantly. For example, a primary culture of striatal basal ganglia isolated from the substantia nigra of adult rat brain was prepared using standard procedures, e.g., by dissociation by trituration with pasteur pipette of substantia nigra tissue, using standard tissue culturing protocols, and grown in a low serum medium, e.g., containing 50% DMEM (Dulbecco's modified Eagle's medium), 50% F-12 medium, heat inactivated horse serum supplemented with penicillin/streptomycin and 4 g/l glucose. Under standard culture conditions, these cells are undergoing significant cell death by three weeks when cultured in a serum-free medium. Cell death is evidenced morphologically by the inability of cells to remain adherent and by changes in their ultrastructural characteristics, e.g., by chromatin clumping and organelle disintegration. Specifically, cells remained adherent and continued to maintain the morphology of viable differentiated neurons. In the absence of thyroid analog alone or in combination with nerve growth factor or other neurogenesis factors treatment, the majority of the cultured cells dissociated and underwent cell necrosis.

Dysfunctions in the basal ganglia of the substantia nigra are associated with Huntington's chorea and parkinsonism in vivo. The ability of the polymeric thyroid hormone analogs alone or in combination with nerve growth factors or other neurogenesis factors defined herein to enhance neuron survival indicates that these polymeric thyroid hormone analogs alone or in combination with nerve growth factors or other neurogenesis factors will be useful as part of a therapy to enhance survival of neuronal cells at risk of dying in vivo due, for example, to a neuropathy or chemical or mechanical trauma. The present invention further provides that these polymeric thyroid hormone analogs alone or in combination with nerve growth factors or other neurogenesis factors provide a useful therapeutic agent to treat neuropathies which affect the striatal basal ganglia, including Huntington's chorea and Parkinson's disease. For clinical applications, the polymeric thyroid hormone analogs alone or in combination with nerve growth factors or other neurogenesis factors may be administered or, alternatively, a polymeric thyroid hormone analog alone or in combination with nerve growth factors or other neurogenesis factors-stimulating agent may be administered.

The thyroid hormone compounds described herein can also be used for nerve tissue protection from chemical trauma. The ability of the polymeric thyroid hormone analogs alone or in combination with nerve growth factors or other neurogenesis factors described herein to enhance survival of neuronal cells and to induce cell aggregation and cell—cell adhesion in redifferentiated cells, indicates that the polymeric thyroid hormone analogs alone or in combination with nerve growth factors or other neurogenesis factors will be useful as therapeutic agents to maintain neural pathways by protecting the cells defining the pathway from the damage caused by chemical trauma. In particular, the polymeric thyroid hormone analogs alone or in combination with nerve growth factors or other neurogenesis factors can protect neurons, including developing neurons, from the effects of toxins known to inhibit the proliferation and migration of neurons and to interfere with cell—cell adhesion. Examples of such toxins include ethanol, one or more of the toxins present in cigarette smoke, and a variety of opiates. The toxic effects of ethanol on developing neurons induces the neurological damage manifested in fetal alcohol syndrome. The polymeric thyroid hormone analogs alone or in combination with nerve growth factors or other neurogenesis factors also may protect neurons from the cytotoxic effects associated with excitatory amino acids such as glutamate.

For example, ethanol inhibits the cell—cell adhesion effects induced in polymeric thyroid analog alone or in combination with nerve growth factor or other neurogenesis factors-treated NG108-15 cells when provided to these cells at a concentration of 25-50 mM. Half maximal inhibition can be achieved with 5-10 mM ethanol, the concentration of blood alcohol in an adult following ingestion of a single alcoholic beverage. Ethanol likely interferes with the homophilic binding of CAMs between cells, rather than their induction, as polymeric thyroid analog alone or in combination with nerve growth factor or other neurogenesis factors-induced N-CAM levels are unaffected by ethanol. Moreover, the inhibitory effect is inversely proportional to polymeric thyroid analog alone or in combination with nerve growth factor or other neurogenesis factors concentration. Accordingly, it is envisioned that administration of a polymeric thyroid analog alone or in combination with nerve growth factor or other neurogenesis factors or polymeric thyroid analog alone or in combination with nerve growth factor or other neurogenesis factors-stimulating agent to neurons, particularly developing neurons, at risk of damage from exposure to toxins such as ethanol, may protect these cells from nerve tissue damage by overcoming the toxin's inhibitory effects. The polymeric thyroid analog alone or in combination with nerve growth factor or other neurogenesis factors described herein also are useful in therapies to treat damaged neural pathways resulting from a neuropathy induced by exposure to these toxins.

The in vivo activities of the polymeric thyroid hormone analogs alone or in combination with nerve growth factors or other neurogenesis factors described herein also are assessed readily in an animal model as described herein. A suitable animal, preferably exhibiting nerve tissue damage, for example, genetically or environmentally induced, is injected intracerebrally with an effective amount of a polymeric thyroid hormone analogs alone or in combination with nerve growth factor or other neurogenesis factors in a suitable therapeutic formulation, such as phosphate-buffered saline, pH 7. The polymeric thyroid hormone analogs alone or in combination with nerve growth factors or other neurogenesis factors preferably is injected within the area of the affected neurons. The affected tissue is excised at a subsequent time point and the tissue evaluated morphologically and/or by evaluation of an appropriate biochemical marker (e.g., by polymeric thyroid hormone analogs alone or in combination with nerve growth factors or other neurogenesis factors or N-CAM localization; or by measuring the dose-dependent effect on a biochemical marker for CNS neurotrophic activity or for CNS tissue damage, using for example, glial fibrillary acidic protein as the marker. The dosage and incubation time will vary with the animal to be tested. Suitable dosage ranges for different species may be determined by comparison with established animal models. Presented below is an exemplary protocol for a rat brain stab model.

Briefly, male Long Evans rats, obtained from standard commercial sources, are anesthetized and the head area prepared for surgery. The calvariae is exposed using standard surgical procedures and a hole drilled toward the center of each lobe using a 0.035K wire, just piercing the calvariae. 25 ml solutions containing either polymeric thyroid analog alone or in combination with nerve growth factor or other neurogenesis factors (e.g., OP-1, 25 mg) or PBS then is provided to each of the holes by Hamilton syringe. Solutions are delivered to a depth approximately 3 mm below the surface, into the underlying cortex, corpus callosum and hippocampus. The skin then is sutured and the animal allowed to recover.

Three days post surgery, rats are sacrificed by decapitation and their brains processed for sectioning. Scar tissue formation is evaluated by immunofluorescence staining for glial fibrillary acidic protein, a marker protein for glial scarring, to qualitatively determine the degree of scar formation. Glial fibrillary acidic protein antibodies are available commercially, e.g., from Sigma Chemical Co., St. Louis, Mo. Sections also are probed with anti-OP-1 antibodies to determine the presence of OP-1. Reduced levels of glial fibrillary acidic protein are anticipated in the tissue sections of animals treated with the polymeric thyroid analog alone or in combination with nerve growth factor or other neurogenesis factors, evidencing the ability of polymeric thyroid analog alone or in combination with nerve growth factor or other neurogenesis factors to inhibit glial scar formation and stimulate nerve regeneration.

Brain Imaging, Diagnosis, and Therapies of Neurodegenerative Diseases

The present invention relates to novel pharmaceutical and radiopharmaceuticals useful for the early diagnosis, prevention, and treatment of neurodegenerative disease, such as, for example, Alzheimer's disease. The invention also includes novel chemical compounds having specific binding in a biological system and capable of being used for positron emission tomography (PET), single photon emission (SPECT) imaging methods, and magnetic resonance (MRI) imaging methods. The ability of T4 and other thyroid hormone analogs to bind to localized ligands within the body makes it possible to utilize such compounds for in situ imaging of the ligands by PET, SPECT, MRI, and similar imaging methods. In principle, nothing need be known about the nature of the ligand, as long as binding occurs, and such binding is specific for a class of cells, organs, tissues or receptors of interest.

PET imaging is accomplished with the aid of tracer compounds labeled with a positron-emitting isotope (Goodman, M. M. Clinical Positron Emission Tomography, Mosby Yearbook, 1992, K. F. Hubner et al., Chapter 14). For most biological materials, suitable isotopes are few. The carbon isotope, $^{11}C$, has been used for PET, but its short half-life of 20.5 minutes limits its usefulness to compounds that can be synthesized and purified quickly, and to facilities that are proximate to a cyclotron where the precursor $C^{11}$ starting material is generated. Other isotopes have even shorter half-lives. $N^{13}$ has a half-life of 10 minutes and $O^{15}$ has an even shorter half-life of 2 minutes. The emissions of both are more energetic than those of $C^{11}$. Nevertheless, PET studies have been carried out with these isotopes (Hubner, K. F., in Clinical Positron Emission Tomography, Mosby Year Book, 1992, K. F. Hubner, et al., Chapter 2). A more useful isotope, $^{18}F$, has a half-life of 110 minutes. This allows sufficient time for incorporation into a radio-labeled tracer, for purification and for administration into a human or animal subject. In addition, facilities more remote from a cyclotron, up to about a 200 mile radius, can make use of $F^{18}$ labeled compounds. Disadvantages of $^{18}F$ are the relative scarcity of fluorinated analogs that have functional equivalence to naturally-occurring biological materials, and the difficulty of designing methods of synthesis that efficiently utilize the starting material generated in the cyclotron. Such starting material can be either fluoride ion or fluorine gas. In the latter case only one fluorine atom of the bimolecular gas is actually a radionuclide, so the gas is designated $F$—$F^{18}$. Reactions using $F$—$F^{18}$ as starting material therefore yield products having only one half the radionuclide abundance of reactions utilizing K. $F^{18}$ as starting material. On the other hand, $F^{18}$ can be prepared in curie quantities as fluoride ion for incorporation into a radiopharmaceutical compound in high specific activity, theoretically 1.7 Ci/nmol using carrier-free nucleophilic substitution reactions. The energy emission of $F^{18}$ is 0.635 MeV, resulting in a relatively short, 2.4 mm average positron range in tissue, permitting high resolution PET images.

SPECT imaging employs isotope tracers that emit high energy photons (.gamma.-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is $I^{123}$ α-gamma.-emitter with a 13.3 hour half life. Compounds labeled with $I^{123}$ can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use. The compounds of the invention can be labeled with Technetium. Technetium-99m is known to be a useful radionuclide for SPECT imaging. The T4 analogs of the invention are joined to a Tc-99m metal cluster through a 4-6 carbon chain which can be saturated or possess a double or triple bond.

Use of $F^{18}$ labeled compounds in PET has been limited to a few analog compounds. Most notably, $^{18}F$-fluorodeoxyglucose has been widely used in studies of glucose metabolism and localization of glucose uptake associated with brain activity. $^{18}F$-L-fluorodopa and other dopamine receptor analogs have also been used in mapping dopamine receptor distribution.

Other halogen isotopes can serve for PET or SPECT imaging, or for conventional tracer labeling. These include $^{75}Br$, $^{76}Br$, $^{77}Br$ and $^{82}Br$ as having usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homolog. Astatine can be substituted for other halogen isotypes. $^{210}At$ for example, emits alpha particles with a half-life of 8.3 h. Other isotopes also emit alpha particles with reasonably useful half-lives. At-substituted compounds are therefore useful for brain therapy, where binding is sufficiently brain-specific.

Numerous studies have demonstrated increased incorporation of carbohydrates and amino acids into malignant brain cells. This accumulation is associated with accelerated proliferation and protein synthesis of such cells. The glucose analog $^{18}F$-2-fluoro-2-deoxy-D-glucose (2-FDG) has been used for distinguishing highly malignant brain brains from normal brain tissue or benign growths (DiChiro, G. et al. (1982) Neurology (NY) 32:1323-1329. However, fluorine-18 labeled 2-FDG is not the agent of choice for detecting low grade brain brains because high uptake in normal tissue can mask the presence of a brain. In addition, fluorine-18 labeled 2-FDG is not the ideal radiopharmaceutical for distinguishing lung brains from infectious tissue or detecting ovarian carcinoma because of high uptake of the 2-FDG radioactivity in infectious tissue and in the bladder, respectively. The naturally occurring amino acid methionine, labeled with carbon-11, has also been used to distinguish malignant tissue from normal tissue. But it too has relatively high uptake in normal tissue. Moreover, the half-life of carbon-11 is only 20 minutes; therefore C11 methionine can not be stored for a long period of time.

Cerebrospinal fluid ("CSF") transthyretin ("TTR"), the main CSF thyroxine (T4) carrier protein in the rat and the human is synthesized in the choroid plexus ("CP"). After injection of $^{125}$I-T4 in the rat, radioactive T4 accumulates first in the CP, then in the CSF and later in the brain (Chanoine J P, Braverman L E. The role of transthyretin in the transport of thyroid hormone to cerebrospinal fluid and brain. Acta Med Austriaca. 1992; 19 Suppl 1:25-8).

Compounds of the invention provide substantially improved PET imaging for areas of the body having amyloid protein, especially of the brain. All the available positron-emitting isotopes which could be incorporated into a biologically-active compound have short half-lives. The practical utility of such labeled compounds is therefore dependent on how rapidly the labeled compound can be synthesized, the synthetic yield and the radiochemical purity of the final product. Even the shipping time from the isotope source, a cyclotron facility, to the hospital or laboratory where PET imaging is to take place, is limited. A rough calculation of the useful distance is about two miles per minute of half-life. Thus $C^{11}$, with a half-life of 20.5 m is restricted to about a 40 mile radius from a source whereas compounds labeled with $F^{18}$ can be used within about a 200 mile radius. Further requirements of an $^{18}$F-labeled compound are that it have the binding specificity for the receptor or target molecule it is intended to bind, that non-specific binding to other targets be sufficiently low to permit distinguishing between target and non-target binding, and that the label be stable under conditions of the test to avoid exchange with other substances in the test environment. More particularly, compounds of the invention must display adequate binding to the desired target while failing to bind to any comparable degree with other tissues or cells.

A partial solution to the stringent requirements for PET imaging is to employ .gamma.-emitting isotopes in SPECT imaging. $I^{123}$ is a commonly used isotopic marker for SPECT, having a half-life of 13 hours for a useful range of over 1000 miles from the site of synthesis. Compounds of the invention can be rapidly and efficiently labeled with $I^{123}$ for use in SPECT analysis as an alternative to PET imaging. Furthermore, because of the fact that the same compound can be labeled with either isotope, it is possible for the first time to compare the results obtained by PET and SPECT using the same tracer.

The specificity of brain binding also provides utility for I-substituted compounds of the invention. Such compounds can be labeled with short-lived $^{123}$I for SPECT imaging or with longer-lived $^{125}$I for longer-term studies such as monitoring a course of therapy. Other iodine and bromine isotopes can be substituted for those exemplified.

In general, the radioactive imaging agents of the present invention are prepared by reacting radioactive 4-halobenzyl derivatives with piperazine derivatives. Preferred are F-18 labeled 4-fluorobenzyl derivatives for PET-imaging. A general method for the preparation of 4-fluoro-.sup.18 F-benzyl halides is described in Iwata et al., Applied Radiation and Isotopes (2000), Vol. 52, pp. 87-92.

For Single Photon Emission Computed Tomography ("SPECT"), $^{99m}$Tc-labeled compounds are preferred. A general synthetic pathway for these compounds starts with non-radioactive TH analogs within the present invention that are reacted with $^{99m}$Tc-binding chelators, e.g. $N_2 S_2$-Chelators. The synthesis of the chelators follows standard procedures, for example, the procedures described in A. Mahmood et al., A $N_2 S_2$-Tetradentate Chelate for Solid-Phase Synthesis: Technetium, Rhenium in Chemistry and Nuclear Medicine (1999), Vol. 5, p. 71, or in Z. P. Zhuang et al., Bioconjugate Chemistry (1999), Vol. 10, p. 159.

One of the chelators is either bound directly to the nitrogen in the —N(R$^4$)R$^5$ group of the non-radioactive compounds of the TH analogs of the present invention, or via a linker moiety comprising an alkyl radical having one to ten carbon atoms, wherein the alkyl radical optionally contains one to ten —C(O)— groups, one to ten —C(O)N(R)— groups, one to ten —N(R)C(O)— groups, one to ten —N(R)— groups, one to ten —N(R)$_2$ groups, one to ten hydroxy groups, one to ten —C(O)OR— groups, one to ten oxygen atoms, one to ten sulfur atoms, one to ten nitrogen atoms, one to ten halogen atoms, one to ten aryl groups, and one to ten saturated or unsaturated heterocyclic rings wherein R is hydrogen or alkyl. A preferred linker moiety is —C(O)—CH$_2$—N(H)—.

The compounds of the invention therefore provide improved methods for brain imaging using PET and SPECT. The methods entail administering to a subject (which can be human or animal, for experimental and/or diagnostic purposes) an image-generating amount of a compound of the invention, labeled with the appropriate isotope and then measuring the distribution of the compound by PET if F$^{18}$ or other positron emitter is employed, or SPECT if I$^{123}$ or other gamma emitter is employed. An image-generating amount is that amount which is at least able to provide an image in a PET or SPECT scanner, taking into account the scanner's detection sensitivity and noise level, the age of the isotope, the body size of the subject and route of administration, all such variables being exemplary of those known and accounted for by calculations and measurements known to those skilled in the art without resort to undue experimentation.

It will be understood that compounds of the invention can be labeled with an isotope of any atom or combination of atoms in the structure. While F$^{18}$, I$^{123}$, and I$^{125}$ have been emphasized herein as being particularly useful for PET, SPECT and tracer analysis, other uses are contemplated including those flowing from physiological or pharmacological properties of stable isotope homolog and will be apparent to those skilled in the art.

The invention also provides for technetium (Tc) labeling via Tc adducts. Isotopes of Tc, notably Tc$^{99m}$, have been used for brain imaging. The present invention provides Tc-complexed adducts of compounds of the invention, which are useful for brain imaging. The adducts are Tc-coordination complexes joined to the cyclic amino acid by a 4-6 carbon chain which can be saturated or possess a double or triple bond. Where a double bond is present, either E (trans) or Z (cis) isomers can be synthesized, and either isomer can be employed. Synthesis is described for incorporating the $^{99m}$Tc isotope as a last step, to maximize the useful life of the isotope.

The following methods were employed in procedures reported herein. $^{18}$F-Fluoride was produced from a Siemens cyclotron using the $^{18}$O(p,n) $^{18}$F reaction with 11 MeV protons on 95% enriched $^{18}$O water. All solvents and chemicals were analytical grade and were used without further purification. Melting points of compounds were determined in capillary tubes by using a Buchi SP apparatus. Thin-layer chromatographic analysis (TLC) was performed by using 250-mm thick layers of silica gel G PF-254 coated on aluminum (obtained from Analtech, Inc.). Column chromatography was performed by using 60-200 mesh silica gel (Aldrich Co.). Infrared spectra (IR) were recorded on a Beckman 18A spectrophotometer with NaCl plates. Proton nuclear magnetic resonance spectra (1H NMR) were obtained at 300 MHz with a Nicolet high-resolution instrument.

In another aspect, the invention is directed to a method of using a compound of the invention for the manufacture of a radiopharmaceutical for the diagnosis of Alzheimer's disease in a human. In another aspect, the invention is directed to a method of preparing compounds of the invention.

The compounds of the invention as described herein are the thyroid hormone analogs or other TTR binding ligands, which bind to TTR and have the ability to pass the blood-brain barrier. The compounds are therefore suited as in vivo diagnostic agents for imaging of Alzheimer's disease. The detection of radioactivity is performed according to well-known procedures in the art, either by using a gamma camera or by positron emission tomography (PET).

Preferably, the free base or a pharmaceutically acceptable salt form, e.g. a monochloride or dichloride salt, of a compound of the invention is used in a galenical formulation as diagnostic agent. The galenical formulation containing the compound of the invention optionally contains adjuvants known in the art, e.g. buffers, sodium chloride, lactic acid, surfactants etc. A sterilization by filtration of the galenical formulation under sterile conditions prior to usage is possible.

The radioactive dose should be in the range of 1 to 100 mCi, preferably 5 to 30 mCi, and most preferably 5 to 20 mCi per application. TH compositions within the scope of the present invention can be used as diagnostic agents in positron emission tomography (PET).

The compounds of the present invention may be administered by any suitable route, preferably in the form of a pharmaceutical composition adapted to such a route, and in a dose effective to bind TTR in the brain and thereby be detected by gamma camera or PET. Typically, the administration is parenteral, e.g., intravenously, intraperitoneally, subcutaneously, intradermally, or intramuscularly. Intraveneous administration is preferred.

Thus, for example, the invention provides compositions for parenteral administration which comprise a solution of contrast media dissolved or suspended in an acceptable carrier, e.g., serum or physiological sodium chloride solution.

Aqueous carriers include water, alcoholic/aqueous solutions, saline solutions, parenteral vehicles such as sodium chloride, Ringer's dextrose, etc. Examples of non-aqueous solvents are propylene glycol, polyethylene glycol, vegetable oil and injectable organic esters such as ethyl oleate. Other pharmaceutically acceptable carriers, non-toxic excipients, including salts, preservatives, buffers and the like, are described, for instance, in REMMINGTON'S PHARMACEUTICAL SCIENCES, 15.sup.th Ed. Easton: Mack Publishing Co., pp. 1405-1412 and 1461-1487 (1975) and THE NATIONAL FORMULARY XIV., 14.sup.th Ed. Washington: American Pharmaceutical Association (1975). Aqueous carriers, are preferred.

Pharmaceutical composition of this invention are produced in a manner known per se by suspending or dissolving the compounds of this invention—optionally combined with the additives customary in galenic pharmacy—in an aqueous medium and then optionally sterilizing the suspension or solution. Suitable additives are, for example, physiologically acceptable buffers (such as, for instance, tromethamine), additions of complexing agents (e.g., diethylenetriaminepentaacetic acid) or—if required—electrolytes, e.g., sodium chloride or—if necessary—antioxidants, such as ascorbic acid, for example.

If suspensions or solutions of the compounds of this invention in water or physiological saline solution are desirable for enteral administration or other purposes, they are mixed with one or several of the auxiliary agents (e.g., methylcellulose, lactose, mannitol) and/or tensides (e.g., lecithins, "Tween", "Myrj") and/or flavoring agents to improve taste (e.g., ethereal oils), as customary in galenic pharmacy.

The compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For the compounds according to the invention having radioactive halogens, these compounds can be shipped as "hot" compounds, i.e., with the radioactive halogen in the compound and administered in e.g., a physiologically acceptable saline solution. In the case of the metal complexes, these compounds can be shipped as "cold" compounds, i.e., without the radioactive ion, and then mixed with Tc-generator eluate or Re-generator eluate.

Inhibiting Angiogenesis

The invention also provides, in another part, compositions and methods for inhibiting angiogenesis in a subject in need thereof. Conditions amenable to treatment by inhibiting angiogenesis include, for example, primary or metastatic tumors and diabetic retinopathy. The compositions can include an effective amount of tetraiodothyroacetic acid (TETRAC), triiodothyroacetic acid (TRIAC), monoclonal antibody LM609, or combinations thereof. Such anti-angiogenesis agents can act at the cell surface to inhibit the pro-angiogenesis agents. The compositions can be in the form of a sterile, injectable, pharmaceutical formulation that includes an anti-angiogenically effective amount of an anti-angiogenic substance in a physiologically and pharmaceutically acceptable carrier, optionally with one or more excipients.

In a further aspect, the invention provides methods for treating a condition amenable to treatment by inhibiting angiogenesis by administering to a subject in need thereof an amount of an anti-angiogenesis agent effective for inhibiting angiogenesis. The compositions of the present invention can be used to inhibit angiogenesis associated with cancers, including head and neck, glioma, skin, lung, breast, and thyroid. The thyroid hormone antagonists, like tetrac, can be administered as polymer conjugates or as nanoparticles.

Nature of Cellular Actions of Tetrac that are Initiated at the Plasma Membrane:

Acting at the plasma membrane receptor for thyroid hormone, tetrac inhibits the proangiogenic effects of T4 and T3 in standard assays of neovascularization (chick chorioallantoic membrane, human dermal microvascular endothelial cells). Tetrac blocks the action of agonist thyroid hormone analogues (T4, T3) on growth of human and animal cancer cells in vitro, as well as in certain in vivo models. Among the human cancer cell models whose proliferation is inhibited by tetrac are breast cancer and lung cancer. Among animal tumor cells are glioma cells that are models for human brain cancer, such as glioma/glioblastoma.

Action of Tetrac Initiated at the Plasma Membrane in the Absence of Agonist Thyroid Hormone Analogues:

The proximity of the hormone receptor site to the RGD site on the integrin underlies the ability of tetrac, in the absence of hormone agonists such as T4 and T3, to block the pro-angiogenic activities of polypeptide endothelial growth factors, such as, but not limited to, vascular endothelial growth factor (VEGF) and basic fibroblast growth factor (bFGF).

Tetrac for Inducing Apoptosis in Glioma and Thyroid Cancer Cells

The figures below demonstrate that tetrac is capable of inducing apoptosis in C6 glioma cells and in thyroid cancer cells (BHP 2-7). Thus, at least part of the decrease in proliferation of cancer cells when they are exposed to tetrac is programmed cell death (apoptosis). When proliferation slows in studies of any cancer cells, the issue is whether the cells survive in a cell cycle arrest mode or whether they die. Cell death is more desirable than cell cycle arrest.

Tetrac for Viral Agents

Tetrac may be used for the West Nile virus. Certain viral agents, such as the West Nile Virus, whose cell entry depends on the alpha v beta 3 integrin via the RGD binding site can be treated with tetrac.

Tetrac for Human Lung Cancer

The thyroid hormone/tetrac effect involves the estrogen receptor (ER) in both small cell and non-small cell human lung carcinoma cells. L-thyroxine (T4) and 3,5,3'-triiodo-L-thyronine (T3) cause proliferation of small cell and non-small cell human lung carcinoma lines and do so via a mechanism that requires the presence in the tumor cells of estrogen receptor-alpha (ERalpha). Tetraiodothyroacetic acid (tetrac) is a probe for the involvement of the cell surface receptor for thyroid hormone on integrin alphaVbeta3 in the cellular actions of T4 and T3. Tetrac, either free or as a nanoparticle, blocks this proliferative action of T4 and T3 on lung carcinoma cells. This indicates that the cell surface receptor for thyroid hormone on integrin alphaVbeta3 mediates the T4 and T3 effects. We have also blocked the proliferative actions of T4 and T3 on lung cancer cells with anti-alphaV and anti-beta3 and with RGD peptide. These observations further support the role of the integrin receptor for thyroid hormone in promotion by T4 and T3 of proliferation of lung cancer cells.

Tetrac, either free or as the nanoparticle, is an attractive and novel strategy for management of human lung carcinoma. In addition to its anti-proliferative action, tetrac, either free or as the nanoparticle, is anti-angiogenic, inhibiting new blood vessel growth that supports lung carcinoma growth. Thus, tetrac has at least two discrete actions that are relevant to inhibition of lung tumor growth.

Among the nanoparticulate formulations of tetrac are tetrac linked by ester or ether bond to polylysyl glycolic acid (PLGA) or to collagen or other molecules of sufficient size to prohibit cell entry by tetrac. These formulations limit actions of tetrac to the cell surface receptor for thyroid hormone on integrin alphaVbeta3.

Cancer-Related New Blood Vessel Growth:

Examples of the conditions amenable to treatment by inhibiting angiogenesis include, but are not limited to, primary or metastatic tumors, including, but not limited to glioma and breast cancer. In such a method, compounds which inhibit the thyroid hormone-induced angiogenic effect are used to inhibit angiogenesis. Details of such a method is illustrated in Example 12. Thyroid hormone antagonists such as tetrac, analogs, polymer conjugates, and nanoparticles thereof can also be used as an anti-angiogenic agent to inhibit angiopoietin-2. This inhibition can help prevent cancer-related new blood vessel growth, as angiopoietin-2 destabilizes blood vessels around tumors, making those blood vessels more susceptible to the induction of sprouts by VEGF.

Diabetic Retinopathy:

Examples of the conditions amenable to treatment by inhibiting angiogenesis include, but are not limited to diabetic retinopathy, and related conditions. In such a method, compounds which inhibit the thyroid hormone-induced angiogenic effect are used to inhibit angiogenesis. Details of such a method is illustrated in Examples 8A and B.

It is known that proliferative retinopathy induced by hypoxia (rather than diabetes) depends upon alphaV ($\alpha$V) integrin expression (E Chavakis et al., Diabetologia 45:262-267, 2002). It is proposed herein that thyroid hormone action on a specific integrin alphaVbeta-3 ($\alpha$V$\beta$3) is permissive in the development of diabetic retinopathy. Integrin $\alpha$V$\beta$3 is identified herein as the cell surface receptor for thyroid hormone. Thyroid hormone, its analogs, and polymer conjugations, act via this receptor to induce angiogenesis.

Dermatology—Nanoparticulate Tetraiodothyroacetic Acid (Tetrac) to Diminish Size of Cutaneous Telangiectasias and Angiomas:

Thyroid hormone antagonists such as tetrac, analogs, polymer conjugates, and nanoparticles thereof can also be used to treat non-cancer skin disorders. This therapeutic and/or cosmetic action of derivatized tetrac is based on its anti-angiogenic activity. Applied locally as an ointment or cream to cutaneous telangiectasias or spider angiomas, derivatized tetrac will oppose the pro-angiogenic actions on endothelial cells of endogenous (circulating) thyroid hormone and of polypeptide vascular growth factors. Systemic effects of the locally applied hormone analogue as a PLGA derivative will be negligible. For low-grade telangiectasias or angiomas, derivatized tetrac may be made available for clinical use in OTC preparations.

Because tetrac opposes the platelet aggregation action of thyroid hormone, trauma at the site of application of tetrac could lead to local bleeding. This is a risk with existing, untreated telangiectasias and angiomas. Successful diminution with application of tetrac of the size of such vascular lesions will, however, reduce the risk of local ecchymoses.

Additional dermatological topical applications for nanoparticulate-conjugated thyroid antagonists include poikiloderma of civatte (long term exposure to sunlight leading to facial neovascularization and dilated blood vessels), acne or facial rosacea, psoriasis alone or in combination with Vitamin D analogs, and skin cancer.

Available anti-angiogenic agents are too expensive for use for the cutaneous lesions targeted here. These agents may also be unsuitable for cutaneous application because they are not locally absorbed.

Methods of Treatment and Formulations:

Thyroid hormone analogs, polymeric forms, and derivatives can be used in a method for promoting angiogenesis in a patient in need thereof. The method involves the co-administration of an effective amount of thyroid hormone analogs, polymeric forms, and derivatives in low, daily dosages for a week or more. The method may be used as a treatment to restore cardiac function after a myocardial infarction. The method may also be used to improve blood flow in patients with coronary artery disease suffering from myocardial ischemia or inadequate blood flow to areas other than the heart, for example, peripheral vascular disease, for example, peripheral arterial occlusive disease, where decreased blood flow is a problem.

The compounds can be administered via any medically acceptable means which is suitable for the compound to be administered, including oral, rectal, topical or parenteral (including subcutaneous, intramuscular and intravenous) administration. For example, adenosine has a very short half-life. For this reason, it is preferably administered intravenously. However, adenosine A.sub.2 agonists have been developed which have much longer half-lives, and which can be administered through other means. Thyroid hormone analogs, polymeric forms, and derivatives can be administered, for example, intravenously, oral, topical, intranasal administration.

In some embodiments, the thyroid hormone analogs, polymeric forms, and derivatives are administered via different means.

The amounts of the thyroid hormone, its analogs, polymeric forms, and derivatives required to be effective in stimulating angiogenesis will, of course, vary with the individual being treated and is ultimately at the discretion of the physician. The factors to be considered include the condition of the patient being treated, the efficacy of the particular adenosine $A_2$ receptor agonist being used, the nature of the formulation, and the patient's body weight. Occlusion-treating dosages of thyroid hormone analogs or its polymeric forms, and derivatives are any dosages that provide the desired effect.

The compounds described above are preferably administered in a formulation including thyroid hormone analogs or its polymeric forms, and derivatives together with an acceptable carrier for the mode of administration. Any formulation or drug delivery system containing the active ingredients, which is suitable for the intended use, as are generally known to those of skill in the art, can be used. Suitable pharmaceutically acceptable carriers for oral, rectal, topical or parenteral (including subcutaneous, intraperitoneal, intramuscular and intravenous) administration are known to those of skill in the art. The carrier must be pharmaceutically acceptable in the sense of being compatible with the other ingredients of the formulation and not deleterious to the recipient thereof.

Formulations suitable for parenteral administration conveniently include sterileaqueous preparation of the active compound, which is preferably isotonic with the blood of the recipient. Thus, such formulations may conveniently contain distilled water, 5% dextrose in distilled water or saline. Useful formulations also include concentrated solutions or solids containing the compound of formula (I), which upon dilution with an appropriate solvent give a solution suitable for parental administration above.

For enteral administration, a compound can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Alternatively, the compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

In one embodiment, the thyroid hormone analogs or its polymeric forms, and adenosine derivatives can be formulated into a liposome or microparticle, which is suitably sized to lodge in capillary beds following intravenous administration. When the liposome or microparticle is lodged in the capillary beds surrounding ischemic tissue, the agents can be administered locally to the site at which they can be most effective. Suitable liposomes for targeting ischemic tissue are generally less than about 200 nanometers and are also typically unilamellar vesicles, as disclosed, for example, in U.S. Pat. No. 5,593,688 to Baldeschweiler, entitled "Liposomal targeting of ischemic tissue," the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,016 to Hubbell et al. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

The formulations may conveniently be presented in unit dosage form and may be prepared by any of the methods well known in the art of pharmacy. All methods include the step of bringing the active compound into association with a carrier, which constitutes one or more accessory ingredients. In general, the formulations are prepared by uniformly and intimately bringing the active compound into association with a liquid carrier or a finely divided solid carrier and then, if necessary, shaping the product into desired unit dosage form.

The formulations can optionally include additional components, such as various biologically active substances such as growth factors (including TGF-.beta., basic fibroblast growth factor (FGF2), epithelial growth factor (EGF), transforming growth factors .alpha. and .beta. (TGF alpha. and beta.), nerve growth factor (NGF), platelet-derived growth factor (PDGF), and vascular endothelial growth factor/vascular permeability factor (VEGF/VPF)), antiviral, antibacterial, anti-inflammatory, immuno-suppressant, analgesic, vascularizing agent, and cell adhesion molecule.

In addition to the aforementioned ingredients, the formulations may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

Formulations and Methods of Treatment

Polymeric thyroid hormone analogs alone or in combination with nerve growth factors or other neurogenesis factors inducers, or agonists of polymeric thyroid hormone analogs alone or in combination with nerve growth factors or other neurogenesis factors receptors of the present invention may be administered by any route which is compatible with the particular polymeric thyroid hormone analog alone or in combination with nerve growth factors or other neurogenesis factors, inducer, or agonist employed. Thus, as appropriate, administration may be oral or parenteral, including intravenous and intraperitoneal routes of administration. In addition, administration may be by periodic injections of a bolus of the polymeric thyroid hormone analog alone or in combination with nerve growth factors or other neurogenesis factors, inducer or agonist, or may be made more continuous by intravenous or intraperitoneal administration from a reservoir which is external (e.g., an i.v. bag) or internal (e.g., a bioerodable implant, or a colony of implanted, polymeric thyroid analog alone or in combination with nerve growth factor or other neurogenesis factors-producing cells).

Therapeutic agents of the invention (i.e., polymeric thyroid hormone analogs alone or in combination with nerve growth factors or other neurogenesis factors, inducers or agonists of polymeric thyroid hormone analogs alone or in combination with nerve growth factors or other neurogenesis factors receptors) may be provided to an individual by any suitable means, directly (e.g., locally, as by injection, implantation or topical administration to a tissue locus) or systemically (e.g., parenterally or orally). Where the agent is to be provided parenterally, such as by intravenous, subcutaneous, intramolecular, ophthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the agent preferably comprises part of an aqueous or physiologically compatible fluid suspension or solution. Thus, the polymeric thyroid hormone analogs alone or in combination with nerve growth factors or other neurogenesis factors carrier or vehicle is physiologically acceptable so that in addition to delivery of the desired agent to the patient, it does not otherwise adversely affect the patient's electrolyte and/or volume balance. The fluid medium for the agent thus can comprise normal physiologic saline (e.g., 9.85% aqueous NaCl, 0.15M, pH 7-7.4).

Association of the dimer with a polymeric thyroid hormone analog pro domain results in the pro form of the polymeric thyroid hormone analog which typically is more soluble in physiological solutions than the corresponding mature form.

Useful solutions for parenteral administration may be prepared by any of the methods well known in the pharmaceutical art, described, for example, in REMINGTON'S PHARMACEUTICAL SCIENCES (Gennaro, A., ed.), Mack Pub., 1990. Formulations of the therapeutic agents of the invention may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide, and glycolide polymers and lactide/glycolide copolymers, may be useful excipients to control the release of the agent in vivo. Other potentially useful parenteral delivery systems for these agents include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration. Suppositories for rectal administration may also be prepared by mixing the polymeric thyroid hormone analogs alone or in combination with nerve growth factors or other neurogenesis factors, inducer or agonist with a non-irritating excipient such as cocoa butter or other compositions which are solid at room temperature and liquid at body temperatures.

Formulations for topical administration to the skin surface may be prepared by dispersing the polymeric thyroid hormone analogs alone or in combination with nerve growth factors or other neurogenesis factors, inducer or agonist with a dermatologically acceptable carrier such as a lotion, cream, ointment or soap. Particularly useful are carriers capable of forming a film or layer over the skin to localize application and inhibit removal. For topical administration to internal tissue surfaces, the agent may be dispersed in a liquid tissue adhesive or other substance known to enhance adsorption to a tissue surface. For example, hydroxypropylcellulose or fibrinogen/thrombin solutions may be used to advantage. Alternatively, tissue-coating solutions, such as pectin-containing formulations may be used.

Alternatively, the agents described herein may be administered orally. Oral administration of proteins as therapeutics generally is not practiced, as most proteins are readily degraded by digestive enzymes and acids in the mammalian digestive system before they can be absorbed into the bloodstream. However, the polymeric thyroid hormone analogs alone or in combination with nerve growth factors or other neurogenesis factors described herein typically are acid stable and protease-resistant (see, for example, U.S. Pat. No. 4,968,590). In addition, OP-1, has been identified in mammary gland extract, colostrum and 57-day milk. Moreover, the OP-1 purified from mammary gland extract is morphogenically-active and is also detected in the bloodstream. Maternal administration, via ingested milk, may be a natural delivery route of TGF-β superfamily proteins. Letterio, et al., Science 264: 1936-1938 (1994), report that TGF-β is present in murine milk, and that radiolabelled TGF-β is absorbed by gastrointestinal mucosa of suckling juveniles. Labeled, ingested TGF-β appears rapidly in intact form in the juveniles' body tissues, including lung, heart and liver. Finally, soluble form polymeric thyroid hormone analogs alone or in combination with nerve growth factors or other neurogenesis factors, e.g., mature polymeric thyroid hormone analogs alone or in combination with nerve growth factors or other neurogenesis factors with or without anti-oxidant or anti-inflammatory agents. These findings, as well as those disclosed in the examples below, indicate that oral and parenteral administration are viable means for administering TGF-β superfamily proteins, including the polymeric thyroid analog alone or in combination with nerve growth factor or other neurogenesis factors, to an individual. In addition, while the mature forms of certain polymeric thyroid analog alone or in combination with nerve growth factor or other neurogenesis factors described herein typically are sparingly soluble, the polymeric thyroid analog alone or in combination with nerve growth factor or other neurogenesis factors form found in milk (and mammary gland extract and colostrum) is readily soluble, probably by association of the mature, morphogenically-active form with part or all of the pro domain of the expressed, full length polypeptide sequence and/or by association with one or more milk components. Accordingly, the compounds provided herein may also be associated with molecules capable of enhancing their solubility in vitro or in vivo.

Where the polymeric thyroid hormone analogs alone or in combination with nerve growth factors or other neurogenesis factors is intended for use as a therapeutic for disorders of the CNS, an additional problem must be addressed: overcoming the blood-brain barrier, the brain capillary wall structure that effectively screens out all but selected categories of substances present in the blood, preventing their passage into the brain. The blood-brain barrier can be bypassed effectively by direct infusion of the polymeric thyroid hormone analogs into the brain, or by intranasal administration or inhalation of formulations suitable for uptake and retrograde transport by olfactory neurons. Alternatively, the polymeric thyroid hormone analogs can be modified to enhance its transport across the blood-brain barrier. For example, truncated forms of the polymeric thyroid hormone analogs alone or in combination with nerve growth factors or other neurogenesis factors or a polymeric thyroid hormone analog alone or in combination with nerve growth factor or other neurogenesis factors-stimulating agent may be most successful. Alternatively, the polymeric thyroid hormone analogs alone or in combination with nerve growth factors or other neurogenesis factors, inducers or agonists provided herein can be derivatized or conjugated to a lipophilic moiety or to a substance that is actively transported across the blood-brain barrier, using standard means known to those skilled in the art. See, for example, Pardridge, Endocrine Reviews 7: 314-330 (1986) and U.S. Pat. No. 4,801,575.

The compounds provided herein may also be associated with molecules capable of targeting the polymeric thyroid hormone analogs alone or in combination with nerve growth factors or other neurogenesis factors, inducer or agonist to the desired tissue. For example, an antibody, antibody fragment, or other binding protein that interacts specifically with a surface molecule on cells of the desired tissue, may be used. Useful targeting molecules may be designed, for example, using the single chain binding site technology disclosed in U.S. Pat. No. 5,091,513. Targeting molecules can be covalently or non-covalently associated with the polymeric thyroid hormone analogs alone or in combination with nerve growth factors or other neurogenesis factors, inducer or agonist.

As will be appreciated by one of ordinary skill in the art, the formulated compositions contain therapeutically-effective amounts of the polymeric thyroid hormone analogs alone or in combination with nerve growth factors or other neurogenesis factors, inducers or agonists thereof. That is, they contain an amount which provides appropriate concentrations of the agent to the affected nervous system tissue for a time sufficient to stimulate a detectable restoration of impaired central or peripheral nervous system function, up to and including a complete restoration thereof. As will be appreciated by those skilled in the art, these concentrations will vary depending upon a number of factors, including the biological efficacy of the selected agent, the chemical characteristics (e.g., hydrophobicity) of the specific agent, the formulation thereof, including a mixture with one or more excipients, the administration route, and the treatment envisioned, including whether the active ingredient will be administered directly into a tissue site, or whether it will be administered systemically. The preferred dosage to be administered is also likely to depend on variables such as the condition of the diseased or damaged tissues, and the overall health status of the particular mammal. As a general matter, single, daily, biweekly or weekly dosages of 0.00001-1000 mg of a polymeric thyroid analog alone or in combination with nerve growth factor or other neurogenesis factors are sufficient in the presence of anti-oxidant and/or anti-inflammatory agents, with 0.0001-100 mg being preferable, and 0.001 to 10 mg being even more preferable. Alternatively, a single, daily, biweekly or weekly dosage of 0.01-1000 µg/kg body weight, more preferably 0.01-10 mg/kg body weight, may be advantageously employed. A Nanoparticle contains between 1 and 100 thyroid hormone molecules per nanoparticle either encapsulated or immobilized on the Nanoparticle surface via chemical bonding. The Nanoparticle can co-encapsulate thyroid hormone analogs along with chemotherapeutic agents, or other known pro-angiogenesis or anti-angiogenesis agents. Furthermore, the Nanoparticle contains inside the chemotherapeutic agents, pro- or anti-angiogenesis agents and the thyroid hormone analogs are immobilized on the surface of the Nanoparticles via stable chemical bonding. The surface of the Nanoparticles contain site directing moiety such αvβ3 ligand bonded to the surface via stable chemical bonding.

The present effective dose can be administered in a single dose or in a plurality (two or more) of installment doses, as desired or considered appropriate under the specific circumstances. A bolus injection or diffusable infusion formulation can be used. If desired to facilitate repeated or frequent infusions, implantation of a semi-permanent stent (e.g., intravenous, intraperitoneal, intracisternal or intracapsular) may be advisable.

The polymeric thyroid hormone analogs alone or in combination with nerve growth factors or other neurogenesis factors, inducers or agonists of the invention may, of course, be administered alone or in combination with other molecules known to be beneficial in the treatment of the conditions described herein. For example, various well-known growth factors, hormones, enzymes, therapeutic compositions, antibiotics, or other bioactive agents can also be administered with the polymeric thyroid hormone analogs alone or in combination with nerve growth factors or other neurogenesis factors. Thus, various known growth factors such as NGF, EGF, PDGF, IGF, FGF, TGF-α, and TGF-β, as well as enzymes, enzyme inhibitors, antioxidants, anti-inflammatory agents, free radical scavenging agents, antibiotics and/or chemoattractant/chemotactic factors, can be included in the present polymeric thyroid hormone analogs alone or in combination with nerve growth factors or other neurogenesis factors formulation.

The following examples are intended to further illustrate certain embodiments of the invention and are not intended to limit the scope of the invention.

Examples 1-7

The following materials and methods were used for examples 1-7. All reagents were chemical grade and purchased from Sigma Chemical Co. (St. Louis, Mo.) or through VWR Scientific (Bridgeport, N.J.). Cortisone acetate, bovine serum albumin (BSA) and gelatin solution (2% type B from bovine skin) were purchased from Sigma Chemical Co. Fertilized chicken eggs were purchased from Charles River Laboratories, SPAFAS Avian Products & Services (North Franklin, Conn.). T4, 3,5,3'-triiodo-L-thyronine (T3), tetraiodothyroacetic acid (tetrac), T4-agarose, 6-N-propyl-2-thiouracil (PTU), RGD-containing peptides, and RGE-containing peptides were obtained from Sigma; PD 98059 from Calbiochem; and CGP41251 was a gift from Novartis Pharma (Basel, Switzerland). Polyclonal anti-FGF2 and monoclonal anti-β-actin were obtained from Santa Cruz Biotechnology and human recombinant FGF2 and VEGF from Invitrogen.

Polyclonal antibody to phosphorylated ERK1/2 was from New England Biolabs and goat anti-rabbit IgG from DAKO. Monoclonal antibodies to αVβ3 (SC73 12) and α-tubulin (E9) were purchased from Santa Cruz Biotechnology (Santa Cruz, Calif.). Normal mouse IgG and HRP-conjugated goat anti-rabbit Ig were purchased from Dako Cytomation (Carpinteria, Calif.). Monoclonal antibodies to αVβ3 (LM609) and αVβ5 (P1F6), as well as purified αVβ3, were purchased from Chemicon (Temecula, Calif.). L-[$^{125}$I]-T4 (specific activity, 1250 µCi/µg) was obtained from Perkin Elmer Life Sciences (Boston, Mass.).

Chorioallantoic membrane (CAM) Model of Angiogenesis: In vivo Neovascularization was examined by methods described previously. 9-12 Ten-day-old chick embryos were purchased from SPAFAS (Preston, Conn.) and incubated at 37° C. with 55% relative humidity. A hypodermic needle was used to make a small hole in the shell concealing the air sac, and a second hole was made on the broad side of the egg, directly over an avascular portion of the embryonic membrane that was identified by candling. A false air sac was created beneath the second hole by the application of negative pressure at the first hole, causing the CAM to separate from the shell. A window approximately 1.0 cm 2 was cut in the shell over the dropped CAM with a small-crafts grinding wheel (Dremel, division of Emerson Electric Co.), allowing direct access to the underlying CAM. FGF2 (1 µg/mL) was used as a standard proangiogenic agent to induce new blood vessel branches on the CAM of 10-day-old embryos. Sterile disks of No. 1 filter paper (Whatman International) were pretreated with 3 mg/mL cortisone acetate and 1 mmol/L PTU and air dried under sterile conditions. Thyroid hormone, hormone analogues, FGF2 or control solvents, and inhibitors were then applied to the disks and the disks allowed to dry. The disks were then suspended in PBS and placed on growing CAMs. Filters treated with T4 or FGF2 were placed on the first day of the 3-day incubation, with antibody to FGF2 added 30 minutes later to selected samples as indicated. At 24 hours, the MAPK cascade inhibitor PD 98059 was also added to CAMs topically by means of the filter disks.

Microscopic Analysis of CAM Sections:

After incubation at 37° C. with 55% relative humidity for 3 days, the CAM tissue directly beneath each filter disk was resected from control and treated CAM samples. Tissues were washed 3× with PBS, placed in 35-mm Petri dishes (Nalge Nunc), and examined under an SV6 stereomicroscope (Zeiss) at ×50 magnification. Digital images of CAM sections exposed to filters were collected using a 3-charge-coupled device color video camera system (Toshiba) and analyzed with Image-Pro software (Media Cybernetics). The number of vessel branch points contained in a circular region equal to the area of each filter disk were counted. One image was counted in each CAM preparation, and findings from 8 to 10 CAM preparations were analyzed for each treatment condition (thyroid hormone or analogues, FGF2, FGF2 antibody, PD 98059). In addition, each experiment was performed 3 times. The resulting angiogenesis index is the mean±SEM of new branch points in each set of samples.

FGF2 Assays:

ECV304 endothelial cells were cultured in M199 medium supplemented with 10% fetal bovine serum. ECV304 cells ($10^6$ cells) were plated on 0.2% gel-coated 24-well plates in complete medium overnight, and the cells were then washed with serum-free medium and treated with T4 or T3 as indicated. After 72 hours, the supernatants were harvested and assays for FGF performed without dilution using a commercial ELISA system (R&D Systems).

MAPK Activation:

ECV304 endothelial cells were cultured in M199 medium with 0.25% hormone-depleted serum 13 for 2 days. Cells were then treated with T4 ($10^{-7}$ mol/L) for 15 minutes to 6 hours. In additional experiments, cells were treated with T4 or FGF2 or with T4 in the presence of PD 98059 or CGP41251. Nuclear fractions were pre-pared from all samples by our method reported previously, the proteins separated by polyacrylamide gel electrophoresis, and transferred to membranes for immunoblotting with antibody to phosphorylated ERK 1/2. The appearance of nuclear phosphorylated ERK1/2 signifies activation of these MAPK isoforms by T4.

Reverse Transcription-Polymerase Chain Reaction:

Confluent ECV304 cells in 10-cm plates were treated with T4 ($10^{-7}$ mol/L) for 6 to 48 hours and total RNA extracted using guanidinium isothiocyanate (Biotecx Laboratories). RNA (1 µg) was subjected to reverse transcription-polymerase chain reaction (RT-PCR) using the Access RT-PCR system (Promega). Total RNA was reverse transcribed into cDNA at 48° C. for 45 minutes, then denatured at 94° C. for 2 minutes. Second-strand synthesis and PCR amplification were performed for 40 cycles with denaturation at 94° C. for 30 s, annealing at 60° C. for 60 s, and extension at 68° C. for 120 s, with final ex-tension for 7 minutes at 68° C. after completion of all cycles. PCR primers for FGF2 were as follows: FGF2 sense strand 5'-TGGTATGTGGCACT-GAAACG-3' (SEQ ID NO:1), antisense strand 5' CTCAAT- GACCTGGCGAAGAC-3' (SEQ ID NO:2); the length of the PCR product was 734 bp. Primers for GAPDH included the sense strand 5'-AAGGTCATCCCTGAGCTGAACG-3' (SEQ ID NO:3), and antisense strand 5'-GGGTGTCGCTGTTGAAGTCAGA-3' (SEQ ID NO:4); the length of the PCR product was 218 bp. The products of RT-PCR were separated by electrophoresis on 1.5% agarose gels and visualized with ethidium bromide. The target bands of the gel were quantified using LabImage software (Kapelan), and the value for [FGF2/GAPDH]×10 calculated for each time point.

Statistical Analysis:

Statistical analysis was performed by 1-way analysis of variance (ANOVA) comparing experimental with respective control group and statistical significance was calculated based on P<0.05.

In Vivo Angiogenesis in Matrigel $FGF_2$ or Cancer Cell Lines Implant in Mice: In Vivo Murine Angiogenesis Model:

The murine matrigel model will be conducted according to previously described methods (Grant et al., 1991; Okada et al., 1995) and as implemented in our laboratory (Powel et al., 2000). Briefly, growth factor free matrigel (Becton Dickinson, Bedford Mass.) will be thawed overnight at 4° C. and placed on ice. Aliquots of matrigel will be placed into cold polypropylene tubes and FGF2, thyroid hormone analogs or cancer cells ($1\times10^6$ cells) will be added to the matrigel. Matrigel with Saline, FGF2, thyroid hormone analogs or cancer cells will be subcutaneously injected into the ventral midline of the mice. At day 14, the mice will be sacrificed and the solidified gels will be resected and analyzed for presence of new vessels. Compounds A-D will be injected subcutaneously at different doses. Control and experimental gel implants will be placed in a micro centrifuge tube containing 0.5 ml of cell lysis solution (Sigma, St. Louis, Mo.) and crushed with a pestle. Subsequently, the tubes will be allowed to incubate overnight at 4° C. and centrifuged at 1,500×g for 15 minutes on the following day. A 200 µl aliquot of cell lysate will be added to 1.3 ml of Drabkin's reagent solution (Sigma, St. Louis, Mo.) for each sample. The solution will be analyzed on a spectrophotometer at a 540 nm. The absorption of light is proportional to the amount of hemoglobin contained in the sample.

Tumor Growth and Metastasis—Chick Chorioallantoic Membrane (CAM) Model of Tumor Implant:

The protocol is as previously described (Kim et al., 2001). Briefly, $1\times10^7$ tumor cells will be placed on the surface of each CAM (7 day old embryo) and incubated for one week. The resulting tumors will be excised and cut into 50 mg fragments. These fragments will be placed on additional 10 CAMs per group and treated topically the following day with 25 µl of compounds (A-D) dissolved in PBS. Seven days later, tumors will then be excised from the egg and tumor weights will be determined for each CAM. FIG. 8 is a diagrammatic sketch showing the steps involved in the in vivo tumor growth model in the CAM.

The effects of TETRAC, TRIAC, and thyroid hormone antagonists on tumor growth rate, tumor angiogenesis, and tumor metastasis of cancer cell lines can be determined.

Tumor Growth and Metastasis—Tumor Xenograft Model in Mice:

The model is as described in our publications by Kerr et al., 2000; Van Waes et al., 2000; Ali et al., 2001; and Ali et al., 2001, each of which is incorporated herein by reference in its entirety). The anti-cancer efficacy for TETRAC, TRIAC, and other thyroid hormone antagonists at different doses and against different tumor types can be determined and compared.

Tumor Growth and Metastasis—Experimental Model of Metastasis:

The model is as described in our recent publications (Mousa, 2002; Amirkhosravi et al., 2003a and 2003b, each of which is incorporated by reference herein in its entirety). Briefly, B16 murine malignant melanoma cells (ATCC, Rockville, Md.) and other cancer lines will be cultured in RPMI 1640 (Invitrogen, Carlsbad, Calif.), supplemented with 10% fetal bovine serum, penicillin and streptomycin (Sigma, St. Louis, Mo.). Cells will be cultured to 70% confluency and harvested with trypsin-EDTA (Sigma) and washed twice with phosphate buffered saline (PBS). Cells will be re-suspended in PBS at a concentration of either $2.0\times10^5$ cells/ml for experimental metastasis. Animals: C57/BL6 mice (Harlan, Indianapolis, Ind.) weighing 18-21 grams will be used for this study. All procedures are in accordance with IACUC and institutional guidelines. The anti-cancer efficacy for TETRAC, TRIAC, and other thyroid hormone antagonists at different doses and against different tumor types can be determined and compared.

Effect of Thyroid Hormone Analogues on Angiogenesis:

T4 induced significant increase in angiogenesis index (fold increase above basal) in the CAM model. T3 at 0.001-1.0 µM or T4 at 0.1-1.0 µM achieved maximal effect in producing 2-2.5 fold increase in angiogenesis index as compared to 2-3 fold increase in angiogenesis index by 1 µg of FGF2 (Table 1 and FIGS. 1a and 1b). The effect of T4 in promoting angiogenesis (2-2.5 fold increase in angiogenesis index) was achieved in the presence or absence of PTU, which inhibit T4 to T3 conversion. T3 itself at 91-100 nM)-induced potent pro-angiogenic effect in the CAM model. T4 agarose produced similar pro-angiogenesis effect to that achieved by T4. The pro-angiogenic effect of either T4 or T4-agarose was 100% blocked by TETRAC or TRIAC.

Enhancement of Pro-Angiogenic Activity of FGF2 by Sub-Maximal Concentrations of $T_4$:

The combination of T4 and FGF2 at sub-maximal concentrations resulted in an additive increase in the angiogenesis index up to the same level like the maximal pro-angiogenesis effect of either FGF2 or T4 (FIG. 2).

Figures 3A, 3B:
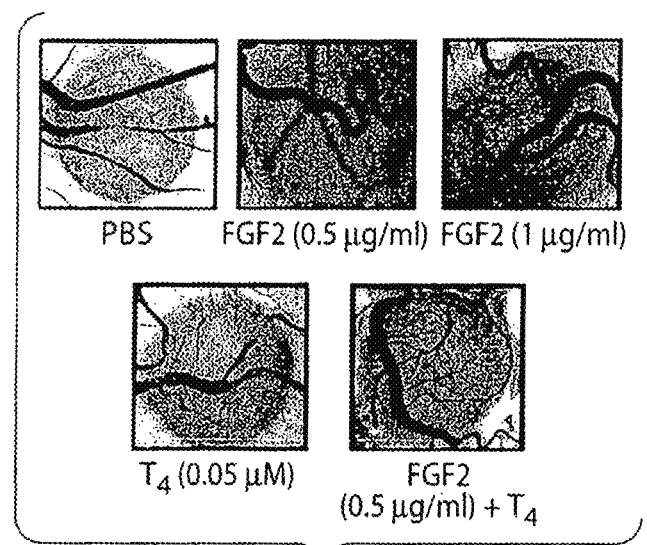
FIG. 3A. Comparison of the proangiogenic effects of FGF2 and T4. Tandem effects of T4 (0.05 µmol/L) and FGF2 (0.5 µg/mL) in submaximal concentrations are additive in the CAM assay and equal the level of angiogenesis seen with FGF2 (1 µg/mL in the absence of T4).
FIG. 3B. Summary of results from 3 experiments that examined actions of FGF2 and T4 in the CAM assay (means±SEM) as in A. *$P<0.05$; **$P<0.001$, comparing results of treated samples with those of PBS-treated control samples in 3 experiments.

Effects of MAPK Cascade Inhibitors on the Pro-Angiogenic Actions of $T_4$ and FGf2 n the CAM Model:

The pro-angiogenesis effect of either T4 or FGF2 was totally blocked by PD 98059 at 0.8-8 µg (FIG. 3).

Effects of Specific Integrin αvβ3 Antagonists on the Pro-Angiogenic Actions of $T_4$ and FGf2 n the CAM Model:

The pro-angiogenesis effect of either T4 or FGF2 was totally blocked by the specific monoclonal antibody LM609 at 10 µs (FIGS. 4a and 4b).

The CAM assay has been used to validate angiogenic activity of a variety of growth factors and other promoters or inhibitors of angiogenesis. In the present studies, $T_4$ in physiological concentrations was shown to be pro-angiogenic, with comparable activity to that of FGF2. The presence of PTU did not reduce the effect of $T_4$, indicating that de-iodination of $T_4$ to generate $T_3$ was not a prerequisite in this model. Because the appearance of new blood vessel growth in this model requires several days, we assumed that the effect of thyroid hormone was totally dependent upon the interaction of the nuclear receptor for thyroid hormone (TR). Actions of iodothyronines that require intranuclear complexing of TR with its natural ligand, $T_3$, are by definition, genomic, and culminate in gene expression. On the other hand, the preferential response of this model system to $T_4$-rather than $T_3$, the natural ligand of TR raised the possibility that angiogenesis might be initiated non-genomically at the plasma membrane by $T_4$ and culminate in effects that require gene transcription. Non-genomic actions of $T_4$ have been widely described, are usually initiated at the plasma membrane and may be mediated by signal transduction pathways. They do not require intranuclear ligand binding of iodothyronine and TR, but may interface with or modulate gene transcription. Non-genomic actions of steroids have also been well-described and are known to interface with genomic actions of steroids or of other compounds. Experiments carried out with $T_4$ and tetrac or with agarose-$T_4$ indicated that the pro-angiogenic effect of $T_4$ indeed very likely was initiated at the plasma membrane. We have shown elsewhere that tetrac blocks membrane-initiated effects of $T_4$, but does not, itself, activate signal transduction. Thus, it is a probe for non-genomic actions of thyroid hormone. Agarose-$T_4$ is thought not to gain entry to the cell interior and has been used by us and others to examine models for possible cell surface-initiated actions of the hormone.

These results suggest that another consequence of activation of MAPK by thyroid hormone is new blood vessel growth. The latter is initiated nongenomically, but of course requires a consequent complex gene transcription program.

The ambient concentrations of thyroid hormone are relatively stable. The CAM model, at the time we tested it, was thyroprival and thus may be regarded as a system, which does not reproduce the intact organism. We propose that circulating levels of $T_4$ serve, with a variety of other regulators, to modulate the sensitivity of vessels to endogenous angiogenic factors, such as VEGF and FGF2.

Three-Dimensional Angiogenesis Assay.

In Vitro Three-Dimensional Sprout Angiogenesis of Human Dermal Micro-Vascular Endothelial Cells (HDMEC) Cultured on Micro-Carrier Beads Coated with Fibrin:

Confluent HDMEC (passages 5-10) were mixed with gelatin-coated Cytodex-3 beads with a ratio of 40 cells per bead. Cells and beads (150-200 beads per well for 24-well plate) were suspended with 5 ml EBM+15% normal human serum, mixed gently every hour for first 4 hours, then left to culture in a $CO_2$ incubator overnight. The next day, 10 ml of fresh EBM+5% HS were added, and the mixture was cultured for another 3 hours. Before experiments, the culture of EC-beads was checked; then 500 ul of PBS was added to a well of 24-well plate, and 100 ul of the EC-bead culture solution was added to the PBS. The number of beads was counted, and the concentration of EC/beads was calculated.

A fibrinogen solution (1 mg/ml) in EBM medium with or without angiogenesis factors or testing factors was prepared. For positive control, 50 ng/ml VEGF+25 ng/ml FGF2 was used. EC-beads were washed with EBM medium twice, and EC-beads were added to fibrinogen solution. The experiment was done in triplicate for each condition. The EC-beads were mixed gently in fibrinogen solution, and 2.5 ul human thrombin (0.05 U/ul) was added in 1 ml fibrinogen solution; 300 ul was immediately transferred to each well of a 24-well plate. The fibrinogen solution polymerizes in 5-10 minutes; after 20 minutes, we added EBM+20% normal human serum+10 ug/ml aprotinin. The plate was incubated in a $CO_2$ incubator. It takes about 24-48 hours for HDMEC to invade fibrin gel and form tubes.

A micro-carrier in vitro angiogenesis assay previously designed to investigate bovine pulmonary artery endothelial cell angiogenic behavior in bovine fibrin gels [Nehls and Drenckhahn, 1995a, b] was modified for the study of human microvascular endothelial cell angiogenesis in three-dimensional ECM environments (FIGS. 1 and 2). Briefly, human fibrinogen, isolated as previously described [Feng et al, 1999], was dissolved in M199 medium at a concentration of 1 mg/ml (pH 7.4) and sterilized by filtering through a 0.22 micron filter. An isotonic 1.5 mg/ml collagen solution was prepared by mixing sterile Vitrogen 100 in 5×M199 medium and distilled water. The pH was adjusted to 7.4 by 1N NaOH. In certain experiments, growth factors and ECM proteins (such as VEGF, bFGF, PDGF-BB, serum, gelatin, and fibronectin) were added to the fibrinogen or collagen solutions. About 500 EC-beads were then added to the 1 mg/ml fibrinogen or 1.5 mg/ml collagen solutions. Subsequently, EC-beads-collagen or EC-beads-fibrinogen suspension (500 EC-beads/ml) was plated onto 24-well plates at 300 ul/well. EC-bead-collagen cultures were incubated at 37° C. to form gel. The gelling of EC-bead-fibrin cultures occurred in less than 5 minutes at room temperature after the addition of thrombin to a final concentration of 0.5 U/ml. After gelation, 1 ml of fresh assay medium (EBM supplemented with 20% normal human serum for HDMEC or EBM supplemented with 10% fetal bovine serum was added to each well. The angiogenic response was monitored visually and recorded by video image capture. Specifically, capillary sprout formation was observed and recorded with a Nikon Diaphot-TMD inverted microscope (Nikon Inc.; Melville, N.Y.), equipped with an incubator housing with a Nikon NP-2 thermostat and Sheldon #2004 carbon dioxide flow mixer. The microscope was directly interfaced to a video system consisting of a Dage-MTI CCD-72S video camera and Sony 12" PVM-122 video monitor linked to a Macintosh G3 computer. The images were captured at various magnifications using Adobe Photoshop. The effect of angiogenic factors on sprout angiogenesis was quantified visually by determining the number and percent of EC-beads with capillary sprouts. One hundred beads (five to six random low power fields) in each of triplicate wells were counted for each experimental condition. All experiments were repeated at least three times.

Cell Culture:

The African green monkey fibroblast cell line, CV-1 (ATCC, Manassas, Va.), which lacks the nuclear receptor for thyroid hormone, was plated at 5000 cells/cm$^2$ and maintained in DMEM, supplemented with 10% (v/v) heat-inactivated FBS, 100 U/ml penicillin, 100 µg/ml streptomycin, and 2 mM L-glutamine. All culture reagents were purchased from Invitrogen Corporation (Carlsbad, Calif.). Cultures were maintained in a 37° C. humidified chamber with 5% $CO_2$. The medium was changed every three days and the cell lines were passaged at 80% confluency. For experimental treatment, cells were plated in 10-cm cell culture dishes (Corning Incorporated, Corning, N.Y.) and allowed to grow for 24 h in 10% FBS-containing medium. The cells were then rinsed twice with phosphate buffered saline (PBS) and fed with serum-free DMEM supplemented with penicillin, streptomycin, and HEPES. After 48 h incubation in serum-free media, the cells were treated with a vehicle control (final concentration of 0.004 N KOH with 0.4% polyethyleneglycol [v/v]) or T4 ($10^{-7}$ M final concentration) for 30 min; media were then collected and free T4 levels were determined by enzyme immunoassays. Cultures incubated with $10^{-7}$ M total T4 have $10^{-9}$ to $10^{-10}$ M free T4. Following treatment, the cells were harvested and the nuclear proteins prepared as previously described.

Transient Transfections with siRNA:

CV-1 cells were plated in 10-cm dishes (150,000 cells/dish) and incubated for 24 h in DMEM supplemented with 10% FBS. The cells were rinsed in OPTI-MEM (Ambion, Austin, Tex.) and transfected with siRNA (100 nM fmal concentration) to αV, β3, or αV and β3 together using siPORT (Ambion) according to manufacturer's directions. Additional sets of CV-1 cells were transfected with a scrambled siRNA, to serve as a negative control. Four hours post-transfection, 7 ml of 10% FBS-containing media was added to the dishes and the cultures were allowed to incubate overnight. The cells were then rinsed with PBS and placed in serum-free DMEM for 48 h before treatment with T4.

RNA Isolation and RT-PCR:

Total RNA was extracted from cell cultures 72 h post-transfection using the RNeasy kit from Qiagen (Valencia, Calif.) as per manufacturer's instructions. Two hundred nanograms of total RNA was reverse-transcribed using the Access RT-PCR system (Promega, Madison, Wis.) according to manufacturer's directions. Primers were based on published species-specific sequences: αV (accession number NM-002210) F-5'-TGGGATTGTGGAAGGAG and R-5'-AAATCCCTGTCCATCAGCAT (319 bp product), β3 (NM000212) F-5'-GTGTGAGTGCTCAGAGGAG and R-5'-CTGACTCAATCTCGTCACGG (5 15 bp product), and GAPDH (AF261085) F-5'-GTCAGTGGTGGACCT-GACCT and R-5'-TGAGCTTGACMGTGGTCG (212 bp product). RT-PCR was performed in the Flexigene thermal cycler eom TECHNE (Burlington, N.J.). After a 2 min incubation at 95° C., 25 cycles of the following steps were performed: denaturation at 94° C. for 1 min, annealing at 57° C. for 1 min, and extension for 1 min at 68° C. for 25 cycles. The PCR products were visualized on a 1.8% (w/v) agarose gel stained with ethidium bromide.

Western Blotting:

Aliquots of nuclear proteins (10 µg/lane) were mixed with Laemmli sample buffer and separated by SDS-PAGE (10% resolving gel) and then transferred to nitrocellulose membranes. After blocking with 5% non-fat milk in Tris-buffered saline containing 1% Tween-20 (TBST) for 30 min, the membranes were incubated with a 1:1000 dilution of a monoclonal antibody to phosphorylated p44/42 MAP kinase (Cell Signaling Technology, Beverly, Mass.) in TBST with 5% milk overnight at 4° C. Following 3×10-min washes in TBST, the membranes were incubated with HRP-conjugated goat anti-rabbit Ig (1:1000 dilution) from DakoCytomation (Carpinteria, Calif.) in TBST with 5% milk for 1 h at room temperature. The membranes were washed 3×5 min in TBST and immunoreactive proteins were detected by chemiluminescence (ECL, Amersham). Band intensity was determined using the VersaDoc 5000 Imaging system (Bio-Rad, Hercules, Calif.).

Radioligand Binding Assay:

Two µg of purified αVβ3 was mixed with indicated concentrations of test compounds and allowed to incubate for 30 min at room temperature. [$^{125}$I]-T4 (2 µCi) was then added and the mixture was allowed to incubate an additional 30 min at 20° C. The samples were mixed with sample buffer (50% glycerol, 0.1M Tris-HCl, pH 6.8, and bromophenol blue) and runout on a 5% basic-native gel for 24 h at 45 mA in the cold. The apparatus was disassembled and the gels were placed on filter paper, wrapped in plastic wrap, and exposed to film. Band intensity was determined using the VersaDoc 5000 Imaging system.

Chick Chorioallantoic Membrane (CAM) Assay (αVβ3 Studies):

Ten-day-old chick embryos were purchased £tom SPA-FAS (Preston, Conn.) and were incubated at 37° C. with 55% relative humidity. A hypodermic needle was used to make a small hole in the blunt end of the egg and a second hole was made on the broad side of the egg, directly over an avascular portion of the embryonic membrane. Mild suction was applied to the first hole to displace the air sac and drop the CAM away from the shell. Using a Dremel model craft drill (Dremel, Racine, Wis.), a approx. 1.0 $cm^2$ window was cut in the shell over the false air sac, allowing access to the CAM. Sterile disks of No. 1 filter paper (Whatman, Clifton, N.J.) were pretreated with 3 mg/ml cortisone acetate and 1rnMmpropylthiouracil and air dried under sterile conditions. Thyroid hormone, control solvents, and the mAb LM609 were applied to the disks and subsequently dried. The disks were then suspended in PBS and placed on growing CAMS. After incubation for 3 days, the CAM beneath the filter disk was resected and rinsed with PBS. Each membrane was placed in a 35 mm Petri dish and examined under an SV6 stereo-microscope at 50× magnification. Digital images were captured and analyzed with Image-Pro software (Mediacybemetics). The number of vessel branch points contained in a circular region equal to the filter disk were counted. One image from each of 8-10 CAM preparations for each treatment condition was counted, and in addition each experiment was performed 3 times.

Example 1. Effect of Thyroid Hormone on Angiogenesis

Figures 1A, 1B:
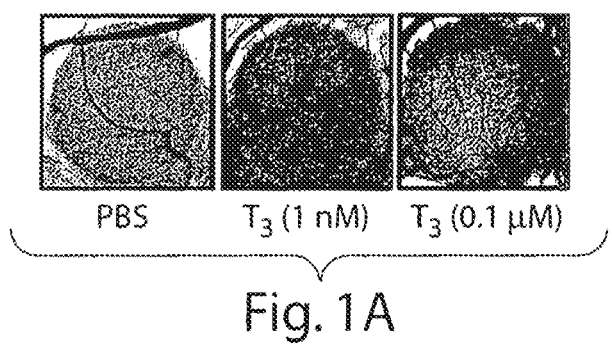
FIG. 1A. Effects of L-T4 and L-T3 on angiogenesis quantitated in the chick CAM assay. Control samples were exposed to PBS and additional samples to 1 nM T3 or 0.1 µmol/L T4 for 3 days. Both hormones caused increased blood vessel branching in these representative images from 3 experiments.
FIG. 1B. Tabulation of mean±SEM of new branches formed from existing blood vessels during the experimental period drawn from 3 experiments, each of which included 9 CAM assays. At the concentrations shown, T3 and T4 caused similar effects (1.9-fold and 2.5-fold increases, respectively, in branch formation). **$P<0.001$ by 1-way ANOVA, comparing hormone-treated with PBS-treated CAM samples.

As seen in FIG. 1A and summarized in FIG. 1B, both L-T4 and L-T3 enhanced angiogenesis in the CAM assay. T4, at a physiologic total concentration in the medium of 0.1 µmol/L, increased blood vessel branch formation by 2.5-fold ($P<0.001$). T3 (1 nmol/L) also stimulated angiogenesis 2-fold. The possibility that T4 was only effective because of conversion of T4 to T3 by cellular 5'-monodeiodinase was ruled out by the finding that the deiodinase inhibitor PTU had no inhibitory effect on angiogenesis produced by T4. PTU was applied to all filter disks used in the CAM model. Thus, T4 and T3 promote new blood vessel branch formation in a CAM model that has been standardized previously for the assay of growth factors.

Example 2. Effects of T4-Agarose and Tetrac

We have shown previously that T4-agarose stimulates cellular signal transduction pathways initiated at the plasma membrane in the same manner as T4 and that the actions of T4 and T4-agarose are blocked by a deaminated iodothyronine analogue, tetrac, which is known to inhibit binding of T4 to plasma membranes. In the CAM model, the addition of tetrac (0.1 µmol/L) inhibited the action of T4 (FIG. 2A), but tetrac alone had no effect on angiogenesis (FIG. 2C). The action of T4-agarose, added at a hormone concentration of 0.1 µmol/L, was comparable to that of T4 in the CAM model (FIG. 2B), and the effect of T4-agarose was also inhibited by the action of tetrac (FIG. 2B; summarized in 2C).

Example 3. Enhancement of Proangiogenic Activity of FGF2 by a Submaximal Concentration of T4

Angiogenesis is a complex process that usually requires the participation of polypeptide growth factors. The CAM assay requires at least 48 hours for vessel growth to be manifest; thus, the apparent plasma membrane effects of thyroid hormone in this model are likely to result in a complex transcriptional response to the hormone. Therefore, we determined whether FGF2 was involved in the hormone response and whether the hormone might potentiate the effect of subphysiologic levels of this growth factor. T4 (0.05 µmol/L) and FGF2 (0.5 µg/mL) individually stimulated angiogenesis to a modest degree (FIG. 3). The angiogenic effect of this submaximal concentration of FGF2 was enhanced by a subphysiologic concentration of T4 to the level caused by 1.0 µg FGF2 alone. Thus, the effects of submaximal hormone and growth factor concentrations appear to be additive. To define more precisely the role of FGF2 in thyroid hormone stimulation of angiogenesis, a polyclonal antibody to FGF2 was added to the filters treated with either FGF2 or T4, and angiogenesis was measured after 72 hours. FIG. 4 demonstrates that the FGF2 antibody inhibited angiogenesis stimulated either by FGF2 or by T4 in the absence of exogenous FGF2, suggesting that the T4 effect in the CAM assay was mediated by increased FGF2 expression. Control IgG antibody has no stimulatory or inhibitory effect in the CAM assay.

Example 4. Stimulation of FGF2 Release from Endothelial Cells by Thyroid Hormone Levels of FGF2 were measured in the media of ECV304 endothelial cells treated with either T4 (0.1 µmol/L) or T3 (0.01 µmol/L) for 3 days. As seen in the Table below, T3 stimulated FGF2 concentration in the medium 3.6-fold, whereas T4 caused a 1.4-fold increase. This finding indicates that thyroid hormone may enhance the angiogenic effect of FGF2, at least in part, by increasing the concentration of growth factor available to endothelial cells.

Effect of T4 and T3 on Release of FGF2 From ECV304 Endothelial Cells

| Cell Treatment | FGF2 (pg/mL/$10^6$ cells) |
|---|---|
| Control | 27.7 ± 3.1 |
| T3 (0.01 µmol/L) | 98.8 ± 0.5* |
| T3 + PD 98059 (2 µmol/L) | 28.4 ± 3.2 |
| T3 + PD 98059 (20 µmol/L) | 21.7 ± 3.5 |
| T4 (0.1 µmol/L) | 39.2 ± 2.8† |
| T4 + PD 98059 (2 µmol/L) | 26.5 ± 4.5 |
| T4 + PD 98059 (20 µmol/L) | 23.2 ± 4.8 |

*P < 0.001, comparing T3-treated samples with control samples by ANOVA;
†P < 0.05, comparing T4-treated samples with control samples by ANOVA.

Example 5. Role of the ERK1/2 Signal Transduction Pathway in Stimulation of Angiogenesis by Thyroid Hormone and FGF2

A pathway by which T4 exerts a nongenomic effect on cells is the MAPK signal transduction cascade, specifically that of ERK1/2 activation. We know that T4 enhances ERK1/2 activation by epidermal growth factor. The role of the MAPK pathway in stimulation by thyroid hormone of FGF2 expression was examined by the use of PD 98059 (2 to 20 µmol/L), an inhibitor of ERK1/2 activation by the tyrosine-threonine kinases MAPK kinase-1 (MEK1) and MEK2. The data in the Table demonstrate that PD 98059 effectively blocked the increase in FGF2 release from ECV304 endothelial cells treated with either T4 or T3. Parallel studies of ERK1/2 inhibition were performed in CAM assays, and representative results are shown in FIG. 5. A combination of T3 and T4, each in physiologic concentrations, caused a 2.4-fold increase in blood vessel branching, an effect that was completely blocked by 3 µmol/L PD 98059 (FIG. 5A). FGF2 stimulation of branch formation (2.2-fold) was also effectively blocked by this inhibitor of ERK1/2 activation (FIG. 5B). Thus, the proangiogenic effect of thyroid hormone begins at the plasma membrane and involves activation of the ERK1/2 pathway to promote FGF2 release from endothelial cells. ERK1/2 activation is again required to transduce the FGF2 signal and cause new blood vessel formation.

Example 6. Action of Thyroid Hormone and FGF2 on MAPK Activation

Stimulation of phosphorylation and nuclear translocation of ERK1/2 MAPKs was studied in ECV304 cells treated with T4 ($10^{-7}$ mol/L) for 15 minutes to 6 hours. The appearance of phosphorylated ERK1/2 in cell nuclei occurred within 15 minutes of T4 treatment, reached a maximal level at 30 minutes, and was still apparent at 6 hours (FIG. 6A). This effect of the hormone was inhibited by PD 98059 (FIG. 6B), a result to be expected because this compound blocks the phosphorylation of ERK1/2 by MAPK kinase. The traditional protein kinase C (PKC)-α, PKC-β, and PKC-γ inhibitor CGP41251 also blocked the effect of the hormone on MAPK activation in these cells, as we have seen with T4 in other cell lines. Thyroid hormone enhances the action of several cytokines and growth factors, such as interferon-γ13 and epidermal growth factor. In ECV304 cells, T4 enhanced the MAPK activation caused by FGF2 in a 15-minute co incubation (FIG. 6C). Applying observations made in ECV304 cells to the CAM model, we propose that the complex mechanism by which the hormone induces angiogenesis includes endothelial cell release of FGF2 and enhancement of the autocrine effect of released FGF2 on angiogenesis.

Example 7. RT-PCR in ECV304 Cells Treated with Thyroid Hormone

The final question addressed in studies of the mechanism of the proangiogenic action of T4 was whether the hormone may induce FGF2 gene expression. Endothelial cells were treated with T4 ($10^{-7}$ mol/L) for 6 to 48 hours, and RT-PCR-based estimates of FGF2 and GAPDH RNA (inferred from cDNA measurements; FIG. 7) were performed. Increase in abundance of FGF2 cDNA, corrected for GAPDH content, was apparent by 6 hours of hormone treatment and was further enhanced by 48 hours.

Example 8A. Retinal Neovascularization Model in Mice (Diabetic and Non-Diabetic)

To assess the pharmacologic activity of a test article on retinal neovascularization. Infant mice are exposed to a high oxygen environment for 7 days and allowed to recover, thereby stimulating the formation of new vessels on the retina. Test articles are evaluated to determine if retinal neovascularization is suppressed. The retinas are examined with hematoxylin-eosin staining and with at least one stain, which demonstrates neovascularization (usually a Selectin stain). Other stains (such as PCNA, PAS, GFAP, markers of angiogenesis, etc.) can be used. A summary of the model is below:

Animal Model

Infant mice (P7) and their dams are placed in a hyperoxygenated environment (70-80%) for 7 days.
On P12, the mice are removed from the oxygenated environment and placed into a normal environment
Mice are allowed to recover for 5-7 days.

Mice are then sacrificed and the eyes collected.
Eyes are either frozen or fixed as appropriate
The eyes are stained with appropriate histochemical stains
The eyes are stained with appropriate immunohistochemical stains
Blood, serum, or other tissues can be collected
Eyes, with special reference to microvascular alterations, are examined for any and all findings. Neovascular growth will be semi quantitatively scored. Image analysis is also available.

Example 8B: Thyroid Hormone and Diabetic Retinopathy

A protocol disclosed in J de la Cruz et al., J Pharmacol Exp Ther 280:454-459, 1997, is used for the administration of Tetrac to rats that have streptozotocin (STZ)-induced experimental diabetes and diabetic retinopathy. The endpoint is the inhibition by Tetrac of the appearance of proliferative retinopathy (angiogenesis).

Example 9A. Wound Healing and Hemostatic Treatment Using Novel Pharmaceutical Polymeric Formulation of Thyroid Hormone and Analogs The present invention also includes a novel wound healing and hemostatic treatment that include an immobilized thyroid hormone analog, preferably T4 analogs, calcium chloride, and collagen. This novel formulation significantly controls both venous and arterial hemorrhage, reduces bleeding time, generates fibrin/platelet plug, releases platelet-derived wound healing factors in a sustained manner in the presence of low level collagen, and safe. Development of such a wound healing and hemostatic dressing can be very valuable for short and long-term use in Combat Casualty Care. Pharmaceutical formulation of immobilized L-thyroxine (T4) and globular hexasaccharide in a hydrogel or dressing containing collagen and calcium chloride can be optimized. This novel Wound healing and Hemostatic (WH formulation) treatment in hydrogel or dressing can also include the addition of a microbicidal.

L-thyroxine conjugated to polymer or immobilized on agarose demonstrated potent stimulation of angiogenesis through activation of an adhesion cell surface receptor (integrin αvβ3) leading to activation of an intracellular signaling event, which in turn leads to up-regulation of various growth factor productions. Additionally, immobilized T4 induced epithelial, fibroblast, and keratinocyte cell migration. Immobilized T4, but not T3 or other analogs, enhanced collagen-induced platelet aggregation and secretion, which would promote formation of the subject's own platelet plug. Furthermore, immobilized T4 also promotes white blood cell migration, which could be critical for fighting infection. Hence, immobilized T4 can help the body make more of a compound used to regenerate damaged blood vessels, and it also increased the amount of white blood cells that makes free radicals in the wound site. Free radicals help clear potentially pathogenic bacteria from a wound.

Thus, T4 or T4-agarose (10-100 nM), but not T3, DIPTA, or GC-1, is effective in enhancing platelet aggregation and secretion (de-granulation). Accordingly, T4 (or analogs and polymeric conjugations thereof, e.g., T4-agarose), in combination with 10 mM calcium chloride, and with or without collagen, is preferred for wound healing. See FIGS. 23A-E.

Thromboelastography:

Thromboelastography (TEG) has been used in various hospital settings since its development by Hartert in 1948. The principle of TEG is based on the measurement of the physical viscoelastic characteristics of blood clot. Clot formation was monitored at 37° C. in an oscillating plastic cylindrical cuvette ("cup") and a coaxially suspended stationary piston ("pin") with a 1 mm clearance between the surfaces, using a computerized Thrombelastograph (TEG Model 3000, Haemoscope, Skokie, Ill.). The cup oscillates in either direction every 4.5 seconds, with a 1 second mid-cycle stationary period; resulting in a frequency of 0.1 Hz and a maximal shear rate of 0.1 per second. The pin is suspended by a torsion wire that acts as a torque transducer. With clot formation, fibrin fibrils physically link the cup to the pin and the rotation of the cup as affected by the viscoelasticity of the clot (Transmitted to the pin) is displayed on-line using an IBM-compatible personal computer and customized software (Haemoscope Corp., Skokie, Ill.). The torque experienced by the pin (relative to the cup's oscillation) is plotted as a function of time.

TEG assesses coagulation by measuring various parameters such as the time latency for the initial initiation of the clot (R), the time to initiation of a fixed clot firmness (k) of about 20 mm amplitude, the kinetic of clot development as measured by the angle (a), and the maximum amplitude of the clot (MA). The parameter A measures the width of the tracing at any point of the MA. Amplitude A in mm is a function of clot strength or elasticity. The amplitude on the TEG tracing is a measure of the rigidity of the clot; the peak strength or the shear elastic modulus attained by the clot, G, is a function of clot rigidity and can be calculated from the maximal amplitude (MA) of the TEG tracing.

The following parameters were measured from the TEG tracing:
  R, the reaction time (gelation time) represents the latent period before the establishment of a 3-dimensional fibrin gel network (with measurable rigidity of about 2 mm amplitude).
  Maximum Amplitude (MA, in mm), is the peak rigidity manifested by the clot.
  Shear elastic modulus or clot strength (G, dynes/cm$^2$) is defined by: G=(5000A)/(100−A).

Blood clot firmness is an important parameter for in vivo thrombosis and hemostasis because the clot must stand the shear stress at the site of vascular injury. TEG can assess the efficacy of different pharmacological interventions on various factors (coagulation activation, thrombin generation, fibrin formation, platelet activation, platelet-fibrin interaction, and fibrin polymerization) involved in clot formation and retraction. The effect of endotoxin (0.63 ug), Xa (0.25 nM), thrombin (0.3 mU), and TF (25 ng) on the different clot parameters measured by computerized TEG in human whole blood is shown in Table 3.

Blood Sampling:
Blood was drawn from consenting volunteers under a protocol approved by the Human Investigations Committee of William Beaumont Hospital. Using the two syringe method, samples were drawn through a 21 gauge butterfly needle and the initial 3 ml blood was discarded. Whole blood (WB) was collected into siliconized Vacutainer tubes (Becton Dickinson, Rutherford, N.J. containing 3.8% trisodium citrate such that a ratio of citrate whole blood of 1:9 (v/v) was maintained. TEG was performed within 3 hrs of blood collection. Calcium was added back at 1-2.5 mM followed by the addition of the different stimulus. Calcium chloride by itself at the concentration used showed only a minimal effect on clot formation and clot strength.

Clot formation is initiated by thrombin-induced cleavage of Fibrinopeptide A from fibrinogen. The resultant fibrin monomers spontaneously polymerize to form fibril strands that undergo linear extension, branching, and lateral association leading to the formation of a three-dimensional network of fibrin fibers. A unique property of network structures is that they behave as rigid elastic solids, capable of resisting deforming shear stress. This resistance to deformation can be measured by elastic modulus—an index of clot strength. Unlike conventional coagulation tests (like the prothrombin time and partial thromboplastin time) that are based only on the time to the onset of clot formation, TEG allows acquisition of quantitative information allowing measurement of the maximal strength attained by clots. Via the GPIIb/IIIa receptor, platelets bind fibrin(ogen) and modulate the viscoelastic properties of clots. Our results demonstrated that clot strength in TF-TEG is clearly a function of platelet concentration and platelets augmented clot strength ~8 fold under shear. Different platelet GPIIb/IIIa antagonists (class I versus class II) behaved with distinct efficacy in inhibiting platelet-fibrin mediated clot strength using TF-TEG under shear.

Statistical Analysis:

Data are expressed as mean±SEM. Data were analyzed by either paired or group analysis using the Student t test or ANOVA when applicable; differences were considered significant at $P<0.05$.

Effect of Calcium Chloride Versus Tissue Factor on Clot Dynamics in Citrated Human Whole Blood Using TEG

| TEG Parameters | 25 ng TF + 2.25 mM $Ca^{+2}$ (Mean ± SEM) | 10 mM $Ca^{+2}$ (Mean ± SEM) |
|---|---|---|
| r (min) | 29.7 ± 2.3 | 14.5 ± 2.5* |
| K (min) | 5.8 ± 1.0 | 7.0 ± 0.7 |
| α (angle) | 45.0 ± 2.6 | 47.3 ± 2.7 |
| MA (mm) | 58.2 ± 1.7 | 56.5 ± 2.2 |

Data represent mean ± SEM, n = 4,
*P < 0.01.

Platelet Aggregation and De-Granulation in Whole Blood Using Impedance Technique:

The Model 560 Whole-Blood Aggregometer and the associated Aggro-Link Software from the Chrono-Log Corporation were used in this study. Two electrodes are placed in diluted blood and an electrical impulse is sent from one to the other. As the platelets aggregate around the electrodes, the Chrono-Log measures the impedance of the electrical signal in ohms of resistance.

Blood Sampling:

Whole blood was drawn daily from healthy donors between the ages of 17 and 21 into 4.5 milliliter Vacutainer vials with 3.8% buffered sodium citrate (Becton Dickinson, Rutherford, N.J.). The blood was kept on a rocker to extend the life of the platelets, and experiments were done within 5 hours of phlebotomy.

Procedure: For the control, 500 microliters of whole blood, 500 microliters of 0.9% saline, and a magnetic stir bar were mixed into a cuvette, and heated for five minutes to 37 degrees Celsius. Sub-threshold aggregation was induced with 5 microliters of 1-2 µg/ml Collagen, which the Aggregometer measured for 6-7 minutes. The effects of T4, T4-agarose versus T3 and other thyroid hormone analogs on collagen-induced aggregation and secretion were tested. Ingerman-Wojenski C, Smith J B, Silver M J. Evaluation of electrical aggregometry: comparison with optical aggregometry, secretion of ATP, and accumulation of radiolabeled platelets. J Lab Clin Med. 1983 January; 101(1):44-52.

Cell Migration Assay:

Human granulocytes are isolated from shed blood by the method of Mousa et al. and cell migration assays carried out as previously described (Methods In Cell Science, 19 (3): 179-187, 1997, and Methods In Cell Science 19 (3): 189-195, 1997). Briefly, a neuroprobe 96 well disposable chemotaxis chamber with an 8 µm pore size will be used. This chamber allow for quantitation of cellular migration towards a gradient of chemokine, cytokine or extracellular matrix proteins. Cell suspension (45 µl of $2\times10^6$) will be added to a polypropylene plate containing 5 µl of test agents such as flavanoids or thyroid hormone derivatives and incubated for 10 minutes at 22° C. IL8 (0.1-100 ng) with or without T3/T4 (33 µl) at 0.001-0.1 µM will be added to the lower wells of a disposable chemotaxis chamber, then assemble the chamber using the pre-framed filter. Add 25 µl of cell/test agent suspension to the upper filter wells then incubate overnight (22 hours at 37° C., 5% CO2) in a humidified cell culture incubator. After the overnight incubation, non-migrated cells and excess media will be gently removed using a 12 channel pipette and a cell scraper. The filters will then washed twice in phosphate buffered saline (PBS) and fixed with 1% formaldehyde in PBS buffer. Membranes of migrated cells will be permeated with Triton X-100 (0.2%) then washed 2-3 times with PBS. The actin filaments of migrated cells will be stained with Rhodamine phalloidin (12.8 IU/ml) for 30 minutes (22° C.). Rhodamine phalloidin will be made fresh weekly and reused for up to 3 days, when stored protected from light at 4° C. Chemotaxis will be quantitatively determined by fluorescence detection using a Cytofluor II micro-filter fluorimeter (530 excitation/590 emission). All cell treatments and subsequent washings will be carried out using a uniquely designed treatment/wash station (Methods In Cell Science, 19 (3): 179-187, 1997). This technique will allow for accurate quantitation of cell migration and provide reproducible results with minimal inter and intra assay variability.

Cellular Migration Assays:

These assays were performed using a Neuroprobe 96 well disposable chemotaxis chamber with an 8 µm pore size. This chamber allowed for quantitation of cellular migration towards a gradient of either vitronectin or osteopontin. Cultured cells were removed following a standardized method using EDTA/Trypsin (0.01%/0.025%). Following removal, the cells were washed twice and resuspended ($2\times10^6$/ml) in EBM (Endothelial cell basal media, Clonetics Inc.). Add either vitronectin or osteopontin (33 µl) at 0.0125-100 µg/ml to the lower wells of a disposable chemotaxis chamber, and then assemble using the preframed filter. The cell suspension (45 µl) was added to a polypropylene plate containing 5 µl of test agent at different concentrations and incubated for 10 minutes at 22° C. Add 25 µl of cell/test agent suspension to the upper filter wells then incubate overnight (22 hours at 37° C.) in a humidified cell culture incubator. After the overnight incubation, non-migrated cells and excess media were gently removed using a 12 channel pipette and a cell scraper. The filters were then washed twice in PBS (no $Ca^{+2}$ or $Mg^{+2}$) and fixed with 1% formaldehyde. Membranes of migrated cells were permeated with Triton X-100 (0.2%) then washed 2-3 times with PBS. The actin filaments of migrated cells were stained with rhodamine phalloidin (12.8 IU/ml) for 30 minutes (22° C.). Rhodamine phalloidin was made fresh weekly and reused for up to 3 days, when stored protected from light at 4° C. Chemotaxis was quantitatively determined by fluorescence detection using a Cytofluor II (530 excitation/590 emission). All cell treatment and subsequent washings were carried out using a uniquely designed treatment/wash station. This station consisted of six individual reagent units each with a 30 ml volume capacity. Individual units were filled with one of the following reagents: PBS, formaldehyde, Triton X-100, or rhodamine-phalloidin. Using this technique, filters were gently dipped into the appropriate solution, thus minimizing migrated cell loss. This technique allowed for maximum quantitation of cell migration and provided reproducible results with minimal inter and intra assay variability.

Migration Toward the Extracellular Matrix Protein Vitronectin

| | Treatments (Fluorescence Units) + SD | Mean EC Migration |
|---|---|---|
| A. | Non-Specific Migration No Matrix in LC | 270 ± 20 |
| B. | Vitronectin (25 ug) in LC | 6,116 ± 185 |
| C. | T3 (0.1 uM) UC/ Vitronectin (25 ug) in LC | 22,016 ± 385 |
| D. | T4 (0.1 uM) UC/ Vitronectin (25 ug) in LC | 13,083 ± 276 |
| | C + XT199 (10 uM) | 4,550 ± 225 |
| | D + XT199 (10 uM) | 3,890 ± 420 |
| | C + PD (0.8 ug) | 7,555 ± 320 |
| | D + PD (0.8 ug) | 6,965 ± 390 |

LC = Lower Chamber, UC = Upper chamber
Similar data were obtained with other potent and specific avb3 antagonists such as LM609 and SM256

Example 9B. In Vitro Human Epithelial and Fibroblast Wound Healing

The in vitro 2-dimensional wound healing method is as described in Mohamed S, Nadijcka D, Hanson, V. Wound healing properties of cimetidine in vitro. Drug Intell Clin Pharm 20: 973-975; 1986, incorporated herein by reference in its entirety. Additionally, a 3-dimensional wound healing method already established in our Laboratory will be utilized in this study (see below). Data show potent stimulation of wound healing by thyroid hormone.

In Vitro 3D Wound Healing Assay of Human Dermal Fibroblast Cells:
Step 1: Prepare Contracted Collagen Gels:
 1) Coat 24-well plate with 350 ul 2% BSA at RT for 2 hr,
 2) 80% confluent NHDF (normal human dermal fibroblast cells, Passage 5-9) are trypsinized and neutralized with growth medium, centrifuge and wash once with PBS
 3) Prepare collagen-cell mixture, mix gently and always on ice:

| Stock solution | Final Concentration |
|---|---|
| 5xDMEC | 1xDMEM |
| 3 mg/ml vitrogen | 2 mg/ml |
| ddH2O | optimal |
| NHDF | 2 × 10~5 cells/ml |
| FBS | 1% |

4) Aspire 2% BSA from 24 well plate, add collagen-cell mixture 350 ul/well, and incubate the plate in 37° C. CO2 incubator.
 5) After 1 hr, add DMEM+5% FBS medium 0.5 ml/well, use a 10 ul tip
 Detach the collagen gel from the edge of each well, then incubate for 2 days. The fibroblast cells will contract the collagen gel Step 2: Prepare 3D Fibrin Wound Clot and Embed Wounded Collagen Culture
 1) Prepare fibrinogen solution (1 mg/ml) with or without testing regents. 350 ul fibrinogen solution for each well in eppendorf tube.

| Stock solution | Final Concentration |
|---|---|
| 5xDMEC | 1xDMEM |
| Fibrinogen | 1 mg/ml |
| ddH2O | optimal |
| testing regents | optimal concentration |
| FBS | 1% or 5% |

2) Cut each contracted collagen gel from middle with scissors. Wash the gel with PBS and transfer the gel to the center of each well of 24 well plate
 3) Add 1.5 ul of human thrombin (0.25 U/ul) to each tube, mix well and then add the solution around the collagen gel, the solution will polymerize in 10 mins.
  After 20 mins, add DMEM+1% (or 5%) FBS with or without testing agent, 450 ul/well and incubate the plate in 37° C. CO2 incubator for up to 5 days. Take pictures on each day.

In Vivo Wound Healing in Diabetic Rats:
Using an acute incision wound model in diabetic rats, the effects of thyroid hormone analogs and its conjugated forms are tested. The rate of wound closure, breaking strength analyses and histology are performed periodically on days 3-21.

Methods:
Animals (Mice and Rats) in the study are given two small puncture wounds—WH is applied to one of the wounds, and the other was covered with saline solution as a control. Otherwise, the wounds are left to heal naturally.

The animals are euthanized five days after they are wounded. A small area of skin—1 to 1.5 millimeters—is excised from the edges of the treated and untreated wounds.

Wound closure and time to wound closure is determined. Additionally, the levels of tenascin, a protein that helps build connective tissue, in the granulation tissue of the wounds is determined. The quality of the granulation tissue (i.e. rough, pinkish tissue that normally forms as a wound heals, new capillaries and connective tissue) is also determined.

Materials and Methods:
Chronic granulating wounds are prepared by methods well known in the art. Male Sprague Dawley rats weighing 300 to 350 grams are acclimatized for a week in our facility prior to use. Under intraperitoneal Nembutal anesthesia (35 mg/kg), the rat dorsum is shaved and depilated. Animals are individually caged and given food and water ad libitum. All experiments were conducted in accordance with the Animal Care and Use Committee guidelines of the Department of Veterans Affairs Medical Center, Albany, N.Y.

Histological characterization of this wound with comparison to a human chronic granulating wound had previously been performed. Sixty four rats are then divided into eight treatment groups (n=8/group). Animals are treated with topical application of vehicle (vehicle controls) on days 5, 9, 12, 15, and 18. The vehicle control can be either agarose (Group 1) or the polymeric form (Group 2) that will be used in conjugation of L-thyroxine. Wounds treated with T4-agarose (Groups 3-5) or T4-polymer (Groups 6-8) at 1, 10, 100 μg/cm$^2$ in the presence of 10 μg globular hexasaccharide, 10

μg collagen, and 10 mM calcium chloride to be applied topically on days 5, 9, 12, 15, and 18. All wounds are left exposed. Every 48 hours the outlines of the wounds can be traced onto acetate sheets, and area calculations can be performed using computerized digital planimetry.

Three full-thickness, transverse strips of granulation tissue are then harvested from the cephalad, middle, and caudal ends of the wounds on day 19 and fixed in 10-percent buffered formalin. Transverse sections (5 μm) are taken from each specimen and stained with hematoxylin and eosin. The thickness of the granulation tissue can be estimated with an ocular micrometer at low power. High-powered fields are examined immediately below the superficial inflammatory layer of the granulation tissue. From each strip of granulation tissue five adjacent high-powered fields can be photographed and coded. Enlarged prints of these exposures are then used for histometric analysis in a blinded fashion. Fibroblasts, "round" cells (macrophages, lymphocytes, and neutrophils), and capillaries are counted. In addition the cellularity of each section is graded for cellularity on a scale of 1 (reduced cell counts) to 5 (highly cellular).

Statistical Analysis:

Serial area measurements were plotted against time. For each animal's data a Gompertz equation will be fitted (typical r 2=0.85). Using this curve the wound half-life can be estimated. Comparison between groups is performed using life table analysis and the Wilcoxon rank test. These statistical analyses are performed using the SAS (SAS/STAT Guide for Personal Computers, Version 6 Edition, Cary, N.C., 1987, p 1028) and BMDP (BMDP Statistical Software Manual, Los Angeles, BMDP Statistical Software, Inc. 1988) packages on a personal computer.

Cell counts for the different treatment groups are pooled and analyzed using a one-way analysis of variance. Post-hoc analyses of differences between groups can be carried out using Tukey's test (all pairwise multiple-comparison test) with $p<0.05$ considered significant. Sigma Stat statistical software (Jandel Scientific, Corte Madera, Calif.) will be used for data analysis.

Example 10. Rodent Model of Myocardial Infarction

The coronary artery ligation model of myocardial infarction is used to investigate cardiac function in rats. The rat is initially anesthetized with xylazine and ketamine, and after appropriate anesthesia is obtained, the trachea is intubated and positive pressure ventilation is initiated. The animal is placed supine with its extremities loosely taped and a median sternotomy is performed. The heart is gently exteriorized and a 6-O suture is firmly tied around the left anterior descending coronary artery. The heart is rapidly replaced in the chest and the thoracotomy incision is closed with a 3-O purse string suture followed by skin closure with interrupted sutures or surgical clips. Animals are placed on a temperature regulated heating pad and closely observed during recovery. Supplemental oxygen and cardiopulmonary resuscitation are administered if necessary. After recovery, the rat is returned to the animal care facility. Such coronary artery ligation in the rat produces large anterior wall myocardial infarctions. The 48 hr. mortality for this procedure can be as high as 50%, and there is variability in the size of the infarct produced by this procedure. Based on these considerations, and prior experience, to obtain 16-20 rats with large infarcts so that the two models of thyroid hormone delivery discussed below can be compared, approximately 400 rats are required.

These experiments are designed to show that systemic administration of thyroid hormone either before or after coronary artery ligation leads to beneficial effects in intact animals, including the extent of hemodynamic abnormalities assessed by echocardiography and hemodynamic measurements, and reduction of infarct size. Outcome measurements are proposed at three weeks post-infarction. Although some rats may have no infarction, or only a small infarction is produced, these rats can be identified by normal echocardiograms and normal hemodynamics (LV end-diastolic pressure <8 mm Hg).

Thyroid Hormone Delivery:

There are two delivery approaches. In the first, thyroid hormone is directly injected into the peri-infarct myocardium. As the demarcation between normal and ischemic myocardium is easily identified during the acute open chest occlusion, this approach provides sufficient delivery of hormone to detect angiogenic effects.

Although the first model is useful in patients undergoing coronary artery bypass surgery, and constitutes proof of principle that one local injection induces angiogenesis, a broader approach using a second model can also be used. In the second model, a catheter retrograde is placed into the left ventricle via a carotid artery in the anesthetized rat prior to inducing myocardial infarction. Alternatively, a direct needle puncture of the aorta, just above the aortic valve, is performed. The intracoronary injection of the thyroid hormone is then simulated by abruptly occluding the aorta above the origin of the coronary vessels for several seconds, thereby producing isovolumic contractions. Thyroid hormone is then injected into the left ventricle or aorta immediately after aortic constriction. The resulting isovolumic contractions propel blood down the coronary vessels perfusing the entire myocardium with thyroid hormone. This procedure can be done as many times as necessary to achieve effectiveness. The number of injections depends on the doses used and the formation of new blood vessels.

Echocardiography:

A method for obtaining 2-D and M-mode echocardiograms in unanesthetized rats has been developed. Left ventricular dimensions, function, wall thickness and wall motion can be reproducibly and reliably measured. The measurement are carried out in a blinded fashion to eliminate bias with respect to thyroid hormone administration.

Hemodynamics:

Hemodynamic measurements are used to determine the degree of left ventricular impairment. Rats are anesthetized with isoflurane. Through an incision along the right anterior neck, the right carotid artery and the right jugular vein are isolated and cannulated with a pressure transducing catheter (Millar, SPR-612, 1.2 Fr). The following measurements are then made: heart rate, systolic and diastolic BP, mean arterial pressure, left ventricular systolic and end-diastolic pressure, and + and −dP/dt. Of particular utility are measurements of left ventricular end-diastolic pressure, progressive elevation of which correlates with the degree of myocardial damage.

Infarct Size:

Rats are sacrificed for measurement of infarct size using TTC methodology.

Morphometry:

Microvessel density [microvessels/mm$^2$] will be measured in the infarct area, peri-infarct area, and in the spared myocardium opposing the infarction, usually the posterior wall. From each rat, 7-10 microscopic high power fields [×400] with transversely sectioned myocytes will be digitally recorded using Image Analysis software. Microvessels will be counted by a blinded investigator. The microcirculation will be defined as vessels beyond third order arterioles with a diameter of 150 micrometers or less, supplying tissue between arterioles and venules. To correct for differences in left ventricular hypertrophy, microvessel density will be divided by LV weight corrected for body weight. Myocardium from sham operated rats will serves as controls.

Example 11. Effects of the αVβ3 Antagonists on the Pro-Angiogenesis Effect of T4 or FGF2

The αVβ3 inhibitor LM609 totally inhibited both FGF2 or T4-induced pro-angiogenic effects in the CAM model at 10 micrograms (FIG. 16).

Example 12. Inhibition of Cancer-Related New Blood Vessel Growth

A protocol disclosed in J. Bennett, Proc Natl Acad Sci USA 99:2211-2215, 2002, is used for the administration of tetraiodothyroacetic (Tetrac) to SCID mice that have received implants of human breast cancer cells (MCF-7). Tetrac is provided in drinking water to raise the circulating level of the hormone analog in the mouse model to $10^{-6}$ M. The endpoint is the inhibitory action of tetrac on angiogenesis about the implanted tumors.

Example 13. Pro-Angiogenesis Promoting Effect of Thyroid Hormone and Analogs Thereof at Subthreshold Levels of VEGF and FGF2 in an In Vitro Three-Dimensional Micro-Vascular Endothelial Sprouting Model Either $T_3$, $T_4$, $T_4$-agarose, or fibroblast growth factor 2 (FGF2) plus vascular endothelial growth factor (VEGF) produced a comparable pro-angiogenesis effect in the in vitro three-dimensional micro-vascular endothelial sprouting model. The pro-angiogenesis effect of the thyroid hormone analogs were blocked by PD 98059, an inhibitor of the mitogen-activated protein kinase (MAPK; ERK1/2) signal transduction cascade. Additionally, a specific αvβ3 integrin antagonist (XT199) inhibited the pro-angiogenesis effect of either thyroid hormone analogs or $T_4$-agarose. Data also demonstrated that the thyroid hormone antagonist Tetrac inhibits the thyroid analog's pro-angiogenesis response. Thus, those thyroid hormone analogs tested are pro-angiogenic, an action that is initiated at the plasma membrane and involves αvβ3 integrin receptors, and is MAPK-dependent.

The present invention describes a pro-angiogenesis promoting effect of $T_3$, $T_4$, or $T_4$-agarose at sub-threshold levels of VEGF and FGF2 in an in vitro three-dimensional microvascular endothelial sprouting model. The invention also provides evidence that the hormone effect is initiated at the endothelial cell plasma membrane and is mediated by activation of the αvβ3 integrin and ERK1/2 signal transduction pathway.

Enhancement by $T_3$, $T_4$, or $T_4$-agarose of the angiogenesis activity of low concentrations of VEGF and FGF2 in the three-dimensional sprouting assay was demonstrated. Either $T_3$, $T_4$ at $10^{-7}$-$10^{-8}$ M, or $T_4$-agarose at $10^{-7}$ M total hormone concentration was comparable in pro-angiogenesis activity to the maximal concentrations of VEGF and FGF2 effect in this in vitro model. Although new blood vessel growth in the rat heart has been reported to occur concomitantly with induction of myocardial hypertrophy by a high dose of $T_4$, thyroid hormone has not been regarded as an angiogenic factor. The present example establishes that the hormone in physiologic concentrations is pro-angiogenic in a setting other than the heart.

$T_4$-agarose reproduced the effects of $T_4$, and this derivative of thyroid hormone is thought not to gain entry to the cell interior; it has been used in our laboratory to examine models of hormone action for possible cell surface-initiated actions of iodothyronines. Further, experiments carried out with $T_4$ and tetrac also supported the conclusion that the action of $T_4$ in this model was initiated at the plasma membrane. Tetrac blocks membrane-initiated effects of $T_4$.

Since thyroid hormone non-genomically activates the MAPK (ERK1/2) signal transduction pathway, the action of the hormone on angiogenesis can be MAPK-mediated. When added to the CAM model, an inhibitor of the MAPK cascade, PD 98059, inhibited the pro-angiogenic action of $T_4$. While this result was consistent with an action on transduction of the thyroid hormone signal upstream of an effect of $T_4$ on FGF2 elaboration, it is known that FGF2 also acts via an MAPK-dependent mechanism. $T_4$ and FGF2 individually cause phosphorylation and nuclear translocation of ERK1/2 in endothelial cells and, when used in sub-maximal doses, combine to enhance ERK1/2 activation further. To examine the possibility that the only MAPK-dependent component of hormonal stimulation of angiogenesis related exclusively to the action of FGF2 on vessel growth, cellular release of FGF2 in response to $T_4$ in the presence of PD 98059 was measured. The latter agent blocked the hormone-induced increase in growth factor concentration and indicated that MAPK activation was involved in the action of $T_4$ on FGF2 release from endothelial cells, as well as the consequent effect of FGF2 on angiogenesis.

Effect of Thyroid Hormone on Angiogenesis:

Either $T_4$, $T_3$, or $T_4$-agarose at 0.01-0.1 μM resulted in significant (P<0.01) stimulation of angiogenesis, see the Table below. This is shown to be comparable to the pro-angiogenesis efficacy of FGF2 (50 ng/ml) plus VEGF (25 ng/ml).

In Vitro Pro-angiogenesis Effect of Growth Factors, Thyroid Hormone, and Analogs in the Three-Dimensional Human Micro-vascular Endothelial Sprouting Assay

| Treatment Groups | Mean Tube Vessel Length (mm) ± SD |
|---|---|
| Control | 0.76 ± 0.08 |
| FGF2 (25 ng) + VEGF (50 ng) | 2.34 ± 0.25* |
| T3 (20 ng) | 1.88 ± 0.21* |
| T4 (23 ng) | 1.65 ± 0.15* |
| T4-agarose (23 ng) | 1.78 ± 0.20* |

Data (means ± SD) were obtained from 3 experiments. Cells were pre-treated with Sub-threshold level of FGF2 (1.25 ng/ml) + VEGF(2.5 ng/ml).
Data represent mean ± SD, n = 3,
*P < 0.01 by ANOVA, comparing treated to control.

Effects of Tetrac on Thyroid Pro-Angiogenesis Action:

$T_3$ stimulates cellular signal transduction pathways initiated at the plasma membrane. These pro-angiogenesis actions are blocked by a deaminated iodothyronine analogue, tetrac, which is known to inhibit binding of $T_4$ to plasma membranes. The addition of tetrac (0.1 μM) inhibited the pro-angiogenesis action of either $T_3$, $T_4$, or $T_4$-agarose (Tables 5-7). This is shown by the inhibition of number of micro-vascular endothelial cell migration and vessel length (Table 5-7).

Role of the ERK1/2 Signal Transduction Pathway in Stimulation of Angiogenesis by Thyroid Hormone:

Parallel studies of ERK1/2 inhibition were carried out in the three-dimensional micro-vascular sprouting assays. Thyroid hormone and analog at 0.01-0.1 μM caused significant increase in tube length and number of migrating cells, an effect that was significantly (P<0.01) blocked by PD 98059 (Tables 5-7). This is shown by the inhibition of number micro-vascular endothelial cell migration and vessel length (Table 5-7).

Role of the Integrin αvβ3 in Stimulation of Angiogenesis by Thyroid Hormone:

Either $T_3$, $T_4$, or $T_4$-agarose at 0.01-0.1 μM-mediated pro-angiogenesis in the presence of sub-threshold levels of VEGF and FGF2 was significantly ($P<0.01$) blocked by the αvβ3 integrin antagonist XT199 (Tables 5-7). This is shown by the inhibition of number of micro-vascular endothelial cell migration and vessel length, see the Tables below.

Thus, the pro-angiogenesis effect of thyroid hormone and its analogs begins at the plasma membrane αvβ3 integrin and involves activation of the ERK1/2.

Pro-Angiogenesis Mechanisms of the Thyroid Hormone $T_3$ in the Three-Dimensional Human Micro-Vascular Endothelial Sprouting Assay

| HDMEC treatment | Mean number of Migrated cells ± SD | Mean vessel Length (mm) ± SD |
| --- | --- | --- |
| Control | 88 ± 14 | 0.47 ± 0.06 |
| $T_3$ (0.1 uM) | 188 ± 15* | 0.91 ± 0.04* |
| $T_3$ (0.1 uM) + PD98059 (3 ug) | 124 ± 29 | 0.48 ± 0.09 |
| $T_3$ (0.1 uM) + XT199 (2 ug) | 118 ± 18 | 0.47 ± 0.04 |
| $T_3$ (0.1 uM) + tetrac (0.15 ug) | 104 ± 15 | 0.58 ± 0.07 |

Human dermal micro-vascular endothelial cells (HDMVC) were used. Cells were pretreated with FGF2 (1.25 ng/ml) + VEGF (2.5 ng/ml). Images were taken at 4 and 10X, day 3. Data represent mean ± SD, n = 3,
*P < 0.01.

Pro-Angiogenesis Mechanisms of the Thyroid Hormone $T_4$ in the Three-Dimensional Human Micro-Vascular Endothelial Sprouting Assay

| HDMEC treatment | Mean number of Migrated cells ± SD | Mean Vessel Length (mm) ± SD |
| --- | --- | --- |
| Control | 88 ± 14 | 0.47 ± 0.06 |
| $T_4$ (0.1 uM) | 182 ± 11* | 1.16 ± 0.21* |
| $T_4$ (0.1 uM) + PD98059 (3 ug) | 110 ± 21 | 0.53 ± 0.13 |
| $T_4$ (0.1 uM) + XT199 (2 ug) | 102 ± 13 | 0.53 ± 0.05 |
| $T_4$ (0.1 uM) + Tetrac (0.15 ug) | 85 ± 28 | 0.47 ± 0.11 |

Human dermal micro-vascular endothelial cells (HDMVC) were used. Cells were pretreated with FGF2 (1.25 ng/ml) + VEGF (2.5 ng/ml). Images were taken at 4 and 10X, day 3. Data represent mean ± SD, n = 3,
*P < 0.01.

Pro-Angiogenesis Mechanisms of the Thyroid Hormone $T_4$-Agarose in the Three-Dimension Human Micro-Vascular Endothelial Sprouting Assay

| HDMEC treatment | Mean number of Migrated cells ± SD | Mean Vessel Length (mm) ± SD |
| --- | --- | --- |
| Control | 88 ± 14 | 0.47 ± 0.06 |
| $T_4$-agarose (0.1 uM) | 191 ± 13* | 0.97 ± 0.08* |
| $T_4$-agarose (0.1 uM) + PD98059 (3 ug) | 111 ± 8 | 0.56 ± 0.03 |
| $T_4$-agarose (0.1 uM) + XT199 (2 ug) | 106 ± 5 | 0.54 ± 0.03 |
| $T_4$-agarose (0.1 uM) + Tetrac (0.15 ug) | 87 ± 14 | 0.45 ± 0.09 |

Human dermal micro-vascular endothelial cells (HDMVC) were used. Cells were pretreated with FGF2 (1.25 ng/ml) + VEGF (2.5 ng/ml). Images were taken at 4 and 10X, day 3. Data represent mean ± SD, n = 3,
*P < 0.01.

Example 14. In Vitro Model for Evaluating Polymeric Thyroid Analogs Transport Across the Blood-Brain Barrier Described below is an in vitro method for evaluating the facility with which selected polymeric thyroid analog alone or in combination with nerve growth factor or other neurogenesis factors likely will pass across the blood-brain barrier. A detailed description of the model and protocol are provided by Audus, et al., Ann. N.Y. Acad. Sci 507: 9-18 (1987), the disclosure of which is incorporated herein by reference.

Briefly, microvessel endothelial cells are isolated from the cerebral gray matter of fresh bovine brains. Brains are obtained from a local slaughter house and transported to the laboratory in ice cold minimum essential medium ("MEM") with antibiotics. Under sterile conditions the large surface blood vessels and meninges are removed using standard dissection procedures. The cortical gray matter is removed by aspiration, then minced into cubes of about 1 mm. The minced gray matter then is incubated with 0.5% dispase (BMB, Indianapolis, Ind.) for 3 hours at 37° C. in a shaking water bath. Following the 3 hour digestion, the mixture is concentrated by centrifugation (1000×g for 10 min.), then resuspended in 13% dextran and centrifuged for 10 min. at 5800×g. Supernatant fat, cell debris and myelin are discarded and the crude microvessel pellet resuspended in 1 mg/ml collagenase/dispase and incubated in a shaking water bath for 5 hours at 37° C. After the 5-hour digestion, the microvessel suspension is applied to a pre-established 50% Percoll gradient and centrifuged for 10 min at 1000×g. The band containing purified endothelial cells (second band from the top of the gradient) is removed and washed two times with culture medium (e.g., 50% MEM/50% F-12 nutrient mix). The cells are frozen (−80° C.) in medium containing 20% DMSO and 10% horse serum for later use.

After isolation, approximately $5\times10^5$ cells/cm$^2$ are plated on culture dishes or 5-12 mm pore size polycarbonate filters that are coated with rat collagen and fibronectin. 10-12 days after seeding the cells, cell monolayers are inspected for confluency by microscopy.

Characterization of the morphological, histochemical and biochemical properties of these cells has shown that these cells possess many of the salient features of the blood-brain barrier. These features include: tight intercellular junctions, lack of membrane fenestrations, low levels of pinocytotic activity, and the presence of gamma-glutamyl transpeptidase, alkaline phosphatase, and Factor VIII antigen activities.

The cultured cells can be used in a wide variety of experiments where a model for polarized binding or transport is required. By plating the cells in multi-well plates, receptor and non-receptor binding of both large and small molecules can be conducted. In order to conduct transendothelial cell flux measurements, the cells are grown on porous polycarbonate membrane filters (e.g., from Nucleopore, Pleasanton, Calif.). Large pore size filters (5-12 mm) are used to avoid the possibility of the filter becoming the rate-limiting barrier to molecular flux. The use of these large-pore filters does not permit cell growth under the filter and allows visual inspection of the cell monolayer.

Once the cells reach confluency, they are placed in a side-by-side diffusion cell apparatus (e.g., from Crown Glass, Sommerville, N.J.). For flux measurements, the donor chamber of the diffusion cell is pulsed with a test substance, then at various times following the pulse, an aliquot is removed from the receiver chamber for analysis. Radioactive or fluorescently-labelled substances permit reliable quantitation of molecular flux. Monolayer integrity is simultaneously measured by the addition of a non-transportable test substance such as sucrose or inulin and replicates of at least 4 determinations are measured in order to ensure statistical significance.

Example 15. Traumatic Injury Model

The fluid percussion brain injury model was used to assess the ability of polymeric thyroid hormone analogs alone or in combination with nerve growth factors or other neurogenesis factors to restore central nervous system functions following significant traumatic brain injury.

I. Fluid Percussion Brain Injury Procedure

The animals used in this study were male Sprague-Dawley rats weighing 250-300 grams (Charles River). The basic surgical preparation for the fluid-percussion brain injury has been previously described. Dietrich, et al., Acta Neuropathol. 87: 250-258 (1994) incorporated by reference herein. Briefly, rats were anesthetized with 3% halothane, 30% oxygen, and a balance of nitrous oxide. Tracheal intubation was performed and rats were placed in a stereotaxic frame. A 4.8-mm craniotomy was then made overlying the right parietal cortex, 3.8 mm posterior to bregma and 2.5 mm lateral to the midline. An injury tube was placed over the exposed dura and bonded by adhesive. Dental acrylic was then poured around the injury tube and the injury tube was then plugged with a gelfoam sponge. The scalp was sutured closed and the animal returned to its home case and allowed to recover overnight.

On the next day, fluid-percussion brain injury was produced essentially as described by Dixon, et al., J. Neurosurg. 67: 110-119 (1987) and Clifton, et al., J. Cereb. Blood Flow Metab. 11: 114-121 (1991). The fluid percussion device consisted of a saline-filled Plexiglas cylinder that is fitted with a transducer housing and injury screw adapted for the rat's skull. The metal screw was firmly connected to the plastic injury tube of the intubated anesthetized rat (70% nitrous oxide, 1.5% halothane, and 30% oxygen), and the injury was induced by the descent of a pendulum that strikes the piston. Rats underwent mild-to-moderate head injury, ranging from 1.6 to 1.9 atm. Brain temperature was indirectly monitored with a thermistor probe inserted into the right temporalis muscle and maintained at 37-37.5° C. Rectal temperature was also measured and maintained at 37° C. prior to and throughout the monitoring period.

Behavioral Testing:

Three standard functional/behavioral tests were used to assess sensorimotor and reflex function after brain injury. The tests have been fully described in the literature, including Bederson, et al., (1986) Stroke 17: 472-476; DeRyck, et al., (1992) Brain Res. 573: 44-60; Markgraf, et al., (1992) Brain Res. 575: 238-246; and Alexis, et al., (1995) Stroke 26: 2338-2346.

A. The Forelimb Placing Test

Forelimb placing to three separate stimuli (visual, tactile, and proprioceptive) was measured to assess sensorimotor integration. DeRyck, et al., Brain Res. 573:44-60 (1992). For the visual placing subtest, the animal is held upright by the researcher and brought close to a table top. Normal placing of the limb on the table is scored as "0," delayed placing (<2 sec) is scored as "1," and no or very delayed placing (>2 sec) is scored as "2." Separate scores are obtained first as the animal is brought forward and then again as the animal is brought sideways to the table (maximum score per limb=4; in each case higher numbers denote greater deficits). For the tactile placing subtest, the animal is held so that it cannot see or touch the table top with its whiskers. The dorsal forepaw is touched lightly to the table top as the animal is first brought forward and then brought sideways to the table. Placing each time is scored as above (maximum score per limb=4). For the proprioceptive placing subtest, the animal is brought forward only and greater pressure is applied to the dorsal forepaw; placing is scored as above (maximum score per limb=2). Finally, the ability of animals to place the forelimb in response to whisker stimulation by the tabletop was tested (maximum score per limb=2). Then subscores were added to give the total forelimb placing score per limb (range=0-12).

B. The Beam Balance Test

Beam balance is sensitive to motor cortical insults. This task was used to assess gross vestibulomotor function by requiring a rat to balance steadily on a narrow beam. Feeney, et al., Science, 217: 855-857 (1982); Goldstein, et al., Behav. Neurosci. 104: 318-325 (1990). The test involved three 60-second training trials 24 hours before surgery to acquire baseline data. The apparatus consisted of a ¾-inch-wide beam, 10 inches in length, suspended 1 ft. above a table top. The rat was positioned on the beam and had to maintain steady posture with all limbs on top of the beam for 60 seconds. The animals' performance was rated with the scale of Clifton, et al., J. Cereb Blood Flow Metab. 11: 1114-121 (1991), which ranges from 1 to 6, with a score of 1 being normal and a score of 6 indicating that the animal was unable to support itself on the beam.

C. The Beam Walking Test

This was a test of sensorimotor integration specifically examining hindlimb function. The testing apparatus and rating procedures were adapted from Feeney, et al., Science, 217: 855-857 (1982). A 1-inch-wide beam, 4 ft. in length, was suspended 3 ft. above the floor in a dimly lit room. At the far end of the beam was a darkened goal box with a narrow entryway. At equal distances along the beam, four 3-inch metal screws were positioned, angling away from the beam's center. A white noise generator and bright light source at the start of the beam motivated the animal to traverse the beam and enter the goal box. Once inside the goal box, the stimuli were terminated. The rat's latency to reach the goal box (in seconds) and hindlimb performance as it traversed the beam (based on a 1 to 7 rating scale) were recorded. A score of 7 indicates normal beam walking with less than 2 foot slips, and a score of 1 indicates that the rat was unable to traverse the beam in less than 80 seconds. Each rat was trained for three days before surgery to acquire the task and to achieve normal performance (a score of 7) on three consecutive trials. Three baseline trials were collected 24 hours before surgery, and three testing trials were recorded daily thereafter. Mean values of latency and score for each day were computed.

Example 16. T4 is a Ligand of αVβ3 Integrin

To determine if T4 is a ligand of the αVβ3 integrin, 2 µg of commercially available purified protein was incubated with [$^{125}$I]T4, and the mixture was run out on a non-denaturing polyacrylamide gel. αVβ3 binds radiolabeled T4 and this interaction was competitively disrupted by unlabeled T4, which was added to αVβ3 prior to the [$^{125}$I]T4 incubation, in a concentration-dependent manner (FIG. 24). Addition of unlabeled T4 reduced binding of integrin to the radiolabeled ligand by 13% at a total T4 concentration of $10^{-7}$ M total ($3\times10^{-10}$ M free T4), 58% at $10^{-6}$ M total ($1.6\times10^{-9}$ M free), and inhibition of binding was maximal with $10^{-5}$ M unlabeled T4. Using non-linear regression, the interaction of αVβ3 with free T4 was determined to have a Kd of 333 pM and an $EC_{50}$ of 371 pM. Unlabeled T3 was less effective in displacing [$^{125}$I]T4-binding to αVβ3, reducing the signal by 28% at $10^{-4}$ M total T3.

Example 17. T4 Binding to αVβ3 is Blocked by Tetrac, RGD Peptide and Integrin Antibody We have shown previously that T4-stimulated signaling pathways activated at the cell surface can be inhibited by the iodothyronine analog tetrac, which is known to prevent binding of T4 to the plasma membrane. In our radioligand-binding assay, while $10^{-8}$ M tetrac had no effect on [$^{125}$I]T4-binding to purified αVβ3, the association of T4 and αVβ3 was reduced by 38% in the presence of $10^{-7}$ M tetrac and by 90% with $10^{-5}$ M tetrac (FIG. 25). To determine specificity of the interaction, an RGD peptide, which binds to the extracellular matrix-biding site on αVβ3, and an RGE peptide, which has a glutamic acid residue instead of an aspartic acid residue and thus does not bind αVβ3, were added in an attempt to displace T4 from binding with the integrin. Application of an RGD peptide, but not an RGE peptide, reduced the interaction of [$^{125}$I]T4 with αVβ3 in a dose-dependent manner (FIG. 25).

To further characterize the interaction of T4 with αVβ3, antibodies to αVβ3 or αVβ5 were added to purified αVβ3 prior to addition of [$^{125}$I]T4. Addition of 1 µg/ml of αVβ3 monoclonal antibody LM609 reduced complex formation between the integrin and T4 by 52%, compared to untreated control samples. Increasing the amount of LM609 to 2 µg, 4 µg, and 8 µg/ml diminished band intensity by 64%, 63% and 81%, respectively (FIG. 26). Similar results were observed when a different αVβ3 monoclonal antibody, SC7312, was incubated with the integrin. SC7312 reduced the ability of T4 to bind αVβ3 by 20% with 1 µg/ml of antibody present, 46% with 2 µg, 47% with 4 µg, and by 59% when 8 µg/ml of antibody were present. Incubation with monoclonal antibodies to αV and β3, separately, did not affect [$^{125}$I]T4-binding to αVβ3, suggesting that the association requires the binding pocket generated from the heterodimeric complex of αVβ3 and not necessarily a specific region on either monomer. To verify that the reduction in band intensity was due to specific recognition of αVβ3 by antibodies, purified αVβ3 was incubated with a monoclonal antibody to αVβ5 (P1F6) or mouse IgG prior to addition of [$^{125}$I]T4, neither of which influenced complex formation between the integrin and radioligand (FIG. 26).

Example 18. T4-Stimulated MAPK Activation is Blocked by Inhibitors of Hormone Binding and of Integrin αVβ3

Nuclear translocation of phosphorylated MAPK (pERK1/2) was studied in CV-1 cells treated with physiological levels of T4 $10^{-7}$ M total hormone concentration, $10^{-10}$ M free hormone) for 30 min. Consistent with results we have previously reported, T4 induced nuclear accumulation of phosphorylated MAPK in CV-1 cells within 30 min (FIG. 27). Pre-incubation of CV-1 cells with the indicated concentrations of αVβ3 antagonists for 16 h reduced the ability of T4 to induce MAPK activation and translocation. Application of an RGD peptide at $10^{-8}$ and $10^{-7}$ M had a minimal effect on MAPK activation. However, $10^{-6}$ M RGD peptide inhibited MAPK phosphorylation by 62% compared to control cultures and activation was reduced maximally when $10^{-5}$ M RGD (85% reduction) and $10^{-4}$ M RGD (87% reduction) were present in the culture media. Addition of the nonspecific RGE peptide to the culture media had no effect on MAPK phosphorylation and nuclear translocation following T4 treatment in CV-1 cells.

Tetrac, which prevents the binding of T4 to the plasma membrane, is an effective inhibitor of T4-induced MAPK activation. When present at a concentration of $10^{-6}$ M with T4, tetrac reduced MAPK phosphorylation and translocation by 86% when compared to cultures treated with T4 alone (FIG. 27). The inhibition increased to 97% when $10^{-4}$ M tetrac was added to the culture media for 16 h before the application of T4. Addition of αVβ3 monoclonal antibody LM609 to the culture media 16 h prior to stimulation with T4 also reduced T4-induced MAPK activation. LM609 at 0.01 and 0.001 µg/ml of culture media did not affect MAPK activation following T4 treatment. Increasing the concentration of antibody in the culture media to 0.1, 1, and 10 µs/ml reduced levels of phosphorylated MAPK found in the nuclear fractions of the cells by 29%, 80%, and 88%, respectively, when compared to cells treated with T4 alone.

CV-1 cells were transiently transfected with siRNA to αV, β3 or both αV and β3 and allowed to recover for 16 h before being placed in serum-free media. Following T4 treatment for 30 min, the cells were harvested and either nuclear protein or RNA was extracted. FIG. 28A demonstrates the specificity of each siRNA for the target integrin subunit. CV-1 cells transfected with either the αV siRNA or both αV and β3 siRNAs showed decreased αV subunit RT-PCR products, but there was no difference in αV mRNA expression when cells were transfected with the siRNA specific for β3, or when exposed to the transfection reagent in the absence of exogenous siRNA. Similarly, cells transfected with β3 siRNA had reduced levels of β3 mRNA, but relatively unchanged levels of αV siRNA. The addition of T4 for 30 min did not alter mRNA levels for either αV or β3, regardless of the siRNA transfected into the cells.

Activated MAPK levels were measured by western blot in CV-I cells transfected with siRNAs to αV and β3, either individually or in combination (FIG. 28B). CV-I cells treated with scrambled negative control siRNA had slightly elevated levels of T4-induced activated MAPK when compared to the parental cell line. Cells exposed to the transfection reagent alone display similar levels and patterns of MAPK phosphorylation as the non-transfected CV-1 cells. When either αV siRNA or β3 siRNA, alone or in combination, was transfected into CV-1 cells, the level of phosphorylated MAPK in vehicle-treated cultures was elevated, but the ability of T4 to induce a further elevation in activated MAPK levels was inhibited.

Example 19. Hormone-Induced Angiogenesis is Blocked by Antibody to αVβ3

Angiogenesis is stimulated in the CAM assay by application of physiological concentrations of T4 (FIG. 29A and summarized in FIG. 29B). $10^{-7}$ M T4 placed on the CAM filter disk induced blood vessel branch formation by 2.3-fold (P<0.001) when compared to PBS-treated membranes. Propylthiouracil, which prevents the conversion of T4 to T3, has no effect on angiogenesis caused by T4. The addition of a monoclonal antibody, LM609 (10 µg/filter disk), directed against αVβ3, inhibited the pro-angiogenic response to T4.

Example 20. Preparation of Tetrac Nanoparticle Formulations and Uses—PLGA

Poly(lactic-co-glycolic acid) (PLGA) nanoparticles encapsulating Tetrac were prepared by single emulsion method. A homogeneous solution of PLGA and the Tetrac were obtained by mixing 30 mg of PLGA and 1.6 mg of Tetrac in 1 ml of acetone. PLGA nanoparticles were prepared with and without the presence of a stabilizer (polyvinyl alcohol was used as a stabilizer). 100 ul of this solution containing both the PLGA and Tetrac were added to 10 ml of deionized water and stir it for 2 hours. For the synthesis of the nanoparticles with a stabilizer 100 ul of the above mentioned solution was added to 1% PVA solution drop wise with constant stirring. The nanoparticles were purified by dialysis for about 12 hours by using appropriate dialysis membrane. The addition of the stabilizer gives the monodispersity and stability to the nanoparticles in aqueous solution. The results are shown in FIG. 33.

Studies in the CAM model of b-FGF-induced angiogenesis demonstrated potent anti-angiogenesis efficacy for free tetrac and Tetrac—PLGA Nanoparticles as shown in FIG. 34.

Example 21. Preparation of PLGA Nanoparticles Co-Encapsulating Tetrac and Temozolomide Another suitable nanoparticle includes PLGA nanoparticles co-encapsulating tetrac and Temozolomide. One of the major advantage of nanoparticles is its ability to co-encapsulate multiple numbers of encapsulating materials in it altogether. A schematic is shown in FIG. 35.

Example 22. T4 Collagen Conjugated Nanoparticles Containing Calcium Phosphate

The release kinetics from inside the collagen Nanoparticles demonstrated 40% release in the first 2 hours with sustained slow release over 20 hours. T4 was immobilized to the outside of the Nanoparticles with >99% stability as shown below. Formulation for wound healing contains T4-immobilized on collagen Nanoparticles and calcium phosphate Nanoparticles inside or can be placed outside the collagen Nanoparticles for topical formulation. The results of the chromatograms are shown in FIGS. 37A-B and FIGS. 38A-B.

Example 23. Preparation of GC-1 Encapsulated PEG-PLGA Nanoparticles

PEG-PLGA Nanoparticles encapsulating GC-1 are prepared by single emulsion method. A solution of PEG-PLGA is prepared in DMSO (e.g. 80 mg/ml). Another solution of GC-1 is prepared in DMSO (e.g. 15 g/ml) separately. Now equal amount of the both solution are mixed (PEG-PLGA and GC-1). Now, 100 ul of this solution is added to 1% PVA (polyvinyl alcohol) solution with constant stirring. After 4 hours the whole solution containing the Nanoparticles encapsulating GC-1 is subjected to dialysis to remove the impurities. A schematic diagram for the preparation of GC-1 encapsulated PEG-PLGA Nanoparticles is shown in FIG. 39.

Example 24. Preparation of GC-1 or T3 Encapsulated PEG-PLGA Nanoparticles

PEG-PLGA nanoparticles encapsulating GC-1 or T3 will be prepared by single emulsion method. A solution of PEG-PLGA will be prepared in DMSO (e.g. 80 mg/ml). Another solution of GC-1 or T3 will be prepared in DMSO (e.g. 15 g/ml) separately. Then, equal amount of both solution will be mixed (PEG-PLGA and GC-1 or T3). 100 µl of this solution will be added to 1% PVA (polyvinyl alcohol) solution with constant stirring. After 4 hours the whole solution containing the nanoparticles encapsulating GC-1 or T3 will be subjected to dialysis to remove the impurities. A schematic diagram for the preparation of T3 encapsulated PEG-PLGA nanoparticles is shown in FIG. 40.

Novel formulations of tetrac include linkage to nanoparticles, a construct that precludes entry of tetrac into the cell and limits its activity to the plasma membrane integrin receptor.

The hydrophobic drug used for entrapment is in solution form or in powder form and the solvent used for dissolving the drug is selected from dimethylformamide (DMF), dimethylsulphoxide (DMSO), dichloromethane, ethylacetate, ethanol.

The block copolymer micelles are made of mucoadhesive and thermosensitive polymer components, and when instilled, it penetrates the mucin membrane, adhere to the membrane pores and at body temperature, it becomes more hydrophobic to release the drug faster.

The random block copolymer of micelles of the present invention may be prepared by mixing monomers such as vinylpyrrolidone (VP), N-isopropyl is acrylamide (NI-PAAM) and acrylic acid (AA) in presence of N,N' methylene bis acrylamide (MBA) and polymerizing the mixture by free radical polymerization reaction using ammonium persulphate as catalyst. The hydrophobic moiety of the polymeric chain remain buried inside the micelles which help dissolution of drug and the hydrophilic moiety such as carboxylic acids are extended outside the surface of the micelles. The clear solution of the micellar dispersion in aqueous solution can be instilled in the patient's eyes much more effectively and the sustained release of the drug encapsulated inside the micelles enhances the therapeutic effect of the drug.

In order to incorporate one or more drugs mentioned above into the block copolymer micelles, various methods described below may be used alone or in combination.

(i) Stirring: A drug is added to an aqueous solution of a block copolymer, and stirred for 2 to 24 hours to obtain micelles containing drug.

(ii) Heating: A drug and an aqueous solution of a block copolymer are mixed and stirred at 30° C. to 80° C. for 5 minutes to a couple of hours and then cooled to room temperature while stirring to obtain micelles containing the drug.

(iii) Ultrasonic Treatment: A mixture of a drug and an aqueous solution of a block copolymer is subjected to an ultrasonic treatment for 10 minutes to 30 minutes and then stirred at room temperature to obtain micelles containing the drug.

(iv) Solvent Evaporation: A drug is dissolved in an organic solvent such as chloroform and was added to an aqueous solution of micelles. Subsequently the organic solvent was evaporated slowly while stirring, and then filtered to remove free drug.

(v) Dialysis: The polymeric micelles solution was added to an organic solution of drug and the mixture is dialyzed against a buffer solution and then water.

The micelle solution of block copolymers is prepared by dissolving amphiphilic monomers in an aqueous medium to obtain micelles, adding aqueous solutions of cross-linking agent, activator and initiator into the said micelles, subjecting the said mixture to polymerization in presence of an inert gas at 30.degree. C.-40.degree. C. till the polymerization of micelles is complete.

The purification step is done by dialysis. The dialysis is carried out for 2-12 hours to eliminate unreacted monomers and free hydrophobic compound (s), if any, in the aqueous phase. A hydrophobic drug may be incorporated into the polymeric micelles of the present invention during the time of polymerization wherein the drug is dissolved into the micelles of the monomers in aqueous solution and the polymerization is done in presence of the drug. As the drug held in the hydrophobic core of the micelles is released on the cornea surface in a controlled manner for a long time, the composition of the present invention is suitable for formulating drugs, which are not amenable to conventional formulating techniques or using non mucoadhesive micelles.

Example 25. Design of Nanoparticles Formulation for Ocular Use

In the initial experiments three different kinds of nanoparticulate formulations based on different polymers will be prepared. The efficacy of these nanoparticles with different variation like surface charge, size and mucoadhesiveness will be examined. TETRAC will be encapsulated in all of these nanoparticles formulations. Broadly PLGA, chitosan and custom made co-polymeric nanoparticles with different ratio of N-isopropylacrylamide, N-3-aminopropylmethacrylamide hydrochloride, and acrylic acid will be synthesized.

The goal is to design different Nanoformulation for TETRAC enhanced ocular kinetics. We will define two different options where the nanoparticles stay on the corneal membrane and deliver TETRAC and another option is to increase nano-uptake across the corneal membrane. The size and surface charge as well as the nature of the nano material will be adjusted to attain optimal eye drop formulation for TETRAC.

Analysis of Nanoparticles:

Based on the original method developed by PRI a modified HPLC analytical method specific for TETRAC Nanoparticles will be developed. Development of analytical method for indirect quantitation of TETRAC inside the nanoparticles is also on agenda. From a set, half of the total amount of the nanoparticles will be disintegrated in 50% acetone and analyzed directly by HPLC for total amount of free and encapsulated TETRAC. On the other hand the other half of nanoparticles will be filtered through a 100 KD centrifugal filter membrane device, and the filtrate will be analyzed by HPLC for the total amount of free TETRAC. Thus, the difference between the amounts of TETRAC in the two analyses would represent the amount of TETRAC inside the nanoparticles.

The sample preparation protocol would have to be tested for each kind of nanoparticles, and adjusted accordingly.

In Vitro Release Kinetics:

To study the release kinetics, a known amount of the nanoparticles formulation encapsulating TETRAC will be suspended in desired medium in which the release kinetics are to be studied. The solution will be distributed as 500 ul aliquots in micro-centrifuge tubes. At predetermined intervals of time the solutions will be filtered through centrifugal filter membrane device (100 KD cut off) as indicated above to separate free TETRAC from the loaded nanoparticles. The concentration of free TETRAC will be determined by HPLC.

$$\% \text{ Release} = \frac{[TETRAC]_{f,t}}{[TETRAC]_0} \times 100$$

Wherein $[TETRAC]_{f,t}$ is the concentration of TETRAC in the filtrate at time t and $[TETRAC]_0$ is the total amount of the encapsulated TETRAC In Vivo Experiments Preliminary in vivo experiment will be performed to test the efficacy of the nanoparticles formulations in New Zealand White rabbits' eyes as compared to a control of the drug without nanoparticles. The procedure of application, collection method of the aqueous humor etc. will be described in details in the animal protocol. The remaining portion of each eye will be saved and stored frozen at $-80°$ C. for possible future analysis.

Four eyes from two rabbits will be used for each formulation at each testing point (n=4). Aqueous humor samples will be collected at 30 and 90 minutes after topical drug administration, where two animals will be sacrificed for each time point. This will require at least 40 rabbits to be sacrificed during the course of the study.

Samples from aqueous humor collected will be frozen at $-80°$ C. until the time of analysis if necessary.

All samples will be analyzed by HPLC. The new specific method for analysis of TETRAC in Nanoparticles will be use for analyzing TETRAC, both free and encapsulated. Filtration of the aqueous humor through 100 KD filters will be used as described earlier to study the two forms of TETRAC.

Depending on the results from the in vivo release kinetics, three formulations will be selected for Phase II. One pilot batch for each formulation will be prepared. The characteristics and stability of these selected formulations will be further studies

Example 26. Preparation of Nanoparticles Containing Tetrac or Analogs

The suspension formulation for the PK and toxicology studies are made using the following procedure:

1. Weight out 50 mg tetrac, add to 10 ml 0.5% CMC (carboxymethylcellulose)
2. Mix well until tetrac is suspended
3. Mix before use.

Another formulation that was made and used for intravenous administration was made using the procedure outlined below:

1. Dissolve 200 mg Tetrac in 1.0 ml DMSO
2. Add 1.0 ml Tween 80, and stir for 5 minutes. Check that all Tween 80 has dissolved.
3. Add drop wise (while stirring) 10 ml PBS.
4. Adjust the pH to 7.4 using 1.0M dibasic sodium phosphate, added slowly while stirring.
5. Q.S to 20 ml with PBS
6. Dilute in PBS to 5 mg/ml (1:1 dilution).

Example 27. Measurement of Particle Size by Dynamic Light Scattering Experiment The nanoparticles were purified by dialysis or about 12 hours by using appropriate dialysis membrane. The addition of the stabilizer gives the monodispersity and stability to the nanoparticles in aqueous solution. The size distribution and zeta potential were determined using zeta size analyzer. The results can be seen in FIG. 41A-B.

Example 28. Inhibition of Angiogenesis by Tetraiodothyroacetic Acid (Tetrac)

Deaminated thyroid hormone analog, Tetraiodothyroacetic acid (tetrac) is a novel, inexpensive anti-angiogenic agent whose activity is proposed to represent an interaction between the thyroid hormone receptor and the RGD recognition site on integrin αVβ3.

This study was designed to examine the effects tetrac on angiogenesis induced by VEGF and FGF2. Induction of angiogenesis by VEGF and FGF2 involves binding of these growth factors to integrin αVβ3 on endothelial cells. Such binding involves ligand protein-specific domains on the integrin, as well as an Arg-Gly-Asp (RGD) recognition site that generically identifies the protein ligands of αVβ3 and several other integrins. RGD peptides also block the proangiogenic actions of $T_4$ and $T_3$, suggesting that the RGD recognition site and the thyroid hormone-tetrac receptor site on integrin αVβ3 are near to one another. Without intending to be bound by theory, because of the proximity of the RGD recognition site and hormone-tetrac binding domain on αVβ3, tetrac is anti-angiogenic in the absence of thyroid hormone. That is, occlusion of the thyroid hormone receptor site might alter the abilities of VEGF and FGF2 to interact with the integrin at the RGD site.

Material and Methods Reagents $T_4$ (≥98% pure by HPLC), $T_3$, tetrac, cortisone acetate, and propylthiouracil (PTU) were purchased from Sigma-Aldrich Corp. (St. Louis, Mo.). FGF2 and VEGF were purchased from Invitrogen Life Technologies, Inc. (Carlsbad, Calif.). Matrigel was purchased from BD Bioscience (San Jose, Calif.).

Cell Culture

Human dermal microvascular endothelial cells (HMVEC-d; Clonetics, San Diego, Calif.) were grown on culture flasks coated with type I collagen (1 mg/ml) and maintained in endothelial growth media-2 (EGM-2MV; Clonetics) supplemented with bovine brain extract (12 μg/ml), recombinant human epidermal growth factor (10 ng/ml), 10% (vol/vol) heat-inactivated fetal bovine serum (FBS), hydrocortisone (1 μg/ml), 100 U/ml penicillin, 100 μg/ml streptomycin, and 2 mM L-glutamine. All culture additives were purchased from Invitrogen. Cultures were maintained in a 37° C. humidified chamber with 5% $CO_2$. The medium was changed every 3 d, and the cell lines were passaged at 80% confluence.

Chick Chorioallantoic Membrane Assay (Chick CAM Assay)

Ten-day-old chick embryos were purchased from SPA-FAS (Preston, Conn.) and were incubated at 37° C. with 55% relative humidity. Chick CAM assays were performed as previously described. Briefly, a hypodermic needle was used to make a small hole in the blunt end of the egg, and a second hole was made on the broad side of the egg, directly over an avascular portion of the embryonic membrane. Mild suction was applied to the first hole to displace the air sac and drop the CAM away from the shell. Using a Dremel model craft drill (Dremel, Racine, Wis.); an approximately 1.0-cm$^2$ window was cut in the shell over the false air sac, allowing access to the CAM. Sterile disks of no. 1 filter paper (Whatman, Clifton, N.J.) were pretreated with 3 mg/ml cortisone acetate and 1 mM propylthiouracil and air dried under sterile conditions. Thyroid hormone, control solvents, and experimental treatments were applied to the disks and subsequently dried. The disks were then suspended in PBS and placed on growing CAMs. After incubation for 3 d, the CAM beneath the filter disk was resected and rinsed with PBS. Each membrane was placed in a 35-mm petri dish and examined under an SV6 stereomicroscope at ×50 magnification. Digital images were captured and analyzed with Image-Pro software (Media Cybernetics, Silver Spring, Md.). The number of vessel branch points contained in a circular region equal to the filter disk was counted.

In Vitro Sprouting Assay

Confluent HMVEC-d cells (passage 5-10) were mixed with gelatin-coated Ctodex-3 beads (Sigma) with a ratio of 40 cells per bead. Cells and beads (150-200 beads per well for 24-well plate) were suspended with 5 ml endothelial basal medium (EBM)+15% (vol/vol) normal human serum (HS) and mixed gently for 4 h at room temperature, then incubated overnight in 37° C. $CO_2$ incubator. Cultures were treated with 10 ml of fresh EBM+15% HS for 3 h. One hundred μl of the HMVEC/bead culture was mixed with 500 μl of phosphate-buffered saline (PBS) and placed in 1 well of a 24 well plate. The number of beads/well was counted, and the concentration of beads/EC was calculated.

Human fibrinogen, isolated as previously described, was dissolved in EBM at a concentration of 1 mg/ml (pH 7.4) and filter sterilized and supplemented with the angiogenesis factors to be tested. VEGF (30 ng/ml)+FGF2 (25 ng/ml) were used as a positive control. The HMVEC/bead culture was washed twice with EBM medium and added to fibrinogen solution. The cultures were mixed gently, and 2.5 μl human thrombin (0.05 U/μl) was added and 300 μl of the culture was transferred to each well of a 24-well plate and allowed to incubate for 20 min. EBM+20% normal HS and 10 μg/ml aprotinin were added and the plate was incubated in a $CO_2$ incubator for 48 h. For each condition, the experiment was carried out in triplicate.

Capillary sprout formation was observed and recorded with a Nikon Diaphot-TMD inverted microscope (Nikon Inc.; Melville, Ky. USA), equipped with an incubator housing with a Nikon KP-2 thermostat and Sheldon #2004 carbon dioxide flow mixer The microscope was directly interfaced to a video system consisting of a Dage-MTI CCD-725 video camera and Sons 12" PVM-12Z video monitor linked to a Macintosh G3 computer. The images were captured at various magnifications using Adobe PhotoShop. The effect of the pro-angiogenesis factors on sprout angiogenesis was quantified visually by determining the number and percent of BC-beads with capillary sprouts. One hundred beads (5 to 6 random low power fields) in each of triplicate wells were counted for each experimental condition. All experiments were repeated at least three times.

Real Time Reverse Transcription-Polymerase Chain Reaction

Total RNA was isolated using the Ambion Aqueous kit (Austin, Tex.). The quality and quantity of the isolated RNA was determined by Bio-Rad Experion automated electrophoresis system (Hercules, Calif.). One μg of total RNA was reverse transcribed using Advantage RT-for-PCR Kit (Clontech; Mountain View, Calif.). PCR was performed using Cepheid Smart Cycler (Sunnyvale, Calif.) by mixing 2 μL cDNA, 10 μL Sybergreen master mix (Qiagen; Valencia, Calif.) and 0.5 μL of 20 μM gene-specific primers. Samples were incubated for 20 min at 25° C. and amplified in 35 PCR cycles with 30 s at 95° C. and 90 s at 60° C. (two-step PCR). The threshold cycle values (CO were determined from semi-log amplification plots (log increase in fluorescence versus cycle number). The specificity and the size of the PCR products were tested by adding a melt curve at the end of the amplifications and by running the PCR products on 2% agarose gel and sequencing the bands. All values were normalized to cyclophilin A. PCR primers were as follows: Angio-1, 5'-GCAACTGGAGCTGATGGACACA-3' (sense) and 5'-CATCTGCACAGTCTCTAAATGGT-3' (antisense), amplicon 116 bp; Angio-2, 5'-TGGGATTTGG- TAACCCTTCA-3' (sense) and 5'-GTAAGCCTCATTC-CCTTCCC-3' (antisense), amplicon 122 bp; integrin $\alpha_v$, 5'-TTGTTGCTACTGGCTGTTTTG-3' (sense) and 5'-TC-CCTTTCTTGTTCTTCTTGAG-3' (antisense), amplicon 89 bp; integrin $\beta_3$, 5'-GTGACCTGAAGGAGAATCTGC-3' (sense) and 5'-TTCTTCGAATCATCTGGCC-3' (antisense), amplicon 184 bp; and cyclophilin A, 5'-CCCACCGTGT-TCTTCGACAT-3' (sense) and 5'-CCAGTGCTCAGAG-CACGAAA-3' (antisense), amplicon 116 bp.

Microarray Analysis: Ten micrograms of total RNA from HMVEC-d cells was amplified and biotin-labeled according to GeneChip Expression Analysis Technical Manual (Affymetrix, Santa Clara, Calif.). Fragmented cRNA was hybridized with human gene chip U133 PLUS 2 (Affymetrix); chips were washed and stained with streptavidin R-phycoerythrin (Molecular Probes, Eugene, Oreg.). The chips were scanned and the data were analyzed with Microarray Suite and Data Mining Tool (Affymetrix).

Tetrac Inhibition of Hormone-Stimulated Angiogenesis: Angiogenesis is stimulated in the CAM assay by application of physiological concentrations of FGF2, VEGF, and T3. As shown 42, FGF2 (1 µg/ml) placed on the CAM filter disk induced blood vessel branch formation by 2.4-fold (P<0.001) compared with PBS-treated membranes. The addition of tetrac (75 ng/filter disc) inhibited the proangiogenic response to FGF2, while tetrac alone had no effect on angiogenesis.

A tetrac dose response curve was performed to find maximum inhibition of FGF2 stimulated angiogenesis. As shown in FIG. 43, seventy five ng/filter disc and 100 ng/filter disc inhibited angiogenesis by 57% and 59% respectively. When the tetrac concentration was increased to 1 µg/filter disc, FGF2 stimulated angiogenesis was inhibited 74%. Maximal inhibition was observed when the tetrac concentrations were further increased to 3 µg/filter disc and this was maintained at 5 µg/filter disc.

Tetrac similarly inhibits the pro-angiogenic effect of VEGF and T3 by 52% and 66% respectively, as shown in FIG. 44.

Tetrac Inhibition of Tube Formation: HMVEC-d cells were cultured on matrigel for 24 hrs and stimulated with VEGF (50 ng/ml) in the presence or absence of increasing amounts of tetrac. Tetrac inhibited the tube formation induced by VEGF as demonstrated by a reduction in the number of junctions, and number of tubes and a decrease in total tubule length, as shown in FIG. 45. This effect is depicted in the photographs in FIG. 46.

The number of tube junctions decreased from 32.0±9.6 (0 µM tetrac) to 18.0±1.5, 4.7±1.8, and 3.0±2.5 with 1 µM, 2.5 µM, and 10 µM tetrac, respectively. Similarly, the number of tubes decreased from 212.3±21.3 (0 µM tetrac) to 180.0±4.0 (1 µM tetrac), 150.0±8.1 (2.5 µM tetrac), and 81.3±24.8 (10 µM tetrac). The total tube length was also decreased in a dose dependent manner; with maximal decrease of 70% of the tube length observed at 10 µM tetrac and was maintained at 25 µM and 50 µM tetrac (data not shown).

mRNA Expression of Integrins αV and β3, and Angiopoietin-2 are Decreased by Tetrac: HMVEC-d cells were grown on matrigel and stimulated with VEGF (50 ng/ml) with and without Tetrac for 2 hours. Messenger RNA was isolated and real-time RT-PCR was performed for integrin αV and integrin 33, as shown in FIG. 47A-B.

Tetrac inhibited mRNA expression of both integrin αV and integrin β3 in a dose response fashion. αV mRNA levels decreased from 0.1149±0.0124 relative fluorescent units (RFUs) in VEGF treated cells to 0.0618±0.00927 RFUs following treatment 1 µM tetrac and decreased further following treatment with 3 µM tetrac. Expression of integrin β3, whose expression is much lower than integrin αV, decreased following tetrac treatment in a similar manner as integrin αV. VEGF treated cells expressed 0.0299±0.0026 RFUs of β3. Expression was decreased to 0.0160±0.0013 and 0.0159±0.0016 RFUs with 1 µM and 3 µM tetrac, respectively. Real-time RT-PCR for angiopoietin-1 and angiopoietin-2 was performed and it was found that tetrac inhibited mRNA expression of angiopoietin-2 in a dose response fashion and did not affect the mRNA levels of angiopoietin-1, as shown in FIG. 48A-B.

In addition, incubation of HMVEC-d cells overnight with tetrac and VEGF did not further alter angiopoietin-1 and angiopoietin-2 expression (data not shown).

Microarray Analysis

To further identify possible mechanisms of tetrac inhibition of VEGF-stimulated angiogenesis, microarray analysis was performed using the Human U133 Plus 2.0 array from Affymetrix. HDMEC cells were incubated with VEGF at 50 ng/ml for 24 hours with and without Tetrac (3 uM). The results of the Affymetrix GeneChip analysis indicated that three different angiopoietin-like transcripts were differentially expressed in the HMVEC-d cells. As shown in FIG. 49A-C, Angiopoietin-like 1 (ANGPTL-1, probe set ID#231773) expression was increased 5.9 fold following VEGF treatment. The stimulated increase in expression was decreased below baseline levels if the cells were co-treated with tetrac and VEGF. Angiopoietin-like 2 (ANGPTL-2, probe set ID#239039) expression was increased 1.6 fold following VEGF treatment when compared to the untreated control. The addition of tetrac reduced the expression of ANGPTL-2 near the baseline levels. Interestingly, angiopoietin-like 3 (ANGPTL-3, probe set ID#231684) expression was unaffected by treatment of HMVEC-d cells with VEGF. However, tetrac reduced expression of ANGPTL-3 1.9 fold when compared to both the untreated control and VEGF treated samples. These data further suggest that tetrac can inhibit the expression of target genes that are necessary for the stimulation of angiogenesis.

Matrix mettaloproteinases (MMPs) have been clearly implicated in angiogenesis. Both synthetic and endogenous MMP inhibitors block angiogenesis in both in vitro and in vivo models. We used the microarray to examine changes in MMP expression following VEGF treatment with and without tetrac. HMVEC-d cells treated with VEGF have a 5.1-fold increase in MMP-15 expression and a 2.9-fold increase in MMP-19 expression. As shown in FIG. 50A-D, when the cells are co-treated with tetrac (3 µM), the expression of MMP-15 and MMP-19 are decreased by 3.2-fold and 8.7-fold, respectively. Interestingly, MMP-24 expression is slightly decreased by VEGF treatment, but is further depressed by the addition of tetrac. Expression of tissue inhibitor of metalloproteinase 3 (TIMP-3), which is a potent inhibitor of several members of the MMP family, is increased 5.4-fold following VEGF and tetrac treatment when compared to VEGF treated HMVEC-d cells. This suggests that part of the mechanism of tetrac inhibition of VEGF-stimulated angiogenesis is regulated by increases in TIMP expression, which in turn blocks the MMPs role in cytoskeletal reorganization that occurs during angiogenesis.

There is much clinical interest currently in anti-angiogenic compounds, primarily for adjunctive use in the setting of cancers. As demonstrated above, the small molecule, tetrac, directed at the plasma membrane receptor for thyroid hormone has potent anti-angiogenic activity. While tetrac is an antagonist of the cell surface-initiated actions of thyroid hormone, tetrac in the absence of thyroid hormone is now shown to inhibit angiogenic activity of VEGF and FGF2 in chick and human endothelial cell assays. Thus, tetrac has the desirable quality of targeting an integrin by which angiogenic VEGF and FGF2 signals are transduced in endothelial cells, but also inhibits the trophic action of physiological concentrations of thyroid hormone on the proliferation of certain tumor cells, including human estrogen receptor (ER)-positive breast cancer MCF-7 cells and murine glioma cell models of glioblastoma.

Without intending to be bound by any theory, it is speculated that thyroid hormone has several effects on tumors at the cellular or molecular level. These effects include a direct proliferative effect on tumor cells, a direct effect on the migration of cancer cells that may support metastasis and indirect support of tumor growth via pro-angiogenic action. In the setting of cancers, unmodified tetrac and triac or modified as nanoparticles or polymer conjugates, acting as anti-thyroid hormone agents, may have therapeutic application.

Significant survival benefit has recently been obtained with administration of tetrac to a mouse model of intracranial implants of murine glioma cells (R. A. Fenstermaker, M. Ciesielski, F. Davis, and P. J. Davis, unpublished observations). Additionally, a recent prospective clinical study indicates that thyroid hormone is a growth factor for glioblastoma multiforme (GBM) and that induction of mild hypothyroidism in GBM patients has a substantial survival benefit. A retrospective analysis of breast cancer experience in hypothyroid patients at M.D. Anderson Cancer Center showed that hypothyroidism conferred a reduced risk of breast cancer and, when the latter occurred in hypothyroid women, was associated with less aggressive lesions. Without intending to be bound by any theory, it is speculated that two effects of thyroid hormone are seen, a directly proliferative effect on tumor cells, and indirect support of tumor growth via angiogenesis. In the settings of these two types of cancer, tetrac may have therapeutic application.

Example 29. Novel $T_4$/Polymeric Conjugates and $T_4$/Nanoparticle Conjugates

The thyroid gland is the source of two fundamentally different types of hormones. The iodothyronine hormones include thyroxine ($T_4$) and 3,5,3'-triiodothyronine ($T_3$). They are essential for normal growth and development and play an important role in energy metabolism. The thyroid hormones are aromatic amino acids ultimately derived from thyrosine. They are chemically and biosynthetically similar to L-DOPA and 5-hydroxytryptophan, the biosynthetic precursors of the neurotransmitters dopamine and serotonine (5-hydroxytryptamine), respectively. The chemical structures of $T_4$ and $T_3$ and their biosynthetic analogs are shown below.

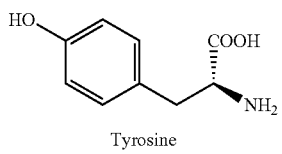
Tyrosine

-continued

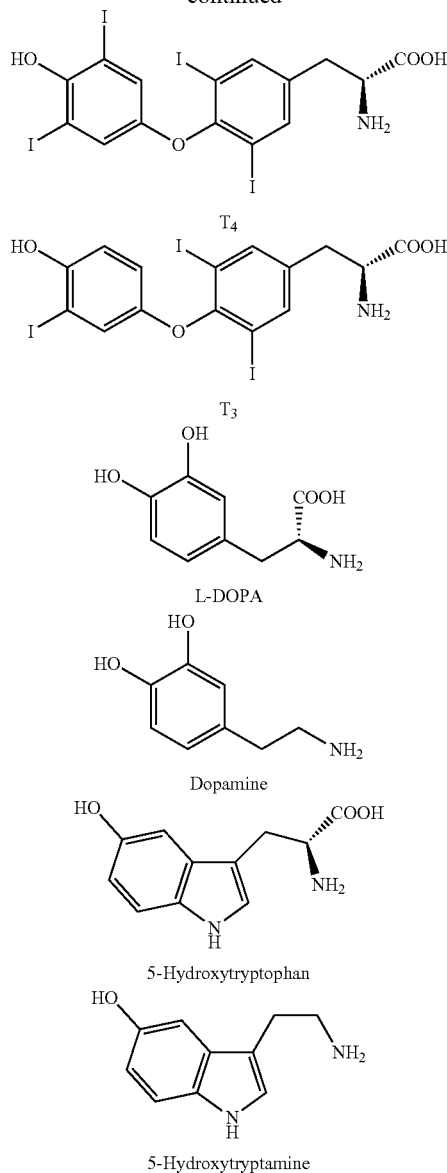

The conjugation of either $T_3$ or $T_4$ with a polymer or immobilization of $T_3$ or $T_4$ with nanoparticles will result in particles with a diameter which does not allow the conjugate to cross the nucleus membrane. Thus, only the cell surface activity of $T_3$ or $T_4$ may be obtained without any undesirable genomic effects.

Both $T_3$ and $T_4$ bear three functional groups which may react to form a polymer conjugate: one carboxylic acid group, one amine group, and one hydroxyl group.

To synthesize the $T_3$ or $T_4$/polymer conjugates, using $T_4$ for illustrative purposes, the reaction site can be any of the following:

1) The carboxylic acid group: The acid group can react to form an ester or an amide. Due to the high reactivity of the amino group in $T_4$, this one should be protected before the conjugating reaction, and then deprotected. Otherwise, the self polymerization will form the $T_4$ oligomers. The candidate polymers include PVA, PEG-$NH_2$, poly(lysine) and related polymers.

2) The amine group: The amine group can react with a polymer carrying a carboxylic acid function or a halogen group. If the polymer has a large amount of activated acid group, the reaction can go through directly. Poly(methylacrylic acid) and poly(acrylic acid) can be used in this way.

3) The hydroxyl group: Due to the existence of a higher reactive amino group, the direct reaction of $T_4$ with a polymer containing a carboxylic acid is difficult. This amino group must be protected before the reaction and deprotected after the conjugating reaction. The common protecting group can be acetic anhydride ($Ac_2O$), N-methyl, N-ethyl, N-Triphenyl or ditertbutyldicarbonate ($BOC_2O$) group.

For each of the following embodiments, $T_3$ may be used instead of $T_4$.

Protection of the Amino Group of L-$T_4$

The protection of the amino group of L-$T_4$ can be done using acetic anhydride ($Ac_2O$), ditertbutyldicarbonate ($BOC_2O$) and butyric anhydride ($Bu_2O$) as the protecting agents, or using any suitable long alipathic groups. An example of a synthesis schematic using a long alipathic group, palmitoyl chloride, is shown in the synthesis schematic below.

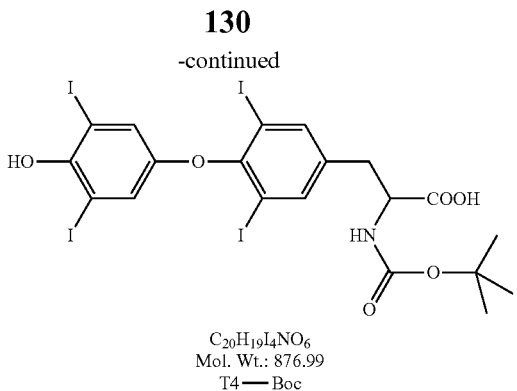

$C_{20}H_{19}I_4NO_6$
Mol. Wt.: 876.99
T4—Boc

L-$T_4$ was selectively protected taking in consideration the reactivity of the amino group compared to the one of the phenol and the zwitterionic form of the commercial L-$T_4$.

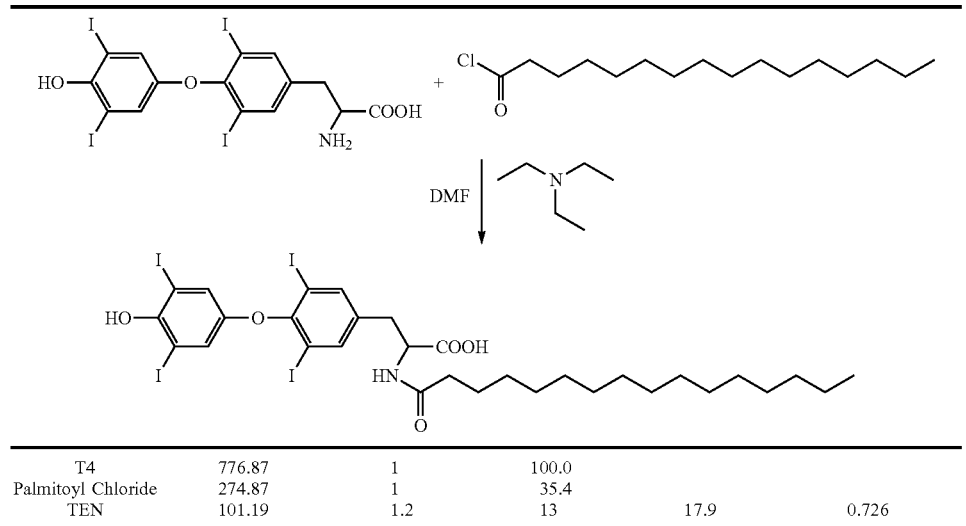

| T4 | 776.87 | 1 | 100.0 | | |
| Palmitoyl Chloride | 274.87 | 1 | 35.4 | | |
| TEN | 101.19 | 1.2 | 13 | 17.9 | 0.726 |

A schematic of the protection of the amino group of L-$T_4$ using ditertbutyldicarbonate ($BOC_2O$) ($T_4$-BOC) is shown below.

This was done using an equimolar amount of products, a mineral base ($Na_2CO_3$) or an organic base (TEA) in polar solvent (DMA or DMF). The compounds PRIAB1, PRIAB4 and PRIAB5 were synthesized under the following reaction conditions shown below.

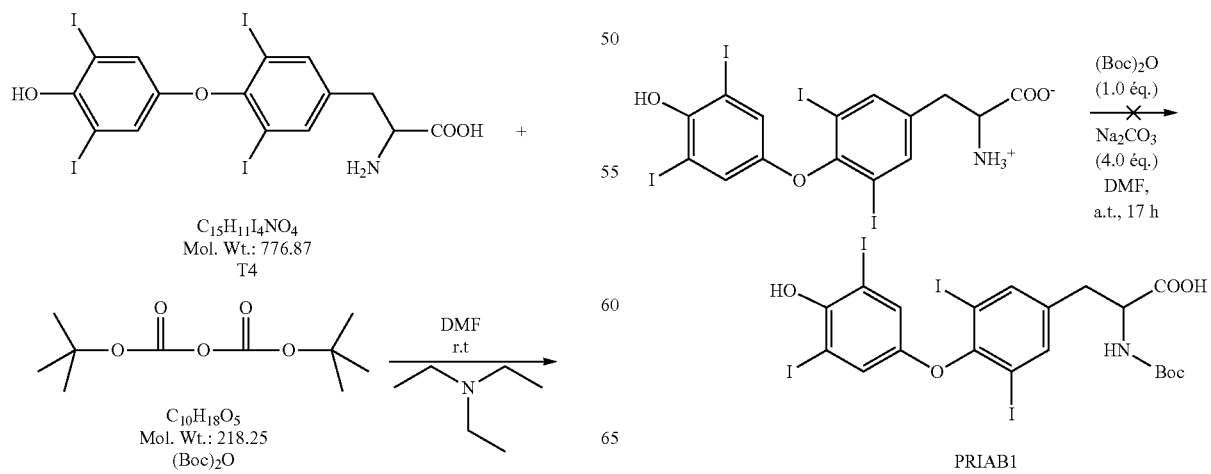

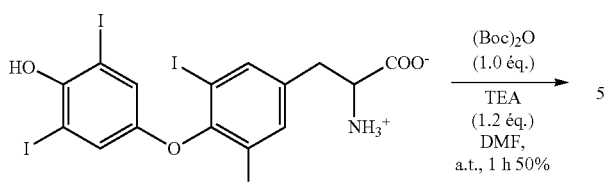

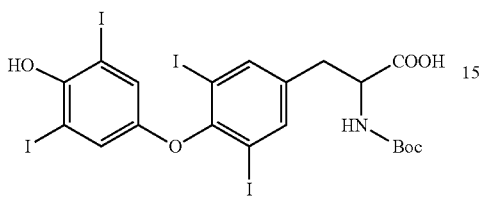

PRIAB1

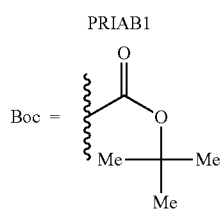

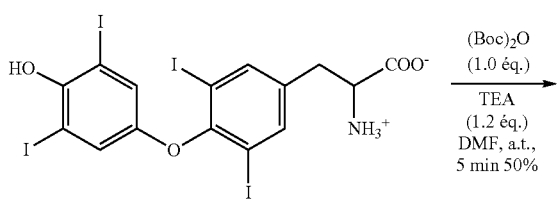

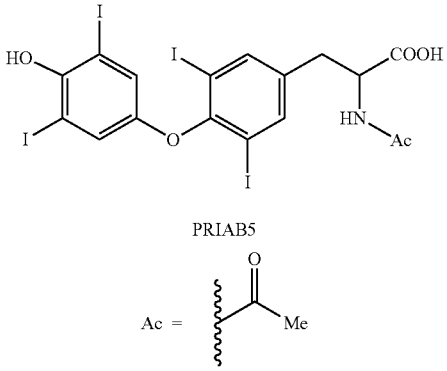

PRIAB5

$$Ac = \text{—C(=O)—Me}$$

The general procedure to get the analytically pure samples for testing is set forth below, using PRIAB1 as an example:

2-[(tert-butoxycarbonyl)amino]-3-[4-(4-hydroxy-3,5-diiodophenoxy)-3,5-diiodophenyl]propanoic acid (PRIAB1).

White solid; Yield 50%; Recrist. Solvt.: AcOEt; Rf=0.79 (DCM/MeOH 5/5); Mp=212° C.; IR (ν cm$^{-1}$): 3407.41 (NH); 1701.65 (CO); 1660.49 (CO); $^1$H NMR (DMSO-d6) δ (ppm): 1.34 (s, 9H, 3 CH$_3$); 2.71-2.79 (t, J=11.7 Hz, 1H, CH); 3.04-3.08 (dd, J=13.6 Hz, J=2.0 Hz, 2H, CH$_2$); 4.16 (br, 1H, NH); 7.05 (s, 2H, ArH); 7.82 (s, 2H, ArH); 11.68 (br, 1H, OH); MS (ESI+): 899.7 [M+Na]$^+$; 821.7 [M-tBu]$^+$; 777.7 [M-Boc]$^+$.

PRIAB2, PRIAB6 and PRIAB12 (shown below) were also synthesized, deprotected and tested for purity, in a similar manner as described above.

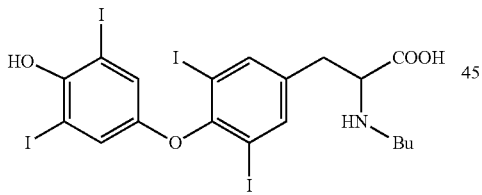

PRIAB4

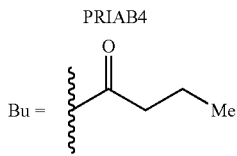

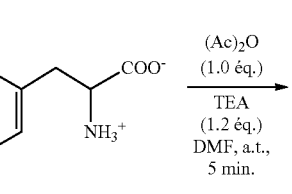

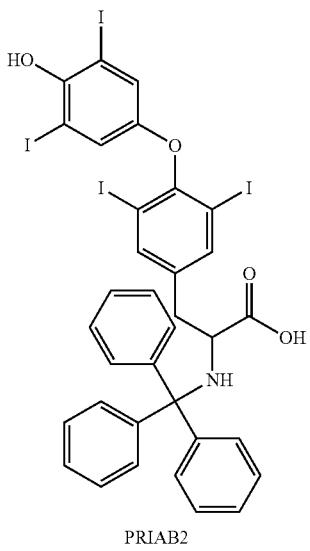

PRIAB2

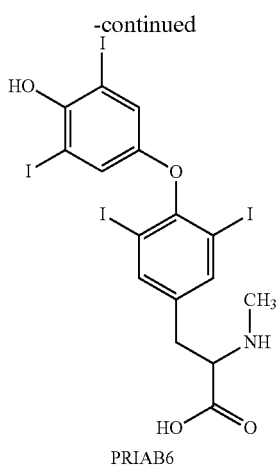

PRIAB6

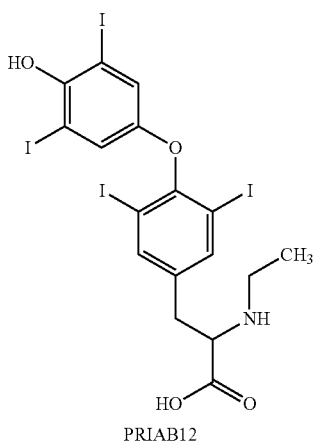

PRIAB12

These novel N-substituted groups (N-Methyl, N-Ethyl or N-Triphenyl) showed comparable pro-angiogenesis efficacy to that of b-FGF or L-T4 as shown in the Table below in the CAM model.

Effect of L-T4 analogs PRIAB2, PRIAB6, PRIAB12 in CAM Model of Angiogenesis

| Treatment | Branch pts ± SEM | % Inhibition ± SEM |
|---|---|---|
| PBS | 76.0 ± 8.5 | |
| FgF (1.25 µg/ml)) | 137.9 ± 7.5 | |
| PRIAB2 (0.1 µM) (T4 analog) | 136.0 ± 18.1 | |
| PRIAB6 (0.1 µM) (T4 analog) | 136.2 ± 12.4 | |
| PRIAB12 (0.1 µM) (T4 analog) | 121.7 ± 13.6 | |

Activation of $T_4$-BOC $T_4$-BOC may be activated using epichlorohydrin, or other suitable activating agent (e.g., epibromohydrin). For example, a synthesis schematic of activated $T_4$-BOC intermediates is shown below.

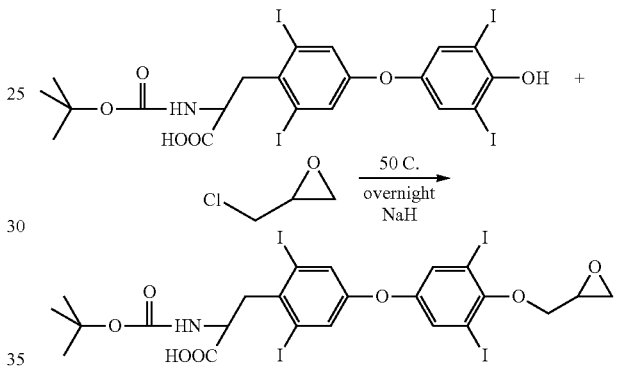

Synthesis of Novel T4/Polymeric Conjugates: Activated T4-BOC can be conjugated to different polymers, including without limitation PVA, PEG, PolyLysine, polyarginine. Conjugation of T4 to a polymer through the phenolic hydroxyl group may be desirable because T4 and T3 are each conjugated to glucuronic acid and sulfonic acid in the liver during degradation. For example, a synthesis schematic of the conjugation of activated T4-Boc to PolyLysine is shown below.

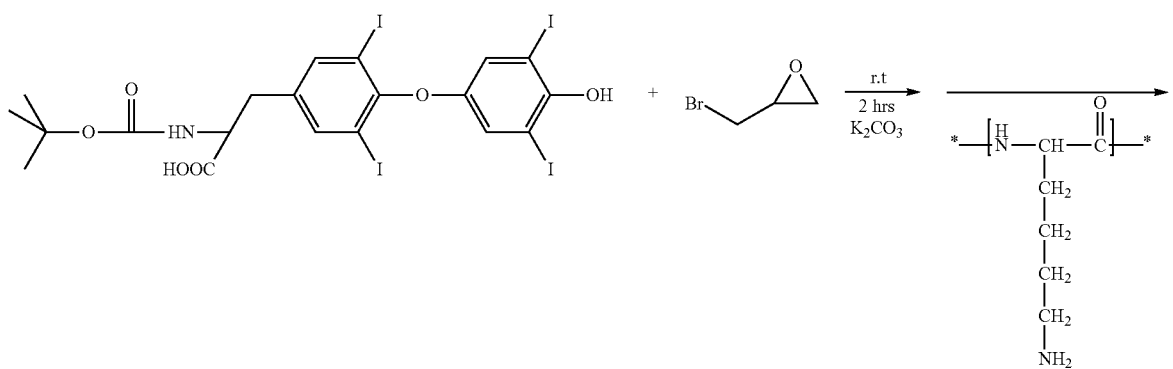

-continued
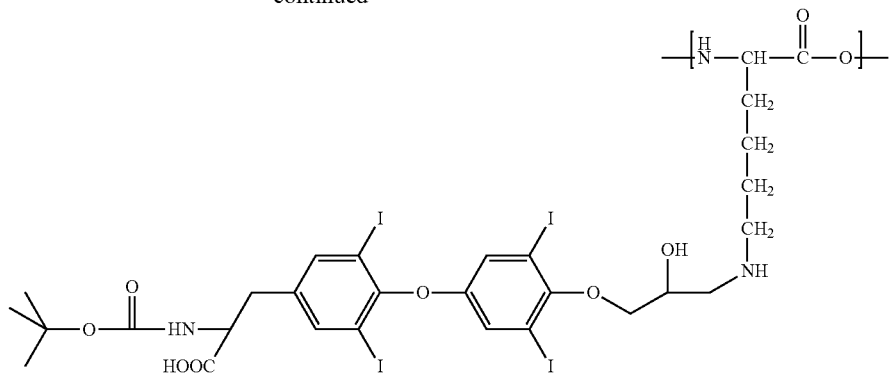
A synthesis schematic of the conjugation of T4-Boc to PolyArginine is shown below.
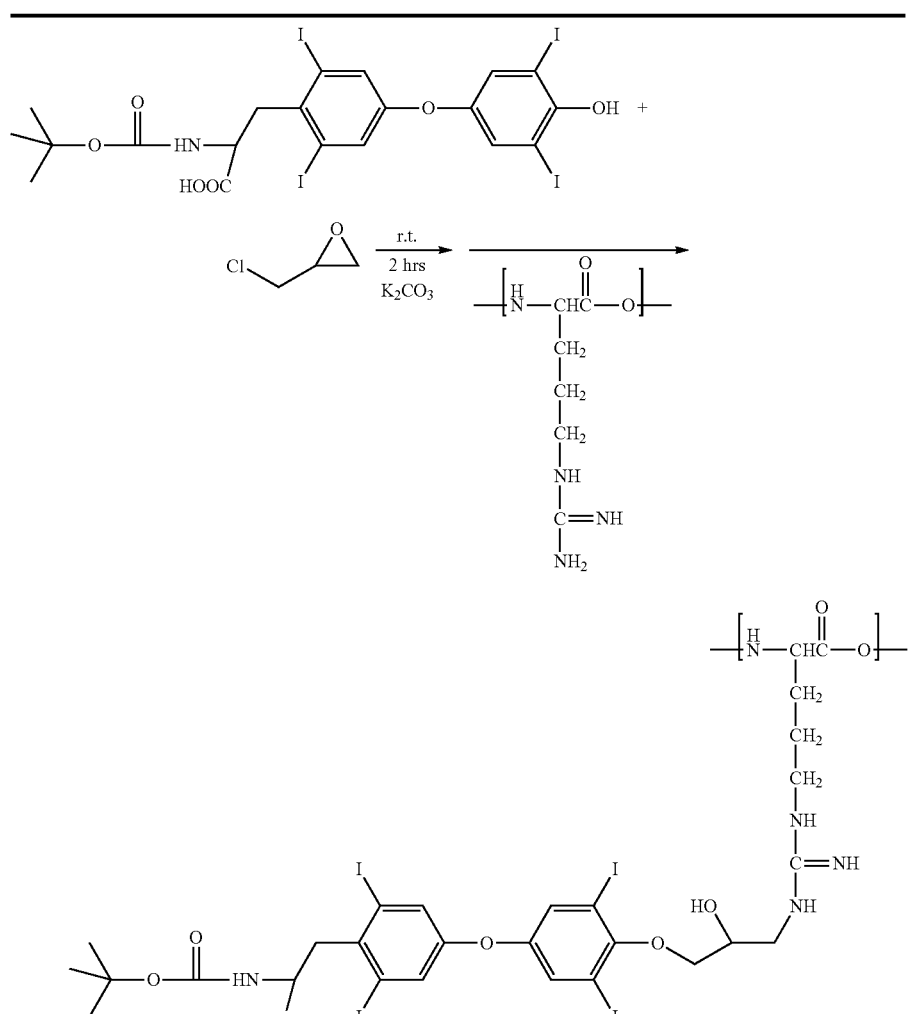
|  | MW | ratio | Weight (mg) | Volume (μl) | Density | mmol |
|---|---|---|---|---|---|---|
| T4-Boc | 876.99 | 1 | 40.0 |  |  | 45.6 |
| Epibromohydrin | 136.98 | 1.5 | 9.4 |  |  | 68.4 |
| PolyArginine |  |  | 60.0 |  |  |  |
| K2CO3 | 138.21 | 1.5 | 9.5 |  |  | 68.4 |
| NaOH | 40 | 1.5 | 2.7 |  |  | 68.4 |

A schematic showing protection of $T_4$ using acetic anhydride ($Ac_2O$) or ditertbutyldicarbonate ($BOC_2O$), deprotection, and subsequent conjugation to PVA or PEG, is shown below.
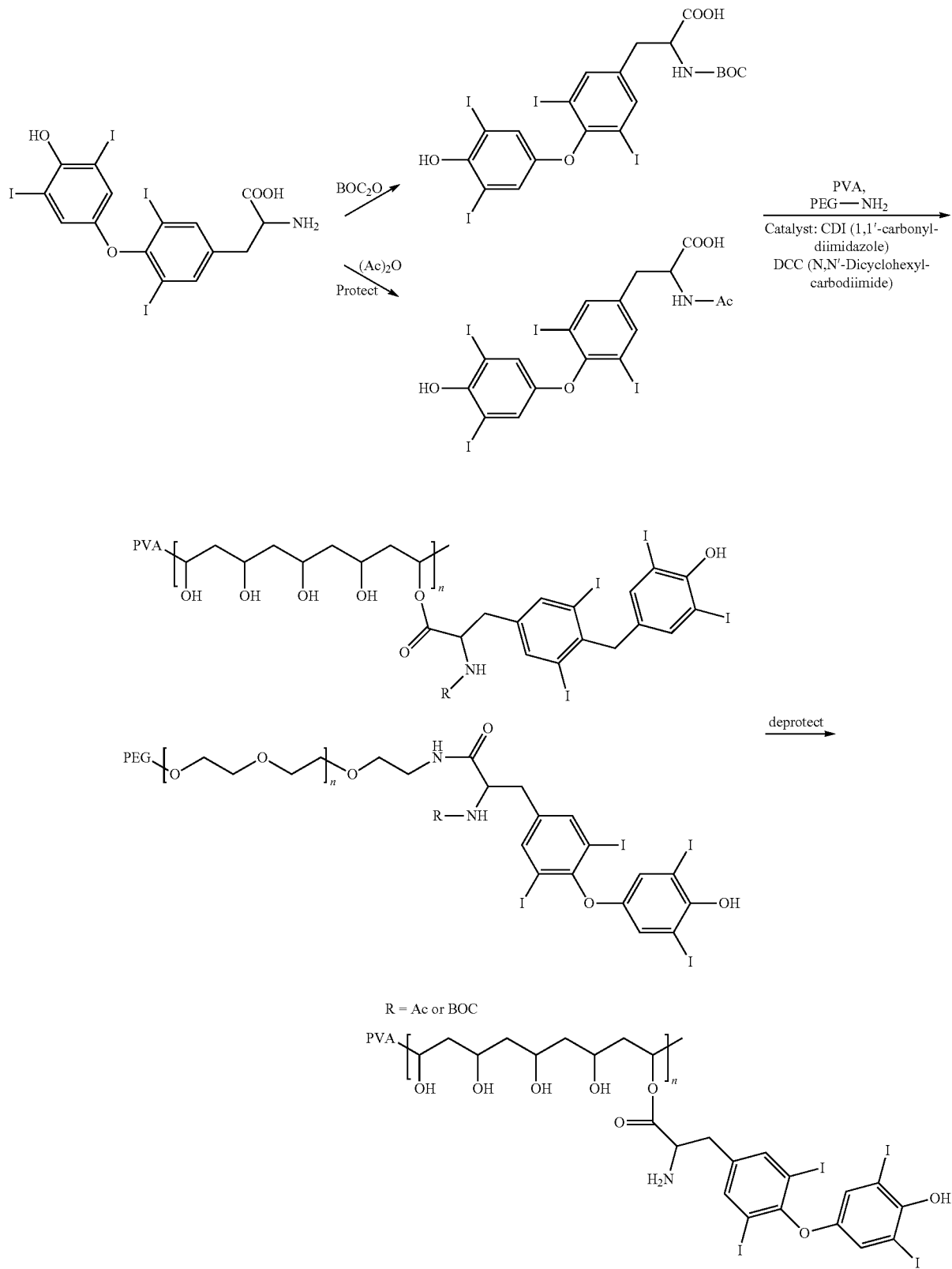

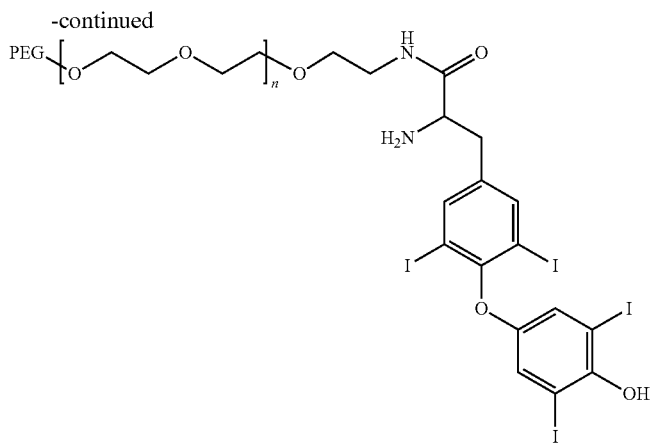

R = Ac or BOC

Preparation of Nanoparticle Encapsulated $T_4$

Subsequent to conjugation, e.g., conjugation to PEG, the $T_4$/PEG conjugates may be used for immobilization with nanoparticles by any method known to one of ordinary skill in the art. For example, without limitation, PEG-PLGA nanoparticles encapsulating N-protected $T_4$ are prepared by single emulsion method as follows (and depicted in FIG. 51). Solutions of PEG-PLGA and N-protected $T_4$ are prepared in DMSO separately (e.g. 80 mg/ml PEG-PLGA and 15 mg/ml N-protected $T_4$) then mixed in equal amounts. 100 μl of this solution is added to 1% PVA (polyvinyl alcohol) solution with constant stirring. After 4 hours the whole solution containing the nanoparticles encapsulating $T_4$ is subjected to dialysis to remove the impurities.

Preparation of $T_4$ Conjugated PEG-PLGA Nanoparticles $T_4$/PEG conjugates may be used for immobilization with nanoparticles by conjugation to a nanoparticles using a suitable conjugation method known to one of ordinary skill in the art. As an illustrative example, the highly reactive amino group present in $T_4$ was blocked first by using either acetic anhydride ($Ac_2O$) or ditertbutyldicarbonate ($BOC_2O$), then activated with epicholorohydrin, and conjugated to nanoparticles, as shown in the schematic below.

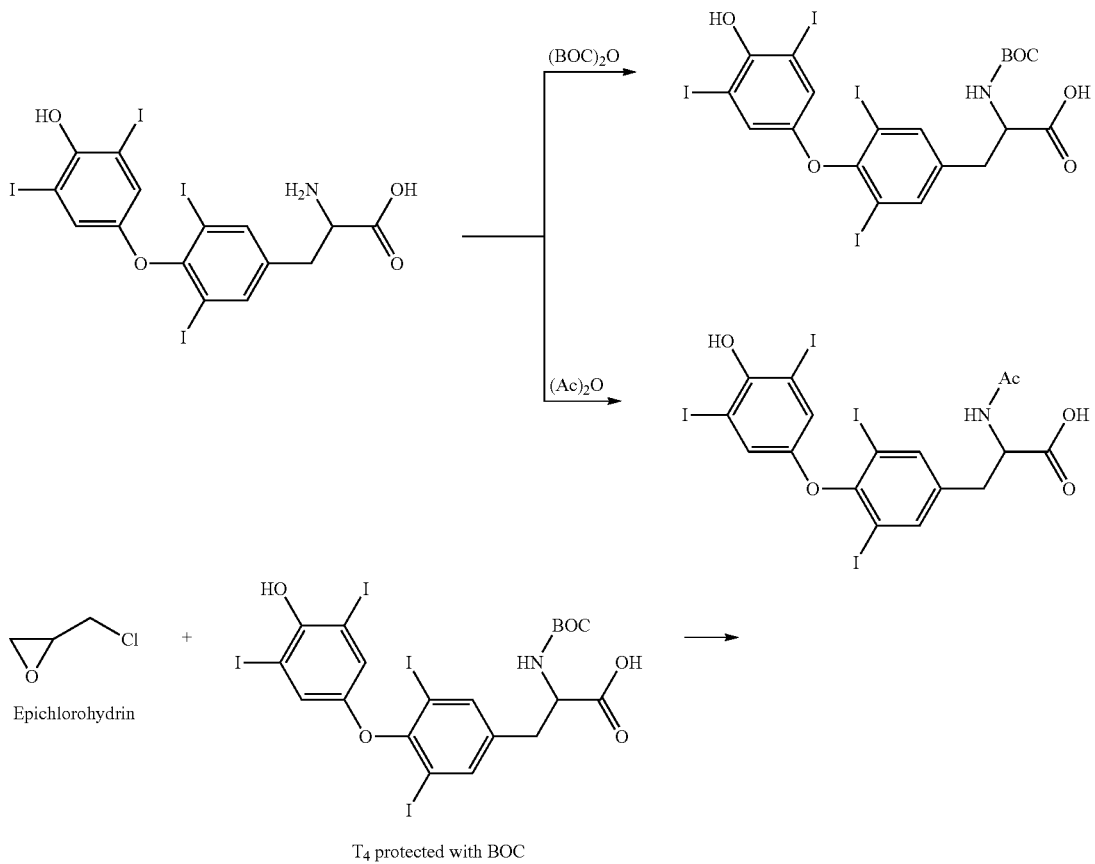

T4 protected with BOC

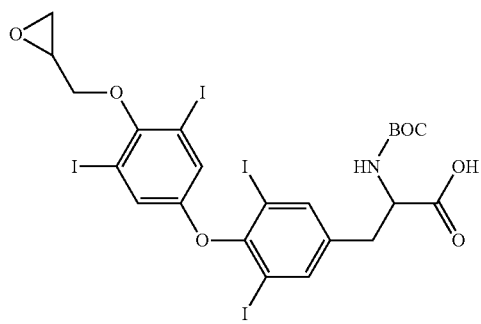
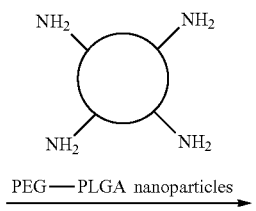

PEG—PLGA nanoparticles

Epoxy activated T4

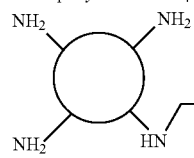
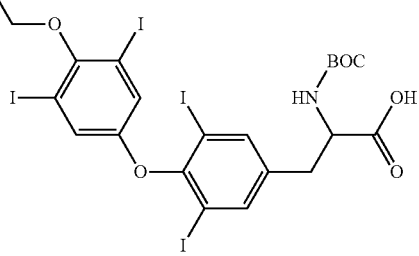

PEG—PLGA nanoparticles conjugated with T4

Pharmacological Tests

PRIAB1, PRIAB4 and PRIAB5, as described above were tested using the chick chlorioallantoic membrane (CAM) assay before conjugation. The results are presented herein for and in FIG. 52 for PRIAB1.

| Treatment | Branch pts ± SEM |
|---|---|
| PBS | 65.2 ± 14.9 |
| T4 (0.1 µM) | 137.3 ± 8.8 |
| PRIAB1 (0.1 µM) | 173 ± 9.9 |

The results of the tests were surprising. The test results showed a clear pro-angiogenesis action by the protected $T_4$ analogs and the bulkiest protective group showed the merest activity. Due to the formation of an amide bound, the free doublet of electrons carried by the secondary nitrogen of those molecules is displaced toward the carbonyl which renders the amine non-nucleophilic (deactivation of the amine by the carbonyl group is shown below). Nevertheless it is still basic.

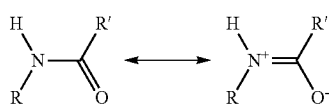

New analogs designed to carry a protected amino group (differing in bulkiness), which render the amine basic and nucleophilic are shown below:

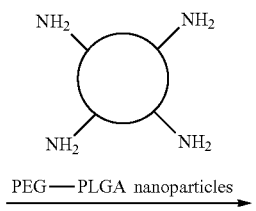

Me = CH₃

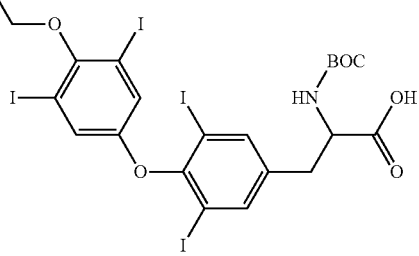

Et = CH₂CH₃

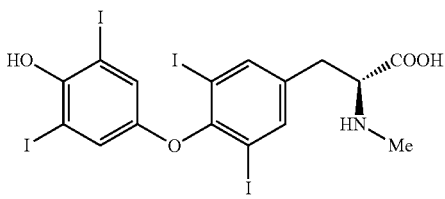

Tr = CPh₃

The results of the present and future investigations on the $T_4$ analogs and their nanoparticles counterparts represent a major step in enhancing the knowledge of the nongenomic action of $T_4$ toward the stimulation of new blood vessel formation. If positive, the results of the alkylated $T_4$ analogs may lead to start numerous new biological assays. These results may contribute towards the design of new dual TR-$\alpha_v\beta_3$ agonists or antagonists.

Example 30. Collateral Regeneration in Coronary, Carotid or Peripheral Tissues

Experimental Limb Ischemic Model:

The present study was carried out on three main groups of rabbits (8-12 months of age): a) ischemic, untreated serving as control group and b) ischemic receiving L-T4 analogs, and c) ischemic group receiving DITPA analogs. Animals were allowed free access to water and food and housed in separate cages at 22° C. ambient temperature and 12 hour light/dark cycle. Immediately after surgery rabbits were injected with a single i.m. dose of tetracycline. Thyroid analogs were given as a loading s.c. dose (1 mg/animal) followed by daily oral administration of the drug (1 mg/animal).

To investigate the feasibility of using thyroid analogs to stimulate angiogenesis and augment collateral vessel development in vivo, we used a rabbit model of hind limb ischemia. Briefly, under anaesthesia (a mixture of ketamine 10 mg/kg and xylazine 2.5 g/kg, i.m.), rabbits were subjected to longitudinal incision which was extended inferiorly from the inguinal ligament to a point just proximal to the patella. Through this incision, the femoral artery was dissected free, along its entire length; all branches of the femoral artery (including the inferior epigastric, deep femoral, lateral circumflex and superficial epigastric arteries) will be dissected free. Extensive dissection of the popliteal and saphenous arteries, was followed by ligation of the external iliac artery and all of the arteries mentioned earlier. This was followed by complete excision of the femoral artery from its proximal origin as a branch of the external iliac artery to the point distally where it bifurcates to form the saphenous and popliteal arteries. Therefore, the blood supply to the distal limb will depend on the collateral arteries which might originate from the ipsilateral internal iliac artery. Muscle samples were taken from the medial thigh.

Angiography:

Development of collateral vessels in the ischemic limb was evaluated by aortic angiography one month after surgery or treatment. As angiography was performed at the end of the study period, the injections were made through a catheter introduced into the aorta. Intra-arterial injection of contrast media (5 ml Isovue-370). Images of the ischemic limb from different groups was recorded.

After angiogram, the animals were sacrificed and blood samples were collected and tissue sections prepared from the hind limb muscles and embedded in paraffin for subsequent immunostaining.

Immunohistochemistry Study:

Expression of CD31:

Paraffin embedded section were deparaffined, rehydrated and subjected to antigen retrieval using microwave and citrate buffer, pH 6.1 for 10 minutes. The sections were then incubated with CD31 monoclonal mouse anti-human (DAKO) diluted 1:1000 in Tris buffered saline. This antibody strongly labels endothelial cells and is a good marker in determination of capillaries. The antigen-antibody complex was visualized using DAB and followed by counterstaining.

Assessment of Capillary Density:

Capillaries identified by positive staining for CD31 were counted by a single observer blinded to the treatment regimen under a 40× objective. (mean number of capillaries per muscle fiber). A total of 10 different fields from tissue sections were randomly selected, the number of capillaries counted and the capillary density was determined by calculating the capillary/muscle fiber ratio.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An imaging compound comprising:
a thyroid hormone analog, wherein the thyroid hormone analog is covalently bonded to a linker selected from the group consisting of diaminopropane, ether, sulfhydryl, ester and anhydride linkages, and the linker is covalently bonded to a radio-labelled tracer selected from the group consisting of iodine-123 ($^{123}$I), iodine-124 ($^{124}$I), iodine-125 ($^{125}$I), iodine-131 ($^{131}$I), fluorine-18 ($^{18}$F), technetium-99m ($^{99m}$Tc), indium-111 ($^{111}$In), carbon-11 ($^{11}$C) and astatine-210 ($^{210}$At), wherein the imaging compound is a nanoparticle.

2. The imaging compound of claim 1, wherein the thyroid hormone analog is tetrac, triac or a combination thereof.

3. The imaging compound of claim 1, wherein the nanoparticle has a diameter between 1 nm and less than 1000 nm.

4. The imaging compound of claim 1, wherein the thyroid hormone analog is covalently bonded to a diaminopropane linker and the diamino propane linker is covalently bonded to indium-111.

5. A method for imaging tumor tissues and neovascularization using the imaging compound of claim 1 comprising the steps of:
administering the imaging compound of claim 1 to a patient, wherein the imaging compound binds to a plurality of αvβ3 integrin receptors;
generating an image representing a distribution of the imaging agent binding to the αvβ3 integrin receptors.

6. The method of claim 5, wherein the step of generating the image is performed by an imaging technique selected from the group consisting of positron emission topography (PET) and single photon emission (SPECT).

7. The method of claim 5, wherein the imaging compound of claim 1 includes a thyroid hormone analog selected from the group consisting of tetrac, triac or a combination thereof.

8. A method for diagnosing a degenerative disease comprising the steps of:
administering the imaging compound of claim 1 to a patient, wherein the imaging compound binds to a plurality of transthyretin; and
generating an image representing a distribution of the imaging compound binding to the plurality of the transthyretin.

9. The method of claim 8, wherein the thyroid hormone analog of the imaging compound of claim 1 is triac or tetrac covalently bound to a the diaminopropane linker.

10. The method of claim 8, wherein the neurodegenerative disease is Alzheimer's disease.

11. The method of claim 8, further comprising the step of inhibiting the formation of amyloid fibrils with the imaging compound of claim 1.

12. The method of claim 8, wherein the step of generating the image is performed by positron emission topography (PET) or single photon emission (SPECT).

13. The imaging method of claim 8, wherein the image representing a distribution of the imaging compound is at least one portion of the brain.

* * * * *

UNITED STATES PATENT AND TRADEMARK OFFICE
CERTIFICATE OF CORRECTION

| | | |
|---|---|---|
| PATENT NO. | : 9,750,709 B2 | Page 1 of 3 |
| APPLICATION NO. | : 14/185010 | |
| DATED | : September 5, 2017 | |
| INVENTOR(S) | : Shaker A. Mousa, Faith B. Davis and Paul J. Davis | |

It is certified that error appears in the above-identified patent and that said Letters Patent is hereby corrected as shown below:

In the Specification

Column 1, Line 35, please change "containing same" to --containing the same--.

Column 4, Line 46, please change "substance" to --substances--.

Column 5, Line 8, please change "XT 1999" to --XT 199--.

Column 6, Line 65, please change "level of" to --levels of--.

Column 8, Line 41, please change "or agent" to --or agents--.

Column 12, Line 16, please change "FIG. 11a" to --FIG. 11A.--.

Column 12, Line 33, please change "FIG. 11b." to --FIG. 11B.--.

Column 12, Line 33, please change "FIG. 11a." to --FIG. 11A.--.

Column 16, Line 14, please change "show ling how" to --showing how--.

Column 17, Line 30, please change "FIG. C" to --FIG. 50C--.

Column 19, Line 20, please change "the related the term" to --the related term--.

Column 22, Line 7, please change "molecule" to --molecules--.

Column 31, Line 66, please change "ideal candidate" to --ideal candidates--.

Column 33, Line 48-49, please change "hydrolysis hydrolysis" to --hydrolysis, hydrolysis--.

Signed and Sealed this
Sixteenth Day of April, 2019

Andrei Iancu
*Director of the United States Patent and Trademark Office*

Column 39, Line 1, please change "can reacted" to --can react--.

Column 51, Line 65, please change "resent invention" to --present invention--.

Column 52, Line 66, please change "be chose" to --be chosen--.

Column 67, Line 4, please change "of is similar" to --is similar--.

Column 70, Line 66, please change "the call." to --the cell.--.

Column 71, Line 3, please change "in a doses" to --in doses--.

Column 72, Line 21, change "in Table" to --in the Table--; and
　　　Line 45, please change "TR-raised" to --TR raises--.

Column 75, Line 24, please change "efforts directed" to --effort directed--.

Column 79, Line 65, please change "$^{18}$F" to --$F^{18}$--.

Column 80, Line 60, please change "brain brains from" to --brains from--; and
　　　Line 64, please change "brain brains because" to --brains because--.

Column 87, Line 54, please change "for parental" to --for parenteral--; and
　　　Line 55, please change "For enteral" to --For parenteral--.

Column 89, Line 41, please change "inducer, or agonist" to --inducers, or agonists--; and
　　　Line 47, please change "inducer, or agonist" to --inducers, or agonists--.

Column 90, Line 45-46, please change "inducer, or agonist" to --inducers, or agonists--; and
　　　Line 52, please change "inducer, or agonist" to --inducers, or agonists--.

Column 92, Line 4, please change "inducer, or agonist" to --inducers, or agonists--; and
　　　Line 14, please change "inducer or agonist" to --inducers, or agonists--.

Column 94, Line 46, please change "were pre-pared" to --were prepared--.

Column 100, Line 3, please change "purchased £tom" to --purchased from--.

Column 106, Line 11, please change "chamber allow" to --chamber allows--; and
　　　Line 24, please change "will then" to --will then be--.

Column 119, Line 25, please change "advantage of" to --advantages of--;
　　　Line 50, please change "amount of the both solution" to --amounts of both solutions--; and
　　　Line 66-67, please change "amount of both solution" to --amounts of both solutions--.

Column 120, Line 19, please change "adhere to" to --adheres to--;

Line 42, please change "containing drug" to --containing the drug--; and
Line 57, please change "free drug" to --the drug--.

Column 121, Line 20, please change "variation like" to --variations like--.

Column 124, Line 34, please change "mixer The" to --mixer. The--.

In the Claims

Column 145, Line 40, please change "the diamino propane" to --the diaminopropane--.

Column 146, Line 38, please change "to a the" to --to the--.